(12) United States Patent
Neville et al.

(10) Patent No.: US 11,786,562 B2
(45) Date of Patent: Oct. 17, 2023

(54) BACTERIOTHERAPY

(71) Applicant: Genome Research Limited, Saffron Walden (GB)

(72) Inventors: Anne Neville, Saffron Walden (GB); Hilary Browne, Saffron Walden (GB); Sam Forster, Saffron Walden (GB); Trevor Lawley, Saffron Walden (GB)

(73) Assignee: Genome Research Limited, Hinxton (GB)

( * ) Notice: Subject to any disclaimer, the term of this patent is extended or adjusted under 35 U.S.C. 154(b) by 884 days.

(21) Appl. No.: 16/094,856

(22) PCT Filed: Apr. 19, 2017

(86) PCT No.: PCT/GB2017/051083
§ 371 (c)(1),
(2) Date: Oct. 18, 2018

(87) PCT Pub. No.: WO2017/182796
PCT Pub. Date: Oct. 26, 2017

(65) Prior Publication Data
US 2022/0184149 A1   Jun. 16, 2022

(30) Foreign Application Priority Data
Apr. 19, 2016 (GB) ...................... 1606801

(51) Int. Cl.
| | |
|---|---|
| *A01N 63/00* | (2020.01) |
| *A61K 35/742* | (2015.01) |
| *A61P 1/06* | (2006.01) |
| *A61P 1/14* | (2006.01) |
| *A61P 1/16* | (2006.01) |
| *A61P 31/04* | (2006.01) |
| *A61P 1/04* | (2006.01) |
| *A61K 9/00* | (2006.01) |

(52) U.S. Cl.
CPC .......... *A61K 35/742* (2013.01); *A61K 9/0031* (2013.01); *A61K 9/0053* (2013.01); *A61P 1/04* (2018.01); *A61P 1/06* (2018.01); *A61P 1/14* (2018.01); *A61P 1/16* (2018.01); *A61P 31/04* (2018.01)

(58) Field of Classification Search
CPC .................................................... A61K 35/742
See application file for complete search history.

(56) References Cited

U.S. PATENT DOCUMENTS

| | | | | |
|---|---|---|---|---|
| 8,906,668 B2 * | 12/2014 | Henn | ..................... | A23L 33/127 |
| | | | | 435/252.4 |
| 10,058,574 B2 * | 8/2018 | Grant | ..................... | A61P 19/02 |
| 10,064,900 B2 * | 9/2018 | Von Maltzahn | ..... | A61K 9/4816 |
| 10,130,665 B2 * | 11/2018 | Lawley | ................ | A61K 35/744 |
| 10,391,130 B2 * | 8/2019 | Grant | ........................ | A61K 9/19 |
| 10,610,550 B2 * | 4/2020 | Mulder | ..................... | C12N 1/20 |
| 10,780,134 B2 * | 9/2020 | Grant | ....................... | A61P 37/06 |
| 10,864,235 B2 * | 12/2020 | Henn | ..................... | A61K 35/742 |
| 2014/0147425 A1 * | 5/2014 | Henn | ..................... | A61K 35/742 |
| | | | | 424/93.41 |
| 2014/0199281 A1 * | 7/2014 | Henn | ..................... | A61K 9/4891 |
| | | | | 424/93.46 |
| 2015/0190435 A1 | 7/2015 | Henn et al. | | |
| 2016/0022746 A1 * | 1/2016 | Lawley | ................. | C12Q 1/689 |
| | | | | 424/93.3 |
| 2017/0319634 A1 * | 11/2017 | Grant | .................. | C12R 2001/01 |
| 2018/0280454 A1 * | 10/2018 | Garcia-Rodenas | ....... | A61P 1/10 |
| 2019/0134109 A1 * | 5/2019 | Mulder | ................. | A61K 31/739 |
| 2019/0209627 A1 * | 7/2019 | Lawley | .................... | C12Q 1/04 |
| 2019/0240269 A1 * | 8/2019 | Lawley | ................ | A61K 35/744 |

FOREIGN PATENT DOCUMENTS

| | | |
|---|---|---|
| JP | 2015537042 A | 12/2015 |
| WO | WO-2012039615 A2 | 3/2012 |
| WO | WO-2013037068 A1 | 3/2013 |
| WO | WO-2014121301 A1 | 8/2014 |
| WO | WO-2015077794 A1 | 5/2015 |
| WO | WO-2015156419 A1 | 10/2015 |
| WO | WO-2017182796 A1 | 10/2017 |

OTHER PUBLICATIONS

Li et al, PNAS, USA, Feb. 12, 2008, 105/6:2117-2122 (Year: 2008).*
Li et al, PLoS ONE, Jun. 2012, 7/6:e26284, 10 pages (Year: 2012).*
Lawley et al, PLoS Pathogens, Oct. 2012, 8/10:e1002995 (Year: 2012).*
Li et al (PNAS vol. 105, No. 6, pp. 2117-2122) (Year: 2008).*
Abecasis, A.B., et al., "A Genomic Signature and the Identification of New Sporulation Genes," Journal of Bacteriology 195(9):2101-2115, American Society for Microbiology, United States (May 2013).
Abujamel, T., et al., "Defining the Vulnerable Period for Re-Establishment of Clostridium Difficile Colonization After Treatment of C. Difficile Infection With Oral Vancomycin or Metronidazole," PloS one 8(10):e76269, Public Library of Science, United States (Oct. 2013).
Ze, X., et al., "Some Are More Equal Than Others: the Role of "Keystone" Species in the Degradation of Recalcitrant Substrates," Gut Microbes 4(3):236-240, Taylor & Francis, United States (May-Jun. 2013).
Xu, M.Q., et al., "Fecal Microbiota Transplantation Broadening Its Application Beyond Intestinal Disorders," World Journal of Gastroenterology 21(1):102-111, Baishideng Publishing Group, United States (Jan. 2015).

(Continued)

*Primary Examiner* — Albert M Navarro
(74) *Attorney, Agent, or Firm* — STERNE, KESSLER, GOLDSTEIN & FOX P.L.L.C.

(57) ABSTRACT

The invention relates to therapeutic compositions comprising at least one isolated bacterium and a pharmaceutically acceptable excipient, as well as methods of preparing such therapeutic compositions. The therapeutic compositions find application in the treatment of dysbiosis, in particular dysbiosis of the gastrointestinal tract.

19 Claims, 18 Drawing Sheets
Specification includes a Sequence Listing.

(56) References Cited

OTHER PUBLICATIONS

Angriman, I., et al., "Relationship Between Pouch Microbiota and Pouchitis Following Restorative Proctocolectomy for Ulcerative Colitis," World Journal of Gastroenterology 20(29):9665-9674, WJG Press, United States (Aug. 2014).

Atarashi, K., et al., "Treg Induction by a Rationally Selected Mixture of Clostridia Strains From the Human Microbiota," Nature 500(7461):232-236, Nature Publishing Group, England (Aug. 2013) including supplemental data.

Bajaj, J.S., et al., "The Intestinal Microbiota and Liver Disease," Gastroenterology 1:9-14, The American Journal of Gastroenterology Supplements (2012).

Bajaj, J.S., "The Role of Microbiota in Hepatic Encephalopathy.," Gut Microbes 5(3):397-403, Taylor & Francis, United States (May 2014).

Blanton, L.V., et al., "Gut Bacteria That Prevent Growth Impairments Transmitted by Microbiota From Malnourished Children," Science 351(6275):aad3311, American Association for the Advancement of Science, United States (Feb. 2016).

Bosshard, P.P., et al., "Ribosomal DNA sequencing for Identification of Aerobic Gram-Positive Rods in the Clinical Laboratory (an 18-month evaluation).," Journal of Clinical Microbiology 41(9):4134-4140, American Society for Microbiology, United States (Sep. 2003).

Britton, R.A., et al., "Role of the Intestinal Microbiota in Resistance to Colonization by Clostridium Difficile," Gastroenterology 146(6):1547-1553, W.B. Saunders, United States (May 2014).

Buffie, C. G., et al., "Precision Microbiome Reconstitution Restores Bile Acid Mediated Resistance to Clostridium Difficile," Nature 517(7533):205-208, Nature Publishing Group, England (Jan. 2015).

Chakraborty, A., et al., "DBETH: a Database of Bacterial Exotoxins for Human," Nucleic Acids Research 40:D615-D620, Oxford University Press, England (Jan. 2012).

Clarridge, J. E., "Impact of 16s rRNA Gene Sequence Analysis for Identification of Bacteria on Clinical Microbiology and Infectious Diseases," Clinical Microbiology Reviews 17(4):840-862, American Society for Microbiology, United States (Oct. 2004).

Cole,J.R., et al., "Ribosomal Database Project: Data and Tools for High Throughput rRNA Analysis," Nucleic Acids Research 42(D):D633-D642, Oxford University Press, England (Jan. 2014).

Collins,S., "A Role for the Gut Microbiota in IBS," Nature Reviews. Gastroenterology & Hepatology 11(8):497-505, Nature Pub. Group, England (Aug. 2014).

Cornely, O.A., et al., "Treatment of First Recurrence of Clostridium Difficile Infection: Fidaxomicin Versus Vancomycin," Clinical Infectious Diseases : An Official Publication of the Infectious Diseases Society of America 55(Suppl 2):S154-S161, Oxford University Press, England (Aug. 2012).

Dominguez-Bello,M.G., et al., "Delivery Mode Shapes the Acquisition and Structure of the Initial Microbiota Across Multiple Body Habitats in Newborns," Proceedings of the National Academy of Sciences of the United States of America 107(26):11971-11975, National Academy of Sciences, United States (Jun. 2010).

Duncan, S.H., et al., "Growth Requirements and Fermentation Products of Fusobacterium Prausnitzii, and a Proposal to Reclassify It as Faecalibacterium Prausnitzil Gen. Nov., Comb. Nov," International Journal of Systematic and Evolutionary Microbiology 52(Pt 6):2141-2146, Microbiology Society, England (Nov. 2002).

Eckburg,P.B., et al., "Diversity of the Human Intestinal Microbial Flora," Science 308(5728):1635-1638, American Association for the Advancement of Science, United States (Jun. 2005).

Fodor,A.A., et al., "The "Most Wanted" Taxa From the Human Microbiome for Whole Genome Sequencing ," PloS one 7(7):e41294, Public Library of Science, United States (Jul. 2012).

Forster,S.C., et al., "HPMCD: The Database of Human Microbial Communities From Metagenomic Datasets and Microbial Reference Genomes," Nucleic Acids Research 44(D1):D604-609, Oxford University Press, England (Jan. 2016).

Francis,M.B., et al., "Bile Acid Recognition by the Clostridium Difficile Germinant Receptor, CspC, Is Important for Establishing Infection," PLoS Pathogens 9(5):e1003356, Public Library of Science, United States (May 2013).

Galperin,M.Y., et al., "Genomic Determinants of Sporulation in Bacilli and Clostridia: Towards the Minimal Set of Sporulation-Specific Genes," Environmental Microbiology 14(11):2870-2890, Blackwell Science, England (Nov. 2012).

Goodman,A.L., et al., "Extensive Personal Human Gut Microbiota Culture Collections Characterized and Manipulated in Gnotobiotic Mice," Proceedings of the National Academy of Sciences of the United States of America 108(15):6252-6257, National Academy of Sciences, United States (Apr. 2011).

Hattori,M and Taylor,T.D.,, "The Human Intestinal Microbiome: a New Frontier of Human Biology," DNA Research : an International Journal for Rapid Publication of Reports on Genes and Genomes 16(1):1-12, Oxford University Press, England (Feb. 2009).

Hold, G.L., et al., "Role of the Gut Microbiota in Inflammatory Bowel Disease Pathogenesis: What Have We Learnt in the Past 10 Years ?," World Journal of Gastroenterology 20(5):1192-1210, WJG Press, United States (Feb. 2014).

Hooper, L.V., et al., "Interactions Between the Microbiota and the Immune System," Science 336(6086):1268-1273, American Association for the Advancement of Science, United States (Jun. 2012).

Hooper, L.V., et al., "Molecular Analysis of Commensal Host-microbial Relationships in the Intestine," Science 291(5505):881-884, American Association for the Advancement of Science, United States (Feb. 2001).

Huse, S.M., et al., "Exploring Microbial Diversity and Taxonomy Using SSU rRNA Hypervariable Tag Sequencing," PLoS Genetics 4(11):e1000255, Public Library of Science, United States (Nov. 2008).

International Search Report and Written Opinion for International Application No. PCT/GB2017/051083, European Patent Office, HV Rijswijk, dated Jul. 5, 2017.

Janoir, C., et al., "Adaptive Strategies and Pathogenesis of Clostridium Difficile From in Vivo Transcriptomics," Infection and Immunity 81(10):3757-3769, American Society for Microbiology, United States (Oct. 2013).

Johnson, M., et al., "NCBI BLAST: a Better Web Interface," Nucleic Acids Research 36:W5-W9, Oxford University Press, England (Jul. 2008).

Jostins, L., et al., "Host-Microbe Interactions Have Shaped the Genetic Architecture of Inflammatory Bowel Disease," Nature 491(7422):119-124, Nature Publishing Group, England (Nov. 2012).

Koenig, J.E., et al., "Succession of Microbial Consortia in the Developing Infant Gut Microbiome," Proceedings of the National Academy of Sciences of the United States of America 108(Suppl 1):4578-4585, National Academy of Sciences, United States (Mar. 2011).

Kozich, J.J ., et al., "Development of a Dual-Index Sequencing Strategy and Curation Pipeline for Analyzing Amplicon Sequence Data on the Miseq Illumina Sequencing Platform," Applied and Environmental Microbiology 79(17):5112-5120, American Society for Microbiology, United States (Sep. 2013).

Lagier, J.C., et al., "The Rebirth of Culture in Microbiology Through the Example of Culturomics to Study Human Gut Microbiota," Clinical Microbiology Reviews 28(1):237-264, American Society for Microbiology, United States (Jan. 2015).

Landy, J., et al., "Review Article: Faecal Transplantation Therapy for Gastrointestinal Disease," Alimentary pharmacology & therapeutics 34(4):409-415, Wiley-Blackwell, England (Aug. 2011).

Lawley, T.D and Walker, A.W., "Intestinal Colonization Resistance," Immunology 138(1):1-11, Blackwell Science, England (Jan. 2013).

Lawley, T.D., et al., "Antibiotic Treatment of Clostridium Difficile Carrier Mice Triggers a Supershedder State, Spore-Mediated Transmission, and Severe Disease in Immunocompromised Hosts," Infection and Immunity 77(9):3661-3669, American Society for Microbiology, United States (Sep. 2009).

Lawley, T.D., et al., "Targeted Restoration of the Intestinal Microbiota With a Simple, Defined Bacteriotherapy Resolves Relapsing Clostridium

(56) References Cited

OTHER PUBLICATIONS

Difficile Disease in Mice," PLoS Pathogens 8(10):e1002995, Public Library of Science, United States (Oct. 2012).

Letunic, I. and Bork, P., "Interactive Tree of Life V2: Online Annotation and Display of Phylogenetic Trees Made Easy," Nucleic Acids Research 39:W475-478, Oxford University Press, England (Jul. 2011).

Louis, P and Flint, H.J., "Diversity, Metabolism and Microbial Ecology of Butyrate-producing Bacteria From the Human Large Intestine," FEMS Microbiology Letters 294(1):1-8, Oxford University Press, England (May 2009).

Lozupone, C and Knight, R., "UniFrac: a New Phylogenetic Method for Comparing Microbial Communities," Applied and Environmental Microbiology 71(12):8228-8235, American Society for Microbiology, United States (Dec. 2005).

Ludwig, W ., et al., "ARB: a Software Environment for Sequence Data," Nucleic Acids Research 32(4):1363-1371, Oxford University Press, England (Feb. 2004).

McArthur, A.G., et al., "The Comprehensive Antibiotic Resistance Database," Antimicrobial Agents and Chemotherapy 57(7):3348-3357, American Society for Microbiology, United States (Jul. 2013).

Meehan, C.J., et al., "A Phylogenomic View of Ecological Specialization in the Lachnospiraceae, a Family of Digestive Tract-Associated Bacteria," Genome Biology and Evolution 6(3):703-713, Oxford University Press, England (Mar. 2014).

Nielsen, H.B., et al., "Identification and Assembly of Genomes and Genetic Elements in Complex Metagenomic Samples Without Using Reference Genomes," Nature Biotechnology 32(8):822-828, Nature America Publishing, United States (Aug. 2014).

Ottman, N., et al., "The Function of Our Microbiota: Who Is Out There and What Do They Do?," Frontiers in Cellular and Infection Microbiology 2:104, Frontiers Media SA, Switzerland (Aug. 2012).

Van Nood, E., et al., "Duodenal Infusion of Donor Feces for Recurrent Clostridium Difficile," The New England Journal of Medicine 368(5):407-415, Massachusetts Medical Society, United States (Jan. 2013).

Perez Martinez, G., et al., "Understanding Gut Microbiota in Elderly's Health Will Enable Intervention Through Probiotics," Beneficial Microbes 5(3):235-246, Wageningen Academic Publishers, Netherlands (Sep. 2014).

Petrof, E.O., et al., "Stool Substitute Transplant Therapy for the Eradication of Clostridium Difficile Infection: 'Repoopulating' the Gut," Microbiome 1(1):3, BioMed Central, England (Jan. 2013).

Price, M.N., et al., "Fasttree 2—approximately Maximum-likelihood Trees for Large Alignments," PLoS One 5(3):e9490, Public Library of Science, United States (Mar. 2010).

Pruesse, E., et al., "SILVA: a Comprehensive Online Resource for Quality Checked and Aligned Ribosomal Rna Sequence Data Compatible With ARB," Nucleic Acids Research 35(21):7188-7196, Oxford University Press, England (2007).

Qin, J., et al., "A Human Gut Microbial Gene Catalogue Established by Metagenomic Sequencing," Nature 464(7285):59-65, Nature Publishing Group, England (Mar. 2010).

Quince, C., et al., "Removing Noise From Pyrosequenced Amplicons," BMC Bioinformatics 12:38, BioMed Central, England (Jan. 2011).

Rajilic-Stojanovi, M and De Vos W.M, "The First 1000 Cultured Species of the Human Gastrointestinal Microbiota," FEMS Microbiology Reviews 38(5):996-1047, Elsevier Science Publishers on behalf of the Federation of European Microbiological Societies, England (Sep. 2014).

NIH Human Microbiome Project, "HMRGD-HMP1," from http://hmpdacc.org/HMRGD, retrieved on Oct. 29, 2018, Institute for Genome Sciences, University of Maryland School of Medicine, 2 pages.

NIH Human Microbiome Project, "Most Wanted Genome-HMP1," from http://hmpdacc.org/most_wanted/#data, retrieved on Oct. 29, 2018, Institute for Genome sciences, University of Maryland School of Medicine, 2 pages.

Riley, T.V., et al., "Comparison of Alcohol Shock Enrichment and Selective Enrichment for the Isolation of Clostridium Difficile," Epidemiology and Infection 99(2):355-359, Cambridge University Press, England (Oct. 1987).

Scheperjans, F., et al., "Gut Microbiota Are Related to Parkinson's Disease and Clinical Phenotype," Movement Disorders 30(3):350-358, Wiley-Liss, United States (Mar. 2015).

Schloss, P.D., et al., "Introducing Mothur: Open-source, Platform-independent, Community-supported Software for Describing and Comparing Microbial Communities," Applied and Environmental Microbiology 75(23):7537-7541, American Society for Microbiology, United States (Dec. 2009).

Schloss, P.D., et al., "Reducing the Effects of Pcr Amplification and Sequencing Artifacts on 16s Rrna-based Studies," PLoS One 6(12):e27310, Public Library of Science, United States (Dec. 2011).

Sekirov, I., et al., "Gut Microbiota in Health and Disease," Physiological Reviews 90(3):859-904, American Physiological Society, United States (Jul. 2010).

Wang, Q., et al., "Naive Bayesian Classifier for Rapid Assignment of Rrna Sequences Into the New Bacterial Taxonomy," Applied and Environmental Microbiology 73(16):5261-5267, American Society for Microbiology, United States (Aug. 2007).

Snyder, A., et al., "Genetic Basis for Clinical Response to CTLA-4 Blockade in Melanoma," The New England Journal of Medicine 371(23):2189-2199, Massachusetts Medical Society, United States (Dec. 2014).

Stewart, E.J, "Growing Unculturable Bacteria," Journal of Bacteriology 194(16):4151-4160, American Society for Microbiology, United States (Aug. 2012).

Adamu, B. O., and Lawley, T. D., "Bacteriotherapy for the treatment of intestinal dysbiosis caused by Clostridium difficile infection," Curr Opin Microbiol 16(5):596-601, Elsevier, Netherlands (published online Jul. 2013, published in print Oct. 2013).

* cited by examiner

A

B

Figure 15 – Characteristics of deposited bacteriotherapy candidates

| 16S rRNA gene sequence | Reference number of deposited bacterial isolate | Closest characterised bacterial species as determined by BLAST analysis | Leibniz-Institut DSMZ (DSMZ) accession number for the deposited bacterial isolate | On Human Microbiome Project's "Most Wanted List" | Average abundance > 0.001% | Reduced average abundance in gastrointestinal dysbiosis | Spore-former (isolated from an ethanol-treated sample) | Present post FMT (CIP2 criteria) | Adheres to CIP2 selection criteria | Pathogen (C. difficile and/or E.coli) inhibition | Co-occurrence with inhibitor | Production of beneficial metabolites (SCFA) | Keystone species | Immunomodulation activity |
|---|---|---|---|---|---|---|---|---|---|---|---|---|---|---|
| 1 | HMI_1 | Clostridium thermocellum | DSM32191 | X | X | X | X | | | | | | | |
| 2 | HMI_2 | Flavonifractor plautii | DSM32147 | X | X | X | X | | | | X | X | | |
| 3 | HMI_3 | Flavonifractor plautii | DSM32149 | | X | X | | | | | | | | |
| 4 | HMI_4 | Clostridium orbiscindens | DSM32175 | X | X | X | X | | | | X | | | X |
| 5 | HMI_5 | Ruminococcus flavefaciens | DSM32153 | X | X | X | | | | | X | X | | |
| 6 | HMI_6 | Anaerotruncus colihominis | DSM32152 | | X | X | X | | | | X | X | | |
| 7 | HMI_7 | Clostridium xylanolyticum | DSM32158 | X | X | X | | | | | X | | | |
| 8 | HMI_8 | Clostridium oroticum | DSM32192 | | X | X | | | | | X | | | |
| 9 | HMI_9 | Eubacterium contortum | DSM32148 | | X | X | | | | | X | X | | X |
| 10 | HMI_10 | Clostridium oroticum | DSM32166 | | X | X | X | | | | X | X | | X |
| 11 | HMI_11 | Lachnospira pectinoschiza | DSM32151 | X | X | X | | | | | X | X | | |
| 12 | HMI_12 | Roseburia faecis | DSM32150 | X | X | X | | | | | X | X | | |
| 13 | HMI_14 | Clostridium hathewayi | DSM32193 | | X | X | | | | | X | X | | |
| 14 | HMI_15 | Fusicatenibacter saccharivorans | DSM32162 | X | X | X | X | | | | X | X | | X |
| 15 | HMI_16 | Clostridium clostridioforme | DSM32194 | X | X | X | | | | | X | | | |
| 16 | HMI_17 | Ruminococcus torques | DSM32163 | X | X | X | X | | | | X | | X | |
| 17 | HMI_18 | Clostridium celerecrescens | DSM32205 | X | X | X | | | | | X | | | |
| 18 | HMI_19 | Clostridium celerescens | DSM32195 | X | X | X | | | | | X | | | |
| 19 | HMI_20 | Eubacterium infirmum | DSM32164 | | X | X | | | | | X | X | | |
| 20 | HMI_21 | Eubacterium infirmum | DSM32177 | | X | X | X | | | | X | | | |
| 21 | HMI_22 | Clostridium thermocellum | DSM32167 | | X | X | X | | | | | | | |
| 22 | HMI_23 | Anaerovorax odorimutans | DSM32165 | | X | X | | | X | X | | X | X | |
| 23 | HMI_24 | Clostridium saccharogumia | DSM32169 | | X | X | | | X | X | | X | X | |
| 24 | HMI_25 | Clostridium saccharogumia | DSM32168 | | X | X | | | X | X | X | X | X | |
| 25 | HMI_26 | Blautia luti | DSM32178 | | X | X | | | X | X | X | X | X | |
| 26 | HMI_27 | Clostridium clostridioforme | DSM32182 | | X | X | | | X | X | X | X | X | X |

Figure 15 continued

| 16S rRNA gene sequence | Reference number of deposited bacterial isolate | Closest characterised bacterial species as determined by BLAST analysis | Leibniz-Institut DSMZ (DSMZ) accession number for the deposited bacterial isolate | On Human Microbiome Project's "Most Wanted List" | Average abundance > 0.001% | Reduced average abundance in gastrointestinal dysbiosis | Spore-former (isolated from an ethanol-treated sample) | Present post FMT (CIP2 criteria) | Adheres to CIP2 selection criteria | Pathogen (C. difficile and/or E.coli) inhibition | Co-occurrence with inhibitor | Production of beneficial metabolites (SCFA) | Keystone species | Immunomodulation activity |
|---|---|---|---|---|---|---|---|---|---|---|---|---|---|---|
| 27 | HMI_28 | Blautia producta | DSM32179 |  | X | X |  | X | X | X | / | X | X | X |
| 28 | HMI_29 | Blautia glucerasea | DSM32180 |  | X | X |  | X | X |  |  | X | X | / |
| 29 | HMI_30 | Clostridium straminisolvens | DSM32184 |  | X | X |  | X | X |  |  | X | X | / |
| 30 | HMI_31 | Butyricicoccus pullicaecorum | DSM32181 |  | X | X |  | X | X |  | X | X | X | / |
| 31 | HMI_32 | Clostridium maritimum | DSM32183 |  | X | X |  | X | X |  |  | X | X | / |
| 32 | HMI_33 | Eubacterium fissicatens | DSM32262 |  | X | X | X | X | / |  | X | X | / | / |
| 33 | HMI_34 | Clostridium saccharolyticum | DSM32211 |  | X | X |  | X | / |  | X | X | / | / |
| 34 | HMI_35 | Ruminococcus obeum | DSM32219 | X | X | X |  | X | / |  | X | X | / | / |
| 35 | HMI_36 | Clostridium methylpentosum | DSM32222 |  | X | X | X |  | / |  |  | / | / | / |
| 36 | HMI_37 | Clostridium xylanolyticum | DSM32261 | X | X | X | X | X | / |  | X | / | / | / |
| 37 | HMI_38 | Oscillibacter valericigenes | DSM32212 | X | X | X | X |  | / |  | X | / | / | X |
| 38 | HMI_39 | Ruminococcus obeum | DSM32220 | X | X | X |  | X | / |  | X | X | / | / |
| 39 | HMI_40 | Megasphaera elsdenii | DSM32213 |  | X | X |  |  | / |  | X | / | / | / |
| 40 | HMI_41 | Blautia luti | DSM32226 |  | X | X |  | X | / |  | X | / | / | / |
| 41 | HMI_42 | Bacteroides coprocola | DSM32215 |  | X | X |  |  | / |  | X | X | / | / |
| 42 | HMI_43 | Bacteroides plebius | DSM32216 |  | X | X |  |  | / |  | X | X | / | / |
| 43 | HMI_44 | Roseburia inulinivorans | DSM32217 |  | X | X | X | X | / |  | X | X | / | / |
| 44 | HMI_45 | Ruminococcus albus | DSM32221 | X | X | X |  | X | / |  |  |  | X | / |
| 45 | HMI_46 | Blautia producta | DSM32218 |  | X | X |  | X | / |  | X | X | / | / |
| 46 | HMI_47 | Clostridium nexile | DSM32224 |  | X | X | X | X | / |  | X | X | / | / |
| 47 | HMI_48 | Butyricicoccus pullicaecorum | DSM32214 |  | X | X | X |  | / |  |  | X | / | / |
| 48 | HMI_49 | Ruminococcus flavefaciens | DSM32263 |  | X | X |  | X | / |  |  | / | X | / |
| 49 | HMI_50 | Flavonifractor plautii | DSM32223 | X | X | X | X |  | / |  |  | X | / | / |
| 50 | HMI_51 | Ruminococcus bromii | DSM32225 | X | X | X | X |  | / |  |  | X | / | X |
| 51 | HMI_52 | Ruminococcus albus | DSM32265 |  | X | X | X | X | / |  |  | X | / | X |

X = Positive/Yes; no fill = Negative/No; slash = No data available/Not tested

BACTERIOTHERAPY

REFERENCE TO SEQUENCE LISTING SUBMITTED ELECTRONICALLY

The content of the electronically submitted sequence listing (Name: P34640USN1 SEQ LIST updated_ST25.txt; Size: 100,657 bytes; and Date of Creation: Aug. 16, 2021) is herein incorporated by reference in its entirety.

FIELD OF THE INVENTION

The present invention relates to therapeutic compositions comprising at least one isolated bacterium as defined herein and a pharmaceutically acceptable excipient, as well as methods of preparing such therapeutic compositions. The therapeutic compositions find application in the treatment of dysbiosis, in particular dysbiosis of the gastrointestinal tract. The dysbiosis may be a dysbiosis associated with an enteric bacterial infection, inflammatory bowel disease, pouchitis, irritable bowel syndrome, a metabolic disease, a neuropsychiatric disorder, an autoimmune disease, an allergic disorder, a cancer, or hepatic encephalopathy.

BACKGROUND TO THE INVENTION

A typical human intestinal microbiota contains 100-1000 bacterial species. There is extensive compositional diversity between individuals, such that each individual's microbiota is as unique as a fingerprint (Qin, Li et al. 2010; Nielsen, Almeida et al. 2014). The majority of the bacterial species within the adult human microbiota are derived from four high level taxonomic classifications or phyla, the Firmicutes, Bacteroidetes, Actinobacteria and Proteobacteria. These groups change in abundance from birth to adulthood to old age, reflecting changing environmental influences such as initial mode of delivery, diet, insults such as pathogen infection and in many cases antibiotic usage (Dominguez-Bello, Costello et al. 2010, Koenig, Spor et al. 2011, Oilman, Smidt et al. 2012). In adulthood, the intestinal microbiota is dominated by the Firmicutes and the Bacteroidetes, both of which are strict anaerobes.

The intestinal microbiota plays a key role in digesting food inaccessible to the human gastrointestinal tract, such as metabolizing carbohydrates into short chain fatty acids (Sekirov, Russell et al. 2010), interacting with the immune system to maintain homeostasis (Hooper, Littman et al. 2012), promoting maturation of the gut (Hooper, Wong et al. 2001) and development of the immune system. The intestinal microbiota also plays an important role in resisting pathogen invasion, termed 'colonisation resistance'. This functions through the diversity and abundance of commensal species present and through the occupation of key niches and utilization of nutrients (Lawley and Walker 2013; Britton and Young 2014). If microbial homeostasis is disturbed, for example through use of antibiotics, a shift towards dysbiosis can occur.

Dysbiosis provides the opportunity for pathogens to establish themselves and cause disease to the individual in question. This has been best studied in terms of a single implicated pathogen such as *Clostridium difficile* (Lawley et al. 2012; Britton and Young 2014; Buffie et al. 2015), but dysbiosis has also been linked with other more complex, multi-factorial diseases such as Inflammatory Bowel Disease (IBD), pouchitis (Angeriman et al. 2014), Irritable Bowel Syndrome (IBS), hepatic encephalopathy (Bajaj 2014; Bajaj et al. 2012) metabolic diseases (including metabolic syndrome, malnutrition, and obesity), neuropsychiatric disorders such as Parkinson's and Alzheimer's disease, autoimmune diseases, allergic disorders, and cancer (Jostins, Ripke et al. 2012, Collins 2014, Hold, Smith et al. 2014, Perez Martinez, Bauerl et al. 2014, Scheperjans, Aho et al. 2015; Blanton et al. 2016, Xu et al. 2015).

Faecal microbiota transplantation (FMT) has proved successful in resolving *C. difficile* associated dysbiosis (Petrof et al. 2013, van Nood et al. 2013), and the administration of specific bacteria has also proved effective for this purpose (Lawley et al. 2012, Buffie et al. 2015). FMT has also showed promising results in the treatment of other intestinal diseases, as well as the management of extra-intestinal disorders associated with gut microbiota, including metabolic diseases, neuropsychiatric disorders, autoimmune diseases, allergic disorders, and tumours (Xu et al. 2015).

Recent years have seen great advances in understanding the role the intestinal microbiota plays in health and disease and how it can be manipulated for the benefit of the host. The majority of our understanding has to date been derived by culture-independent studies, i.e. by studying the compositional components of the microbiota and how they change during disease using molecular and genomic techniques. This process allows identification of potential therapeutic candidates that can resolve disease. However, the isolation, purification and acquisition of such candidate therapeutic bacteria has proven difficult.

There is therefore a need in the art to identify and isolate specific bacteria, as well as combinations of bacteria, which can be used to treat dysbiosis. Therapeutic compositions based on known, defined, bacteria or bacterial mixtures are advantageous as they improve patient safety because they comprise only defined and well characterised bacteria that are known to promote, and not harm, human health, and eliminate the possibility of inadvertently transferring pathogenic material to a recipient by FMT. In addition, such therapeutic compositions can be prepared in vitro in a large-scale manner using standardised, reproducible procedures, thereby providing batch consistency, and do not rely on regular donations from healthy human donors. Therapeutic compositions comprising known, defined, bacteria or bacterial mixtures can also be therapeutically delivered e.g. in a capsule, as a tablet, or as an enema, which is more acceptable to patients and health care professionals than suspensions of faecal material used in the case of FMT. The bacteria included in such therapeutic compositions can further be tailored to the treatment of specific dysbiotic states and diseases associated therewith by specifically altering the bacterial composition to optimally resolve the dysbiotic state in question and thus improve efficacy.

However, in order to isolate such candidate therapeutic bacteria for the treatment of dysbiosis, a thorough understanding of the biology of the candidates in question is required, as well as a large initial panel of candidates to select from. This poses a problem as the majority of the bacteria in the intestinal microbiota are considered to be unculturable and have never been isolated in the laboratory (Eckburg, Bik et al. 2005, Hattori and Taylor 2009, Stewart 2012). Thus, gaining a basic understanding of the functional attributes of the microbiota and developing a multi-species bacteria-based therapeutic with fastidious, anaerobic commensal isolates presents a formidable challenge. While recent efforts have made progress in resolving this issue (Goodman, Kallstrom et al. 2011, Lagier, Hugon et al.

2015), there remains a need in the art to identify and isolate bacteria capable of treating dysbiosis.

STATEMENTS OF INVENTION

The present invention relates to therapeutic compositions, in particular therapeutic compositions for use in the treatment of dysbiosis in an individual. Dysbiosis can occur in any part of the human or animal body which is normally colonized by bacteria and other microbes. The present invention particularly concerns dysbiosis of the gastrointestinal tract in humans.

The present inventors have surprisingly found that the majority of bacteria present in the human intestinal microbiota can be cultured, contrary to the prevailing view in the art which was that the majority of the human intestinal microbiota is unculturable. This major breakthrough now allows the majority of bacteria present in the human microbiota to be isolated and characterised, and evaluated for their activity in treating dysbiosis. This is possible not only for individual bacterial isolates but also for combinations of bacteria isolated from the intestinal microbiota. In addition, isolation of these bacteria allows the bacteria to be screened, for example, for the absence of virulence factors and antibiotic resistance prior to their inclusion in a therapeutic composition, thereby improving safety. In addition, the bacteria included in a therapeutic composition can be tailored to the treatment of a specific dysbiotic state and/or disease associated therewith by optimising the bacterial composition to resolve the dysbiosis in question, thereby improving efficacy. None of this is possible in FMT where undefined mixes of bacteria are used, usually obtained from a faecal sample of a healthy human donor. The use of isolated bacteria for the treatment of dysbiosis has the further advantage that it allows the bacteriotherapy treatment to be standardised, making patient outcomes more predictable, as well as facilitating evaluation of the therapeutic potential of bacteriotherapy in the context of particular diseases by removing the variability in bacterial composition associated with the use of FMT.

Through surprisingly being able to culture the majority of bacteria present in the human intestinal microbiota, the present inventors were able to prepare libraries of intestinal bacteria which were then subjected to whole-genome sequencing and screened using both in silico analysis and in vitro experiments to identify bacteria which are expected to be useful in treating dysbiosis, in particular dysbiosis of the gastrointestinal tract. Using this approach, the present inventors identified 51 bacteria which are expected to be useful for this purpose, including several families, genera, and species of bacteria which have not previously been described, let alone isolated or employed in the treatment of dysbiosis. As already explained above, the majority of the human microbiota was thought in the art to be unculturable, so the mere disclosure of a 16S ribosomal RNA sequence of one of these bacteria does not in itself enable the isolation of such a bacterium from its natural environment. Nor does the disclosure of such a 16S ribosomal RNA sequence suggest that a bacterium with such a sequence has previously been isolated, as 16S ribosomal RNA sequence information can be obtained from bacterial populations, including faecal samples, without the need to isolate individual bacteria. However, the ability to isolate bacteria in pure form from their natural environment is a prerequisite for their inclusion in therapeutic compositions according to the present invention.

Thus, in a first aspect, the present invention provides a therapeutic composition comprising at least one isolated bacterium and a pharmaceutically acceptable excipient. The bacterium preferably comprises a gene encoding a 16S ribosomal RNA (rRNA), wherein said gene comprises a sequence with at least 90% sequence identity with the sequence set forth in any one of SEQ ID NOs 1 to 51.

The therapeutic composition may comprise more than one isolated bacterium, in addition to the pharmaceutically acceptable excipient. Where more than one bacterium is included in the therapeutic composition, the bacteria are preferably distinct, wherein each bacterium comprises a gene encoding a 16S rRNA, wherein said gene comprises a sequence with at least 90% sequence identity with the sequence set forth in any one of SEQ ID NOs 1 to 51. Thus, for example, the therapeutic composition may comprise two distinct isolated bacteria, wherein the first bacterium comprises a gene encoding a 16S rRNA, wherein said gene comprises a sequence with at least 90% sequence identity with the sequence set forth in SEQ ID NO: 1 and the second bacterium comprises a gene encoding a 16S rRNA, wherein said gene comprises a sequence with at least 90% sequence identity with the sequence set forth in SEQ ID NO: 2.

As mentioned above, the therapeutic compositions of the present invention find application in the treatment of dysbiosis, in particular the treatment of a dysbiosis of the intestinal tract. Thus, in a second aspect, the present invention provides a therapeutic composition according to the invention for use in a method of treating a dysbiosis, preferably a dysbiosis of the gastrointestinal tract, in an individual. Also provided is a method of treating a dysbiosis in an individual, the method comprising administering a therapeutically effective amount of a therapeutic composition according to the invention to an individual in need thereof, as well as the use of a therapeutic composition according to the present invention for the manufacture of a medicament for the treatment of a dysbiosis in an individual. Also provided is the use of at least one isolated bacterium, as described herein, and optionally a pharmaceutically acceptable excipient, for the manufacture of a medicament for the treatment of a dysbiosis in an individual, the bacterium preferably comprising a gene encoding a 16S rRNA and said gene comprises a sequence with at least 90% sequence identity with the sequence set forth in any one of SEQ ID NOs 1 to 51.

Methods of preparing or manufacturing a therapeutic composition according to the present invention also form part of the invention. Thus, in a third aspect, the present invention provides a method of preparing or manufacturing a therapeutic composition according to the present invention, wherein the method preferably comprises the steps of:
  (i) culturing an isolated bacterium as described herein; and
  (ii) mixing the bacteria obtained in (i) with a pharmaceutically acceptable excipient.

As mentioned above, the therapeutic compositions of the present invention may comprise at least two distinct isolated bacteria as described herein. Where the therapeutic composition comprise more than one distinct isolated bacteria, the method of preparing or manufacturing a therapeutic composition preferably comprises steps of:
  (i) culturing a first isolated bacterium as described herein;
  (ii) culturing a second isolated bacterium as described herein; and
  (ii) mixing the bacteria obtained in (i) and (ii) with a pharmaceutically acceptable excipient. The bacteria cultured in steps (i) and (ii) preferably have distinct 16S rRNA sequences. Steps (i) and (ii) are preferably performed independently. The above method can be adapted to include further steps to allow the culturing of more than two distinct isolated bacteria, preferably bacteria with distinct 16S rRNA sequences, by including an additional step or steps for the culturing of a third or further isolated bacterium as disclosed herein. In this case, all bacteria cultured in the method are mixed with a pharmaceutically acceptable excipient.

A therapeutic composition obtainable by a method of preparing or manufacturing a therapeutic composition, as disclosed herein also forms part of the present invention.

BRIEF DESCRIPTION OF THE FIGURES

FIG. 2 shows the relative abundance of bacteria in faecal samples (x axis) compared to the relative abundance of bacteria growing on YCFA agar plates (y axis) as determined by metagenomic sequencing. The results demonstrate that the bacteria grown on YCFA agar are representative of the bacteria present in complete faecal samples as indicated by Spearman Rho=0.75.

FIG. 4A shows that the culture conditions employed by the present inventors enabled isolation of representatives from 21 of the 25 most abundant faecal bacterial genera as determined by metagenomic sequencing. A black dot indicates the number of species cultured and archived from each genus. Lachnospiraceae incertae sedis, unclassified Lachnospiraceae, *Clostridium* IV and *Clostridium* XI are not strict genera and represent currently unclassified species. FIG. 4B shows the 24 most abundant bacterial species (comprising 90% of the total bacterial abundance at the species level) as determined by metagenomic sequencing. All were cultured and archived except for Odoribacter splanchnicus. FIG. 4C shows that intestinal microbiota members present at low abundance were also cultured. At least one representative species from each of the genera presented was cultured. Genera are listed in order of decreasing abundance.

FIG. 5 shows a phylogenetic tree of bacteria cultured from the 6 donors constructed from full length 16S rRNA gene sequences. Novel candidate species (filled black circles), genera (grey filled circles) and families (filled stars) are shown by dot colours. Major phyla and family names are indicated. Proteobacteria were not cultured, but are included for context.

FIG. 6 shows the results of a principal component analysis of the donors, recipients and controls at 2-3 months after FMT. The clustering of the faecal samples indicates a similar microbial community structure. Antibiotic use and exposure to *C. difficile* likely leads to a shift from the healthy state, as seen in the metronidazole-treated control samples. Treatment of *C. difficile* infection (CDI) with vancomycin, an antibiotic that targets Gram-positive organisms would presumably lead to further disruption of the intestinal microbiota. FMT led to a shift from a diseased microbiota to a healthy one with most of the post-FMT samples clustering with the donors and healthy control samples.

FIG. 10 shows part of a YCFA agar plate on which a bacteriotherapy candidate was streaked in an X-shape and allowed to grow. Following growth of the bacteriotherapy candidate, the plate was covered with overlay agar comprising *C. difficile* or *E. coli*. Inhibition of *C. difficile* or *E. coli* growth by a bacteriotherapy candidate was measured by determining the width of the zone of clearing around the bacteriotherapy candidate strain grown on the plate. The black diagonal line in FIG. 10 indicates the distance measured and recorded as the width of the zone of clearing for an exemplary bacteriotherapy candidate. Four such measurements were taken per plate.

FIG. 11 shows the mean measurement±standard deviation from a representative experiment.

FIG. 12A shows the reduced relative *C. difficile* growth in Cell Free Supernatant (CFS) of bacteriotherapy candidate cultures at the 18.17 h time-point, while FIG. 12B shows reduced relative *E. coli* growth in CFS from the candidate bacteriotherapy isolates. The relative growth of either pathogen in the control YCFA medium was high (*C. difficile*=8.96±0.39 rel. growth units; *E. coli* 11.61±2.55 rel. growth units, at the 18.17 h time-point). When the mean and two standard deviations of relative growth of either pathogen in CFS derived from a bacteriotherapy candidate culture was more than two standard deviations below its mean growth in YCFA at the 18.17 h time-point, growth of the pathogen was considered to be inhibited. Where only one relative growth value was available for a particular CFS (vs *C. difficile*, FIG. 12A: HMI 15, HMI 26, HMI 27, HMI 28), the bacteriotherapy candidate was considered to be inhibitory if the relative growth of *C. difficile* was two standard deviations below the mean growth of *C. difficile* in YCFA broth. Only the results from inhibitory CFS are shown.

FIG. 15 shows characteristics of deposited bacteriotherapy candidates.

DETAILED DESCRIPTION

Figure 1:
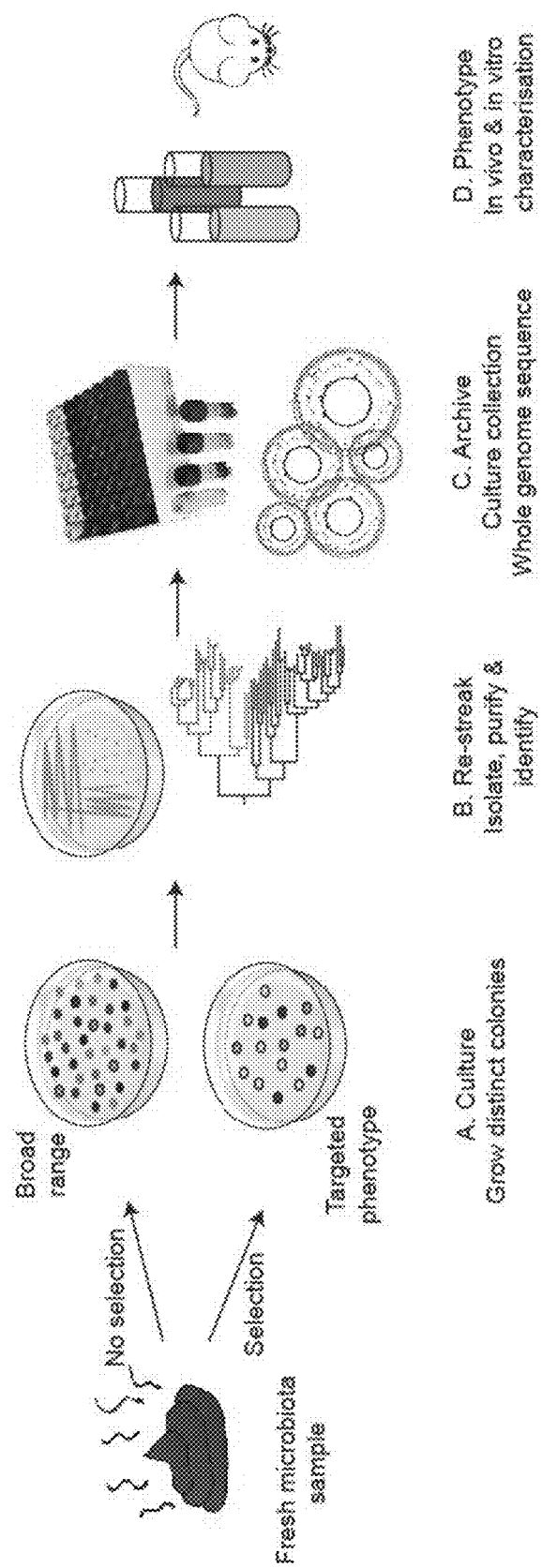
FIG. 1 shows a schematic diagram of the workflow used to culture, archive and characterise the intestinal microbiota. The process incorporates several steps which are: culture, re-streak, archive and phenotype. (A) Fresh faecal samples were left untreated or were treated to select for bacteria with a desired phenotype (such as sporulation). The stool was homogenised and then serially diluted before aliquots of the homogenate were inoculated on YCFA agar to culture the bacteria present in the faecal samples. (B) Bacterial isolates were identified by selecting single colonies that were then streaked to purity before full-length 16S rRNA gene amplification and sequencing was performed. (C) Each unique, novel and desired bacterial isolate was archived frozen in a culture collection and a whole genome sequence was generated for each. (D) Phenotypic characterisation and functional validation of metagenomics studies was then performed using in vitro and in vivo methods.

The bacteria disclosed herein have been obtained from human stool samples, and thus are naturally present in the gastrointestinal tract of at least some healthy human individuals. However, these bacteria have been cultured in vitro for the first time by the present inventors, thereby isolating them from their environment in pure form, and making it possible to include them as defined active ingredients in therapeutic compositions. The bacterium present in the therapeutic composition of the present invention is thus isolated. In other words, the bacterium present in the therapeutic composition is provided in isolated and/or purified form, e.g. isolated and/or purified from the environment in which it is normally present, such as the gastrointestinal tract and/or stool samples. The isolated bacterium present in the therapeutic composition may be in substantially pure, or in homogeneous form. For example, the bacterium may be free, or substantially free, of material with which it is found in the environment in which it is normally present (e.g. the gastrointestinal tract and/or stool samples).

The bacterium present in the therapeutic composition of the present invention is preferably a human intestinal bacterium, i.e. a bacterium found in the human intestine. The bacteria whose 16S rRNA gene sequences are set out in SEQ ID NOs 1 to 51 are all intestinal bacteria.

The bacterium is preferably a non-pathogenic bacterium. In other words, the bacterium preferably does not cause disease in a healthy human individual when administered to said individual, in particular the gastrointestinal tract of said individual. The therapeutic composition can be administered to an individual in a variety of ways as described in more detailed elsewhere herein, including in the form of a tablet or enema.

The bacterium present in the therapeutic composition of the present invention is preferably susceptible to treatment with one or more antibiotics. In other words, the bacterium is preferably not resistant to treatment with at least one antibiotic. This allows antibiotic treatment of an individual in the event that one or more of the bacteria included in a therapeutic composition administered to the individual causes disease in the individual, contrary to expectations. All of the 51 bacteria disclosed herein where found to carry no known genes conferring resistance to the following antibiotics: beta-lactams, fusidic acid, elfamycin, aminoglycoside, fosfomycin, and tunicamycin. Thus, in a preferred embodiment, the bacterium is susceptible to treatment with one or more antibiotics selected from the group consisting of: a beta-lactam, fusidic acid, elfamycin, aminoglycoside, fosfomycin, and tunicamycin. In vitro and in silico methods for screening bacteria for antibiotic resistance are known in the art. Exemplary in silico methods are also described in Example 1.

The bacterium included in the therapeutic composition of the present invention preferably does not comprise one or more genes encoding one or more virulence factors and/or preferably does not produce one or more virulence factors. Virulence factors in this context are properties which enhance the potential of a bacterium to cause disease in an individual. Virulence factors include the production of bacterial toxins, such as endotoxins and exotoxins by a bacterium, as well as the production of hydrolytic enzymes that may contribute to the pathogenicity of the bacterium. Methods for screening bacteria for genes encoding virulence factors are known in the art and include the in silico methods described in Example 1. The 51 bacteria disclosed herein were found not to carry any known virulence factors using in silico analysis. Methods for screening bacteria for the production of virulence factors are similarly known in the art.

Bacteria can be taxonomically classified based on the sequence of the gene encoding the 16S ribosomal RNA (rRNA) in the bacterium. This gene sequence is also referred to as the ribosomal DNA sequence (rDNA). A bacterium comprising a gene which encodes a 16S rRNA which has 90% or more sequence identity with the 16S rRNA encoded by a second bacterium belongs to the same family as said second bacterium. A bacterium comprising a gene which encodes a 16S rRNA which has 95% or more sequence identity with the 16S rRNA encoded by a second bacterium belongs to the same genus as said second bacterium. A bacterium comprising a gene which encodes a 16S rRNA which has 97% or more, or 98.7% or more sequence identity with the 16S rRNA encoded by a second bacterium belongs to the same species as said second bacterium. A bacterium included in the therapeutic composition of the present invention may be a bacterium which belongs to the same family, genus, and/or species as a bacterium disclosed herein.

A bacterium which belongs to the same family, genus, and/or species as a bacterium disclosed herein is expected to retain one or more properties of the disclosed bacterium. Thus, in a preferred embodiment, a bacterium present in the therapeutic composition of the present invention belongs to the same family, genus, and/or species as a bacterium disclosed herein and retains at least one property of the bacterium disclosed herein. Various properties of the bacteria disclosed herein are described and include, for example, a lack of production of one or more virulence factors, susceptibility to treatment with one or more antibiotics, and a lack of pathogenicity.

The therapeutic composition of the present invention may comprise at least one isolated bacterium, wherein the bacterium comprises a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 1 to 51.

For example, the therapeutic composition of the present invention may comprise at least one isolated bacterium, wherein the bacterium comprises a gene encoding a 16S rRNA, wherein said gene comprises a sequence with at least 90% sequence identity with the sequence set forth in any one of SEQ ID NOs 1 to 51. In a preferred embodiment, the therapeutic composition comprises an isolated bacterium, wherein the bacterium comprises a gene encoding a 16S rRNA, and wherein said gene comprises a sequence with at least 90% sequence identity with the sequence set forth in SEQ ID NO: 1. In addition, or alternatively, the therapeutic composition may comprise an isolated bacterium, wherein the bacterium comprises a gene encoding a 16S rRNA, and wherein said gene comprises a sequence with at least 90% sequence identity with the sequence set forth in SEQ ID NO: 21.

In addition, or alternatively, the therapeutic composition may comprise at least one isolated bacterium, wherein the bacterium comprises a gene encoding a 16S rRNA, wherein said gene comprises a sequence with at least 95% sequence identity with the sequence set forth in any one of SEQ ID NOs 1 to 51. In a preferred embodiment, the therapeutic composition comprises at least one isolated bacterium, wherein said bacterium comprises a gene encoding a 16S rRNA, and wherein said gene comprises a sequence with at least 95% sequence identity with the sequence set forth in any one of SEQ ID NOs 2 to 20, or 22 to 51, more preferably any one of SEQ ID NOs 5, 6, 11, 13, 14, 15, 17, 18, 19, 20, 22, 23, 24, 26, 29, 33, 35, 41, 43, 45, 46, 47, 49, or 50, yet more preferably any one of SEQ ID NOs 5, 6, 11, 13, 15, 19, 22, 23, 29, 33, 35, 41, 43, 45, 46, or 50.

In addition, or alternatively, the therapeutic composition may comprise at least one isolated bacterium, wherein the bacterium comprises a gene encoding a 16S rRNA, wherein said gene comprises a sequence with at least 97%, or at least 98.7%, sequence identity with the sequence set forth in any one of SEQ ID NOs 1 to 51. In a preferred embodiment, the therapeutic composition comprises at least one isolated bacterium, wherein said bacterium comprises a gene encoding a 16S rRNA, and wherein said gene comprises a sequence with at least 97% sequence identity with the sequence set forth in any one of SEQ ID NOs 2 to 20, or 22 to 51, more preferably any one of SEQ ID NOs 2 to 3, 5 to 8, 10 to 20, 22 to 26, 29 to 37, or 39 to 50, yet more preferably any one of SEQ ID NOs 3, 5 to 8, 10 to 13, 15, 16, 19, 22, 23, 29, 32 to 37, 39 to 46, or 48 to 50. In an alternative preferred embodiment, the therapeutic composition may comprise at least one isolated bacterium, wherein said bacterium comprises a gene encoding a 16S rRNA, and wherein said gene comprises a sequence with at least 98.7% sequence identity with the sequence set forth in any one of SEQ ID NOs 2 to 20, or 22 to 51, more preferably any one of SEQ ID NOs 2 to 4, 5 to 20, 22 to 26, 29 to 37 to 51, yet more preferably any one of SEQ ID NOs 2 to 8, 10 to 13, 15, 16, 17, 19, 20, 22, 23, 29, 31, 32 to 37 to 46, or 48 to 51.

As mentioned above, in a preferred embodiment, the therapeutic composition of the present invention may comprise at least one isolated bacterium, wherein the bacterium comprises a gene encoding a 16S rRNA, wherein said gene comprises a sequence with at least 90% sequence identity with the sequence set forth in SEQ ID NO: 1 or SEQ ID NO: 21. In addition, or alternatively, the therapeutic composition may comprise at least one isolated bacterium, wherein the bacterium comprises a gene encoding a 16S rRNA, wherein said gene comprises a sequence with at least 91% sequence identity with the sequence set forth in SEQ ID NO: 29. In addition, or alternatively, the therapeutic composition may comprise at least one isolated bacterium, wherein the bacterium comprises a gene encoding a 16S rRNA, wherein said gene comprises a sequence with at least 92% sequence identity with the sequence set forth in any one of SEQ ID NOs 6, 11, 19 or 24. In addition, or alternatively, the therapeutic composition may comprise at least one isolated bacterium, wherein the bacterium comprises a gene encoding a 16S rRNA, wherein said gene comprises a sequence with at least 93% sequence identity with the sequence set forth in any one of SEQ ID NOs 13, 22, 26 or 35. In addition, or alternatively, the therapeutic composition may comprise at least one isolated bacterium, wherein the bacterium comprises a gene encoding a 16S rRNA, wherein said gene comprises a sequence with at least 94% sequence identity with the sequence set forth in any one of SEQ ID NOs 5, 14, 15, 17, 18, 23, or 50. In addition, or alternatively, the therapeutic composition may comprise at least one isolated bacterium, wherein the bacterium comprises a gene encoding a 16S rRNA, wherein said gene comprises a sequence with at least 95% sequence identity with the sequence set forth in any one of SEQ ID NOs 20, 33, 41, 43, 45, 46, 47, or 49. In addition, or alternatively, the therapeutic composition may comprise at least one isolated bacterium, wherein the bacterium comprises a gene encoding a 16S rRNA, wherein said gene comprises a sequence with at least 96% sequence identity with the sequence set forth in any one of SEQ ID NOs 2, 7, 8, 10, 12, 30, 32, 39, 42, 44, or 48. In addition, or alternatively, the therapeutic composition may comprise at least one isolated bacterium, wherein the bacterium comprises a gene encoding a 16S rRNA, wherein said gene comprises a sequence with at least 97% sequence identity with the sequence set forth in any one of SEQ ID NOs 3, 16, 25, 31, 34, 36, 37, or 40. In addition, or alternatively, the therapeutic composition may comprise at least one isolated bacterium, wherein the bacterium comprises a gene encoding a 16S rRNA, wherein said gene comprises a sequence with at least 98% sequence identity with the sequence set forth in any one of SEQ ID NOs 4 or 9. In addition, or alternatively, the therapeutic composition may comprise at least one isolated bacterium, wherein the bacterium comprises a gene encoding a 16S rRNA, wherein said gene comprises a sequence with at least 99% sequence identity with the sequence set forth in any one of SEQ ID NOs 27, 28, 38, or 51.

More preferably, the therapeutic composition of the present invention may comprise at least one isolated bacterium, wherein the bacterium comprises a gene encoding a 16S rRNA, wherein said gene comprises a sequence with at least 90% sequence identity with the sequence set forth in SEQ ID NO: 1 or SEQ ID NO: 21. In addition, or alternatively, the therapeutic composition may comprise at least one isolated bacterium, wherein the bacterium comprises a gene encoding a 16S rRNA, wherein said gene comprises a sequence with at least 92% sequence identity with the sequence set forth in any one of SEQ ID NOs 6, or 11. In addition, or alternatively, the therapeutic composition may comprise at least one isolated bacterium, wherein the bacterium comprises a gene encoding a 16S rRNA, wherein said gene comprises a sequence with at least 93% sequence identity with the sequence set forth in SEQ ID NO: 35. In addition, or alternatively, the therapeutic composition may comprise at least one isolated bacterium, wherein the bacterium comprises a gene encoding a 16S rRNA, wherein said gene comprises a sequence with at least 94% sequence identity with the sequence set forth in any one of SEQ ID NOs 5, 19, 22, 23, or 50. In addition, or alternatively, the therapeutic composition may comprise at least one isolated bacterium, wherein the bacterium comprises a gene encoding a 16S rRNA, wherein said gene comprises a sequence with at least 95% sequence identity with the sequence set forth in any one of SEQ ID NOs 13, 15, 29, 33, 41, 43, 45, or 46. In addition, or alternatively, the therapeutic composition may comprise at least one isolated bacterium, wherein the bacterium comprises a gene encoding a 16S rRNA, wherein said gene comprises a sequence with at least 96% sequence identity with the sequence set forth in any one of SEQ ID NOs 7, 12, 32, 39, 42, or 44, at least 97% sequence identity with the sequence set forth in any one of SEQ ID NOs 3, 8, 10, 16, 34, 36, 37, 40, 48, or 49. In addition, or alternatively, the therapeutic composition may comprise at least one isolated bacterium, wherein the bacterium comprises a gene encoding a 16S rRNA, wherein said gene comprises a sequence with at least 98% sequence identity with the sequence set forth in any one of SEQ ID NOs 4, 9, 17 or 31. In addition, or alternatively, the therapeutic composition may comprise at least one isolated bacterium, wherein the bacterium comprises a gene encoding a 16S rRNA, wherein said gene comprises a sequence with at least 99% sequence identity with the sequence set forth in any one of SEQ ID NOs 2, 20, 38, or 51. In addition, or alternatively, the therapeutic composition may comprise at least one isolated bacterium, wherein the bacterium comprises a gene encoding a 16S rRNA, wherein said gene comprises a sequence with 100% sequence identity with the sequence set forth in any one of SEQ ID NOs 14, 18, 24, 25, 26, 27, 28, 30, or 47.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Other algorithms suitable for the alignment of nucleotide sequences may be used instead of GAP, e.g. BLAST (Basic Local Alignment Search Tool) (which uses the method of Altschul et al. (1990) J. Mol. Biol. 215: 405-410), FASTA (which uses the method of Pearson and Lipman (1988) PNAS USA 85: 2444-2448), the Smith-Waterman algorithm (Smith and Waterman (1981) J. Mol Biol. 147: 195-197), the TBLASTN program, of Altschul et al. (1990) supra, or the psi-Blast algorithm (Nucl. Acids Res. (1997) 25 3389-3402), generally employing default parameters. In particular, BLAST may be used, preferably employing default parameters.

Sequence alignment algorithms, such as BLAST, calculate the similarity score between a query sequence and a subject sequence. The sequence identity of the query sequence to the subject sequence may be dependent on the percentage of the query sequence that is required to overlap with the subject sequence. This is also referred to as query coverage. In a preferred embodiment, the isolated bacterium present in the therapeutic composition of the present invention comprises a gene encoding a 16S rRNA, wherein said gene comprises a sequence, which (in addition to the specified sequence identity) has a query coverage of at least 98%, at least 99%, or 100%, preferably at least 98%. The query coverage refers to the percentage of said sequence which overlaps with the sequence with which it has the specified sequence identity, e.g. SEQ ID NO: 1. For example, the bacterium present in the therapeutic composition may comprise a gene encoding a 16S rRNA, wherein said gene comprises a sequence with at least 90% sequence identity with the sequence set forth in any one of SEQ ID NOs 1 to 51 and at least 98% query coverage.

Yet more preferably, the therapeutic composition of the present invention may comprise at least one isolated bacterium, wherein the bacterium is a bacterium as deposited under the Budapest Treaty on the International Recognition of the Deposit of Microorganisms for the Purposes of Patent Procedures at the Leibniz-Institut DSMZ—Deutsche Sammlung von Mikroorganismen and Zellkulturen GmbH (DSMZ), Inhoffenstr. 7B, 38124 Braunschweig by Genome Research Limited under an accession number as listed in FIG. 15. Specifically, the therapeutic composition of the present invention may comprise at least one isolated bacterium, wherein the bacterium is a bacterium as deposited under the Budapest Treaty at DSMZ under one of the following accession numbers (the date of deposit with DSMZ for each bacterium deposited is indicated in brackets after the accession number): DSM32191 (27 Oct. 2015), DSM32147 (23 Sep. 2015), DSM32149 (23 Sep. 2015), DSM32175 (6 Oct. 2015), DSM32153 (27 Oct. 2015), DSM32152 (23 Sep. 2015), DSM32158 (23 Sep. 2015), DSM32192 (27 Oct. 2015), DSM32148 (23 Sep. 2015), DSM32166 (6 Oct. 2015), DSM32151 (23 Sep. 2015), DSM32150 (23 Sep. 2015), DSM32193 (27 Oct. 2015), DSM32162 (6 Oct. 2015), DSM32194 (27 Oct. 2015), DSM32163 (6 Oct. 2015), DSM32205 (1 Mar. 2016), DSM32195 (27 Oct. 2015), DSM32164 (6 Oct. 2015), DSM32177 (13 Oct. 2015), DSM32167 (6 Oct. 2015), DSM32165 (6 Oct. 2015), DSM32169 (6 Oct. 2015), DSM32168 (6 Oct. 2015), DSM32178 (13 Oct. 2015), DSM32182 (13 Oct. 2015), DSM32179 (13 Oct. 2015), DSM32180 (13 Oct. 2015), DSM32184 (13 Oct. 2015), DSM32181 (13 Oct. 2015), DSM32183 (13 Oct. 2015), DSM 32262 (2 Feb. 2016), DSM32211 (2 Dec. 2015), DSM 32219 (8 Dec. 2015), DSM 32222 (8 Dec. 2015), DSM 32261 (2 Feb. 2016), DSM32212 (2 Dec. 2015), DSM32220 (8 Dec. 2015), DSM32213 (2 Dec. 2015), DSM 32226 (8 Dec. 2015), DSM32215 (2 Dec. 2015), DSM32216 (2 Dec. 2015), DSM 32217 (2 Feb. 2016), DSM32221 (8 Dec. 2015), DSM32218 (2 Dec. 2015), DSM 32224 (8 Dec. 2015), DSM 32214 (2 Dec. 2015), DSM 32263 (2 Feb. 2016), DSM 32223 (8 Dec. 2015), DSM 32225 (8 Dec. 2015), and DSM 32265 (10 Feb. 2016). The putative genus and species names of the deposited bacteria, as well as their known characteristics, are listed in FIG. 15.

Yet more preferably, the therapeutic composition of the present invention comprises at least one isolated bacterium, wherein the bacterium is a bacterium as deposited under the Budapest Treaty at DSMZ under one of the following accession numbers: DSM32191 and DSM32177. In addition, or alternatively, the therapeutic composition may comprise at least one isolated bacterium, wherein the bacterium is a bacterium as deposited under the Budapest Treaty at DSMZ under one of the following accession numbers:

DSM32153, DSM32152, DSM32151, DSM32193, DSM32162, DSM32194, DSM32205, DSM32195, DSM32164, DSM32177, DSM32165, DSM32169, DSM32168, DSM32182, DSM32184, DSM32211, DSM32222, DSM32215, DSM32217, DSM32218, DSM32224, DSM32214, DSM32223, and DSM32225; more preferably a bacterium as deposited under one of the following accession numbers: DSM32153, DSM32152, DSM32151, DSM32193, DSM32194, DSM32164, DSM32165, DSM32169, DSM32184, DSM32211, DSM32222, DSM32215, DSM32217, DSM32218, DSM32224, and DSM32225.

Alternatively, the therapeutic composition of the present invention may comprise at least one isolated bacterium, said bacterium comprising a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

The therapeutic composition of the invention may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, at least thirty-five, at least thirty-six, at least thirty-seven, at least thirty-eight, at least thirty-nine, at least forty, at least forty-one, at least forty-two, at least forty-three, at least forty-four, at least forty-five, at least forty-six, at least forty-seven, at least forty-eight, at least forty-nine, at least fifty, or at least fifty-one bacteria as disclosed herein.

The therapeutic composition of the invention may comprise one, up to two, up to three, up to four, up to five, up to six, up to seven, up to eight, up to nine, up to ten, up to eleven, up to twelve, up to thirteen, up to fourteen, up to fifteen, up to sixteen, up to seventeen, up to eighteen, up to nineteen, up to nineteen, up to twenty, up to twenty-one, up to twenty-two, up to twenty-three, up to twenty-four, up to twenty-five, up to twenty-six, up to twenty-seven, up to twenty-eight, up to twenty-nine, up to thirty, up to thirty-one, up to thirty-two, up to thirty-three, up to thirty-four, up to thirty-five, up to thirty-six, up to thirty-seven, up to thirty-eight, up to thirty-nine, up to forty, up to forty-one, up to forty-two, up to forty-three, up to forty-four, up to forty-five, up to forty-six, up to forty-seven, up to forty-eight, up to forty-nine, up to fifty, or up to fifty-one bacteria as disclosed herein. Preferably, the therapeutic composition of the invention comprise up to twenty, preferably up to ten, bacteria as disclosed herein.

Where a therapeutic composition comprises more than one isolated bacterium, the isolated bacteria are preferably distinct. "Distinct" may refer to the isolated bacteria encoding distinct 16S rRNA sequences.

The therapeutic composition of the invention may comprise at least one isolated bacterium which forms spores. Such a bacterium is also referred to as a spore-forming bacterium. Spores are metabolically dormant structures that are resilient to environmental insults and are used by certain bacteria as a survival strategy upon encountering adverse conditions. Bacteriotherapy candidates HMI 1, HMI 2, HMI 4, HMI 6, HMI 10, HMI 15, HMI 17, HMI_21, HMI_22, HMI_33, HMI_36, HMI_37, HMI_38, HMI_44, HMI_47, HMI_48, HMI_50, HMI_51, and HMI_52 were isolated from ethanol-treated samples and are thus expected to be capable of forming spores. In addition, HMI_3, HMI_7, HMI_8, HMI_16, HMI_18, HMI_19, HMI_24, HMI_25, HMI_26, HMI_27, HMI_28, HMI_29, HMI_30, HMI_34, HMI_41, and HMI_46 are expected to be spore formers based on phylogenetic analysis.

Thus, the therapeutic composition of the present invention may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, or at least thirty-five isolated spore-forming bacteria. In one embodiment, the bacteria in the therapeutic composition may consist of spore forming bacteria.

The spore-forming bacterium may thus be a bacterium comprising a gene encoding a 16S ribosomal RNA (rRNA), wherein said gene comprises a sequence with at least 90% sequence identity with the sequence set forth in any one of SEQ ID NOs 1, 2, 3, 4, 6, 7, 8, 10, 14, 15, 16, 17, 18, 20, 21, 23, 24, 25, 26, 27, 28, 29, 32, 33, 35, 36, 37, 40, 43, 45, 46, 47, 49, 50, or 51. Alternatively, the spore forming bacterium may be a bacterium comprising a gene encoding a 16S ribosomal RNA (rRNA), wherein said gene comprises a sequence with at least 90% sequence identity with the sequence set forth in any one of SEQ ID NOs 1, 2, 4, 6, 10, 14, 16, 20, 21, 32, 35, 36, 37, 43, 46, 47, 49, 50, or 51.

The spore-forming bacterium may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 1, 2, 3, 4, 6, 7, 8, 10, 14, 15, 16, 17, 18, 20, 21, 23, 24, 25, 26, 27, 28, 29, 32, 33, 35, 36, 37, 40, 43, 45, 46, 47, 49, 50, or 51. Alternatively, the spore forming bacterium may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 1, 2, 4, 6, 10, 14, 16, 20, 21, 32, 35, 36, 37, 43, 46, 47, 49, 50, or 51.

Preferably, the spore forming bacterium is a bacterium comprising a gene encoding a 16S ribosomal RNA (rRNA), wherein said gene comprises a sequence with at least 90% sequence identity with the sequence set forth in SEQ ID NOs 1 or SEQ ID NO: 21, and/or at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 2, 3, 4, 6, 7, 8, 10, 14, 15, 16, 17, 18, 20, 23, 24, 25, 26, 27, 28, 29, 32, 33, 35, 36, 37, 40, 43, 45, 46, 47, 49, 50, or 51. More preferably, the spore forming bacterium may be a bacterium comprising a gene encoding a 16S ribosomal RNA (rRNA), wherein said gene comprises a sequence with at least 90% sequence identity with the sequence set forth in SEQ ID NOs 1 or SEQ ID NO: 21, and/or at least 91%, at least 92%, at least 93%, at least 94%, at least 95%, at least 96%, at least 97%, at least 98%, at least 98.7%, at least 99%, or 100% sequence identity with the sequence set forth in any one of SEQ ID Nos 2, 4, 6, 10, 14, 16, 20, 32, 35, 36, 37, 43, 46, 47, 49, 50, or 51.

More preferably, the spore forming bacterium may be a bacterium comprising a gene encoding a 16S ribosomal RNA (rRNA), wherein said gene comprises a sequence with at least 90% sequence identity with the sequence set forth SEQ ID NO: 1 or SEQ ID NO: 21, at least 92% sequence identity with the sequence set forth in SEQ ID NO: 29, at least 92% sequence identity with the sequence set forth in SEQ ID NOs 6, or 24 at least 93% sequence identity with the sequence set forth in SEQ ID NOs 35 or 26, at least 94% sequence identity with the sequence set forth in any one of SEQ ID NOs 14, 15, 17, 18, 23, or 50, at least 95% sequence identity with the sequence set forth in any one of SEQ ID NOs 20, 33, 43, 45, 46, 47, or 49, at least 96% sequence identity with the sequence set forth in any one of SEQ ID NOs 2, 7, 8, 10, or 32, at least 97% sequence identity with the sequence set forth in any one of SEQ ID NOs 3, 16, 25, 36, 37 or 40, at least 98% sequence identity with the sequence set forth in SEQ ID NO: 4, or at least 99% sequence identity with the sequence set forth in SEQ ID NOs 27, 28, or 51. Yet more preferably, the spore forming bacterium may be a bacterium comprising a gene encoding a 16S ribosomal RNA (rRNA), wherein said gene comprises a sequence with at least 90% sequence identity with the sequence set forth SEQ ID NO: 1 or SEQ ID NO: 21, at least 92% sequence identity with the sequence set forth in SEQ ID NO: 6, at least 93% sequence identity with the sequence set forth in SEQ ID NO: 35, at least 94% sequence identity with the sequence set forth in any one of SEQ ID NOs 14, or 50, at least 95% sequence identity with the sequence set forth in any one of SEQ ID NOs 20, 43, 46, 47, or 49, at least 96% sequence identity with the sequence set forth in any one of SEQ ID NOs 2, 10, or 32, at least 97% sequence identity with the sequence set forth in any one of SEQ ID NOs 16, 36, or 37, at least 98% sequence identity with the sequence set forth in SEQ ID NO: 4, or at least 99% sequence identity with the sequence set forth in SEQ ID NO: 51.

More preferably, the spore forming bacterium may be a bacterium comprising a gene encoding a 16S ribosomal RNA (rRNA), wherein said gene comprises a sequence with at least 90% sequence identity with the sequence set forth in SEQ ID NO: 1 or SEQ ID NO: 21, at least 92% sequence identity with the sequence set forth SEQ ID NO: 6, at least 93% sequence identity with the sequence set forth in SEQ ID NO: 35, at least 94% sequence identity with the sequence set forth in SEQ ID NOs 23 or 50, at least 95% sequence identity with the sequence set forth in any one of SEQ ID NOs 15, 29, 33, 43, 45 or 46, at least 96% sequence identity with the sequence set forth in SEQ ID NOs 7 or 32, at least 97% sequence identity with the sequence set forth in any one of SEQ ID NOs 3, 10, 16, 36, 37, or 49, at least 98% sequence identity with the sequence set forth in SEQ ID NOs 4, 8 or 17, at least 99% sequence identity with the sequence set forth in any one of SEQ ID NOs 2, 20, or 51, or 100% sequence identity with the sequence set forth in any one of SEQ ID NOs 14, 18, 25, 26, 27, 28, or 47. Even more preferably, the spore forming bacterium may be a bacterium comprising a gene encoding a 16S ribosomal RNA (rRNA), wherein said gene comprises a sequence with at least 90% sequence identity with the sequence set forth in SEQ ID NO: 1 or SEQ ID NO: 21, at least 92% sequence identity with the sequence set forth SEQ ID NO: 6, at least 93% sequence identity with the sequence set forth in SEQ ID NO: 35, at least 94% sequence identity with the sequence set forth in SEQ ID NO: 50, at least 95% sequence identity with the sequence set forth in any one of SEQ ID NOs 43, or 46, at least 96% sequence identity with the sequence set forth in SEQ ID NO: 32, at least 97% sequence identity with the sequence set forth in any one of SEQ ID NOs 10, 16, 36, 37, or 49, at least 98% sequence identity with the sequence set forth in SEQ ID NO: 4, at least 99% sequence identity with the sequence set forth in any one of SEQ ID NOs 2, 20, or 51, or 100% sequence identity with the sequence set forth in any one of SEQ ID NOs 14, or 47.

Yet more preferably, the spore forming bacterium may be a bacterium as deposited at DSMZ under accession number DSM32191, DSM32147, DSM32175, DSM32152, DSM32166, DSM32162, DSM32163, DSM32177, DSM32167, DSM 32262, DSM 32222, DSM 32261, DSM32212, DSM32217, DSM32224, DSM32214, DSM32223, DSM32225, DSM32265, DSM32149, DSM32158, DSM32192, DSM32194, DSM32205, DSM32195, DSM32169, DSM32168, DSM32178, DSM32182, DSM32179, DSM32180, DSM32211, DSM32226, or DSM32218. Most preferably, the spore forming bacterium is a bacterium as deposited at DSMZ under accession number DSM32191, DSM32147, DSM32175, DSM32152, DSM32166, DSM32162, DSM32163, DSM32177, DSM32167, DSM 32262, DSM 32222, DSM 32261, DSM32212, DSM32217, DSM32224, DSM32214, DSM32223, DSM32225, or DSM32265. Alternatively, the therapeutic composition of the present invention may comprise at least one isolated spore-forming bacterium, said bacterium comprising a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

The isolated bacterium present in the therapeutic composition may be antagonistic towards an intestinal bacterium, inhibit or prevent the growth or sporulation of an intestinal bacterium, and/or neutralize or protect against a toxin produced by an intestinal bacterium. Preferably the bacterium inhibits or prevents the growth of an intestinal bacterium. The intestinal bacterium may be a pathogenic or non-pathogenic intestinal bacterium. Preferably, the intestinal bacterium is a pathogenic bacterium. This is particularly preferred in the context of a therapeutic composition for use in the treatment of a dysbiosis associated with an enteric bacterial infection. However, other diseases are also known to be characterised by an increase in certain types of bacteria in the gastrointestinal tract. For example, inflammatory bowel disease is known to be characterised by an increase in bacteria from the Proteobacteria phylum, such as *Escherichia coli*, in the intestinal microbiota. Similarly, irritable bowel syndrome, obesity and malnutrition are known to be characterised by an increase in certain types of bacteria in the gastrointestinal tract. A bacterial composition comprising at least one bacterium which is antagonistic towards an intestinal bacterium, inhibits or prevents the growth or sporulation of an intestinal bacterium, and/or neutralizes or protects against a toxin produced by an intestinal bacterium thus also finds application in the treatment of dysbiosis associated with inflammatory bowel disease, irritable bowel syndrome, obesity, or malnutrition.

The pathogenic bacterium may be a Gram positive bacterium, or a Gram negative bacterium. Exemplary pathogenic bacteria include pathogenic bacteria of the genera

*Clostridium, Escherichia, Enterococcus, Klebsiella, Enterobacter, Proteus, Salmonella, Shigella, Staphylococcus, Vibrio, Aeromonas, Campylobacter, Bacillus, Helicobacter, Listeria, Plesiomonas,* or *Yersinia*. In a preferred embodiment, the pathogenic bacterium is a pathogenic bacterium of the genera *Clostridium* or *Escherichia*, such as *Clostridium difficile* or *Escherichia coli*.

Examples of pathogenic *Escherichia coli* include adherent-invasive *Escherichia coli* (AIEC), enteroaggregative *Escherichia coli*, enterohemorrhagic *Escherichia coli*, enteroinvasive *Escherichia coli*, enterotoxigenic *Escherichia coli*, and *Escherichia coli* O157:H7. An enterotoxigenic *Escherichia coli* may produce a heat-labile enterotoxin, or heat-stable enterotoxin.

For example, the pathogenic bacterium may be *Clostridium difficile* or adherent-invasive *E. coli* (AIEC).

Bacteriotherapy candidates HMI_14, HMI_25, HMI_42, HMI_26, HMI_28, HMI_35 and HMI_46 have been shown to inhibit growth of *Clostridium difficile* in an overlay assay. In addition, HMI_2, HMI_4, HMI_5, HMI_6, HMI_15, HMI_26, HMI_27, HMI_28, HMI_34, HMI_35, HMI_39, HMI_40, HMI_43, HMI_44, HMI_46 and HMI_47 have been shown to inhibit growth of *Clostridium difficile* in a CFS-relative growth inhibition assay (see Example 2, FIG. 13, and Table 1).

Bacteriotherapy candidates HMI_4, HMI_10, HMI_11, HMI_14, HMI_26, HMI_28, HMI_33, HMI_35, HMI_42 and HMI_46 have been shown to inhibit growth of *Escherichia coli* in an overlay assay. In addition, HMI_46 and HMI_28, have been shown to inhibit growth of *Escherichia coli* in a CFS-relative growth inhibition assay (see Example 2, FIG. 13, and FIG. 15).

It is expected that a bacterium which inhibits the growth of *Escherichia coli* also inhibits the growth of other Proteobacteria. Thus, the pathogenic bacterium may be a proteobacterium. Proteobacteria include (apart from *Escherichia* species), *Salmonella* species, *Campylobacter* species, *Vibrio* species, *Helicobacter* species, and *Yersinia* species.

It is expected that a bacterium which inhibits the growth of *Clostridium difficile* also inhibits the growth of other bacteria of the genus *Clostridium*. Thus, the pathogenic bacterium may be a bacterium of the genus *Clostridium*. Pathogenic bacteria of the genus *Clostridium* (apart from *Clostridium difficile*), include *Clostridium perfringens, Clostridium botulinum,* and *Clostridium tetani.*

The therapeutic composition may thus comprise at least one isolated bacterium which inhibits the growth of *Clostridium difficile* and/or *Escherichia coli*. For example, the therapeutic composition may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, or at least twenty-two isolated bacteria which inhibit the growth of *Clostridium difficile* and/or *Escherichia coli*. In one embodiment, the bacteria in the therapeutic composition may consist of one or more isolated bacteria which have been shown to inhibit the growth of *Clostridium difficile* and/or *Escherichia coli*.

In a preferred embodiment, the therapeutic composition may comprise at least one isolated bacterium which has been shown to inhibit the growth of *Clostridium difficile*. This is preferred in the context of a therapeutic composition for use in the treatment of a dysbiosis associated with an enteric infection, in particular a dysbiosis associated with an infection with a pathogenic *Clostridium*-related species, such as *Clostridium difficile, Clostridium perfringens, Clostridium botulinum,* or *Clostridium tetani*, most preferably *Clostridium difficile*.

For example, the therapeutic composition may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or at least nineteen isolated bacteria which inhibit the growth of *Clostridium difficile*. In one embodiment, the bacteria in the therapeutic composition may consist of bacteria which inhibit the growth of *Clostridium difficile*.

A bacterium inhibits the growth of *Clostridium difficile* may be a bacterium comprising a gene encoding a 16S ribosomal RNA (rRNA), wherein said gene comprises a sequence with at least 90% sequence identity with the sequence set forth in any one of SEQ ID NOs 2, 4, 5, 6, 13, 14, 24, 25, 26, 27, 33, 34, 38, 39, 41, 42, 43, 45 and 46.

Alternatively, a bacterium which inhibits the growth of *Clostridium difficile* may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 99%, or 100% sequence identity with the sequence set forth in any one of SEQ ID NOs 2, 4, 5, 6, 13, 14, 24, 25, 26, 27, 33, 34, 38, 39, 41, 42, 43, 45 and 46.

More preferably, a bacterium which inhibits the growth of *Clostridium difficile* may be a bacterium comprising a gene encoding a 16S ribosomal RNA (rRNA), wherein said gene comprises a sequence with at least 92% sequence identity with the sequence set forth in any one of SEQ ID NOs 6, or 24, at least 93% sequence identity with the sequence set forth in any one of SEQ ID NOs 13, or 26, at least 94% sequence identity with the sequence set forth in any one of SEQ ID NOs 5, or 14, at least 95% sequence identity with the sequence set forth in any one of SEQ ID NOs 33, 41, 43, 45, or 46, at least 96% sequence identity with the sequence set forth in any one of SEQ ID NOs 2, 39, or 42, at least 97% sequence identity with the sequence set forth in any one of SEQ ID NOs 25, or 34, at least 98% sequence identity with the sequence set forth in SEQ ID NO: 4, or at least 99% sequence identity with the sequence set forth in any one of SEQ ID NOs 27, or 38.

Even more preferably, a bacterium which inhibits the growth of *Clostridium difficile* may be a bacterium comprising a gene encoding a 16S ribosomal RNA (rRNA), wherein said gene comprises a sequence with at least 92% sequence identity with the sequence set forth SEQ ID NO: 6, at least 94% sequence identity with the sequence set forth in SEQ ID NO: 5, at least 95% sequence identity with the sequence set forth in any one of SEQ ID NOs 13, 33, 41, 43, 45, or 46, at least 96% sequence identity with the sequence set forth in any one of SEQ ID NOs 39, or 42, at least 97% sequence identity with the sequence set forth in SEQ ID NO: 34, at least 98% sequence identity with the sequence set forth in SEQ ID NO: 4, at least 99% sequence identity with the sequence set forth in any one of SEQ ID NOs 2, or 38, or 100% sequence identity with the sequence set forth in any one of SEQ ID NOs 14, 24, 25, 26, or 27.

Most preferably, the bacterium which inhibits the growth of *Clostridium difficile* may be a bacterium as deposited at DSMZ under accession number DSM32147, DSM32175, DSM32153, DSM32152, DSM32193, DSM32162, DSM32168, DSM32178, DSM32182, DSM32179, DSM32211, DSM 32219, DSM32220, DSM32213, DSM32215, DSM32216, DSM 32217, DSM32218, DSM 32224. Alternatively, the therapeutic composition of the present invention may comprise at least one isolated bacterium which inhibits the growth of *Clostridium difficile*, wherein said bacterium comprising a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

In an alternative preferred embodiment, the therapeutic composition may comprise at least one isolated bacterium which inhibits the growth of *Escherichia coli*. This is preferred in the context of a therapeutic composition for use in the treatment of a dysbiosis associated with an enteric infection, in particular a dysbiosis associated with an infection with a Proteobacterium, such as *Escherichia* species, *Salmonella* species, *Campylobacter* species, *Vibrio* species, *Helicobacter* species, and *Yersinia* species, most preferably a dysbiosis associated with an infection with *Escherichia coli*.

For example, the therapeutic composition may comprise at least one, at least two, at least three, at least four, at least five, at least six, at least seven, at least eight, at least nine, or at least ten, isolated bacteria which inhibit the growth of *Escherichia coli*. In one embodiment, the bacteria in the therapeutic composition may consist of bacteria which inhibit the growth of *Escherichia coli*.

A bacterium which inhibits the growth of *Escherichia coli* may be a bacterium comprising a gene encoding a 16S ribosomal RNA (rRNA), wherein said gene comprises a sequence with at least 90% sequence identity with the sequence set forth in any one of SEQ ID NOs 4, 10, 11, 13, 25, 27, 32, 34, 41, and 45.

Alternatively, a bacterium which inhibits the growth of *Escherichia coli* may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 99%, or 100% sequence identity with the sequence set forth in any one of SEQ ID NOs 4, 10, 11, 13, 25, 27, 32, 34, 41, and 45.

More preferably, a bacterium which inhibits the growth of *Escherichia coli* may be a bacterium comprising a gene encoding a 16S ribosomal RNA (rRNA), wherein said gene comprises a sequence with at least 92% sequence identity with the sequence set forth in SEQ ID NO: 11, at least 93% sequence identity with the sequence set forth in SEQ ID NO: 13, at least 95% sequence identity with the sequence set forth in any one of SEQ ID NOs 41, or 45, at least 96% sequence identity with the sequence set forth in any one of SEQ ID NOs 10, or 32, at least 97% sequence identity with the sequence set forth in any one of SEQ ID NOs 25, or 34, at least 98% sequence identity with the sequence set forth in SEQ ID NO: 4, or at least 99% sequence identity with the sequence set forth in SEQ ID NO: 27.

Even more preferably, a bacterium which inhibits the growth of *Escherichia coli* may be a bacterium comprising a gene encoding a 16S ribosomal RNA (rRNA), wherein said gene comprises a sequence with at least 92% sequence identity with the sequence set forth in SEQ ID NO: 11, at least 95% sequence identity with the sequence set forth in any one of SEQ ID NOs 13, 41, or 45, at least 96% sequence identity with the sequence set forth in SEQ ID NO: 32, at least 97% sequence identity with the sequence set forth in any one of SEQ ID NOs 10, or 34, at least 98% sequence identity with the sequence set forth in SEQ ID NO: 4, or 100% sequence identity with the sequence set forth in any one of SEQ ID NOs 25, or 27.

Most preferably, the bacterium which inhibits the growth of *Escherichia coli* may be a bacterium as deposited at DSMZ under accession number DSM32175, DSM32166, DSM32151, DSM32193, DSM32178, DSM32179, DSM 32262, DSM 32219, DSM32215, DSM32218. Alternatively, the therapeutic composition of the present invention may comprise at least one isolated bacterium which inhibits the growth of *Escherichia coli*, wherein said bacterium comprising a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

In addition to an isolated bacterium which inhibits the growth of *Clostridium difficile* and/or *Escherichia coli*, the therapeutic composition may comprise at least one isolated bacterium which co-occurs with a bacterium which inhibits the growth of *Clostridium difficile* and/or *Escherichia coli* as disclosed herein. Bacteriotherapy candidates which have been shown to co-occur with a bacterium which inhibits the growth of *Clostridium difficile* and/or *Escherichia* coil as disclosed herein are HMI 2, HMI 5, HMI 6, HMI 7, HMI 8, HMI 9, HMI 10, HMI_11, HMI_12, HMI_14, HMI_15, HMI_16, HMI_17, HMI_18, HMI_19, HMI_20, HMI_26, HMI_27, HMI_31, HMI_33, HMI_34, HMI_35, HMI_37, HMI_38, HMI_39, HMI_41, HMI_42, HMI_43, HMI 44, HMI 46, HMI_47, HMI_48, HMI_50, HMI_51, and HMI_52 (see FIG. 15 for details).

Thus, the therapeutic composition may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, at least thirty-four, or thirty-five isolated bacteria which co-occur with a bacterium which inhibits the growth of *Clostridium difficile* and/or *Escherichia coli* as disclosed herein.

The bacterium which co-occurs with a bacterium which inhibits the growth of *Clostridium difficile* and/or *Escherichia coli* as disclosed herein, may be a bacterium comprising a gene encoding a 16S ribosomal RNA (rRNA), wherein said gene comprises a sequence with at least 90% sequence identity with the sequence set forth in any one of SEQ ID NOs 2, 5, 6, 7, 8, 9, 10, 11, 12, 13, 14, 15, 16, 17, 18, 19, 25, 26, 30, 32, 33, 34, 36, 37, 38, 40, 41, 42, 43, 45, 46, 47, 49, 50, or 51.

Alternatively, the bacterium which co-occurs with a bacterium which inhibits the growth of *Clostridium difficile* and/or *Escherichia coli* as disclosed herein, may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 2, 5, 6, 7, 8, 9, 10, 11, 12, 13, 14, 15, 16, 17, 18, 19, 25, 26, 30, 32, 33, 34, 36, 37, 38, 40, 41, 42, 43, 45, 46, 47, 49, 50, or 51.

Preferably, the bacterium which co-occurs with a bacterium which inhibits the growth of *Clostridium difficile* and/or *Escherichia coli* as disclosed herein, is a bacterium comprising a gene encoding a 16S ribosomal RNA (rRNA), wherein said gene comprises a sequence with at least 92% sequence identity with the sequence set forth in any one of SEQ ID NOs 6, 11, or 19, at least 93% sequence identity with the sequence set forth in any one of SEQ ID NOs 13 or 26, at least 94% sequence identity with the sequence set forth in any one of SEQ ID NOs 5, 14, 15, 17, 18, or 50, at least 95% sequence identity with the sequence set forth in any one of SEQ ID NOs 33, 41, 43, 45, 46, 47, or 49, at least 96% sequence identity with the sequence set forth in any one of SEQ ID NOs 2, 7, 8, 10, 12, 30, 32, or 42, at least 97% sequence identity with the sequence set forth in any one of SEQ ID NOs 16, 25, 34, 36, 37, or 40, at least 98% sequence identity with the sequence set forth in SEQ ID NO: 9, or at least 99% sequence identity with the sequence set forth in any one of SEQ ID NOs 38, or 51.

More preferably, the bacterium which co-occurs with a bacterium which inhibits the growth of *Clostridium difficile* and/or *Escherichia coli* as disclosed herein, is a bacterium comprising a gene encoding a 16S ribosomal RNA (rRNA), wherein said gene comprises a sequence with at least 92% sequence identity with the sequence set forth in any one of SEQ ID NOs 6, or 11, at least 94% sequence identity with the sequence set forth in any one of SEQ ID NOs 5, 19, or 50, at least 95% sequence identity with the sequence set forth in any one of SEQ ID NOs 13, 15, 33, 41, 43, 45, or 46, at least 96% sequence identity with the sequence set forth in any one of SEQ ID NOs 7, 12, 32, or 42, at least 97% sequence identity with the sequence set forth in any one of SEQ ID NOs 8, 10, 16, 34, 36, 37, 40, or 49, at least 98% sequence identity with the sequence set forth in any one of SEQ ID NOs 9 or 17, at least 99% sequence identity with the sequence set forth in any one of SEQ ID NOs 2, 38, 51, or at least 100% sequence identity with the sequence set forth in any one of SEQ ID NOs 14, 18, 25, 26, 30, or 47.

Most preferably, the bacterium which co-occurs with a bacterium which inhibits the growth of *Clostridium difficile* and/or *Escherichia coli* as disclosed herein, is a bacterium as deposited at DSMZ under accession number DSM32147, DSM32153, DSM32152, DSM32158, DSM32192, DSM32148, DSM32166, DSM32151, DSM32150, DSM32193, DSM32162, DSM32194, DSM32163, DSM32205, DSM32195, DSM32164, DSM32178, DSM32182, DSM32181, DSM32262, DSM32211, DSM32219, DSM32261, DSM32212, DSM32220, DSM32226, DSM32215, DSM32216, DSM32217, DSM32218, DSM32224, DSM32214, DSM32223, DSM32225, or DSM32265. Alternatively, the therapeutic composition of the present invention may comprise at least one isolated bacterium which co-occurs with a bacterium which inhibits the growth of *Clostridium difficile* and/or *Escherichia coli* as disclosed herein, wherein said bacterium comprises a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

Bacteria related to the genus *Clostridium* have been shown to be beneficial in reducing inflammation through interactions with the host immune system (Atarashi, Tanoue et al. 2013). The isolated bacterium present in the therapeutic composition may thus be a bacterium which has immunomodulatory activity. For example, the bacterium may reduce inflammation in the individual, e.g. in the gastrointestinal tract of the individual. Bacteriotherapy candidates which are in the same genus as bacteria which have been shown to be beneficial in reducing inflammation through interactions with the host immune system are HMI_4, HMI_9, HMI_10, HMI_15, HMI_27, HMI_28 and HMI_38. The bacteria ar therefore expected to have immunomodulatory activity, such as reducing inflammation in the individual, e.g. in the gastrointestinal tract of the individual.

Thus, the therapeutic composition may comprise at least one, at least two, at least three, at least four, at least five, at least six, or at least seven isolated bacteria which have immunomodulatory activity. In one embodiment, the bacteria in the therapeutic composition may consist of bacteria which reduce inflammation in the individual.

The bacterium which has immunomodulatory activity may be a bacterium comprising a gene encoding a 16S ribosomal RNA (rRNA), wherein said gene comprises a sequence with at least 90% sequence identity with the sequence set forth in any one of SEQ ID NOs 4, 9, 10, 14, 26, 27, or 37.

Alternatively, a bacterium which has immunomodulatory activity may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 99%, or 100% sequence identity with the sequence set forth in any one of SEQ ID NOs 4, 9, 10, 14, 26, 27, or 37.

Preferably, a bacterium which has immunomodulatory activity may be a bacterium comprising a gene encoding a 16S ribosomal RNA (rRNA), wherein said gene comprises a sequence with at least 93% sequence identity with the sequence set forth in SEQ ID NO: 26, at least 94% sequence identity with the sequence set forth in SEQ ID NO: 14, at least 96% sequence identity with the sequence set forth in SEQ ID NO:10, at least 97% sequence identity with the sequence set forth in SEQ ID NO: 37, at least 98% sequence identity with the sequence set forth in any one of SEQ ID NOs 4 or 9, or at least 99% sequence identity with the sequence set forth in SEQ ID NO: 27. More preferably, a bacterium which has immunomodulatory activity may be a bacterium comprising a gene encoding a 16S ribosomal RNA (rRNA), wherein said gene comprises a sequence with at least 97% sequence identity with the sequence set forth in in any of SEQ ID NOs 10 or 37, at least 98% sequence identity with the sequence set forth in any one of SEQ ID NOs 4 or 9, or at least 100% sequence identity with the sequence set forth in any one of SEQ ID NOs 14, 26, or 27.

Most preferably, the bacterium which has immunomodulatory activity may be a bacterium as deposited at DSMZ under accession number DSM32175, DSM32148, DSM32166, DSM32162, DSM32182, DSM32179, or DSM32212. Alternatively, the therapeutic composition of the present invention may comprise at least one isolated bacterium which has immunomodulatory activity, wherein said bacterium comprising a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

The therapeutic composition of the invention may comprise at least one isolated bacterium which is on the Human Microbiome Project's (HMP) "most wanted" list. Bacteriotherapy candidates HMI 1, HMI 2, HMI 4, HMI 5, HMI 7, HMI 11, HMI 12, HMI 15, HMI 16, HMI_17, HMI_18, HMI_19, HMI_35, HMI_37, HMI_38, HMI_39, HMI_45, HMI_50, and HMI_51 are on HMP's "most wanted" list.

Thus, the therapeutic composition of the present invention may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, or nineteen bacteria which are on HMP's "most wanted" list. In one embodiment, the bacteria in the therapeutic composition may consist of bacteria which are on HMP's "most wanted" list.

The bacterium which is on HMP's "most wanted" list may be a bacterium comprising a gene encoding a 16S ribosomal RNA (rRNA), wherein said gene comprises a sequence with at least 90% sequence identity with the sequence set forth in any one of SEQ ID NOs 1, 2, 4, 5, 7, 11, 12, 14, 15, 16, 17, 18, 34, 36, 37, 38, 44, 49, or 50.

Alternatively, the bacterium which is on HMP's "most wanted" list may be a bacterium comprising a gene encoding a 16S ribosomal RNA (rRNA), wherein said gene comprises a sequence with at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 1, 2, 4, 5, 7, 11, 12, 14, 15, 16, 17, 18, 34, 36, 37, 38, 44, 49, or 50.

Preferably, the bacterium which is on HMP's "most wanted" list is a bacterium comprising a gene encoding a 16S ribosomal RNA (rRNA), wherein said gene comprises a sequence with at least 90% sequence identity with the sequence set forth SEQ ID NO: 1, at least 92% sequence identity with the sequence set forth SEQ ID NO: 11, at least 94% sequence identity with the sequence set forth in any one of SEQ ID NOs 5, 14, 15, 17, 18, or 50, at least 95% sequence identity with the sequence set forth SEQ ID NO: 49, at least 96% sequence identity with the sequence set forth in any one of SEQ ID NOs 2, 7, 12, or 44, at least 97% sequence identity with the sequence set forth in any one of SEQ ID NOs 16, 34, 36, or 37, at least 98% sequence identity with the sequence set forth in SEQ ID NO: 4, or at least 99% sequence identity with the sequence set forth in SEQ ID NO: 38.

More preferably, the bacterium which is on HMP's "most wanted" list is a bacterium comprising a gene encoding a 16S ribosomal RNA (rRNA), wherein said gene comprises a sequence with at least 90% sequence identity with the sequence set forth SEQ ID NO: 1, at least 92% sequence identity with the sequence set forth SEQ ID NO: 11, at least 94% sequence identity with the sequence set forth in any one of SEQ ID NOs 5 or 50, at least 95% sequence identity with the sequence set forth SEQ ID NO: 15, at least 96% sequence identity with the sequence set forth in any one of SEQ ID NOs 7, 12, or 44, at least 97% sequence identity with the sequence set forth in any one of SEQ ID NOs 16, 34, 36, 37, 49, at least 98% sequence identity with the sequence set forth in any one of SEQ ID NOs 4, or 17, at least 99% sequence identity with the sequence set forth in any one of SEQ ID NOs 2, or 38, or 100% sequence identity with the sequence set forth in any one of SEQ ID NOs 14, or 18.

Most preferably, the bacterium which is on HMP's "most wanted" list is a bacterium as deposited at DSMZ under accession number DSM32191, DSM32147, DSM32175, DSM32153, DSM32158, DSM32151, DSM32150, DSM32162, DSM32194, DSM32163, DSM32205, DSM32195, DSM32219, DSM32261, DSM32212, DSM32220, DSM32221, DSM32223, or DSM32225. Alternatively, the therapeutic composition of the present invention may comprise at least one bacterium which is on HMP's "most wanted" list, wherein said bacterium comprises a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

The therapeutic composition of the invention may comprise at least one isolated bacterium which is a keystone species. Bacteriotherapy candidates HMI_17, HMI_23, HMI_24, HMI_25, HMI_26, HMI_27, HMI_28, HMI_29, HMI_30, HMI_31, HMI_32, HMI_45, HMI_49, HMI_51, and HMI_52 are expected to be keystone species.

Thus, the therapeutic composition of the present invention may comprise at least one, at least two, at least three, at least four, at least five, at least six, at least seven, at least eight, at least nine, at least ten, at least eleven, at least twelve, at least thirteen, at least fourteen, or fifteen bacteria which are keystone species. In one embodiment, the bacteria in the therapeutic composition may consist of bacteria which are keystone species.

The bacterium which is a keystone species may be a bacterium comprising a gene encoding a 16S ribosomal RNA (rRNA), wherein said gene comprises a sequence with at least 90% sequence identity with the sequence set forth in any one of SEQ ID NOs 16, 22, 23, 24, 25, 26, 27, 28, 29, 30, 31, 44, 48, 50, or 51.

Alternatively, the bacterium which is a keystone species may be a bacterium comprising a gene encoding a 16S ribosomal RNA (rRNA) wherein said gene comprises a sequence with at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 16, 22, 23, 24, 25, 26, 27, 28, 29, 30, 31, 44, 48, 50, or 51.

Preferably, the bacterium which is a keystone species is a bacterium comprising a gene encoding a 16S ribosomal RNA (rRNA) wherein said gene comprises a sequence with at least 91% sequence identity with the sequence set forth in SEQ ID NO: 29, at least 92% sequence identity with the sequence set forth in SEQ ID NO: 24, at least 93% sequence identity with the sequence set forth in any one of SEQ ID NOs 22, or 26, at least 94% sequence identity with the sequence set forth in any one of SEQ ID NOs 23, or 50, at least 96% sequence identity with the sequence set forth in any one of SEQ ID NOs 30, 44, or 48, at least 97% sequence identity with the sequence set forth in any one of SEQ ID NOs 16, 25, or 31, or at least 99% sequence identity with the sequence set forth in any one of SEQ ID NOs 27, 28, or 51.

More preferably, the bacterium which is a keystone species is a bacterium comprising a gene encoding a 16S ribosomal RNA (rRNA) wherein said gene comprises a sequence with at least 94% sequence identity with the sequence set forth in any one of SEQ ID NOs 22, 23, or 50, at least 95% sequence identity with the sequence set forth in SEQ ID NO: 29, at least 96% sequence identity with the sequence set forth in SEQ ID NO: 44, at least 97% sequence identity with the sequence set forth in any one of SEQ ID NOs 16, or 48, at least 98% sequence identity with the sequence set forth in SEQ ID NO: 31, at least 99% sequence identity with the sequence set forth in SEQ ID NO: 51, or 100% sequence identity with the sequence set forth in any one of SEQ ID NOs 24, 25, 26, 27, 28, or 30.

Most preferably, the bacterium which is a keystone species is a bacterium as deposited at DSMZ under accession number DSM32163, DSM32165, DSM32169, DSM32168, DSM32178, DSM32182, DSM32179, DSM32180, DSM32184, DSM32181, DSM32183, DSM32221, DSM32263, DSM32225, or DSM32265. Alternatively, the therapeutic composition of the present invention may comprise at least one bacterium which is a keystone species, wherein said bacterium comprises a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

In addition, or alternatively, the therapeutic composition of the invention may comprise at least one isolated bacterium which has been shown to be present post-FMT. The bacteriotherapy candidates to which this applies are set out in FIG. 15. For example, the therapeutic composition may comprise at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one or twenty two bacteria which has been shown to be present post-FMT. For example the bacterium which has been shown to be present post-FMT may comprise a gene encoding a 16S ribosomal RNA (rRNA), wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 22, 23, 24, 25, 26, 27, 28, 29, 30, 31, 32, 33, 34, 36, 38, 40, 43, 44, 45, 46, 48, or 51. Preferably, the bacterium which has been shown to be present post-FMT is a bacterium as deposited at DSMZ under accession number DSM32165, DSM32169, DSM32168, DSM32178, DSM32182, DSM32179, DSM32180, DSM32184, DSM32181, DSM32183, DSM32262, DSM32211, DSM32219, DSM32261, DSM32220, DSM32226, DSM32217, DSM32221, DSM32218, DSM32224, DSM32263, or DSM32265. Alternatively, the therapeutic composition of the present invention may comprise at least one bacterium which has been shown to be present post-FMT, wherein said bacterium comprises a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

In addition, or alternatively, the therapeutic composition of the invention may comprise at least one isolated bacterium which is expected to produce one or more beneficial metabolites, such as short chain fatty acids (SCFA). The bacteriotherapy candidates to which this applies are set out in FIG. 15. For example, the therapeutic composition may comprise at least one, at least two, at least three, at least four, at least five, at least six, at least seven, at least eight, at least nine, at least ten, at least eleven, at least twelve, at least thirteen, or fourteen bacteria which produce one or more beneficial metabolites. For example the bacterium which produces one or more beneficial metabolites may comprise a gene encoding a 16S ribosomal RNA (rRNA), wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence set forth in any one of SEQ ID NOs 9, 12, 19, 20, 22, 23, 24, 25, 26, 27, 28, 29, 30, or 31. Preferably, the bacterium which is expected to produce one or more beneficial metabolites is a bacterium as deposited at DSMZ under accession number DSM32148, DSM32150, DSM32164, DSM32177, DSM32165, DSM32169, DSM32168, DSM32178, DSM32182, DSM32179, DSM32180, DSM32184, DSM32181, or DSM32183. Alternatively, the therapeutic composition of the present invention may comprise at least one bacterium which produces one or more beneficial metabolites, wherein said bacterium comprises a gene encoding a 16S rRNA, wherein said gene comprises a sequence with at least 90%, at least 91%, at least 92%, at least 93%, at least 94%, at least 95%, at least 96%, at least 97%, at least 98%, at least 98.7%, at least 99%, or 100% sequence identity with the sequence of the gene encoding the 16S rRNA in a deposited bacterium as described above.

The isolated bacterium or isolated bacteria present in a therapeutic composition may make up at least 1%, 5%, 10%, 15%, 20%, 25%, 30%, 35%, 40%, 45%, 50%, 55%, 60%, 65%, 7%, 75%, 80%, 85%, or 90% of the therapeutic composition by volume or weight.

The therapeutic composition may comprise no other active ingredient other than the isolated bacterium or isolated bacteria in question, and optionally a prebiotic. Thus, the active ingredient of the therapeutic composition may consist of one or more isolated bacteria disclosed herein, and optionally a prebiotic. This may also be referred to as a defined active ingredient.

The therapeutic composition of the present invention is not a faecal microbiota transplant (FMT). FMTs usually consist of a stool sample from a healthy human donor which is administered directly to the recipient, e.g. in the form of an enema, without bacteria present in the stool sample being isolated prior to the administration of the FMT to the recipient. An advantage of the therapeutic composition of the invention is that it may comprise no undefined components, which are present in FMTs, thereby allowing the therapeutic composition to be standardised and increasing safety.

The therapeutic composition of the present invention may be prepared by a method comprising culturing the one or more isolated bacteria present in the therapeutic composition in a suitable medium or media. Media and conditions suitable for culturing the bacteria to be included in the therapeutic composition of the present invention are described in detail elsewhere herein. For example, a method of preparing a therapeutic composition according to the present invention may comprise the steps of:
  (i) culturing a first isolated bacterium;
  (ii) optionally culturing a second isolated bacterium; and
  (iii) mixing the bacteria obtained in (i) and optionally (ii) to prepare the therapeutic composition. The isolated bacteria to be included in the therapeutic composition are preferably cultured in separate steps. In other words, a separate culture of each bacterium to be included in the therapeutic composition is preferably prepared. This allows the growth of each bacterium to be evaluated and the amount of each bacterium to be included in the pharmaceutical composition to be controlled as desired. The bacteria cultured in steps (i) and (ii) preferably have distinct 16S rRNA sequences.

The above method may include steps of culturing each isolated bacterium which is to be included in the therapeutic composition. Thus, the method may e.g. further include steps of culturing a third, fourth, fifth, sixth, seventh, eighth, ninth, and/or tenth distinct isolated bacterium, as required. In this way, the method comprise steps of culturing up to 51 distinct isolated bacteria. The bacterium or bacteria cultured by said method may be any bacterium as disclosed herein.

The method may optionally comprise one or more further steps in which the bacteria are mixed with one or more additional ingredients, such as a pharmaceutically acceptable excipient, prebiotic, carrier, insoluble fibre, buffer, osmotic agent, antifoaming agent, and/or preservative. In addition, or alternatively, the method may comprise suspending the bacteria obtained in (i) and optionally (ii) in a chemostat medium, or saline, e.g. 0.9% saline. The bacteria obtained in (i) and optionally (ii) may be provided under a reduced atmosphere, such as $N_2$, $CO_2$, Hz, or a mixture thereof, e.g. $N_2$:$CO_2$:$H_2$. The gases may be present in appropriate ratios for the preservation of the bacteria present in the therapeutic composition. For Example, the reduced atmosphere may comprise 80% $N_2$, 10% $CO_2$ and 10% $H_2$. In addition, or alternatively, the method may comprise a step of lyophilising the bacteria obtained in (i) and optionally (ii), optionally in the presence of a stabiliser and/or crypro-tectant. The method may also comprise a step of preparing a capsule, tablet, or enema comprising the bacteria obtained in (i) and optionally (ii). The capsule or tablet may be enteric-coated, pH dependent, slow-release, and/or gastro-resistant.

The present invention also encompasses a therapeutic composition obtainable by, or obtained by, a method as disclosed herein. Such a therapeutic composition may further be used for a therapeutic purpose, in a therapeutic method, or for the manufacture of a medicament, as described herein, such as treatment of a dysbiosis, in particular a dysbiosis of the gastrointestinal tract.

It is expected that the bacteria disclosed herein will be suitable for the treatment of a dysbiosis, in particular a dysbiosis of the gastrointestinal tract. Without wishing to be limited by theory, it is expected that administration of one or more of the bacteria disclosed herein to an in individual will resolve a gastrointestinal dysbiosis, where present, and/or prevent the occurrence of gastrointestinal dysbiosis, in the individual. "Individual", as used herein, refers to a human individual or human patient.

Treatment of a dysbiosis may refer to the cure, prevention, or amelioration of a dysbiosis or the amelioration of at least one symptom associated with dysbiosis. Where the dysbiosis is associated with a disease, such as inflammatory bowel disease, treatment of the dysbiosis may refer to the cure, prevention, or amelioration of said disease, or the amelioration of at least one symptom associated with said disease.

The therapeutic compositions of the present invention thus find application in the treatment of dysbiosis, in particular dysbiosis of the gastrointestinal tract. Accordingly, the invention provides a method of treating a dysbiosis comprising administering a therapeutically effective amount of a therapeutic composition of the invention to an individual in need thereof, a therapeutic composition according to the invention for use in a method of treating a dysbiosis in an individual, and the use of a therapeutic composition of the invention for the manufacture of a medicament for the treatment of a dysbiosis in an individual.

"Dysbiosis" in the context of the present invention refers to a state in which the normal diversity and/or function of the microbiota or microbiome, in particular the human gastrointestinal microbiota, is disrupted. Any disruption from the normal state of the microbiota in a healthy individual can be considered a dysbiosis, even if the dysbiosis does not result in a detectable decrease in health in the individual. In a preferred embodiment, the dysbiosis may be associated with one or more pathological symptoms. For example, "dysbiosis" may refer to a decrease in the microbial diversity of the microbiota. In addition, or alternatively, "dysbiosis" may refer to an increase in the abundance of one or more bacteria, e.g. one or more pathogenic bacteria, in the microbiota of an individual relative to the abundance of said bacterium or bacteria in the microbiota of a healthy individual, i.e. an individual without a dysbiosis. The pathogenic bacteria present during dysbiosis are often Proteobacteria and resistant to one or more antibiotics. Examples of Proteobacteria include *Escherichia, Salmonella, Campylobacter, Vibrio, Helicobacter*, and *Yersinia* species.

The dysbiosis may be a dysbiosis associated with an enteric bacterial infection, such as an infection of the gastrointestinal tract with a pathogenic bacterium. Many bacteria capable of causing infections of the gastrointestinal tract in humans are known and include: gram positive bacteria, and gram negative bacteria. The pathogenic bacterium is preferably a pathogenic species of the genus *Clostridium, Escherichia, Enterococcus, Klebsiella, Enterobacter, Proteus, Salmonella, Shigella, Staphylococcus, Vibrio, Aeromonas, Campylobacter, Plesiomonas, Bacillus, Helicobacter, Listeria,* or *Yersinia*. Preferred examples of such pathogenic bacteria include *Clostridium difficile, Clostridium perfringens, Clostridium botulinum, Escherichia coli, Salmonella typhi, Staphylococcus aureus, Vibrio cholerae, Vibrio parahaemolyticus, Vibrio vulnificus, Campylobacter fetus, Campylobacter jejuni, Aeromonas hydrophila, Plesiomonas shigelloides, Bacillus cereus, Helicobacter pylori, Listeria monocytogenes,* and *Yersinia enterocolitica*. More preferably, the pathogenic bacterium is a pathogenic species of the genus *Clostridium* or *Escherichia*. Most preferably, the pathogenic bacterium is *Clostridium difficile* or *Escherichia coli*.

The pathogenic bacterium may resistant to one or more antibiotics. For example, the pathogenic bacterium, e.g. *Clostridium difficile*, may be resistant to fluoroquinolones. In addition, or alternatively, the pathogenic bacterium may be resistant to one or more carbapenems. Carbapenems are antibiotics used for the treatment of infections by multidrug-resistant (MDR) bacteria, and examples include imipenem, meropenem, ertapenem, doripenem, panipenem, and biapenem.

Treatment of a dysbiosis associated with an infection with a pathogenic bacterium may comprise reducing the abundance of the pathogenic bacterium, e.g. in the gastrointestinal tract of the individual, relative to the abundance of the pathogenic bacterium prior to treatment.

The dysbiosis may be a recurrent or chronic dysbiosis. For example, *Clostridium difficile* is known to result in recurrent infections in some individuals, with the infection reoccurring once antibiotic treatment is stopped. This may be referred to as a recurrent or chronic dysbiosis.

Dysbiosis of the gastrointestinal tract is known to be associated with, and is thought to play a causal role in, a number of diverse diseases, including inflammatory bowel disease, irritable bowel syndrome, metabolic disease, a neuropsychiatric disorder, an autoimmune disease, an allergic disorder, or a cancer. Thus the dysbiosis may be a dysbiosis associated with inflammatory bowel disease, irritable bowel syndrome, a metabolic disease, a neuropsychiatric disorder, an autoimmune disease, an allergic disorder, a cancer, or hepatic encephalopathy. Examples of inflammatory bowel disease include ulcerative colitis and Crohn's disease.

Metabolic disease in which dysbiosis of the gastrointestinal tract has been shown to play a role include metabolic syndrome, obesity, type 2 diabetes mellitus, a cardiovascular disease, and non-alcoholic fatty liver.

Neuropsychiatric disorder in which dysbiosis of the gastrointestinal tract has been shown to play a role include Parkinson's disease, Alzheimer's disease, multiple sclerosis, myoclonus dystonia, autism and chronic fatigue syndrome.

Autoimmune diseases in which dysbiosis of the gastrointestinal tract has been shown to play a role include idiopathic thrombocytopenic purpura, arthritis, Sjögren's syndrome, systemic lupus erythematosus, and Hashimoto's thyroiditis.

Allergic disorder in which dysbiosis of the gastrointestinal tract has been shown to play a role include atopy, and asthma.

Cancers in which dysbiosis of the gastrointestinal tract has been shown to play a role include colorectal cancer, extra-intestinal tumours, mammary tumours, hepatocellular carcinoma, lymphoma, melanoma, and lung cancer.

The therapeutic composition of the invention may comprise a pharmaceutically acceptable excipient, carrier, buffer, stabilizer or other materials well known to those skilled in the art. Such materials should be non-toxic and should not interfere with the efficacy of the isolated bacteria present in the therapeutic composition. The precise nature of the pharmaceutically acceptable excipient or other material will depend on the route of administration, which may be oral or rectal. Many methods for the preparation of therapeutic compositions are known to those skilled in the art. See e.g. Robinson ed., Sustained and Controlled Release Drug Delivery Systems, Marcel Dekker, Inc., New York, 1978.

The therapeutic composition of the invention may comprise a prebiotic, a carrier, insoluble fibre, a buffer, an osmotic agent, an anti-foaming agent and/or a preservative.

Prebiotics may provide nutrients for the isolated bacteria present in the therapeutic composition to assist their early growth and colonisation after administration to the individual. Any prebiotic known in the art may be used. Non-limiting examples of prebiotics include oligosaccharides, e.g., fructooligosaccharides such as oligofructose and inulin, mannan oligosaccharides and galactooligosaccharides, soluble, oligofructose-enriched inulin and soluble fiber. Insoluble fiber may be included in the therapeutic composition as a carrier, e.g., to provide protection during transit or storage. A buffer may be included in the therapeutic composition to promote the viability of the isolated bacteria present. An anti-fungal agent may included in the therapeutic composition as a preservative.

The therapeutic composition may be made or provided in chemostat medium. Alternatively, the therapeutic composition may be made or provided in saline, e.g., 0.9% saline. It will be understood that any carrier or solution which does not impair viability of the bacteria present in the therapeutic composition and is compatible with administration to an individual may be used.

The therapeutic composition may be made or provided under reduced atmosphere, i.e., in the absence of oxygen. The synthetic stool preparation may be made or provided under $N_2$, $CO_2$, $H_2$, or a mixture thereof, optionally with controlled levels of partial pressure of $N_2$:$CO_2$:$H_2$.

The therapeutic composition may be for oral or rectal administration to the individual. Where the therapeutic composition is for oral administration, the therapeutic composition may be in the form of a capsule, or a tablet. Where the therapeutic composition is for rectal administration, the therapeutic composition may be in the form of an enema. The preparation of suitable capsules, tablets and enema is well-known in the art. The capsule or tablet may comprise a coating to protect the capsule or tablet from stomach acid. For example, the capsule or tablet may be enteric-coated, pH dependent, slow-release, and/or gastro-resistant. Such capsules and tablets are used, for example, to minimize dissolution of the capsule or tablet in the stomach but allow dissolution in the small intestine.

The therapeutic composition may be lyophilized. The lyophilized therapeutic composition may comprise one or more stabilisers and/or cryoprotectants. The lyophilized therapeutic composition may be reconstituted using a suitable diluent prior to administration to the individual.

A therapeutic composition according to the present invention may be administered alone or in combination with other treatments, concurrently or sequentially or as a combined preparation with another therapeutic agent or agents, for the treatment of dysbiosis, or a disease associated with dysbiosis as described herein. For example, a conjugate of the invention may be used in combination with an existing therapeutic agent for inflammatory bowel disease, irritable bowel syndrome, a metabolic disease, a neuropsychiatric disorder, an autoimmune disease, an allergic disorder, a cancer, or hepatic encephalopathy.

For example, where the therapeutic composition is for the treatment of a dysbiosis associated with cancer, the therapeutic composition may optionally be administered in combination a cancer immunotherapy, such as an immune check-point inhibitor, to the individual. Examples of check-point inhibitors which may be employed in this context include Programmed cell death protein 1 (PD-1) inhibitors, Programmed death-ligand 1 (PD-L1) inhibitors, cytotoxic T-lymphocyte-associated protein 4 (CTLA-4) inhibitors. Manipulation of the gut microbiota in combination with immune check-point inhibitor treatment has been shown to improve efficacy of immune check-point inhibitors in treating cancer (Snyder et al. 2015). In a preferred embodiment, the cancer in this context is lung cancer or melanoma. Immune check-point inhibitors have been approved for the treatment of these cancers and bacteriotherapy has been shown to improve efficacy of check-point inhibitors in the treatment of melanoma (Snyder et al. 2015).

The therapeutic compositions of the invention may be administered to an individual, preferably a human individual. Administration may be in a "therapeutically effective amount", this being sufficient to show benefit to the individual. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the dysbiosis, the site of delivery of the composition, the type of therapeutic composition, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. A therapeutically effective amount or suitable dose of a therapeutic composition of the invention can be determined by comparing its in vitro activity and in vivo activity in an animal model. Methods for extrapolation of effective dosages in mice and other test animals to humans are known. The precise dose will depend upon a number of factors, including whether the therapeutic composition is for prevention or for treatment.

Further aspects and embodiments of the invention will be apparent to those skilled in the art given the present disclosure including the following experimental exemplification.

All documents mentioned in this specification are incorporated herein by reference in their entirety.

Unless the context dictates otherwise, the singular includes the plural.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Identification and Isolation of Bacteriotherapy Candidates

Materials and Methods

Two different approaches were used to isolate bacterial species for inclusion in a therapeutic composition for treating dysbiosis. The first relied on a broad culturing approach from healthy adult donors to establish a culture collection which is as representative as possible of the bacterial component of the intestinal microbiota of healthy individuals. This process also incorporated a targeted culturing approach to preferentially select bacteria displaying a particular phenotype or function e.g. spore formation. The second approach was more targeted in nature and aimed to isolate bacterial species specifically associated with resolving gastrointestinal dysbiosis by comparing the microbiota of individuals before and after Faecal Microbiota Transplantation (FMT) administered to resolve dysbiosis associated with *C. difficile* infection. These two approaches are respectively referred to as Candidate Isolation Process 1 (CIP1) and Candidate Isolation Process 2 (CIP2) below.

Sample Collection and Culturing

For CIP1, fresh faecal samples were obtained from six consenting healthy adult human donors (one faecal sample per donor—minimum 0.5 g). The samples were placed in anaerobic conditions within one hour of passing to preserve the viability of anaerobic bacteria. All sample processing and culturing took place under anaerobic conditions in a Whitley DG250 workstation (Don Whitley, West Yorkshire, UK) at 37° C. Culture media, phosphate-buffered saline (PBS) and all other materials that were used for culturing were placed in the anaerobic cabinet 24 hours before use. The faecal samples were divided into two portions. One portion was homogenised in reduced PBS (0.1 g stool/ml PBS) and was serially diluted and plated directly onto YCFA (Duncan, Hold et al. 2002) agar supplemented with 0.002 g/ml each of glucose, maltose and cellobiose in large (13.5 cm diameter) petri dishes. This sample was also subjected to metagenomic sequencing to profile the entire community. The other portion was treated with an equal volume of 70% (v/v) ethanol for 4 hours at room temperature under ambient aerobic conditions to kill vegetative cells. Then, the solid material was washed 3 times with PBS and it was eventually resuspended in PBS. Plating was performed in same manner as described for the non-ethanol treated samples above.

For the ethanol-treated samples of CIP1, the medium was supplemented with 0.1% sodium taurocholate to stimulate spore germination. Colonies were picked 72 hours after plating from petri dishes of both ethanol-treated and non-ethanol-treated conditions harbouring non-confluent growth, (i.e. plates on which the colonies were distinct and not touching). The colonies that were picked were re-streaked to confirm purity.

For CIP2, twelve individuals who had each experienced more than three recurrences of *Clostridium difficile* infection (CDI), having failed treatment with metronidazole and vancomycin were selected for Faecal Microbiota Transplantation (FMT). The donors were screened for pathogens and other viral infections as previously described (Landy, Al-Hassi et al. 2011). The patients discontinued oral vancomycin 1-2 days before FMT. FMT was administered to recipients by enema (n=3), pills (n=6), a combination of both (n=2, R8 and R10), or by nasogastric infusion (n=1, R7). Faecal samples were collected from the patients 1-2 days after stopping vancomycin treatment (pre-FMT) and at different times post-FMT. Stool samples used for FMT were also collected from the donors. Samples from healthy individuals and individuals infected with *C. difficile* treated with antibiotics were also included as controls. Faecal samples were collected in sterile containers and were frozen at −80° C. DNA was extracted from all samples for 454 sequencing and subsequent analysis as described below.

For the culturing of samples from the faecal microbiota transplant (FMT) recipients (CIP2), 50 mg of each faecal sample was mixed thoroughly in 0.5 ml sterile, reduced phosphate buffered saline (PBS). The homogenate was serially diluted to $10^{-6}$ and aliquots of this dilution were plated on a panel of media under anaerobic conditions. The following media were used: fastidious anaerobic agar (FAA, Lab M Ltd, Lancashire, UK) containing 2% defibrinated horse blood, Brain Heart Infusion (BHI, Oxoid UK), de Man Rogosa Sharpe and CCEY (Bioconnections, UK) agars with and without the addition of 10 µg/ml vancomycin (Appli-Chem, Germany). All plated media were incubated anaerobically at 37° C. for 48-72 hours except for the BHI agar, which was incubated aerobically at 37° C. for 24-48 hours.

Microbiota Profiling and Sequencing

Identification of each cultured isolate was performed by PCR amplification of the full length 16S rRNA gene (using 7F (5-AGAGTTTGATYMTGGCTCAG-3) (SEQ ID NO: 52) forward primer and 1510R (5-ACGGYTACCTTGT-TACGACTT-3) (SEQ ID NO: 53) reverse primer followed by capillary sequencing. For both CIP1 and CIP2, 16S rRNA gene sequence reads were aligned in the Ribosomal Database Project (RDP) and manually curated in ARB (Ludwig, Strunk et al. 2004). For CIP1, the R package seqinr version 3.1 was used to determine sequence similarity between 16S rRNA gene sequences and, as full-length 16S rRNA gene sequence reads were generated, 98.7% was used as the species-level cut-off to classify reads to Operational Taxonomic Units (OTUs) (Bosshard, Abels et al. 2003, Clarridge 2004). As only partial length 16S rRNA gene sequence reads were generated for candidate bacteria from CIP2, 97% was used as the species-level cut-off (Bosshard, Abels et al. 2003, Clarridge 2004) and the OTUs at this cut-off were determined using mothur (Schloss, Westcott et al. 2009). For both CIP1 and CIP2, the 16S rRNA gene sequence of each species-level OTU was then compared to the Ribosomal Database Project (RDP) reference database to assign taxonomic designations down to the genus level (Wang, Garrity et al. 2007). A BLASTn search was then performed with the 16S rRNA gene sequences to determine whether the OTU represented either a previously character- ised or a novel species (Altschul, Gish et al. 1990).

Comparisons of the OTUs with the Human Microbiome Project (HMP) "Most Wanted" list and reference genomes database were carried out using 97% sequence identity of the 16S rRNA gene sequences to define a bacterial species because only partial 16S rRNA gene sequences were available for the bacteria on the HMP "Most Wanted" list and reference genomes database. HMP data regarding the most wanted taxa and the completed sequencing projects were downloaded from the NIH Human Microbiome Project's "Most Wanted" Taxa from the Human Microbiome for Whole Genome Sequencing (Web 8 Mar. 2016 hmpdacc.org/most_wanted/#data) and the NIH Human Microbiome Project's Reference Genomes Data (Web 8 Mar. 2016 hmp-dacc.org/HMRGD/), respectively. Genomic DNA was extracted from at least one representative of each unique OTU using a phenol-chloroform based DNA isolation procedure. DNA was sequenced on the Illumina HiSeq platform generating read lengths of 100 bp and these were assembled and annotated for further analysis.

DNA was also extracted directly from each faecal sample for whole community metagenomic and 16S rRNA gene amplicon sequencing using the MP Biomedical FastDNA SPIN Kit for soil. To enable comparisons with the complete community samples, non-confluent cultures were scraped from agar plates 72 hours after inoculation with the initial faecal sample and DNA was extracted from this community using the same DNA isolation process. 16S rRNA gene amplicon libraries were made by PCR amplification of variable regions 1 and 2 of the 16S rRNA gene using the Q5 High-Fidelity Polymerase Kit supplied by New England Biolabs. Primers 27F AATGATACGGCGAC-CACCGAGATCTACAC TATGGTAATT CC AGMGTTY-GATYMTGGCTCAG (SEQ ID NO: 54) ($1^{st}$ part=Illumina adapter, $2^{nd}$=forward primer pad, $3^{rd}$=Forward primer linker and $4^{th}$=Forward primer) and 338R CAAGCAGAA-GACGGCATACGAGAT ACGAGACTGATT AGTCAGTCAG AA GCTGCCTCCCGTAGGAGT (SEQ ID NO: 55) (1st part=reverse complement of 3' Illumina adapter, $2^{nd}$=golay barcode, $3^{rd}$=reverse primer pad, $4^{th}$=reverse primer linker and $5^{th}$=reverse primer) were used. Four PCR amplification reactions per sample were carried out; products were pooled and combined in equimolar amounts for sequencing using the Illumina MiSeq platform, generating 150 bp reads.

For 454 amplicon sequencing of the CIP2 derived faecal samples, DNA was extracted directly from the faecal samples (70 mg) using the FastDNA Spin Kit for Soil on a Fastprep instrument (MP Biomedicals, USA) following the manufacturer's instructions. The V3-V5 regions of the 16S rRNA gene were amplified using barcoded primers 338F (5'-ACTCCTACGGGAGGCAGCAG-3') (SEQ ID NO: 56) and 926R (5'-CCG TCA ATT CMT TTR AGT-3') (SEQ ID NO: 57) adapted with linkers. Thermocycling involved an initial 2-min denaturation step at 94° C. followed by 20 cycles of denaturation (94° C. for 30 s), annealing (53° C. for 30 s) and elongation (68° C. for 2 min). The PCR products were purified using the Wizard SV Gel and PCR Clean-Up System (Promega, UK) following the manufacturer's protocol and quantified using the Qubit® dsDNA HS Assay Kit (Life Technologies, UK). Equimolar volumes of each cleaned-up products of each PCR reaction were sequenced on the Roche 454 FLX-Titanium platform.

Microbiota Analysis

A maximum likelihood phylogeny of the culture derived bacteria from CIP1 was generated from the aligned RDP sequence using FastTree version 2.1.3 (Price, Dehal et al. 2010) with the following settings: a Generalised Time-Reversible (GTR) model of nucleotide substitution and CAT approximation of the variation in rates across sites with 20 rate categories. The ethanol resistant phylogeny was derived directly from the entire culture phylogeny. All phylogenetic trees were edited in ITOL (Letunic and Bork 2011).

Analysis of the partial 16S rRNA gene sequence generated from the 16S rRNA gene amplicon libraries from the CIP1 derived faecal samples was carried out using the mothur MiSeq SOP (Kozich, Westcott et al. 2013) on Aug. 29 2014, identifying 7549 OTUs across all samples. A sequence identity threshold of 97% was again used to define an OTU.

For the 454 sequence analysis from CIP2 derived faecal samples the sequence reads were trimmed, filtered and pre-processed using the mothur software 454 SOP accessed in November 2012 (Schloss, Westcott et al. 2009, Schloss, Gevers et al. 2011). To ensure high quality sequence data for analysis, the sequences were trimmed using a window size of 50 bp (average quality score of 35 bp), homopolymers >8 bp were removed and no ambiguous bases or mismatches in the primer sequence were allowed. Redundant sequence reads were removed to generate unique sequences, which were aligned to the SILVA alignment database (Pruesse, Quast et al. 2007). These aligned sequences were screened to ensure that sequences overlapped in the same alignment space using the screen.seqs command in mothur. Unique sequences were again generated and the sequences were preclustered to remove sequences that were likely due to pyrosequencing errors (Huse, Dethlefsen et al. 2008). Chimeric sequences were removed using Perseus (Quince, Lanzen et al. 2011) and other contaminants such as chloroplast and mitochrondria were also removed. Sequences with 97% sequence identity and their assigned taxonomy from phylum to genus level according to the Ribosomal Database Project (RDP) (Cole, Wang et al. 2014) and SILVA (Pruesse, Quast et al. 2007) databases were regarded as belonging to the same operational taxonomic units (OTUs). The species diversity in each sample was measured by calculating the Shannon diversity Index (SDI), which takes into account both species richness and relative proportional abundance (Schloss, Westcott et al. 2009). The OTUs were then used to cluster dendrograms, using the Bray Curtis calculator in the mothur package. Other analyses, such as Invsimpson index, principal component analysis (PCA) and the UniFrac method of comparing microbial communities were performed as described previously using the mothur software (Lozupone and Knight 2005, Lawley, Clare et al. 2012).

Metagenomic Analysis

Microbial abundance was calculated using the Human Pan-Microbe Community Database (Forster, Browne et al. 2015) against 1883 healthy individuals (3218 samples) and 458 diseased individuals (628 samples). Occurrence was calculated as greater than 1000, independent, normalised reads with abundance calculated relative to total high quality reads within the sample. Antimicrobial resistance and virulence factor identification were performed using automated sequence homology search against protein sequences annotated in the complete genome sequence. The antimicrobial resistance reference list was defined based on the comprehensive antimicrobial CARD database (McArthur, Waglechner et al. 2013) while toxins were identified by occurrence in the Database of Bacterial Exotoxins for Humans (DBETH) (Chakraborty, Ghosh et al. 2012).

Experimental Set-Up and Results

The inventors established methods to isolate and identify bacteria for incorporation into a therapeutic composition tailored to the treatment of dysbiosis of the gastrointestinal tract, as well as e.g. enteric infections, such as, but not limited to, those caused by *Clostridium difficile*. As mentioned above, two different approaches for acquiring bacterial candidates for inclusion in a therapeutic were employed. The first (CIP1) relied on a broad culturing approach from healthy adult donors to establish a culture collection which is as representative as possible of the bacterial component of the healthy human intestinal microbiota. This process also incorporated a targeted culturing approach to preferentially select bacteria displaying a particular phenotype or function e.g. spore formation. The second process (CIP2) was more targeted in nature and aimed to acquire bacterial species specifically associated with resolving gastrointestinal dysbiosis by comparing individuals before and FMT to resolve *C. difficile* associated dysbiosis. These two approaches are described in more detail below.

Figure 2:
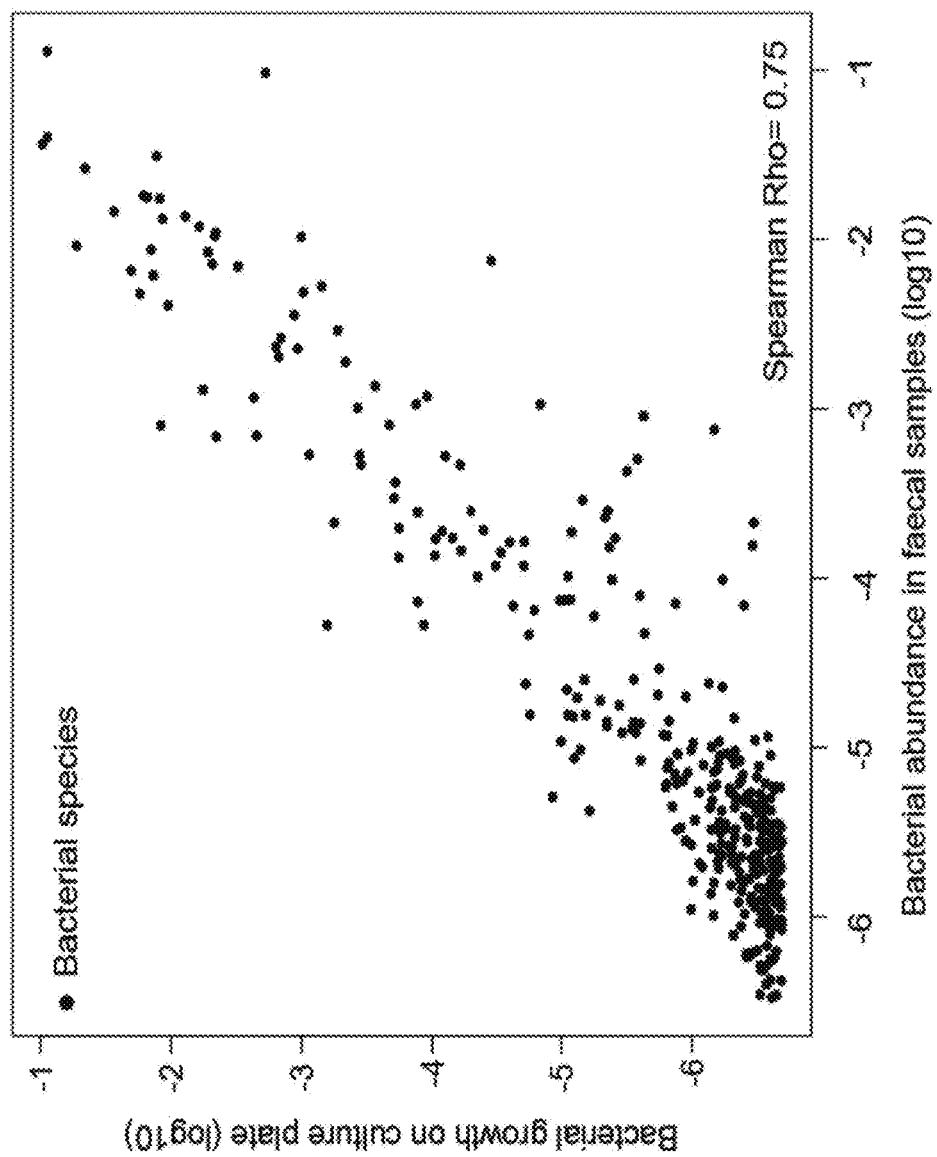
FIG. 2: Targeted phenotypic culturing facilitates bacterial discovery from healthy human faecal microbiota.

CIP1—Broad Culturing Approach to Identify Therapeutic Candidates:

The inventors first sought to establish a genomic-based workflow that could be used as a platform for targeted culturing of specific bacterial phenotypes (FIG. 1). Fresh faecal samples were collected from 6 healthy humans and defined the resident bacterial communities with a combined metagenomic sequencing and bacterial culturing approach. Applying shotgun metagenomic sequencing, the inventors profiled and compared the bacterial species present in the original faecal samples to those that grew as distinct colonies on agar plates containing the complex, broad range bacteriological medium, YCFA (Duncan, Hold et al. 2002) supplemented with glucose, maltose and cellobiose. Importantly, a strong correlation was observed between the two samples at the species level (Spearman Rho=0.75, p<0.01) (FIG. 2). When sequenced, the original faecal sample and the cultured bacterial community shared an average of 93% of raw reads across the 6 donors.

These results demonstrate that surprisingly, and contrary to the established view in the art, a significant proportion of the bacteria within the faecal microbiota can be cultured with a single growth medium. Thus, a broad range culturing method was established that, when combined with high throughput archiving or specific phenotypic selection, can be utilised to isolate and identify novel bacteria from the human gastrointestinal tract.

The human intestinal microbiota is dominated by strict anaerobic bacteria that are extremely sensitive to ambient oxygen. Certain members of the Firmicutes, including *Clostridium difficile*, produce metabolically dormant and highly resistant spores during colonisation that facilitate both persistence within the host and environmental transmission (Lawley, Clare et al. 2009, Francis, Allen et al. 2013, Janoir, Deneve et al. 2013). Relatively few intestinal spore-forming bacteria have been cultured to date and while metagenomic studies suggest that other unexpected members of the intestinal microbiota possess potential sporulation genes, they remain poorly characterised (Galperin, Mekhedov et al. 2012, Abecasis, Serrano et al. 2013, Meehan and Beiko 2014, Rajilic-Stojanovic and de Vos 2014).

Figure 3:
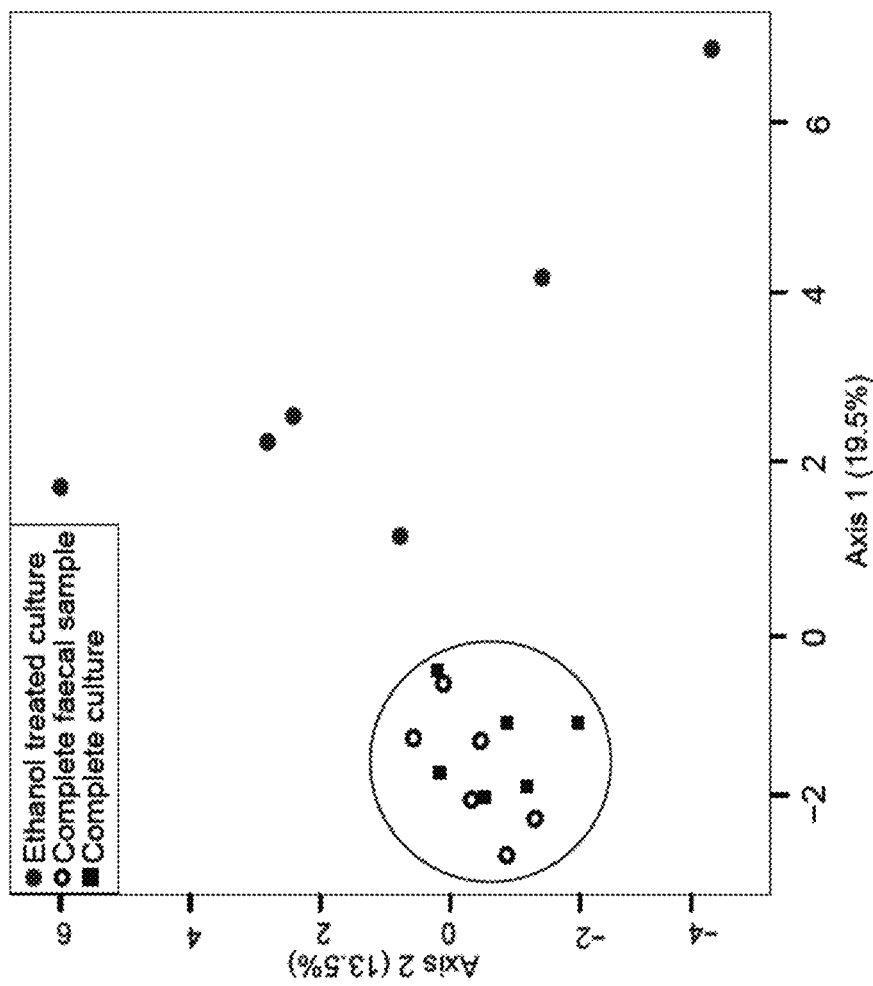
FIG. 3 shows a principal component analysis (PCoA) plot of 16S rRNA gene sequences detected from 6 donor faecal samples representing bacteria in the complete faecal samples (unfilled circles), faecal bacterial colonies recovered from YCFA agar plates without ethanol pre-treatment (filled black squares) or with ethanol pre-treatment to select for ethanol-resistant spore-forming bacteria (filled black circles). These results demonstrate that culturing without ethanol selection is representative of the complete faecal sample, while ethanol treatment shifts the profile, enriching for ethanol-resistant spore-forming bacteria and allowing their subsequent isolation.

The inventors hypothesized that sporulation might be an unappreciated basic phenotype of the human intestinal microbiota that may have a profound impact on microbiota persistence and spread between humans. Spore-formation is also viewed as desirable for bacteriotherapy formulations since the resistant nature of the spore structure would promote survival of the medicine during production and subsequent storage. Spores from *C. difficile* are resistant to ethanol and this phenotype can be used to select for spores from a mixed population of spores and ethanol-sensitive vegetative cells (Riley, Brazier et al. 1987). Faecal samples with or without ethanol treatment were processed using our combined culture and metagenomics workflow (FIG. 1). Principle component analysis demonstrated that ethanol treatment profoundly altered the culturable bacterial composition and when compared to the original profile, efficiently enriched for ethanol-resistant bacteria, facilitating their isolation (FIG. 3). ~2,000 individual bacterial colonies were picked from both ethanol-treated and non-ethanol-treated conditions, re-streaked them to purity and performed full-length 16S rRNA gene sequencing to enable taxonomic characterisation. Unique taxa were then archived as frozen stocks for future phenotypic analysis.

Figure 4:
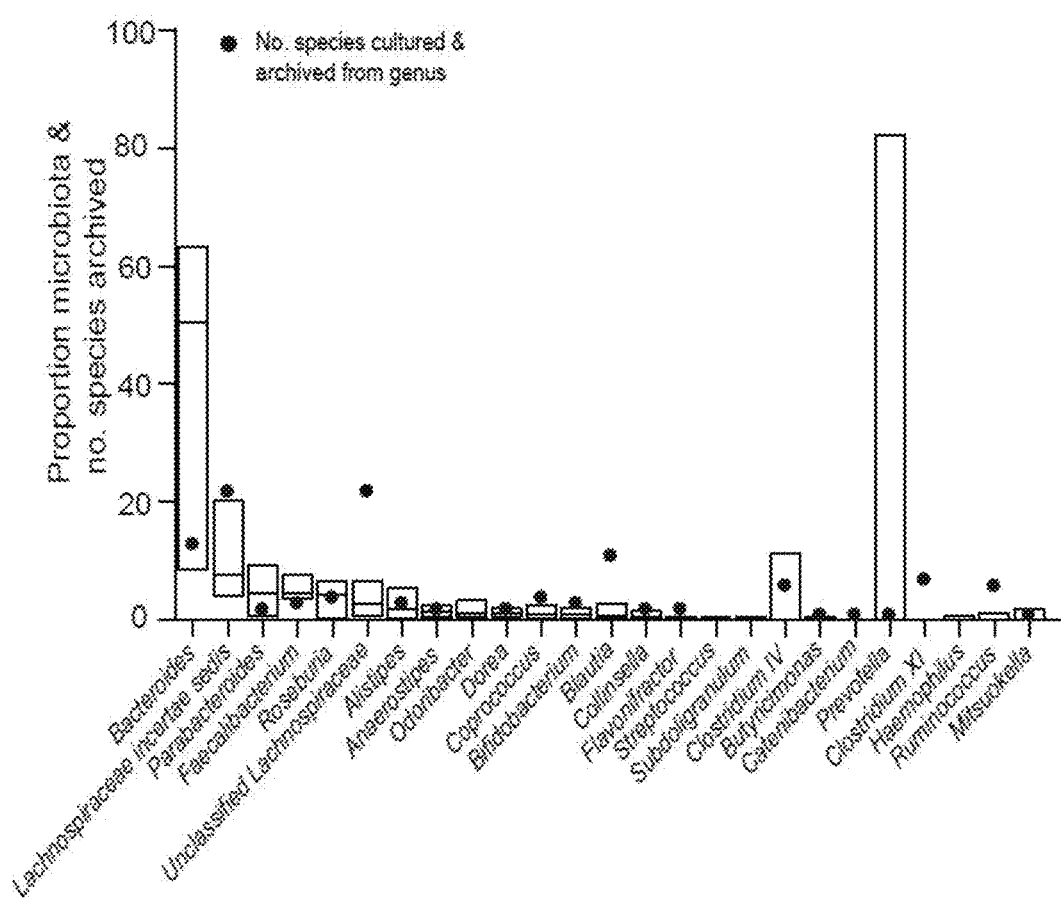
FIG. 4: Archiving of bacterial diversity and novelty through anaerobic culturing.
Figure 4:
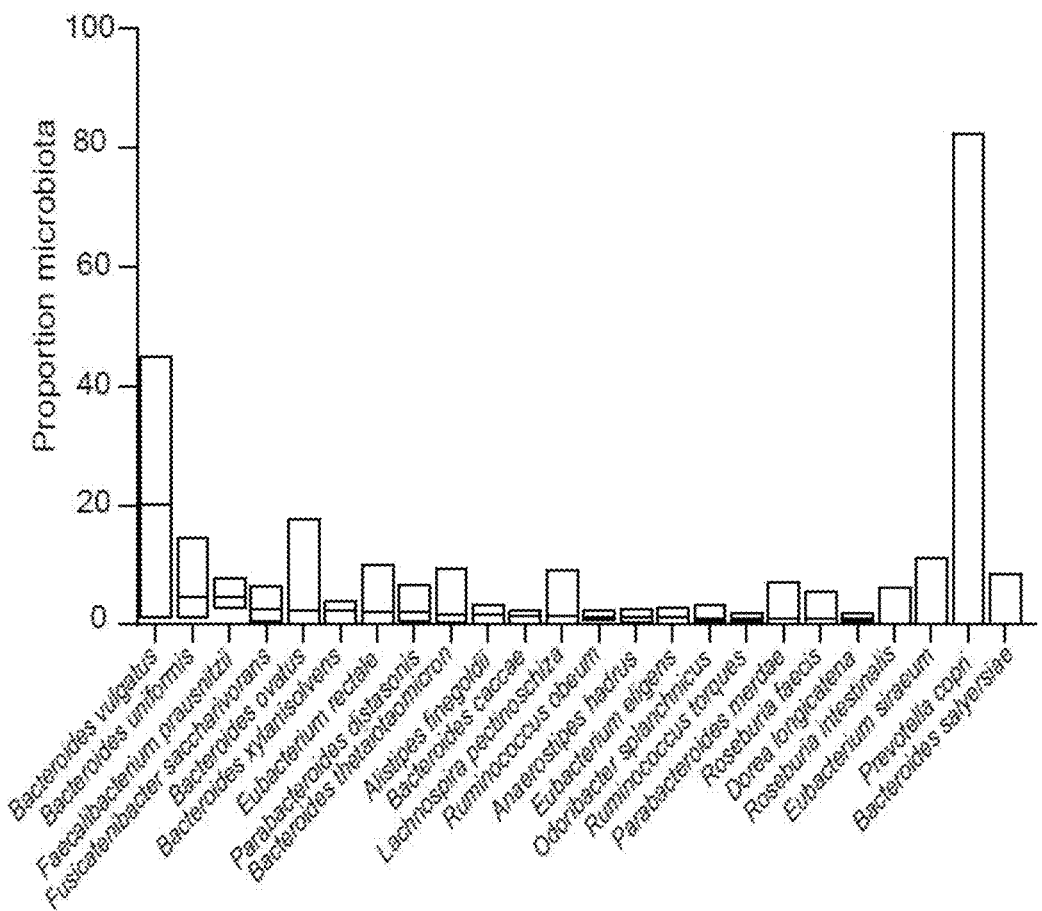
Figure 4:
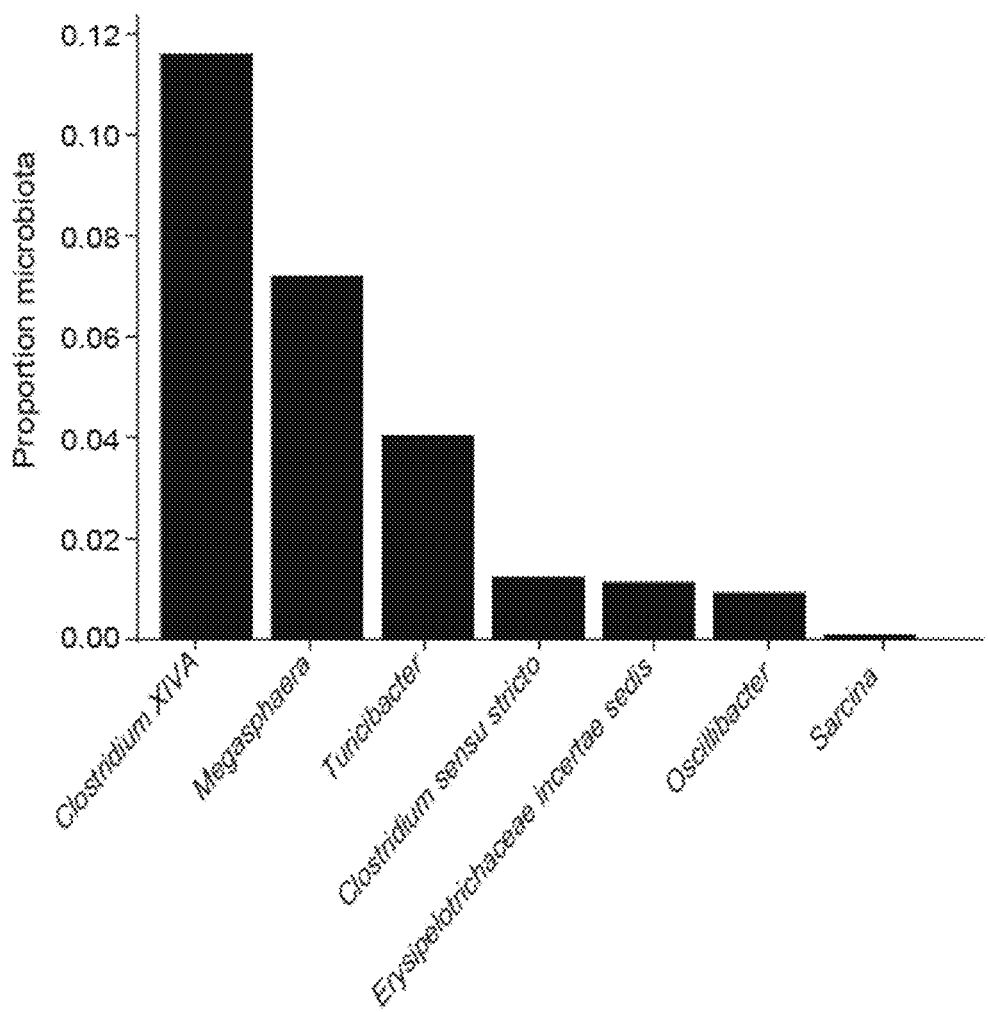
Figure 5:
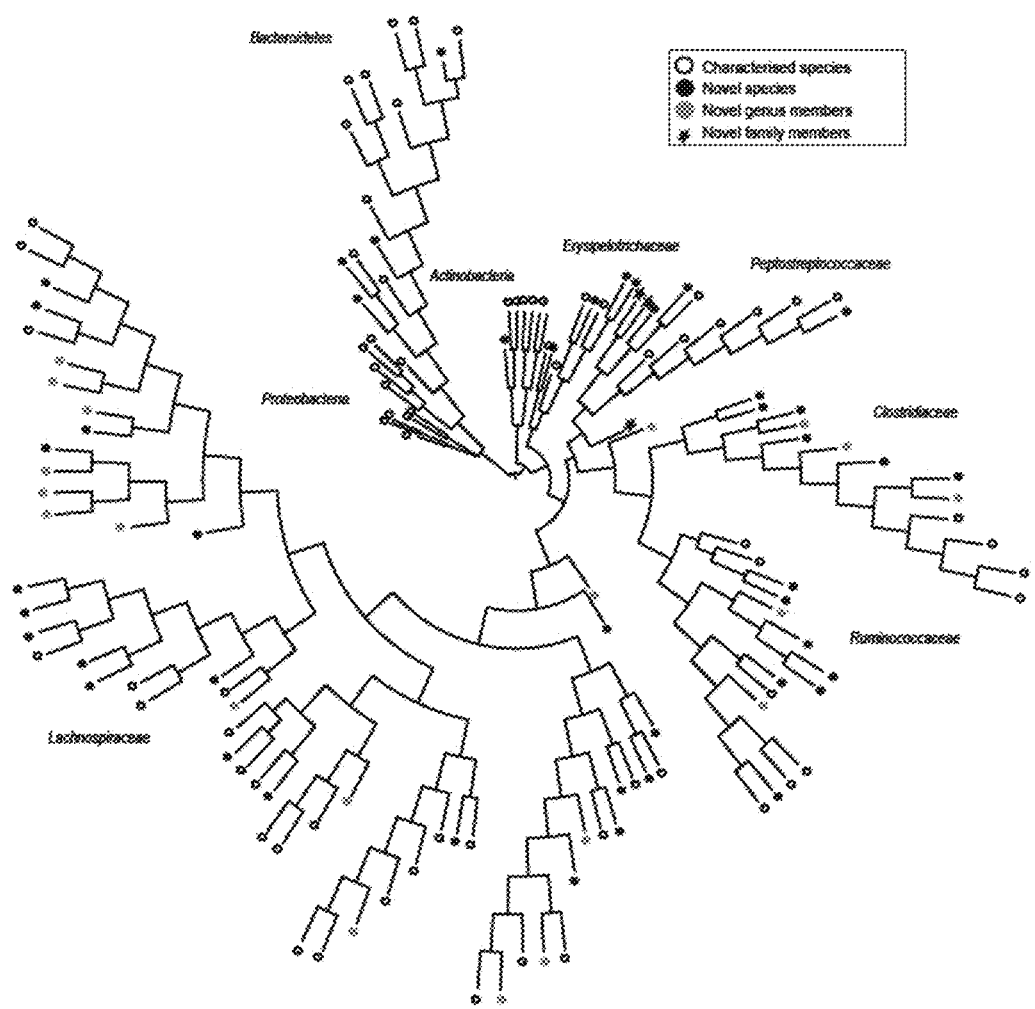
FIG. 5: Phylogeny of cultured and archived bacteria from healthy human faecal microbiota.

In total, bacteria representing 96% of the bacterial abundance at the genus level and 90% of the bacterial abundance at the species level based on average relative abundance across the 6 donors (FIGS. 4A and 4B) were archived. Even genera that were present at low average relative abundance (<0.2%) were isolated and purified (FIG. 4C). Ethanol-resistant species were isolated from 5 known families (Clostridiaceae, Peptostreptococcaceae, Lachnospiraceae, Ruminococcaceae and Erysipelotrichaceae) and 2 newly identified candidate families (bacterial isolates HMI_1 and HMI_22) (see FIG. 15 for details). The identification of these new and unexpected spore-formers highlights the broad taxonomic distribution of this phenotype among the enteric species of the Firmicutes. Overall, 137 distinct bacterial species including 45 candidate novel species and isolates representing 20 candidate novel genera and 2 candidate novel families were archived (FIG. 5). Our collection contains 90 species from the Human Microbiome Project's (HMP) 'most wanted' list of previously uncultured and unsequenced microbes (Fodor, Desantis et al. 2012). 19 of the deposited bacterial isolates listed in FIG. 15 are included in the HMP's "Most Wanted" list, namely: HMI 1, HMI 2, HMI 4, HMI 5, HMI 7, HMI 11, HMI 12, HMI_15, HMI_16, HMI_17, HMI_18, HMI_19, HMI_35, HMI_37, HMI_38, HMI_39, HMI_45, HMI_50 and HMI_51 (see FIG. 15 for details). Thus, our broad-range YCFA based culturing approach led to the discovery of large numbers of novel bacteria (including novel families, genera, species, and isolates) and challenges the prevailing perception in the art that the majority of the intestinal microbiota is "unculturable".

Figure 7:
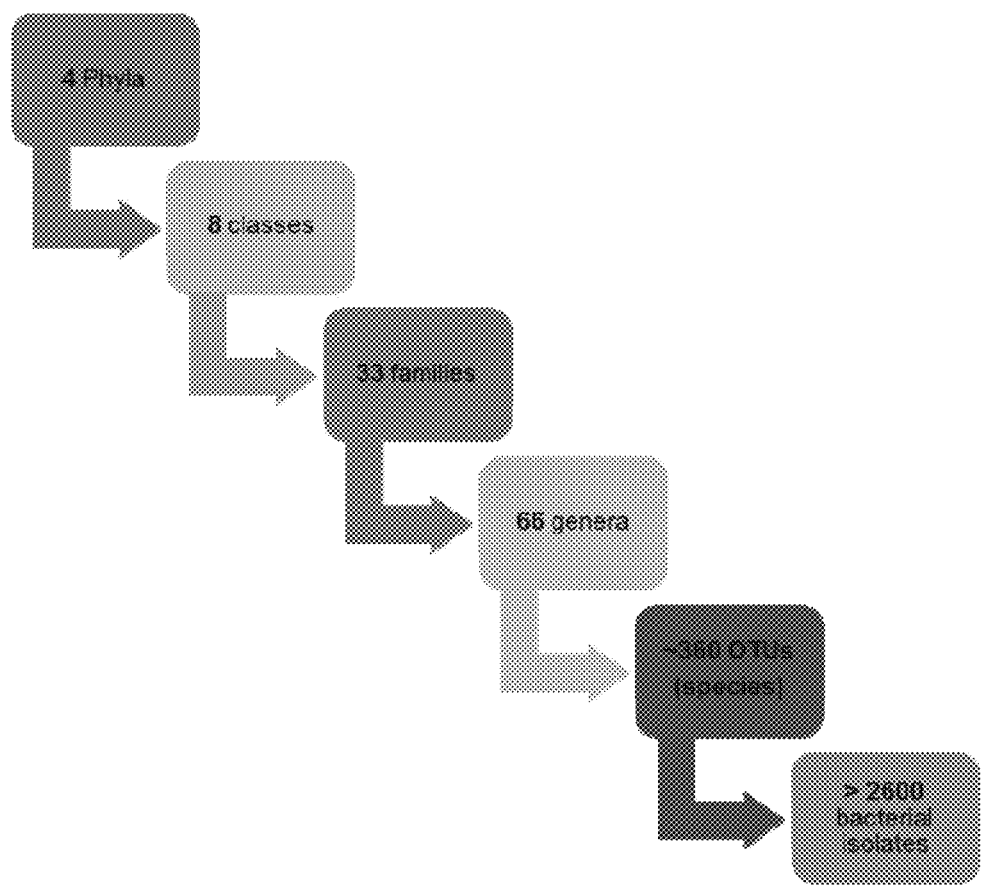
FIG. 7: Taxonomic summary of the bacteria isolated from faecal samples of the donors, recipients and controls from a study to treat *C. difficile* using FMT. These bacterial isolates represent a large cross-section of intestinal microbiota diversity.

CIP2: Targeted Identification of Candidates to Resolve Gastrointestinal Dysbiosis As described above, FMT has proven effective in resolving CDI. The inventors therefore sought to culture from faecal samples from FMT donors and recipients to isolate candidate bacteria that could be used in therapy. A panel of different microbiological media were tested to recover the broadest range of bacterial species from the faecal samples (see Methods). This approach allowed culturing and archival of bacterial candidates. Over 2600 bacterial isolates were cultured and using 16S rRNA gene sequencing these were taxonomically classified (FIG. 7). These bacterial isolates were members of the 4 major phyla (Actinobacteria, Bacteroidetes, Proteobacteria and Firmicutes) in the intestinal microbiota. These bacterial isolates represented more than 350 different OTUs based on alignments of the partial length 16S rRNA gene.

In Silico Analysis of Candidate Bacteria:

Having established a culture collection through the two approaches described above (CIP1 and CIP2), the inventors next sought to screen these bacteria to identify bacterial candidates for bacteriotherapy.

Figure 6:
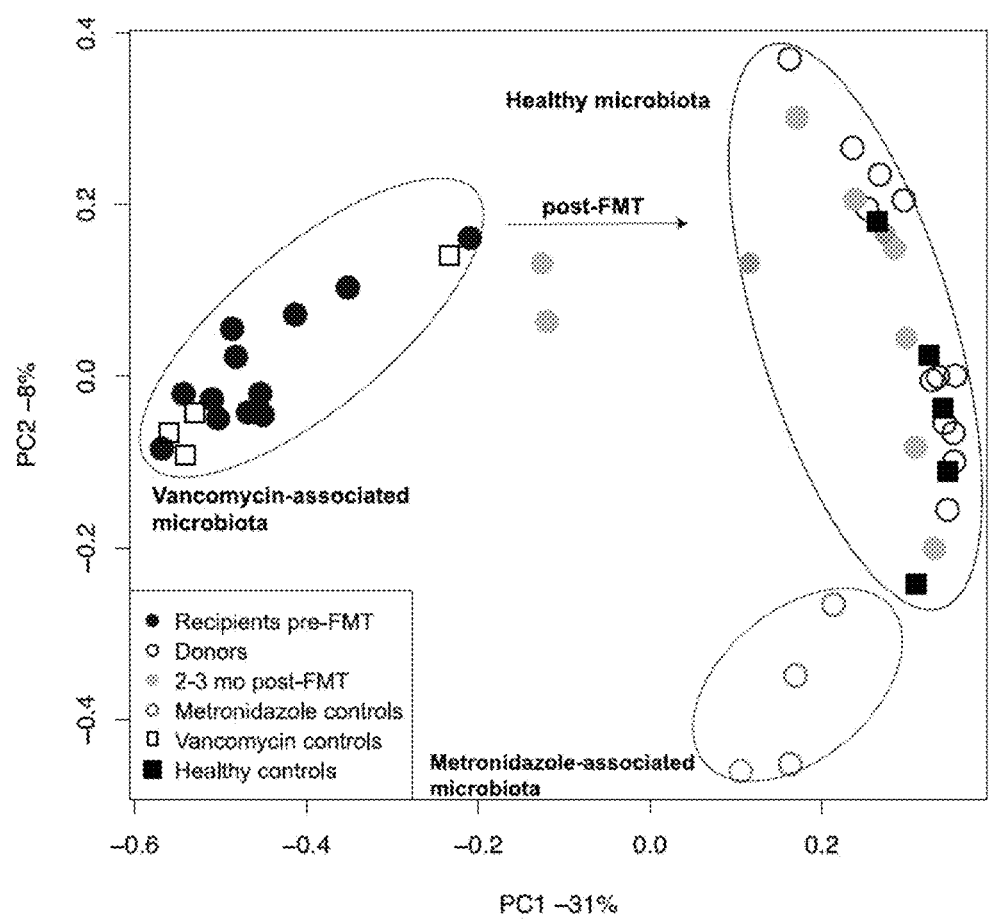
FIG. 6: Faecal Microbiota Transplant (FMT) restores the intestinal microbiota of patients with recurrent *C. difficile* infection to a healthy state.

The inventors first sought to analyse the isolates cultured from FMT donors and recipients. At one to three months post-FMT, the faecal microbiota profiles of the recipients were similar to those of the donors and the healthy controls. In particular, the relative abundances of the four major bacterial phyla present in the gut microbiota were also similar across these groups. The microbiota community structure in the donors and recipients (before and after FMT) was visualised for evaluation using principal component analysis (PCA) (FIG. 6).

The PCA plot demonstrates the presence of two distinct compositional profiles representing a "health-associated" microbiota, and a "vancomycin" microbiota. The health-associated profile contained samples from FMT donors, healthy controls and FMT recipients at 2-3 months post treatment. The "vancomycin" microbiota profile was separated from the health-associated microbiota along Principal Component 1 and only contained individuals treated with vancomycin. These vancomycin control individuals became infected with C. difficile while taking antibiotics to treat other disease conditions. Additionally, the "metronidazole-associated" profile was separated from the "health-associated" profile along Principal Component 2 and contained samples from C. difficile infected patients treated with metronidazole.

The donor-recipient profiles of each pair were compared before and after FMT to identify taxa that were present in the donor sample, and which increased in relative abundance in the recipient's profile after FMT. A total of 786 OTUs from all recipient samples were detected after FMT but singleton OTUs present at the different time points were removed. This resulted in 375 OTUs for further analysis. Given that recurrence of CDI typically occurs 3-4 weeks after the withdrawal of antibiotic treatment, (Comely, Miller et al. 2012, Abujamel, Cadnum et al. 2013) OTUs that were increased in relative proportional abundances at 2-3 months post-FMT were analysed further.

Figure 8:
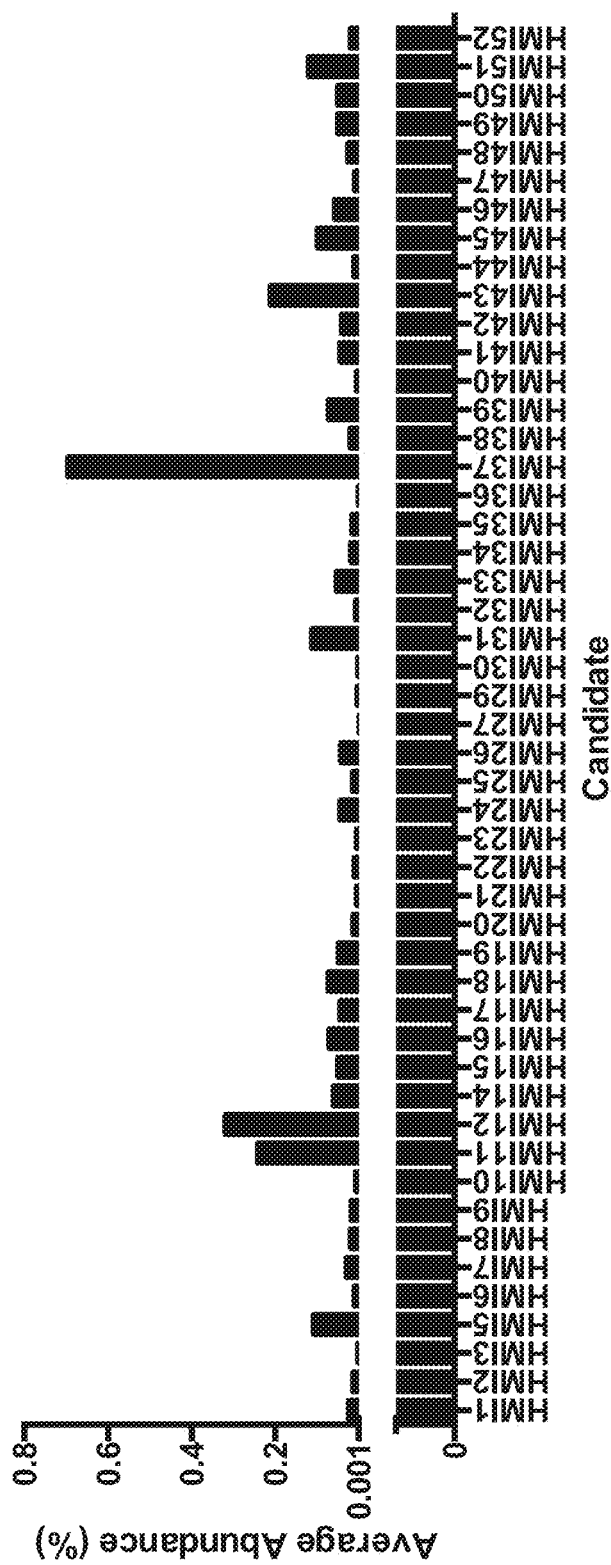
FIG. 8: Average relative abundance of bacteriotherapy candidates in healthy individuals. The bacteriotherapy candidates occur at an average abundance of greater than 0.001% within the gastrointestinal microbiota of 1883 healthy individuals (3218 samples).
Figure 9:
FIG. 9: The bacteriotherapy candidates are depleted in dysbiotic and disease states. The average fold change in the relative abundance of each bacteriotherapy candidate in diseased and dysbiotic states in comparison to its relative abundance in a healthy microbiota is plotted. *Escherichia coli*, a marker of dysbiosis is also included for comparison. The relative abundance of a bacterium refers to the proportion of the total microbiota represented by the bacterium in question.

Next, the inventors undertook in silico analysis to further screen the bacteriotherapy candidates from both of our culturing approaches (CIP1 and CIP2). As described above a healthy intestinal microbiota is based on a diverse and abundant microbial community. Using the whole genome sequences that the inventors generated from bacterial isolates from CIP1 and CIP2, the inventors computationally assessed their prevalence in healthy and diseased individuals in public metagenomic data-sets using the HPMC database tool (Forster, Browne et al. 2015). Candidate bacteria were first filtered to include only those isolates with greater than 0.001% average abundance within the bacterial community across all healthy individuals in which they were detected (FIG. 8). All of the bacteria deposited with DSMZ thus had greater than 0.001% average abundance within the bacterial community across all healthy individuals in which they were detected (see FIG. 15). In addition to being health-associated, preferred candidates for bacteriotherapy applications are expected to ameliorate gastrointestinal dysbiosis. To identify such candidates, the distribution of each of our isolates in publicly available metagenomics datasets was examined. Bacterial species whose total average abundance was substantially decreased (greater than four-fold decrease) in individuals with gastrointestinal dysbiosis relative to healthy individuals were selected and subjected to further analysis as described below (FIG. 9). All of the bacteria deposited with DSMZ thus showed a decreased total average abundance (greater than four-fold decrease) in individuals with gastrointestinal dysbiosis relative to healthy individuals (see FIG. 15).

The list of bacteriotherapy candidates was further analysed on the basis of computationally predicted antimicrobial resistance (AMR) and virulence factors. Bacteriotherapy candidates with overall predicted resistance scores below 20% of the overall predicted resistance scores of the known pathogens C. difficile, Enterococcus faecalis and Escherichia coli were included. Candidates were also selected for the absence of in-silico predicted resistance to beta-lactams, fusidic acid, elfamycin, aminoglycoside, fosfomycin and tunicamycin and by the absence of known toxins as listed in Chakrabory A. et al, 2012, A Database of Bacterial Exotoxins for Humans (DBETH). Based on this analysis the inventors identified 51 candidates for use in bacteriotherapy from CIP1 and CIP2 (see FIG. 15). 10 of these bacteriotherapy candidates were identified using CIP2, namely: HMI_23, HMI_24, HMI_25, HMI_26, HMI_27, HMI_28, HMI_29, HMI_30, HMI_31 and HMI_32 (see FIG. 15 for details). All of these 10 isolates were cultured from healthy donors. The remaining bacteriotherapy candidates were identified using CIP1.

The bacteriotherapy candidates identified using CIP1 and CIP2, with the exception of HMI_17, were then subjected to in vitro analysis to establish their therapeutic efficacy in treating C. difficile and E. coli infection as described in Example 2 below.

Example 2—In Vitro Analysis of Bacteriotherapy Candidates

Figure 10:
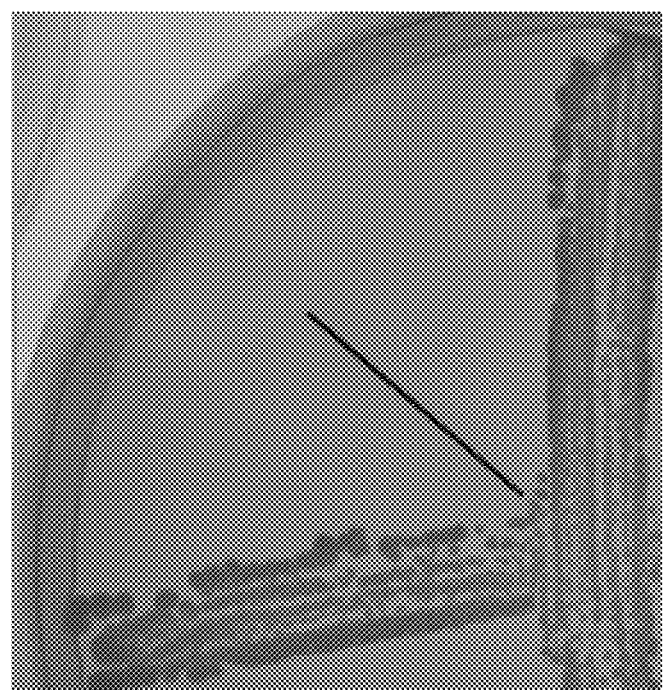
FIG. 10 demonstrates how the zone of clearing around bacteriotherapy candidates was measured in the overlay assays.
Figure 11:
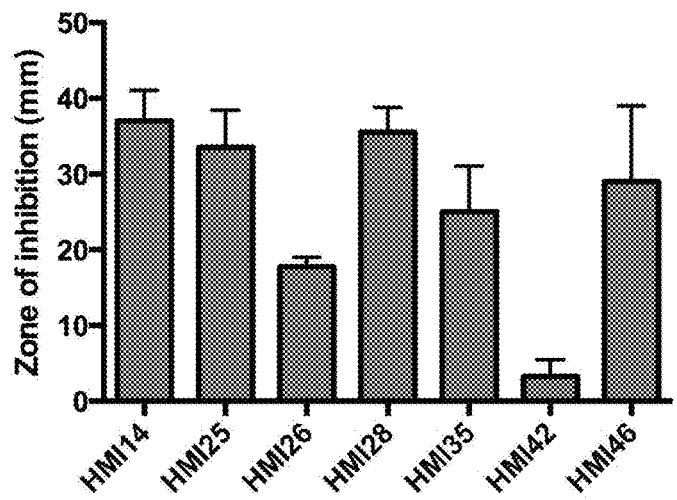
FIG. 11 shows the results of *C. difficile* and *E. coli* growth overlay assays to determine the anti-pathogen activity of bacteriotherapy candidates. The zones of clearing were measured with a ruler as described in FIG. 10. Millimetre (mm) measurements were taken.
Figure 11:
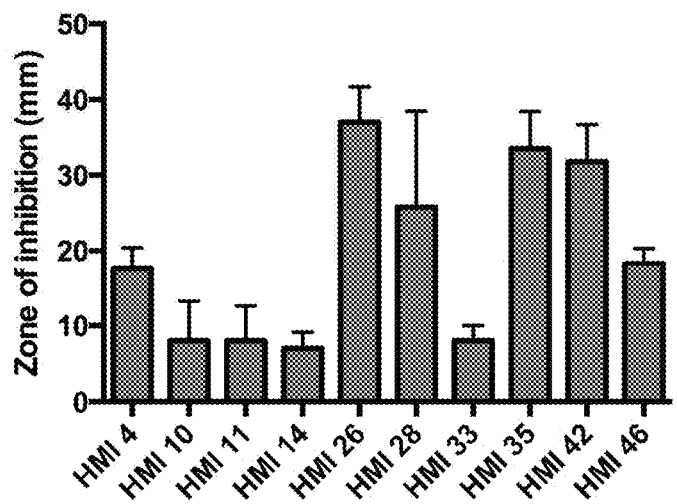

Detection of Anti-Pathogen Activities of the Bacteriotherapy Candidates by an Overlay Assay The bacterial isolates of interest identified in Example 1 were streaked in an "X" shape over the surface of a standard Petri dish containing warmed and reduced YCFA agar. These inoculated plates were then incubated anaerobically at 37° C. for 3 to 6 days, until bacterial growth was clearly visible. Overlay agar was prepared by adding 0.8% agar to an appropriate broth. For C. difficile, BHI broth+0.8% agar was used. For E. coli, LB+0.8% agar was prepared. The overlay agar was held molten at 50° C. before use. The overlay agar was inoculated (1% inoculum) with an aliquot of a turbid culture of the pathogen of interest, in this case either C. difficile M7404 or E. coli (AIEC). A 10 ml aliquot of the inoculated overlay agar was added to the surface of the agar plates bearing each commensal strain of interest. The overlay agar was allowed to set and the plates were incubated anaerobically at 37° C. for one to two days. Following incubation, zones of clearing could be observed if the commensal strain of interest was capable of inhibiting the growth of the pathogen in the overlay layer. The width of each zone of clearing was measured with a ruler as shown in FIG. 10. The results are shown in FIG. 11.

Detection of Anti-Pathogen Activity by CFS-Relative Growth Inhibition Assay.

Bacteriotherapy candidates were grown in 1 ml aliquots of reduced YCFA broth at 37° C. under anaerobic conditions for two days. Cell free supernatant (CFS) was prepared by centrifuging each culture to remove the bacteria and by passing the resulting supernatant through a 0.22 μm filter to sterilise it. Uninoculated YCFA broth was also filter sterilised. The CFSs and filtered YCFA broth aliquots were frozen at −20° C. until they were required. These filtrates were thawed under anaerobic conditions at 37° C. and a 100 μl aliquot of each CFS was added to one well of a flat-bottomed 96-well plate. Several wells were filled with filter-sterilised YCFA broth to serve as positive controls for pathogen growth. Each well was inoculated (2-5% inoculum) with a turbid, early-mid exponential phase C. difficile M7404 culture. Alternatively, a 5% inoculum of a stationary phase E. coli culture adjusted to $OD_{600}$ was used. The 96-well plate was sealed with an optically clear film and it was transferred to a FLUOstar Omega microplate-reader (BMG Labtech). The plate was incubated static at 37° C. in the plate-reader and $OD_{600}$ readings were taken every 10 min for 18.17 hours. The plate was shaken for 10 seconds before each OD reading was taken. All isolates, except HMI17 were tested.

Figure 12:
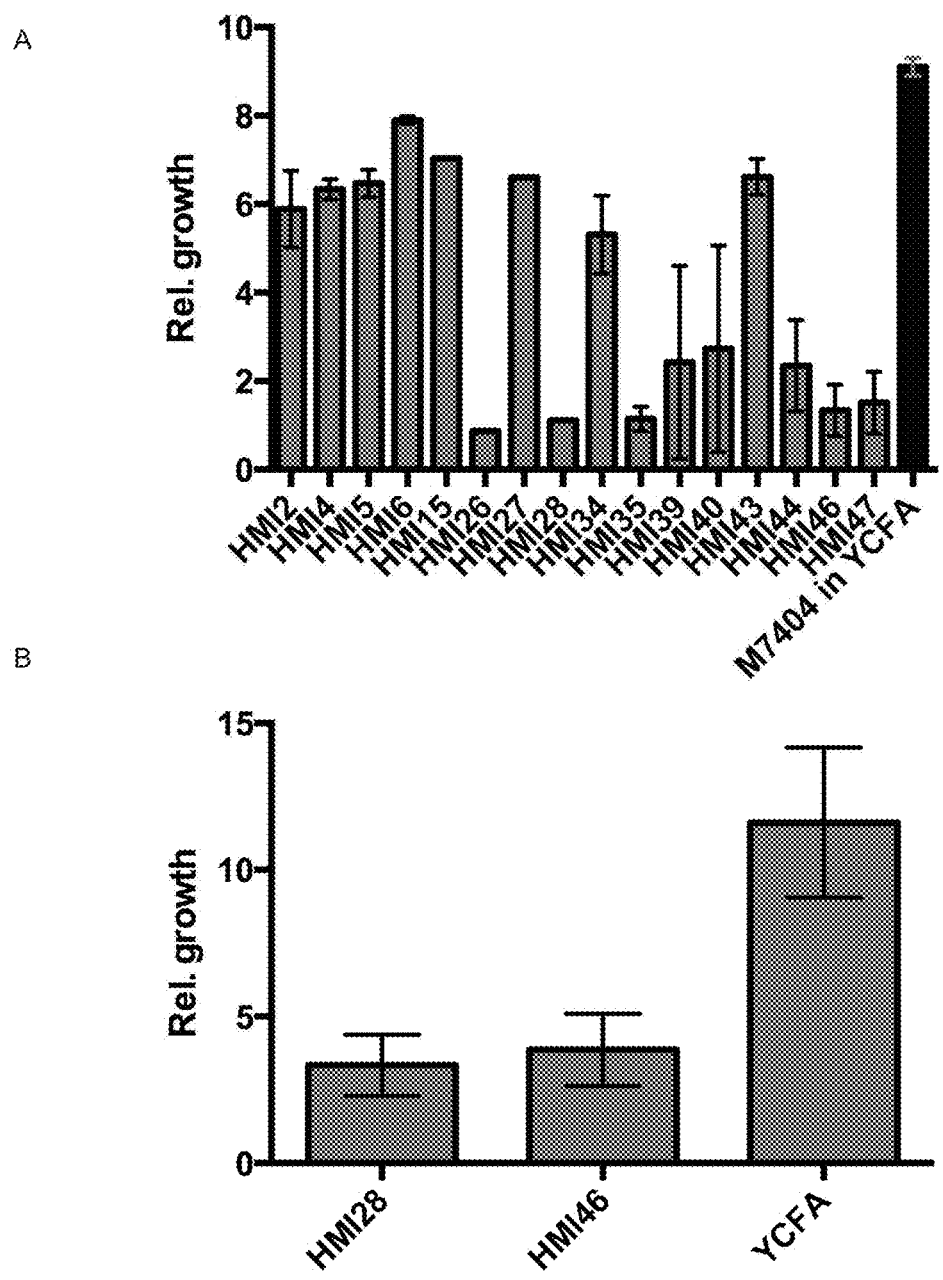
FIG. 12 shows the results of *C. difficile* and *E. coli* growth inhibition assays to determine the anti-pathogen activity of bacteriotherapy candidates.

The relative growth of the pathogen of interest in each of the CFSs tested was then calculated as follows: For each CFS tested, every raw-data value was expressed relative to its $OD_{600}$ reading that was taken at the ten minute time-point. Such data normalisation permitted direct comparison of C. difficile or E. coli growth in the various CFSs by eliminating the initial inherent variation in the optical density of the CFSs (due to the pre-fermentation of the media) from consideration. The relative growth achieved at the 18.17 h time-point by C. difficile or E. coli in each of the CFSs was compared to the relative growth of the pathogen of interest that was achieved in YCFA broth. A commensal strain was considered a potential inhibitor of C. difficile or E. coli if the relative growth plus two standard deviations of the pathogen of interest in the CFS derived from that same commensal isolate, was less than the mean minus two standard deviations of the relative growth of the pathogen in YCFA broth. Where only one relative growth value was available, a CFS was considered as potentially inhibitory if the relative pathogen growth was more than two standard deviations below the mean relative growth in YCFA broth. The results for bacteriotherapy candidates found to have inhibitory activity are shown in FIG. 12.

Results

Figure 13:
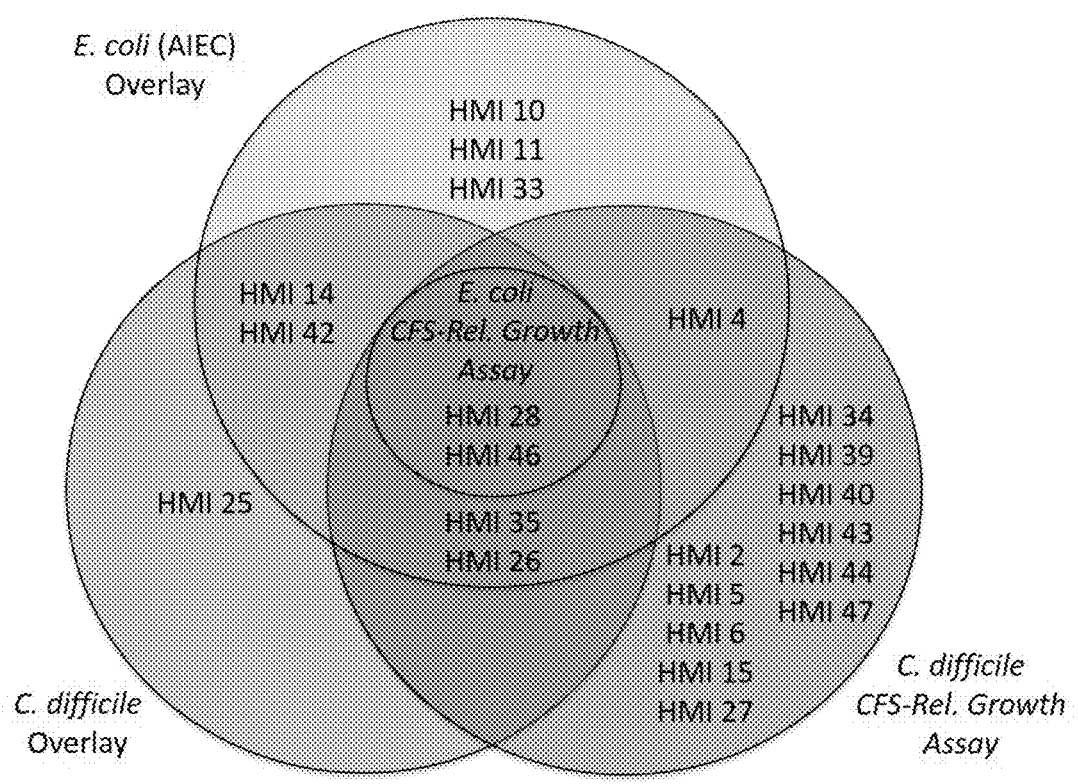
FIG. 13 shows a summary of the results obtained in the growth overlay and growth inhibition assays. Bacterial isolates shown to have inhibitory activity in the *E. coli* (AIEC) overlay assay, *C. difficile* overlay assay and *C. difficile* and *E. coli* growth assays are shown. Bacterial isolates showing inhibitory activity in two or more assays are shown in the overlapping regions. Bacterial isolates are referred to by their isolate number. See FIG. 15 for details of the bacterial isolates listed.

A summary of the results obtained in the growth overlay and growth inhibition assays is shown in FIG. 13 and FIG. 15. The bacteriotherapy candidates which showed activity in each of the in vitro assays are indicated in this figure.

Of the 50 bacteriotherapy candidates tested, 22 demonstrate growth inhibition of at least one of C. difficile M7404 or E. coli (AIEC) in one of the assays performed. 11 of the bacteriotherapy candidates inhibited the growth of at least one of either C. difficile or E. coli in overlay assays, suggesting that the inhibition conferred by these bacteriotherapy candidates is direct. According to the overlay assay data, 5 of the bacteriotherapy candidates inhibit only the growth of either C. difficile or E. coli, suggesting that the inhibitory activity of these bacteriotherapy candidates is not generic, i.e. that the inhibitory activity is specific for one or more pathogenic bacteria.

Of the 50 bacteriotherapy candidates tested, 6 inhibited the growth of both C. difficile and E. coli in overlay assays, suggesting that they have a broad-spectrum of inhibitory activity and are likely to also have inhibitory activity against other pathogenic bacteria.

The results from the CFS-relative growth inhibition assay demonstrate that the CFS from 16 of the 50 bacteriotherapy candidates tested, only supported the relative growth of C. difficile to levels more than two standard deviations below the mean relative growth in YCFA broth at the 18.17 h time-point. These bacteriotherapy candidates are thus considered to inhibit C. difficile growth. 5 of these bacteriotherapy candidates were also shown to directly inhibit C. difficile and/or E. coli growth in the overlay assays. This suggests that these 5 bacteriotherapy candidates secrete one or more substances which inhibit the growth of these pathogenic bacteria. The remaining 11 bacteriotherapy candidates which showed inhibitory activity in the CFS-relative growth inhibition assay are likely to compete with C. difficile for nutrients. CFS from two of the bacteriotherapy candidates did not support growth of E. coli to within two standard deviations of the mean growth observed for E. coli in YCFA broth. These isolates are therefore considered to inhibit the growth of E. coli.

Example 3—in Silico Co-Abundance Network Analysis

To identify bacteria that, while not capable of directly inhibiting pathogen growth as tested in Example 2, may support the growth or survival of those bacteria that exhibited direct inhibition of pathogen growth in Example 2, co-abundance network analysis was performed.

This analysis was performed as described previously using the complete list of healthy datasets in the HPMC database tool (Forster, Browne et al. 2015). For each candidate bacterium that demonstrated inhibition of pathogen growth in Example 2, a complete list of first degree neighbour species that exhibited co-occurrence with the candidate bacterium across at least 95% of faecal samples with an average abundance greater than 0.001% and a minimum of 100 reads was generated. Bacteria that exhibited extensive co-occurrence with candidate bacteria exhibiting direct inhibitory activity of pathogen growth are predicted to provide a metabolic, environmental and/or immunomodulatory support function required for colonization of the gastrointestinal tract by the candidate bacteria. The deposited bacteria demonstrating such co-occurrence is indicated in FIG. 15.

Discussion

Bacterial isolates that inhibited the growth of one or more pathogenic bacteria as shown in Example 2 are expected to be suitable for treating gastrointestinal dysbiosis in humans.

However, bacterial isolates that did not show evidence of pathogen inhibition in Example 2 are still expected to be useful for the treatment of gastrointestinal dysbiosis.

Firstly, based on the co-occurrence data obtained in Example 3, a large number of the deposited bacteria are expected to support the colonization of the gastrointestinal tract by the inhibitory bacteria identified in Example 2 through direct or indirect interaction. Metabolic networks in which consortia of bacteria thrive by cross-feeding, structural networks, such as biofilms, or the interactions of 'keystone species', allow the microbiota to establish and stabilise (Ze and Mougen et al. 2013). Co-occurrence analysis identified 35 candidates that formed first degree co-occurrence neighbours with direct inhibitors at a rate above 95% (HMI_2, HMI 5, HMI 6, HMI 7, HMI 8, HMI 9, HMI 10, HMI 11, HMI 12, HMI_14, HMI_15, HMI_16, HMI_17, HMI_18, HMI_19, HMI_20, HMI_26, HMI_27, HMI_31, HMI_33, HMI_34, HMI_35, HMI_37, HMI_38, HMI_39, HMI 41, HMI_42, HMI 43, HMI_44, HMI_46, HMI_47, HMI_48, HMI_50, HMI_51, HMI_52; see FIG. 15 for details). In addition, several of the bacterial isolates listed in FIG. 15 reside within the same genera as known keystone species (HMI_17, HMI_23 to HMI_32, HMI_45, HMI_49, HMI_51 and HMI_52; see FIG. 15 for details) and thus are expected to represent keystone species themselves.

Figure 14:
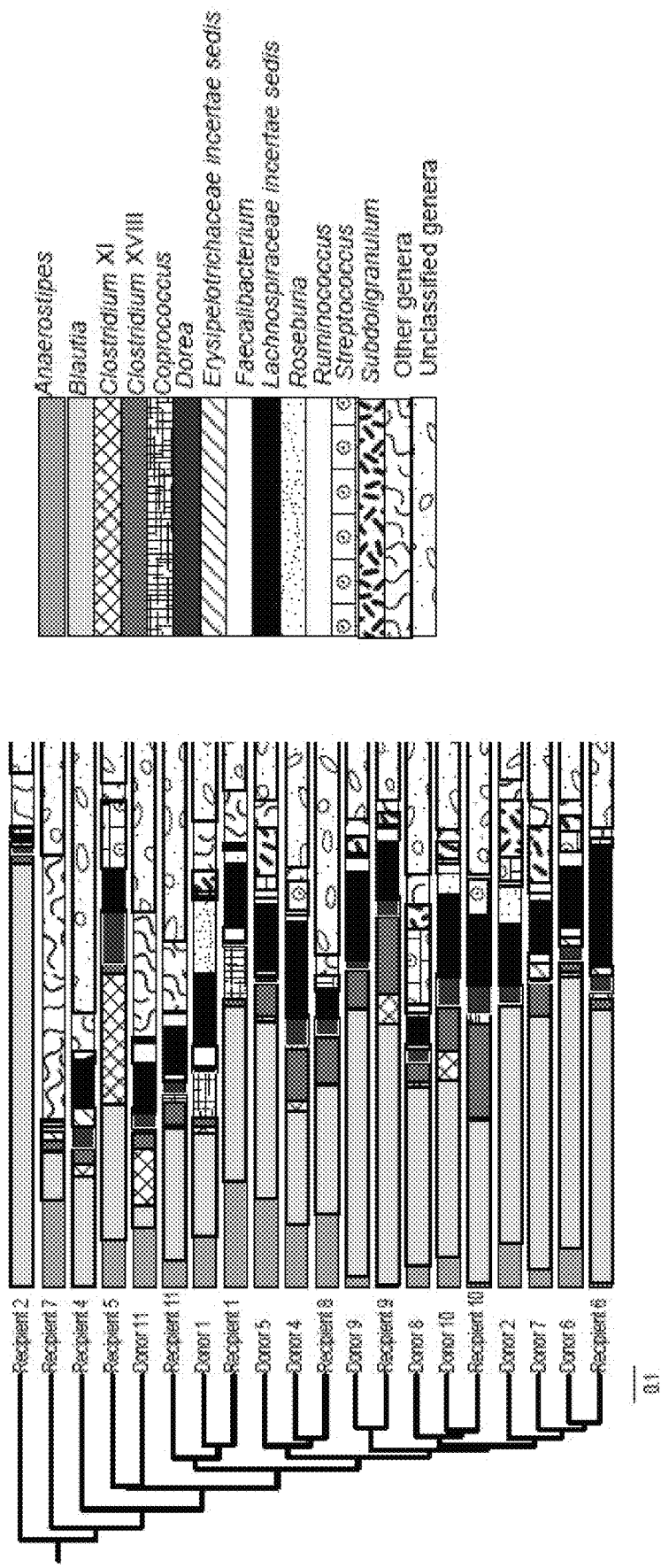
FIG. 14: Dendrogram and bar plots showing the relative abundance of each genus indicated in FIG. 14 at 3 months post-FMT in both donors and recipients. The dendrogram clusters samples based on the phylogenetic relationship of the microbial community present within the samples. The composition of donor and recipient profiles were similar when assessed at the genus level post-FMT.

Secondly, the bacterial isolates listed in FIG. 15 are shown in Example 1 to contribute to the overall diversity of the gastrointestinal microbiota, which is low during dysbiosis. Specifically, a number of these bacteria (HMI_23 to HMI_32 inclusive) were recovered from the intestinal microbiota of FMT donors as part of CIP2. When the microbiota of a healthy donor was transferred to an individual with dysbiosis due to antibiotic treatment for recurrent *C. difficile* infection, all were restored to health (FIG. 6), which was determined as the absence of *C. difficile* at 2-3 months post-FMT. The criteria for identifying bacteriotherapy candidates by the CIP2 process required that a certain candidate bacterial species was present in the microbiota of half the recipients at more than >0.6% average relative abundance at 2-3 months post-FMT. Moreover, genera representing several of the 51 bacteria listed in FIG. were also identified in healthy donors and in cured recipients post-FMT (FIG. 14). Furthermore, the in silico analysis presented herein (FIGS. 8 and 9) revealed that the 51 candidate bacteriotherapy isolates are prevalent in healthy individuals, in whom they occur at an average relative abundance >0.001% and these bacteria tend to be depleted under conditions of dysbiosis (FIG. 9). Together, these data strongly suggest that the 51 bacterial isolates listed in FIG. 15 are suitable in the treatment of gastrointestinal dysbiosis.

Thirdly, the bacterial isolates listed in FIG. 15 are expected to compete with enteric pathogens in the gastrointestinal tract, and thus find application in the treatment of gastrointestinal dysbiosis. Specifically, the widespread occurrence of these bacteria in healthy individuals implies that they efficiently colonise the gastrointestinal tract. When the microbiota is populated by these health-associated bacteria, the likelihood of enteric infection with any pathogenic bacterium is known to be low, as such infections usually do not occur in individuals with a healthy gastrointestinal microbiota. Indeed, following FMT, during which genera representing many of the 51 bacteria listed in FIG. 15 were identified in individuals treated for a dysbiosis of the gastrointestinal tract following antibiotic treatment for *C. difficile* infection (FIG. 14), a healthy microbiota profile was restored (FIG. 6 and FIG. 14) and *C. difficile* infection did not recur within 3 months. This indicates that these bacteria promote health according to the principles of colonisation resistance, in which pathogens are excluded or suppressed by competition with the resident health-associated bacteria for nutrients and attachment sites (Britton & Young 2014; Lawley & Walker 2013).

Fourthly, several of the bacterial isolates listed in FIG. 15 are expected, on the basis of extrapolation from investigations of other species in the same genera or clades (Louis & Flint, 2009), to produce metabolites, such as short chain fatty acids, which have known benefits for gastrointestinal health (e.g. HMI_9, HMI_12, HMI_20, HMI_21 and HMI_23-HMI_32; see FIG. 15 for details).

Finally some *Clostridium* related species have been shown to be immunomodulatory and can be beneficial in reducing inflammation (Atarashi, Tanoue et al. 2013). Based on a comparison of 16S rRNA gene sequences using 95% sequence identity as a cut-off to define a genus (Bosshard, Abels et al. 2003), examples in this context that are in the same genus as these bacteria are HMI 4, HMI_9, HMI_10, HMI_15, HMI_27, HMI_28 and HMI_38.

SEQUENCE LISTING 16S rRNA gene sequences of the 51 deposited bacterial isolates listed in FIG. 15 are set out below. For each bacteriotherapy candidate a putative genus and species name is give. The genus was and species names were assigned based on the Ribosomal Database Project (RDP) reference database and BLASTn analysis as explained in Example 1. The genus and species names assigned to each of the bacteriotherapy candidates are thus that of the most closely related known bacterium and hence subject to change.

```
HMI_1 Clostridium thermocellum 16S rDNA sequence
                                                                            (SEQ ID NO: 1)
CAGGACGAACGCTGGCGGCGTGCCTAACACATGCAAGTCGAACGAGAATCTTTGAACAGA

TCTTTTCGGAGTGACGTTCAAAGAGGAAAGTGGCGGACGGGCGAGTAACGCGTGAGTAAC

CTGCCCATAAGAGGGGGATAATCCATGGAAACGTGGACTAATACCGCATATTGTAGTCAA

GTCGCATGACTAGATTATGAAAGATTTATCGCTTATGGATGGACTCGCGTCAGATTAGAT

AGTTGGTGAGGTAACGGCTCACCAAGTCAACGATCTGTAGCCGAACTGAGAGGTTGATCG

GCCGCATTGGGACTGAGACACGGCCCAGACTCCTACGGGAGGCAGCAGTGGGGAATATTG

CGCAATGGGGGCAACCCTGACGCAGCAACGCCGCGTGCAGGAAGAAGGTCTTCGGATTGT

AAACTGTTGTCGCAAGGGAAGAAGACAGTGACGGTACCTTGTGAGAAAGTCACGGCTAAC

TACGTGCCAGCAGCCGCGGTAATACGTAGGTGACAAGCGTTGTCCGGATTTACTGGGTGT

AAAGGGCGCGTAGGCGGACTGTCAAGTCAGTCGTGAAATACCGGGGCTTAACCCCGGGGC

TGCGATTGAAACTGACAGCCTTGAGTATCGGAGAGGAAAGCGGAATTCCTAGTGTAGCGG

TGAAATGCGTAGATATTAGGAGGAACACCAGTGGCGAAGGCGGCTTTCTGGACGACAACT

GACGCTGAGGCGCGAAAGTGTGGGGAGCAAACAGGATTAGATACCCTGGTAGTCCACACC

GTAAACGATGGATACTAGGTGTAGGAGGTATCGACCCCTTCTGTGCCGCAGTTAACACAA

TAAGTATCCCACCTGGGGAGTACGACCGCAAGGTTGAAACTCAAAGGAATTGACGGGGC

CCGCACAAGCAGTGGAGTATGTGGTTTAATTCGAAGCAACGCGAAGAACCTTACCTGGGC
```

-continued

```
TTGACATCCCTGGAATCGAGTAGAGATACTTGAGTGCCTTCGGGAATCAGGTGACAGGTG

GTGCATGGTTGTCGTCAGCTCGTGTCGTGAGATGTTGGGTTAAGTCCCGCAACGAGCGCA

ACCCCTATTGTCAGTTGCCATCATTAAGTTGGGCACTCTGGCGAGACTGCCGGTGACAAA

TCGGAGGAAGGTGGGGACGACGTCAAATCATCATGCCCCTTATGCCCAGGGCTACACACG

TACTACAATGGCCGATAACAAAGTGCAGCGAAACCGTGAGGTGGAGCGAATCACAAAACT

CGGTCTCAGTTCAGATTGCAGGCTGCAACTCGCCTGCATGAAGTTGGAATTGCTAGTAAT

CGCGGATCAGAATGCCGCGGTGAATACGTTCCCGGGCCTTGTACACACCGCCCGTCACAC

CATGAGAGTCGATAACACCCGAAGCCTGTGAGCTAACCTATTAGGAGGCAGCAGTCGAAG

GTGGGGTTGATGATTGGGGTGAAGTCG
```

HMI_2 *Flavonifractor plautii* 16S rDNA sequence (SEQ ID NO: 2)

```
GAGTGCTCATGACAGAGGATTCGTCCAATGGAGTGAGTTACTTAGTGGCGGACGGGTGAGTAACGCGTGAGTAAC

CTGCCTTGGAGTGGGGAATAACAGGTGGAAACATCTGCTAATACCGCATGATGCAGTTGGGTCGCATGGCTCTGA

CTGCCAAAGATTTATCGCTCTGAGATGGACTCGCGTCTGATTAGCTGGTTGGCGGGGTAACGGCCCACCAAGGCG

ACGATCAGTAGCCGGACTGAGAGGTTGGCCGGCCACATTGGGACTGAGACACGGCCCAGACTCCTACGGGAGGCA

GCAGTGGGGAATATTGGGCAATGGGCGCAAGCCTGACCCAGCAACGCCGCGTGAAGGAAGAAGGCTTTCGGGTTG

TAAACTTCTTTTCTCAGGGACGAAGCAAGTGACGGTACCTGAGGAATAAGCCACGGCTAACTACGTGCCAGCAGC

CGCGGTAATACGTAGGTGGCGAGCGTTATCCGGATTTACTGGGTGTAAAGGGCGTGTAGGCGGGACTGCAAGTCA

GATGTGAAAACCATGGGCTCAACCTGTGGCCTGCATTTGAAACTGTAGTTCTTGAGTACTGGAGAGGCAGACGGA

ATTCCTAGTGTAGCGGTGAAATGCGTAGATATTAGGAGGAACACCAGTGGCGAAGGCGGTCTGCTGGACAGCAAC

TGACGCTGAGGCGCGAAAGCGTGGGGAGCAAACAGGATTAGATACCCTGGTAGTCCACGCTGTAAACGATGGATA

CTAGGTGTGGGGGGTCTGACCCCCTCCGTGCCGCAGTTAACACAATAAGTATCCCACCTGGGGAGTACGATCGCA

AGGTTGAAACTCAAAGGAATTGACGGGGGCCCGCACAAGCGGTGGAGTATGTGGTTTAATTCGAAGCAACGCGAA

GAACCTTACCAGGGCTTGACATCCCGGTGACCGGTGTAGAGATACACCTTCTTCTTCGGAAGCGCCGGTGACAGG

TGGTGCATGGTTGTCGTCAGCTCGTGTCGTGAGATGTTGGGTTAAGTCCCGCAACGAGCGCAACCCTTATTGTTA

GTTGCTACGCAAGAGCACTCTAGCGAGACTGCCGTTGACAAAACGGAGGAAGGTGGGGACGACGTCAAATCATCA

TGCCCCTTATGTCCTGGGCCACACACGTACTACAATGGTGGTCAACAGAGGGAAGCAAGACCGCGAGGTGGAGCA

AACCCCTAAAAGCCATCCCAGTTCGGATTGCAGGCTGCAACTCGCCTGTATGAAGTTGGAATCGCTAGTAATCGC

GGATCAGCATGCCGCGGTGAATACGTTCCCGGGCCTTGTACACACCGCCCGTCACACCATGAGAGTCGGGAACAC

CCGAAGTCCGTAGCCTAACCGCAAGGGGGCGCGGCCGAAGGTGGGTTCGATAATTGGGGTGAAGTCGT
```

HMI_3 *Flavonifractor plautii* 16S rDNA sequence (SEQ ID NO: 3)

```
TGGCTGTTTAGTGGCGGACGGGTGAGTAACGCGTGAGTAACCTGCCTTGGAGTGGGGAATAACACAGTGAAAACT

GTGCTAATACCGCATGACATATTGGTGTCGCATGGCACTGATATCAAAGATTTATCGCTCTGAGATGGACTCGCG

TCTGATTAGATAGTTGGCGGGGTAACGGCCCACCAAGTCGACGATCAGTAGCCGGACTGAGAGGTTGGCCGGCCA

CATTGGGACTGAGACACGGCCCAGACTCCTACGGGAGGCAGCAGTGGGGAATATTGGGCAATGGGCGCAAGCCTG

ACCCAGCAACGCCGCGTGAAGGAAGAAGGCTTTCGGGTTGTAAACTTCTTTTAACAGGGACGAAGTAAGTGACGG

TACCTGTTGAATAAGCCACGGCTAACTACGTGCCAGCAGCCGCGGTAATACGTAGGTGGCAAGCGTTATCCGGAT

TTACTGGGTGTAAAGGGCGTGTAGGCGGGACTGCAAGTCAGATGTGAAAACTATGGGCTCAACCCATAGCCTGCA

TTTGAAACTGTAGTTCTTGAGTGTCGGAGAGGCAATCGGAATTCCGTGTGTAGCGGTGAAATGCGTAGATATACG

GAGGAACACCAGTGGCGAAGGCGGATTGCTGGACGATAACTGACGCTGAGGCGCGAAAGCGTGGGGAGCAAACAG

GATTAGATACCCTGGTAGTCCACGCCGTAAACGATGGATACTAGGTGTGGGGGGTCTGACCCCCTCCGTGCCGCA

GCTAACGCAATAAGTATCCCACCTGGGGAGTACGATCGCAAGGTTGAAACTCAAAGGAATTGACGGGGGCCCGCA
```

-continued

```
CAAGCGGTGGAGTATGTGGTTTAATTCGAAGCAACGCGAAGAACCTTACCAGGGCTTGACATCCTACTAACGAAC
CAGAGATGGATTAGGTGCCCTTCGGGGAAAGTAGAGACAGGTGGTGCATGGTTGTCGTCAGCTCGTGTCGTGAGA
TGTTGGGTTAAGTCCCGCAACGAGCGCAACCCTTATTGTTAGTTGCTACGCAAGAGCACTCTAGCGAGACTGCCG
TTGACAAAACGGAGGAAGGTGGGGACGACGTCAAATCATCATGCCCCTTATGTCCTGGGCCACACACGTACTACA
ATGGCGGTTAACAGAGGGAGGCAAAGCCGCGAGGCAGAGCAAACCCCTAAAAGCCGTCCCAGTTCGGATTGCAGG
CTGAAACCCGCCTGTATGAAGTCGGAATCGCTAGTAATCGCGGATCAGCATGCCGCGGTGAATACGTTCCCGGGC
CTTGTACACACCGCCCGTCACACCATGAGAGTCGGGAACACCCGAAGTCCGTAGCCTAACTGCAAAGGGGGCGCG
GCCGAAGGTGGGTTCGATAATTGGGGTGAAGTCGTAACAGGGTAACCG
```

HMI_4 Clostridium orbiscindens 16S rDNA sequence
(SEQ ID NO: 4)
```
TGGCGGACGGGTGAGTAACGCGTGAGGAACCTGCCTCGGAGTGGGGAATAACAGACCGAAAGGCCTGCTAATACC
GCATGATGCAGTTGGACCGCATGGTCCTGACTGCCAAAGATTTATCGCTCTGAGATGGCCTCGCGTCTGATTAGC
TTGTTGGCGGGGTAATGGCCCACCAAGGCGACGATCAGTAGCCGGACTGAGAGGTTGGCCGGCCACATTGGGACT
GAGACACGGCCCAGACTCCTACGGGAGGCAGCAGTGGGGAATATTGGGCAATGGGCGCAAGCCTGACCCAGCAAC
GCCGCGTGAAGGAAGAAGGCTTTCGGGTTGTAAACTTCTTTTCTCAGGGACGAACAAATGACGGTACCTGAGGAA
TAAGCCACGGCTAACTACGTGCCAGCAGCCGCGGTAATACGTAGGTGGCAAGCGTTATCCGGATTTACTGGGTGT
AAAGGGCGTGTAGGCGGGAAGGCAAGTCAGATGTGAAAACTATGGGCTCAACCCATAGCCTGCATTTGAAACTGT
TTTTCTTGAGTGCTGGAGAGGCAATCGGAATTCCGTGTGTAGCGGTGAAATGCGTAGATATACGGAGGAACACCA
GTGGCGAAGGCGGATTGCTGGACAGTAACTGACGCTGAGGCGCGAAAGCGTGGGGAGCAAACAGGATTAGATACC
CTGGTAGTCCACGCTGTAAACGATGGATACTAGGTGTGGGGGGTCTGACCCCCTCCGTGCCGCAGTTAACACAAT
AAGTATCCCACCTGGGGAGTACGATCGCAAGGTTGAAACTCAAAGGAATTGACGGGGGCCCGCACAAGCGGTGGA
GTATGTGGTTTAATTCGAAGCAACGCGAAGAACCTTACCAGGGCTTGACATCCTACTAACGAAGCAGAGATGCAT
TAGGTGCCCTTCGGGGAAAGTAGAGACAGGTGGTGCATGGTTGTCGTCAGCTCGTGTCGTGAGATGTTGGGTTAA
GTCCCGCAACGAGCGCAACCCTTATTGTTAGTTGCTACGCAAGAGCACTCTAGCGAGACTGCCGTTGACAAAACG
GAGGAAGGCGGGGACGACGTCAAATCATCATGCCCCTTATGTCCTGGGCTACACACGTACTACAATGGTGGTAAA
CAGAGGGAAGCAAGACCGCGAGGTGGAGCAAATCCCTAAAAGCCATCCCAGTTCGGATTGCAGGCTGAAACCCGC
CTGTATGAAGTTGGAATCGCTAGTAATCGCGGATCAGCATGCCGCGGTGAATACGTTCCCGGGCCTTGTACACAC
CGCCCGTCACACCATGAGAGTCGGGAACACCCGAAGTCCGTAGTCTAACCGCAAGGGGGACGCGGCCGAAGGTGG
GTTCGATAATTGGGGTGAAGTCGTAACAGGGTAACC
```

HMI_5 Ruminococcus flavefaciens 16S rDNA sequence
(SEQ ID NO: 5)
```
CGGATCAGTGGCGGACGGGTGAGTAACACGTGAGCAACCTGCCTTTAAGAGGGGGATAACGTTTGGAAACGAACG
CTAATACCGCATAACATAGAAGATTCACATGTTTCTTCTATCAAAGATTTATCGCTTAAAGATGGGCTCGCGTCT
GATTAGCTAGTTGGTGAGGTAACGGCTCACCAAGGCGACGATCAGTAGCCGTACTGAGAGGTAGAACGGCCACAT
TGGGACTGAGACACGGCCCAGACTCCTACGGGAGGCAGCAGTGGGGAATATTGCACAATGGAGGAAACTCTGATG
CAGCGATGCCGCGTGAGGGAAGAAGGTTTTCGGATTGTAAACCTCTGTCTTCAGGGACGATAATGACGGTACCTG
AGGAGGAAGCTCCGGCTAACTACGTGCCAGCAGCCGCGGTAATACGTAGGGAGCGAGCGTTGTCCGGAATTACTG
GGTGTAAAGGGAGCGTAGGCGGGATCTTAAGTCAGGTGTGAAAACTATGGGCTCAACCCATAGACTGCACTTGAA
ACTGAGGTTCTTGAGTGAAGTAGAGGCAGGCGGAATTCCTAGTGTAGCGGTGAAATGCGTAGATATTAGGAGGAA
CATCAGTGGCGAAGGCGGCCTGCTGGGCTTTTACTGACGCTGAGGCTCGAAAGCGTGGGGAGCAAACAGGATTAG
ATACCCTGGTAGTCCACGCTGTAAACGATGATTACTAGGTGTGGGGGACTGACCCCTTCCGTGCCGCAGTTAAC
ACAATAAGTAATCCACCTGGGGAGTACGGCCGCAAGGTTGAAACTCAAAGGAATTGACGGGGGCCCGCACAAGCA
```

-continued

GTGGAGTATGTGGTTTAATTCGAAGCACGCGAAGAACCTTACCGGGTCTTGACATCTACAGAATCCTTTAGAGAT

AAGGGAGTGCCCTTCGGGGAACTGTAAGACAGGTGGTGCATGGTTGTCGTCAGCTCGTGTCGTGAGATGTTGGGT

TAAGTCCCGCAACGAGCGCAACCCCTATCATTAGTTGCTACGCAAGAGCACTCTAATGAGACTGCCGTTGACAAA

ACGGAGGAAGGTGGGGATGACGTCAAATCATCATGCCCCTTATGACCCGGGCTACACACGTACTACAATGGCGTA

ACAGAGGGAAGCAACATCGCGAGGTGAAGCAAATCTCTAAAAAACGTCCCAGTTCAGATTGCAGGCTGCAACTCG

CCTGCATGAAGACGGAATTGCTAGTAATCGCAGATCAGCATGCTGCGGTGAATACGTTCCCGGGCCTTGTACACA

CCGCCCGTCACACCATGGGAGTCGGTAACACCCGAAGTCGCTTGTCTAA

HMI_6 *Anaerotruncus colihominis* 16S rDNA sequence (SEQ ID NO: 6)

AGTCGACGGACACATCCGACGGAATAGCTTGCTAGGAAGATGGATGTTGTTAGTGGCGGACGGGTGAGTAACACG

TGAGCAACCTACCTCAGAGTGGGGGACAACAGTTGGAAACGACTGCTAATACCGCATAAGATGGCAGGGTCGCAT

GGCCTGGTCATAAAAGGAGCAATTCGCTCTGAGATGGGCTCGCGTCTGATTAGCTAGTTGGTGAGGTAACGGCTC

ACCAAGGCAACGATCAGTAGCCGGACTGAGAGGTTGAACGGCCACATTGGGACTGAGACACGGCCCAGACTCCTA

CGGGAGGCAGCAGTGGGGAATATTGCACAATGGGGGAAACCCTGATGCAGCGACGCCGCGTGAGGGAAGACGGTT

TTCGGATTGTAAACCTCTGTCTTGTGGGACGATAGTGACGGTACCACAGGAGGAAGCCATGGCTAACTACGTGCC

AGCAGCCGCGGTAATACGTAGATGGCGAGCGTTGTCCGGAATTACTGGGTGTAAAGGGAGTGTAGGCGGGCTGGT

AAGTTGAATGTGAAACCTTCGGGCTCAACCCGGAGCGTGCGTTCAAAACTGCTGGTCTTGAGTGAAGTAGAGGCA

GGCGGAATTCCCGGTGTAGCGGTGGAATGCGTAGATATCGGGAGGAACACCAGTGGCGAAGGCGGCCTGCTGGGC

TTTTACTGACGCTGAGGCTCGAAAGCATGGGTAGCAAACAGGATTAGATACCCTGGTAGTCCATGCCGTAAACGA

TGATTACTAGGTGTGGGGGATTGACCCCCTCCGTGCCGGAGTTAACACAATAAGTAATCCACCTGGGGAGTACG

ACCGCAAGGTTGAAACTCAAAGGAATTGACGGGGGCCCGCACAAGCAGTGGAGTATGTGGTTTAATTCGAAGCAA

CGCGAAAAACCTTACCAGGTCTTGACATCCATCGCCAGGCTAAGAGATTAGCTGTTCCCTCCGGGGACGATGAGA

CAGGTGGTGCATGGTTGTCGTCAGCTCGTGTCGTGAGATGTTGGGTTAAGTCCCGCAACGAGCGCAACCCTTACT

ATTAGTTGCTACGCAAGAGCACTCTAATGGGACTGCCGTTGACAAAACGGAGGAAGGTGGGGATGACGTCAAATC

ATCATGCCCCTTATGACCTGGGCTACACACGTACTACAATGGCCGTTAACAGAGAGCAGCGATACCGCGAGGTGG

AGCGAATCTAGAAAAACGGTCTCAGTTCGGATTGCAGGCTGAAACTCGCCTGCATGAAGTCGGAATTGCTAGTAA

TCGCGGATCAGCATGCCGCGGTGAATACGTTCCCGGGCCTTGTACACACCGCCCGTCACACCATGAGAGCCGGTA

ACACCCGAAGTCAGTAGCCTAACCGCAAGGAGGGCGCTGCCGAAGGTGGGGCTGGTAATTGGGGTGAAGTCGTAA

C

HMI_7 *Clostridium xylanolyticum* 16S rDNA sequence (SEQ ID NO: 7)

GTAACGCGTGGGTAACCTGCCTCATACAGGGGGATAACAGTTAGAAATGACTGCTAATACCGCATAAGCGCACAG

GGTCGCATGACCTAGTGTGAAAAACTCCGGTGGTATGAGATGGACCCGCGTCTGATTAGCTAGTTGGTGAGGTAA

CGGCTCACCAAGGCGACGATCAGTAGCCGACCTGAGAGGGTGATCGGCCACATTGGGACTGAGACACGGCCCAAA

CTCCTACGGGAGGCAGCAGTGGGGAATATTGCACAATGGGGGAAACCCTGATGCAGCGACGCCGCGTGAAGGAAG

AAGTATTTCGGTATGTAAACTTCTATCAGCAGGGAAGAAAATGACGGTACCTGACTAAGAAGCCCCGGCTAACTA

CGTGCCAGCAGCCGCGGTAATACGTAGGGGGCAAGCGTTATCCGGATTTACTGGGTGTAAAGGGAGCGTAGGCGG

TCTGACAAGTCAGAAGTGAAAGCCCGGGGCTCAACTCCGGGACTGCTTTTGAAACTGCCGGACTAGATTGCAGGA

GAGGTAAGTGGAATTCCTAGTGTAGCGGTGAAATGCGTAGATATTAGGAGGAACACCAGTGGCGAAGGCGGCTTA

CTGGACTGTAAATGACGCTGAGGCTCGAAAGCGTGGGGAGCAAACAGGATTAGATACCCTGGTAGTCCACGCCGT

AAACGATGAATACTAGGTGTTGGGGAGCACAGCTCTTCGGTGCCGCAGCAAACGCAATAAGTATTCCACCTGGGG

AGTACGTTCGCAAGAATGAAACTCAAAGGAATTGACGGGACCCGCACAAGCGGTGGAGCATGTGGTTTAATTCG

AAGCAACGCGAAGAACCTTACCAAGTCTTGACATCCCGATGACCGTCCCGTAACGGGGGCTTCTCTTCGGAGCAT

```
CGGTGACAGGTGGTGCATGGTTGTCGTCAGCTCGTGTCGTGAGATGTTGGGTTAAGTCCCGCAACGAGCGCAACC

CTTATCTTTAGTAGCCAGCGGTACGGCCGGGCACTCTAGAGAGACTGCCAGGGATAACCTGGAGGAAGGTGGGGA

TGACGTCAAATCATCATGCCCCTTATGATTTGGGCTACACACGTGCTACAATGGCGTAAACAAAGGGAAGCGAAA

CTGTGAAGTCTAGCAAATCTCAAAAATAACGTCTCAGTTCGGATTGTAGTCTGCAACTCGACTACATGAAGCTGG

AATCGCTAGTAATCGCGAATCAGCATGTCGCGGTGAATACGTTCCCGGGTCTTGTACACACCGCCCGTCACACCA

TGGGAGTTGGAAACGCCCGAAGTCAGTGACCCAACCGTAAGGAGGGAGCTGCCGAAGGCGGGTCTGATAACTGGG

GTGAAGTCGTAACAAGGTAACCG
```

HMI_8 *Clostridium oroticum* 16S rDNA sequence (SEQ ID NO: 8)

```
TTTTGATTGATTTCTTCGGAAAGAGAGAGACTGTGACTGAGTGGCGGACGGGTGAGTAACGCGTGGGTAACCTGC

CTCATACAGGGGGATAACAGTTAGAAATGACTGCTAATACCGCATAAGCACACAGCTTCGCATGAAGCAGTGTGA

AAAACTCCGGTGGTATGAGATGGACCCGCGTCTGATTAGGTAGTTGGTGGGGTAACGGCCCACCAAGCCGACGAT

CAGTAGCCGACCTGAGAGGGTGACCGGCCACATTGGGACTGAGACACGGCCCAAACTCCTACGGGAGGCAGCAGT

GGGGAATATTGCACAATGGGGGAAACCCTGATGCAGCGACGCCGCGTGAAGGATGAAGTATTTCGGTATGTAAAC

TTCTATCAGCAGGGAAGAAAATGACGGTACCTGACTAAGAAGCCCCGGCTAACTACGTGCCAGCAGCCGCGGTAA

TACGTAGGGGGCAAGCGTTATCCGGATTTACTGGGTGTAAAGGGAGCGTAGACGGTAATGCAAGTCTGGAGTGAA

AACCCGGGGCTCAACCCCGGGACTGCTTTGGAAACTGTGTAACTAGAGTGTCGGAGAGGCAAGTGGAATTCCTAG

TGTAGCGGTGAAATGCGTAGATATTAGGAGGAACACCAGTGGCGAAGGCGGCTTGCTGGACGATGACTGACGTTG

AGGCTCGAAAGCGTGGGGAGCAAACAGGATTAGATACCCTGGTAGTCCACGCCGTAAACGATGACTACTAGGTGT

CGGTAAGCAAAGCTTATCGGTGCCGCAGCAAACGCAATAAGTAGTCCACCTGGGGAGTACGTTCGCAAGAATGAA

ACTCAAAGGAATTGACGGGGACCCGCACAAGCGGTGGAGCATGTGGTTTAATTCGAAGCAACGCGAAGAACCTTA

CCTGGTCTTGACATCCCTCTGACAGCTGAGTAATGTCGGTTTTCTTTCGGGACAGAGGAGACAGGTGGTGCATGG

TTGTCGTCAGCTCGTGTCGTGAGATGTTGGGTTAAGTCCCGCAACGAGCGCAACCCCTATCTTCAGTAGCCAGCA

TATGAGATGGGCACTCTGGAGAGACTGCCAGGGATAACCTGGAGGAAGGTGGGGATGACGTCAAATCATCATGCC

CCTTATGATCAGGGCTACACACGTGCTACAATGGCGTAAACAAAGGGAAGCGAGCCTGCGAGGGGGAGCAAATCC

CAAAAATAACGTCTCAGTTCGGATTGTAGTCTGCAACTCGACTACATGAAGCTGGAATCGCTAGTAATCGCGAAT

CAGAATGTCGCGGTGAATACGTTCCCGGGTCTTGTACACACCGCCCGTCACACCATGGGAGTCAGTAACGCCCGA

AGTCAGTGACCCAACCTTTCAGGAGGGAGCTGCCGAAGGCGGGACCGATAACTGGGGTGAAGTCGT
```

HMI_9 *Eubacterium contortum* 16S rDNA sequence (SEQ ID NO: 9)

```
CTTAAGTTTGATTCTTCGGATGAAGACTTTTGTGACTGAGTGGCGGACGGGTGAGTAACGCGTGGGTAACCTGCC

TCATACAGGTGGATAACAGTTAGAAATGACTGCTAATACCGCATAAGACCACAGCACCGCATGGTGCAGGGGTAA

AAACTCCGGTGGTATGAGATGGACCCGCGTCTGATTAGCTAGTTGGTGGGGTAACGGCCTACCAAGGCGACGATC

AGTAGCCGACCTGAGAGGGTGACCGGCCACATTGGGACTGAGACACGGCCCAAACTCCTACGGGAGGCAGCAGTG

GGGAATATTGCACAATGGGGGAAACCCTGATGCAGCGACGCCGCGTGAAGGATGAAGTATTTCGGTATGTAAACT

TCTATCAGCAGGGAAGAAAATGACGGTACCTGACTAAGAAGCCCCGGCTAACTACGTGCCAGCAGCCGCGGTAAT

ACGTAGGGGGCAAGCGTTATCCGGATTTACTGGGTGTAAAGGGAGCGTAGACGGTATGGCAAGTCTGATGTGAAA

GGCCAGGGCTCAACCCTGGGACTGCATTGGAAACTGTCGAACTAGAGTGTCGGAGAGGCAAGTGGAATTCCTAGT

GTAGCGGTGAAATGCGTAGATATTAGGAGGAACACCAGTGGCGAAGGCGGCTTGCTGGACGATGACTGACGTTGA

GGCTCGAAAGCGTGGGGAGCAAACAGGATTAGATACCCTGGTAGTCCACGCCGTAAACGATGACTACTAGGTGTC

GGGTAGCAGAGCTATTCGGTGCCGCAGCCAACGCAATAAGTAGTCCACCTGGGGAGTACGTTCGCAAGAATGAAA

CTCAAAGGAATTGACGGGACCCGCACAAGCGGTGGAGCATGTGGTTTAATTCGAAGCAACGCGAAGAACCTTAC
```

-continued

```
CTGCTCTTGACATCTCCCTGACCGGCAAGTAATGTTGCCTTTCCTTCGGGACAGGGATGACAGGTGGTGCATGGT
TGTCGTCAGCTCGTGTCGTGAGATGTTGGGTTAAGTCCCGCAACGAGCGCAACCCCTATCTTTAGTAGCCAGCGG
TTTGGCCGGGCACTCTAGAGAGACTGCCAGGGATAACCTGGAGGAAGGTGGGGATGACGTCAAATCATCATGCCC
CTTATGAGCAGGGCTACACACGTGCTACAATGGCGTAAACAAAGGGAAGCGAGCCTGCGAGGGTAAGCAAATCTC
AAAAATAACGTCTCAGTTCGGATTGTAGTCTGCAACTCGACTACATGAAGCTGGAATCGCTAGTAATCGCGAATC
AGAATGTCGCGGTAATACGTTCCCGGGTCTTGTACACACCGCCCGTCACACCATGGGAGTTGGTAACGCCCGAA
GTCAGTGACCCAACCGCAAGGAGGGAGCTGCCGAAGGTGGGACCGATAACTGGGGTGAAGTCGTAACAAGGTAAC
CG
```

HMI_10 *Clostridium oroticum* 16S rDNA sequence (SEQ ID NO: 10)
```
ACATGCAAGTCGAGCGAGCGCTTTAGTGGAATTCTACGGAAGGAAAGTGAAGTGACTGAGCGGCGGACGGGTGAG
TAACGCGTGGGTAACCTGCCTCATACAGGGGGATAACAGTTAGAAATGACTGCTAATACCGCATAAGACCCCAGT
ACCGCATGGTACAGAGGTAAAAACTGAGGTGGTATGAGATGGACCCGCGTCTGATTAGCTAGTTGGTGAGGTAGA
GGCTCACCAAGGCGACGATCAGTAGCCGACCTGAGAGGGTGACCGGCCACATTGGGACTGAGACACGGCCCAAAC
TCCTACGGGAGGCAGCAGTGGGGAATATTGCACAATGGGGGAAACCCTGATGCAGCGACGCCGCGTGAGCGAAGA
AGTATTTCGGTATGTAAAGCTCTATCAGCAGGGAAGAAAATGACGGTACCTGACTAAGAAGCACCGGCTAAATAC
GTGCCAGCAGCCGCGGTAATACGTATGGTGCAAGCGTTATCCGGATTTACTGGGTGTAAAGGGAGCGTAGACGGA
GCAGCAAGTCTGATGTGAAAACCCGGGGCTCAACCCCGGGAGTGCATTGGAAACTGTTGATCTAGAGTGCTGGAG
AGGTAAGTGGAATTCCTAGTGTAGCGGTGAAATGCGTAGATATTAGGAGGAACACCAGTGGCGAAGGCGGCTTAC
TGGACAGTGACTGACGTTGAGGCTCGAAAGCGTGGGGAGCAAACAGGATTAGATACCCTGGTAGTCCACGCCGTA
AACGATGACTACTAGGTGTCGGGTAGCAAAGCTATTCGGTGCCGCAGCCAACGCAATAAGTAGTCCACCTGGGGA
GTACGTTCGCAAGAATGAAACTCAAAGGAATTGACGGGGACCCGCACAAGCGGTGGAGCATGTGGTTTAATTCGA
AGCAACGCGAAGAACCTTACCTGCCCTTGACATCCGGGTGACCGGCGAGTAATGTCGCCTTCTCTTCGGAGCAGC
CGAGACAGGTGGTGCATGGTTGTCGTCAGCTCGTGTCGTGAGATGTTGGGTTAAGTCCCGCAACGAGCGCAACCC
TTATCTTTAGTAGCCAGCGGATAAGCCGGGACTCTAGAGAGACTGCCAGGGATAACCTGGAGGAAGGTGGGGAT
GACGTCAAATCATCATGCCCCTTATGGGCAGGGCTACACACGTGCTACAATGGCGTAAACAAAGGGAAGCGAAGC
TGTGAAGCGGAGCGAATCTCAAAAATAACGTCTCAGTTCGGATTGTAGTCTGCAACTCGACTACATGAAGCTGGA
ATCGCTAGTAATCGCGAATCAGAATGTCGCGGTAATACGTTCCCGGGTCTTGTACACACCGCCCGTCACACCAT
GGGAGTCAGTAACGCCCGAAGTCAGTGACCCAACCGTAAGGAGGGAGCTGCCGAAGGCGGGACGGATAACTGGGG
TGAAGTCGTAACAAGGTAACCG
```

HMI_11 *Lachnospira pectinoschiza* 16S rDNA sequence (SEQ ID NO: 11)
```
AGTGGCGGACGGGTGAGTAACGCGTGGGTAACCTGCCCTGTACAGGGGGACAACAGCTGGAAACGGCTGCTAATA
CCGCATAAGCCCTTAGCACTGCATGGTGCATAGGGAAAAGGAGCAATCCGGTACAGGATGGACCCGCGTCTGATT
AGCCAGTTGGCAGGGTAACGGCCTACCAAAGCGACGATCAGTAGCCGATCTGAGAGGATGTACGGCCACATTGGG
ACTGAGACACGGCCCAGACTCCTACGGGAGGCAGCAGTGGGGAATATTGCACAATGGAGGAAACTCTGATGCAGC
GACGCCGCGTGAGTGAAGAAGTATTTCGGTATGTAAAGCTCTATCAGCAGGGAAGAAAATGACGGTACCTGACTA
AGAAGCACCGGCTAAATACGTGCCAGCAGCCGCGGTAATACGTATGGTGCAAGCGTTATCCGGATTTACTGGGTG
TAAAGGGAGCGTAGGTGGCAAGGCAAGCCAGAAGTGAAAACCCGGGGCTCAACCGCGGGATTGCTTTTGGAACTG
TCATGCTAGAGTGCAGGAGGGGTGAGCGGAATTCCTAGTGTAGCGGTGAAATGCGTAGATATTAGGAGGAACACC
GGAGGCGAAGGCGGCTCACTGGACTGTAACTGACACTGAGGCTCGAAAGCGTGGGGAGCAAACAGGATTAGATAC
CCTGGTAGTCCACGCGGTAAACGATGAATACTAGATGTCGGGTAGCAAAGCTACTCGGTGTCGTCGAAACGCAA
TAAGTATTCCACCTGGGGAGTACGTTCGCAAGAATGAAACTCAAAGGAATTGACGGGGACCCGCACAAGCGGTGG
```

```
AGCATGTGGTTTAATTCGAAGCAACGCGAAGAACCTTACCTGCTCTTGACATCCCATTCGATAGAGGGTAATGCT
TCTAGCCCTTCGGGGGAATGGAGACAGGTGGTGCATGGTTGTCGTCAGCTCGTGTCGTGAGATGTTGGGTTAAGT
CCCGCAACGAGCGCAACCCTTATTGTCAGTAGCCAGCAGGTGAAGCTGGGCACTCTGATGAGACTGCCGGGGATA
ACCCGGAGGAAGGTGGGGATGACGTCAAATCATCATGCCCCTTATGAGCAGGGCTACACACGTGCTACAATGGCG
TAAACAGAGGGAAGCGAAGGAGTGATCTGGAGCAAATCTCAAAAATAACGTCTCAGTTCGGATTGTAGTCTGCAA
CTCGACTACATGAAGCTGGAATCGCTAGTAATCGCAGATCAAAATGCTGCGGTGAATACGTTCCCGGGTCTTGTA
CACACCGCCCGTCACACCATGGGAGTCGGTAATGCCCGAAGTCAGTGACTCAACCGAAAGGAAAAAGCTGCCGAA
GGCAGGACTGGTAACTGGGGTGAAGTCGT
```

HMI_12 *Roseburia faecis* 16S rDNA sequence (SEQ ID NO: 12)
```
AGTCGAACGAAGCACTTTATTACGATTTCTTCGGAATGACGATTTAGTGACTGAGTGGCGGACGGGTGAGTAACG
CGTGGGTAACCTGCCTTATACAGGGGGATAACAGTTAGAAATGACTGCTAATACCGCATAAGCGCACAGGATTGC
ATGATCTGGTGTGAAAAACTCCGGTGGTATAAGATGGACCCGCGTCTGATTAGCTGGTTGGTGAGGTAACGGCCC
ACCAAGGCGACGATCAGTAGCCGACCTGAGAGGGTGACCGGCCACATTGGGACTGAGACACGGCCCAAACTCCTA
CGGGAGGCAGCAGTGGGGAATATTGCACAATGGGGGAAACCCTGATGCAGCGACGCCGCGTGAGCGAAGAAGTAT
TTCGGTATGTAAAGCTCTATCAGCAGGGAAGAAAAAAATGACGGTACCTGACTAAGAAGCCCCGGCTAACTACGT
GCCAGCAGCCGCGGTAATACGTAGGGGGCAAGCGTTATCCGGATTTACTGGGTGTAAAGGGAGCGCAGGCGGTGC
GGCAAGTCTGATGTGAAAGCCCGGGGCTCAACCCCGGGACTGCATTGGAAACTGTCGTACTTGAGTATCGGAGAG
GTAAGTGGAATTCCTAGTGTAGCGGTGAAATGCGTAGATATTAGGAGGAACACCAGTGGCGAAGGCGGCTTACTG
GACGATAACTGACGCTGAGGCTCGAAAGCGTGGGGAGCAAACAGGATTAGATACCCTGGTAGTCCACGCCGTAAA
CGATGAATACTAGGTGTCGGGGGACATAGTCCTTCGGTGCCGCAGCAAACGCAATAAGTATTCCACCTGGGGAGT
ACGTTCGCAAGAATGAAACTCAAAGGAATTGACGGGACCCGCACAAGCGGTGGAGCATGTGGTTTAATTCGAAG
CAACGCGAAGAACCTTACCAAGTCTTGACATCCCGGTGACAAAGTATGTAATGTACTCTTTCTTCGGAACACCGG
TGACAGGTGGTGCATGGTTGTCGTCAGCTCGTGTCGTGAGATGTTGGGTTAAGTCCCGCAACGAGCGCAACCCCT
GTTCTTAGTAGCCAGCGGTTCGGCCGGGCACTCTAGGGAGACTGCCAGGGATAACCTGGAGGAAGGCGGGGATGA
CGTCAAATCATCATGCCCCTTATGACTTGGGCTACACACGTGCTACAATGGCGTAAACAAAGGGAAGCGAAAAGG
TGACTTCTAGCAAATCCCAAAAATAACGTCCCAGTTCGGACTGTAGTCTGCAACTCGACTACACGAAGCTGGAAT
CGCTAGTAATCGCGAATCAGAATGTCGCGGTGAATACGTTCCCGGGTCTTGTACACACCGCCCGTCACACCATGG
GAGTCGGGAATGCCCGAAGCCGGTGACTCAACCGAAAGGAGAGAGCCGTCGAAGGCAGGTCTGATAACTGGGGTG
AAGTCGTAACAAGGTAACC
```

HMI_14 *Clostridium hathewayi* 16S rDNA sequence (SEQ ID NO: 13)
```
AGTCGACGGAGATGCGATGTGAGCGAGAGGTGCTTGCACTGATCAATCTTTTCGTATCTTAGTGGCGGACGGGTG
AGTAACGCGTGGGTAACCTGCCTTATACCGGGGGATAACACTTAGAAATAGGTGCTAATACCGCATAAGCGCACG
GTGTCGCATGACACAGTGTGAAAAACTCCGGTGGTATAAGATGGACCCGCGTCTGATTAGCCAGTTGGCAGGGTA
ACGGCCTACCAAAGCGACGATCAGTAGCCGGCCTGAGAGGGTGAACGGCCACATTGGGACTGAGACACGGCCCAA
ACTCCTACGGGAGGCAGCAGTGGGGAATATTGCACAATGGGGGAAACCCTGATGCAGCGACGCCGCGTGAGTGAA
GAAGTATTTCGGTATGTAAAGCTCTATCAGCAGGGAAGAAGAAATGACGGTACCTGACTAAGAAGCCCCGGCTAA
CTACGTGCCAGCAGCCGCGGTAATACGTAGGGGGCAAGCGTTATCCGGATTTACTGGGTGTAAAGGGAGCGTAGA
CGGTGAAGCAAGTCTGAAGTGAAAGGTTGGGGCTCAACCCCGAAACTGCTTTGGAAACTGTTTAACTGGAGTACA
GGAGAGGTAAGTGGAATTCCTAGTGTAGCGGTGAAATGCGTAGATATTAGGAGGAACACCAGTGGCGAAGGCGGC
TTACTGGACTGTAACTGACGTTGAGGCTCGAAAGCGTGGGGAGCAAACAGGATTAGATACCCTGGTAGTCCACGC
```

```
CGTAAACGATGATTACTAGGTGTTGGTGGATATGGATCCATCGGTGCCGCAGCAAACGCAATAAGTAATCCACCT

GGGGAGTACGTTCGCAAGAATGAAACTCAAAGGAATTGACGGGGACCCGCACAAGCGGTGGAGCATGTGGTTTAA

TTCGAAGCAACGCGAAGAACCTTACCTGATCTTGACATCCCTATGAATACAGGGTAATGCCTGTAGTACTTCGGT

ACATAGGAGACAGGTGGTGCATGGTTGTCGTCAGCTCGTGTCGTGAGATGTTGGGTTAAGTCCCGCAACGAGCGC

AACCCCTATCTTTAGTAGCCAGCAGTAAGATGGGCACTCTAGAGAGACTGCCGGGGATAACCCGGAGGAAGGTGG

GGATGACGTCAAATCATCATGCCCCTTATGACCAGGGCTACACACGTGCTACAATGGCGTAAACAGAGGGAAGCG

AAGTGGTGACATGGAGCAAATCCCAAAAATAACGTCCCAGTTCGGATTGCAGGCTGCAACTCGCCTGCATGAAGC

TGGAATCGCTAGTAATCGCAGATCAGAATGCTGCGGTGAATACGTTCCCGGGTCTTGTACACACCGCCCGTCACA

CCATGGGAGTAGGTAATGCCCGAAGTCGGTGACCTAACCGCAAGGAAGGAGCCGCCGAAGGCAGGACTTATAACT

GGGGTGAAGTCGTAACAAGGTAACCGT
```

HMI_15 *Fusicatenibacter_saccharivorans* 16S rDNA sequence (SEQ ID NO: 14)
```
CGGATGGAATCGGTATAACTTAGTGGCGGACGGGTGAGTAACGCGTGGGAAACCTGCCCTGTACCGGGGGATAAC

ACTTAGAAATAGGTGCTAATACCGCATAAGCGCACGGAACTGCATGGTTCTGTGTGAAAAACTCCGGTGGTACAG

GATGGTCCCGCGTCTGATTAGCCAGTTGGCAGGGTAACGGCCTACCAAAGCGACGATCAGTAGCCGGCCTGAGAG

GGTGAACGGCCACATTGGGACTGAGACACGGCCCAAACTCCTACGGGAGGCAGCAGTGGGGAATATTGCACAATG

GGGGAAACCCTGATGCAGCGACGCCGCGTGAGTGAAGAAGTATTTCGGTATGTAAAGCTCTATCAGCAGGGAAGA

AAATGACGGTACCTGACTAAGAAGCCCCGGCTAACTACGTGCCAGCAGCCGCGGTAATACGTAGGGGGCAAGCGT

TATCCGGATTTACTGGGTGTAAAGGGAGCGTAGACGGCATGGCAAGCCAGATGTGAAAACCCAGGGCTCAACCTT

GGGATTGCATTTGGAACTGCCAGGCTGGAGTGCAGGAGAGGTAAGCGGAATTCCTAGTGTAGCGGTGAAATGCGT

AGATATTAGGAGGAACACCAGTGGCGAAGGCGGCTTACTGGACTGTAACTGACGTTGAGGCTCGAAAGCGTGGGG

AGCAAACAGGATTAGATACCCTGGTAGTCCACGCCGGTAAACGATGATTGCTAGGTGTAGGTGGGTATGGACCCAT

CGGTGCCGCAGCTAACGCAATAAGCAATCCACCTGGGGAGTACGTTCGCAAGAATGAAACTCAAAGGAATTGACG

GGGACCCGCACAAGCGGTGGAGCATGTGGTTTAATTCGAAGCAACGCGAAGAACCTTACCAAGTCTTGACATCCC

AATGACGCACCTGTAAAGAGGTGTTCCCTTCGGGGCATTGGAGACAGGTGGTGCATGGTTGTCGTCAGCTCGTGT

CGTGAGATGTTGGGTTAAGTCCCGCAACGAGCGCAACCCTTATTCTTAGTAGCCAGCAGGTGAAGCTGGGCACTC

TAAGGAGACTGCCGGGGATAACCCGGAGGAAGGCGGGGATGACGTCAAATCATCATGCCCCTTATGATTTGGGCT

ACACACGTGCTACAATGGCGTAAACAAAGGGAAGCGAGACAGTGATGTGGAGCAAATCCCAGAAATAACGTCTCA

GTTCGGATTGTAGTCTGCAACTCGACTACATGAAGCTGGAATCGCTAGTAATCGCGAATCAGCATGTCGCGGTGA

ATACGTTCCCGGGTCTTGTACACACCGCCCGTCACACCATGGGAGTTGGAAATGCCCGAAGTCTGTGACCTAACC

GAAAGGGAGGAGCAGCCGAAGGCAGGTCTGATAACTGGGGTGAAGTCGTA
```

HMI_16 *Clostridium_clostridioforme* 16S rDNA sequence (SEQ ID NO: 15)
```
CTGCTTTGATGAAGTTTTCGGATGGATTTAAAACAGCTTAGTGGCGGACGGGTGAGTAACGCGTGGGTAACCTGC

CTCACACTGGGGGATAACAGTTAGAAATAGCTGCTAATACCGCATAAGCGCACGGTTCCGCATGGAACAGTGTGA

AAAACTCCGGTGGTGTGAGATGGACCCGCGTCTGATTAGCCAGTTGGCGGGGTAACGGCCCACCAAAGCGACGAT

CAGTAGCCGGCCTGAGAGGGTGAACGGCCACATTGGGACTGAGACACGGCCCAAACTCCTACGGGAGGCAGCAGT

GGGGAATATTGCACAATGGGGGAAACCCTGATGCAGCGACGCCGCGTGAGTGAAGAAGTATTTCGGTATGTAAAG

CTCTATCAGCAGGGAAGAAAGTGACGGTACCTGAATAAGAAGCCCCGGCTAACTACGTGCCAGCAGCCGCGGTAA

TACGTAGGGGGCAAGCGTTATCCGGATTTACTGGGTGTAAAGGGAGCGTAGACGGCAAGGCAAGTCTGAAGTGAA

AGCCCGGTGCTTAACGCCGGGACTGCTTTGGAAACTGTTTAGCTGGAGTGCCGGAGAGGTAAGCGGAATTCCTAG

TGTAGCGGTGAAATGCGTAGATATTAGGAAGAACACCAGTGGCGAAGGCGGCTTACTGGACGGTAACTGACGTTG

AGGCTCGAAAGCGTGGGGAGCAAACAGGATTAGATACCCTGGTAGTCCACGCCGTAAACGATGATTGCTAGGTGT
```

-continued

AGGTGGGTATGGACCCATCGGTGCCGCAGCTAACGCAATAAGCAATCCACCTGGGGAGTACGTTCGCAAGAATGA

AACTCAAAGGAATTGACGGGGACCCGCACAAGCGGTGGAGCATGTGGTTTAATTCGAAGCAACGCGAAGAACCTT

ACCAGGTCTTGACATCCCGATGAAAAACCCGTAACGGGGTTCCCTCTTCGGAGCATCGGAGACAGGTGGTGCATG

GTTGTCGTCAGCTCGTGTCGTGAGATGTTGGGTTAAGTCCCGCAACGAGCGCAACCCTTATTCTTAGTAGCCAGC

AGGTAAGGCTGGGCACTCTAAGGAGACTGCCGGGGATAACCCGGAGGAAGGTGGGGATGACGTCAAATCATCATG

CCCCTTATGATCTGGGCTACACACGTGCTACAATGGCGTAACAAAGGGAAGCGAGCCTGCGAGGGTGAGCAAATC

CCAAAAATAACGTCCCAGTTCGGACTGTAGTCTGCAACCCGACTACACGAAGCTGGAATCGCTAGTAATCGCGAA

TCAGAATGTCGCGGTGAATACGTTCCCGGGTCTTGTACACACCGCCCGTCACACCATGGGAGTCGGAAATGCCCG

AAGTCTGTGACTCAACCGCAAGGAGAGAGCAGCCGAAGGCAGGTCTGATAACTGGGGTGAAGTCGT

HMI_17 *Ruminococcus_torques* 16S rDNA sequence (SEQ ID NO: 16)

CGGTATGAGATGGACCCGCGTCTGATTAGCTAGTTGGTGGGGTAACGGCCTACCAAGGCG

ACGATCAGTAGCCGACCTGAGAGGGTGACCGGCCACATTGGGACTGAGACACGGCCCAAA

CTCCTACGGGAGGCAGCAGTGGGGAATATTGCACAATGGGGGAAACCCTGATGCAGCGAC

GCCGCGTGAGCGAAGAAGTATTTCGGTATGTAAAGCTCTATCAGCAGGGAAGAAAATGAC

GGTACCTGACTAAGAAGCCCCGGCTAACTACGTGCCAGCAGCCGCGGTAATACGTAGGGG

GCAAGCGTTATCCGGATTTACTGGGTGTAAAGGGAGCGTAGACGGCGAGGCAAGTCTGAT

GTGAAAACCCGGGGCTCAACCCCGTGACTGCATTGGAAACTGTTTTGCTTGAGTGCCGGA

GAGGTAAGCGGAATTCCTAGTGTAGCGGTGAAATGCGTAGATATTAGGAGGAACACCAGT

GGCGAAGGCGGCTTACTGGACGGCAACTGACGTTGAGGCTCGAAAGCGTGGGGAGCAAAC

AGGATTAGATACCCTGGTAGTCCACGCCGTAAACGATGAATACTAGGTGTCGGGGAGCAA

AGCTCTTCGGTGCCGCCGCAAACGCAATAAGTATTCCACCTGGGGAGTACGTTCGCAAGA

ATGAAACTCAAAGGAATTGACGGGGACCCGCACAAGCGGTGGAGCATGTGGTTTAATTCG

AAGCAACGCGAAGAACCTTACCAAGCCTTGACATCCCATTGACAGAGCATGTAATGTGCT

TTCCCTTCGGGGCAGTGGTGACAGGTGGTGCATGGTTGTCGTCAGCTCGTGTCGTGAGAT

GTTGGGTTAAGTCCCGCAACGAGCGCAACCCCTATCTTCAGTAGCCAGCGGTTTGGCCGG

GCACTCTGGAGAGACTGCCAGGGATAACCTGGAGGAAGGTGGGGATGACGTCAAATCATC

ATGCCCCTTATGGCTTGGGCTACACACGTGCTACAATGGCGTAAACAAAGGGAAGCGAGC

CTGCGAGGGGAGCAAATCCCAAAAATAACGTCTCAGTTCGGATTGTAGTCTGCAACTCG

ACTACATGAAGCTGGAATCGCTAGTAATCGCGAATCAGAATGTCGCGGTGAATACGTTCC

CGGGTCTTGTACACACCGCCCGTCACACCATGGGAGTCGGCAACGCCCGAAGCCAGTGAC

CCAACCGAAAG

HMI_18 *Clostridium_celerecrescens* 16S rDNA sequence (SEQ ID NO: 17)

AGTCGACGAGGTAATGAGATGAAGTTTTCGGATGGATTCTTATTTCCGAGTGGCGGACGGGTGAGTAACGCGTGG

GTAACCTGCCTCATACAGGGGGATAACGATTGGAAACGATTGCTAATACCGCATAAGCGCACAGTACCACATGGT

ACAGTGTGAAAAACTCCGGTGGTATGAGATGGACCCGCGTCTGATTAGCTAGTTGGTGAGGTAACGGCCCACCAA

GGCAACGATCAGTAGCCGACCTGAGAGGGTGACCGGCCACATTGGGACTGAGACACGGCCCAGACTCCTACGGGA

GGCAGCAGTGGGGATATTGCACAATGGAGGAAACTCTGATGCAGCGACGCCGCGTGAGTGAAGAAGTATTTCGG

TATGTAAAGCTCTATCAGCAGGGAAGAAAATGACGGTACCTGACTAAGAAGCCCCGGCTAACTACGTGCCAGCAG

CCGCGGTAATACGTAGGGGGCAAGCGTTATCCGGATTTACTGGGTGTAAAGGGAGCGTAGACGGCGATGCAAGTC

TGAAGTGAAATACCCGGGCTCAACCTGGGAACTGCTTTGGAAACTGTATGGCTAGAGTGCTGGAGAGGTAAGCGG

-continued

AATTCCTAGTGTAGCGGTGAAATGCGTAGATATTAGGAAGAACACCAGTGGCGAAGGCGGCTTACTGGACAGTAA
CTGACGTTCAGGCTCGAAAGCGTGGGGAGCAAACAGGATTAGATACCCTGGTAGTCCACGCCGTAAACGATGAAT
ACTAGGTGTCGGGGGACAAAGTCTTTCGGTGCCGCCGCAAACGCAATAAGTATTCCACCTGGGGAGTACGTTCGC
AAGAATGAAACTCAAAGGAATTGACGGGGACCCGCACAAGCGGTGGAGCATGTGGTTTAATTCGAAGCAACGCGA
AGAACCTTACCAAATCTTGACATCCCTCTGAAAAGCCTTTAATCGAGCTCCTCCTTCGGGACAGAGGTGACAGGT
GGTGCATGGTTGTCGTCAGCTCGTGTCGTGAGATGTTGGGTTAAGTCCCGCAACGAGCGCAACCCCTATTGTCAG
TAGCCAGCAGGTAAAGCTGGGCACTCTGATGAGACTGCCAGGGATAACCTGGAGGAAGGTGGGGATGACGTCAAA
TCATCATGCCCCTTATGATTTGGGCTACACACGTGCTACAATGGCGTAAACAAAGAGAGGCGAAGCTGTGAGGCA
GAGCAAATCTCAAAAATAACGTCTCAGTTCGGATTGTAGTCTGCAACTCGACTACATGAAGCTGGAATCGCTAGT
AATCGCGGATCAGAATGCCGCGGTGAATACGTTCCCGGGTCTTGTACACACCGCCCGTCACACCATGGGAGTCGG
AAATGCCCGAAGCCAGTGACCCAAGCGAAAGCAGGGAGCTGTCGAAGGCAGGTCTGATAACTGGGGTGAAGTCGT

HMI_19 *Clostridium_celerescens* 16S rDNA sequence (SEQ ID NO: 18)
TCGACGAGGTATTTTGATTGAAGTTTTCGGATGGATTTCAGATACCGAGTGGCGGACGGGTGAGTAACGCGTGGG
TAACCTGCCTCATACAGGGGGATAACGGTTAGAAATGACTGCTAATACCGCATAAGCGCACAGTACCGCATGGTA
CGGTGTGAAAAACTCCGGTGGTATGAGATGGACCCGCGTCTGATTAGCTAGTTGGTGGGGTAACGGCCCACCAAG
GCGACGATCAGTAGCCGACCTGAGAGGGTGACCGGCCACATTGGGACTGAGACACGGCCCAGACTCCTACGGGAG
GCAGCAGTGGGGATATTGCACAATGGAGGAAACTCTGATGCAGCGACGCCGCGTGAGTGAAGAAGTATTTCGGT
ATGTAAAGCTCTATCAGCAGGGAAGAAAATGACGGTACCTGACTAAGAAGCCCCGGCTAACTACGTGCCAGCAGC
CGCGGTAATACGTAGGGGGCAAGCGTTATCCGGATTTACTGGGTGTAAAGGGAGCGTAGACGGCGACGCAAGTCT
GAAGTGAAATACCCGGGCTCAACCTGGGAACTGCTTTGGAAACTGTGTTGCTAGAGTGCTGGAGAGGTAAGCGGA
ATTCCTAGTGTAGCGGTGAAATGCGTAGATATTAGGAAGAACACCAGTGGCGAAGGCGGCTTACTGGACAGTAAC
TGACGTTGAGGCTCGAAAGCGTGGGGAGCAAACAGGATTAGATACCCTGGTAGTCCACGCCGTAAACGATGAATA
CTAGGTGTTGGTGAGCAAAGCTCATCGGTGCCGCCGCAAACGCAATAAGTATTCCACCTGGGGAGTACGTTCGCA
AGAATGAAACTCAAAGGAATTGACGGGACCCGCACAAGCGGTGGAGCATGTGGTTTAATTCGAAGCAACGCGAA
GAACCTTACCAAATCTTGACATCCCTCTGAAACGCCCTTAATCGGGCTCCTCCTTCGGGACAGAGGTGACAGGTG
GTGCATGGTTGTCGTCAGCTCGTGTCGTGAGATGTTGGGTTAAGTCCCGCAACGAGCGCAACCCCTATTGTCAGT
AGCCAGCAGGTAAAGCTGGGCACTCTGATGAGACTGCCAGGGATAACCTGGAGGAAGGTGGGGATGACGTCAAAT
CATCATGCCCCTTATGATTTGGGCTACACACGTGCTACAATGGCGTAAACAAAGAGAAGCGAGCCTGCGAGGGGG
AGCAAATCTCAAAAATAACGTCTCAGTTCGGATTGTAGTCTGCAACTCGACTACATGAAGCTGGAATCGCTAGTA
ATCGCAGATCAGAATGCTGCGGTGAATACGTTCCCGGGTCTTGTACACACCGCCCGTCACACCATGGGAGTCGGA
AATGCCCGAAGCCAGTGACCCAAGCGAAAGCAGGGAGCTGTCGAAGGCAGGTCTGATAACTGGGGTGAAGTCGTA
ACAGGGTAACCG HMI_20 *Eubacterium_infirmum* 16S rDNA sequence (SEQ ID NO: 19)
GAGCTCATCACAGATGCTTCGGTTGAAGTGATGAGTGGAAAGCGGCGGACGGGTGAGTAA
CGCGTAGGCAACCTGCCCTTTGCAGAGGGATAGCCTCGGGAAACCGGGATTAAAACCTCA
TGACACCTCTTAAAGACATCTTTGAGAGGTCAAAGATTTATCGGCAGAGGATGGGCCTGC
GTCTGATTAGCTAGTTGGTGGGGTAACGGCCTACCAAGGCGACGATCAGTAGCCGACCTG
AGAGGGTGATCGGCCACATTGGAACTGAGACACGGTCCAAACTCCTACGGGAGGCAGCAG
TGGGGAATATTGCACAATGGGGGAAACCCTGATGCAGCAACGCCGCGTGAAGGAAGAAGG
CCTTTGGGTCGTAAACTTCTGTTCTAAGGGAAGATAATGACGGTACCTTAGGAGCAAGTC
CCGGCTAACTACGTGCCAGCAGCCGCGGTAATACGTAGGGGGCAAGCGTTATCCGGAATT -continued

ATTGGGCGTAAAGAGTACGTAGGTGGTTACCTAAGCACGAGGTATAAGGCAATGGCTTAA

CCATTGTTCGCCTTGTGAACTGGGCTACTTGAGTGCAGGAGAGGAAAGCGGAATTCCTAG

TGTAGCGGTGAAATGCGTAGATATTAGGAGGAACACCAGTGGCGAAGGCGGCTTTCTGGA

CTGTAACTGACACTGAGGTACGAAAGCGTGGGGAGCAAACAGGATTAGATACCCTGGTAG

TCCACGCCGTAAACGATGAGCACTAGGTGTCGGGGTCGCAAGACTTCGGTGCCGCAGTTA

ACGCAATAAGTGCTCCGCCTGGGGAGTACGTTCGCAAGAATGAAACTCAAAGGAATTGAC

GGGGACCCGCACAAGCAGCGGAGCATGTGGTTTAATTCGAAGCAACGCGAAGAACCTTAC

CAGGACTTGACATCCCTCTGACAGCCTTTTAATCGAGGTTTTCTACGGACAGAGGAGACA

GGTGGTGCATGGTTGTCGTCAGCTCGTGTCGTGAGATGTTGGGTTAAGTCCCGCAACGAG

CGCAACCCTTGTCATTAGTTGCCAGCAGTAAGATGGGCACTCTAGTGAGACTGCCGGGGA

TAACTCGGAGGAAGGTGGGGATGACGTCAAATCATCATGCCCCTTATGTTCTGGGCTACA

CACGTGCTACAATGGCCGGTACAGAGAGAAAGCGAGACTGCGAAGTGGAGCGAAACTCAA

AAGCCGGTCCCAGTTCGGATTGCAGGCTGCAACTCGCCTGCATGAAGTCGGAGTTGCTAG

TAATCGCAGATCAGAATGCTGCGGTGAATGCGTTCCCGGGTCTTGTACACACCGCCCGTC

ACACCATGGAAGTTGGGGGCGCCCGAAGTTGGCAGATAAATATGTTACCTAAGGCGAAAT

CAATGACTGGGGTGAAGTCGT

HMI_21 Eubacterium_infirmum 16S rDNA sequence                                    (SEQ ID NO: 20)

TCGGTAAAGGGATATGGCGGAAAGCGGCGGACGGGTGAGTAACGCGTAGGCAACCTGCCC

CTTACAGAGGGATAGCCATTGGAAACGATGATTAAGACCTCATAACGCCTCCCTCCCACA

TGAGGGGGAGGCCAAAGATTCATCGGTAAGGGATGGGCCTGCGTCTGATTAGCTTGTTGG

CGGGGTAACGGCCCACCAAGGCGACGATCAGTAGCCGACCTGAGAGGGTGATCGGCCACA

TTGGAACTGAGACACGGTCCAAACTCCTACGGGAGGCAGCAGTGGGGAATATTGCACAAT

GGGCGGAAGCCTGATGCAGCAACGCCGCGTGAGGGATGAAGGCCTTCGGGTCGTAAACCT

CTGTCCTTGGGGAAGAAACAAATGACGGTACCCATGGAGGAAGCCCCGGCTAACTACGTG

CCAGCAGCCGCGGTAATACGTAGGGGGCGAGCGTTATCCGGAATTATTGGGCGTAAAGAG

TGCGTAGGTGGTTACCTAAGCGCAGGGTCTAAGGCAATGGCTCAACCATTGTTCGCCCTG

CGAACTGGGCTACTTGAGTGCAGGAGAGGAAAGCGGAATTCCTAGTGTAGCGGTGAAATG

CGTAGATATTAGGAGGAACACCAGTGGCGAAGGCGGCTTTCTGGACTGTTACTGACACTG

AGGCACGAAAGCGTGGGGAGCAAACAGGATTAGATACCCTGGTAGTCCACGCCGTAAACG

ATGAGCACTAGGTGTCGGGCCGCAAGGCTTCGGTGCCGCAGTTAACGCATTAAGTGCTC

CGCCTGGGGAGTACGCACGCAAGTGTGAAACTCAAAGGAATTGACGGGGACCCGCACAAG

CAGCGGAGCATGTGGTTTAATTCGAAGCAACGCGAAGAACCTTACCAGGACTTGACATCC

CCCTGACAGATCCTTAACCGGATCCTTCTTCGGACAGGGGAGACAGGTGGTGCATGGTTG

TCGTCAGCTCGTGTCGTGAGATGTTGGGTTAAGTCCCGCAACGAGCGCAACCCTTGCCAT

TAGTTGCCATCATTCAGTTGGGCACTCTAATGGGACTGCCGGGACAACTCGGAGGAAGG

TGGGGATGACGTCAAATCATCATGCCCCTTATGTTCTGGGCTACACACGTGCTACAATGG

CCGGTACAGCAGGAAGCGATCCCGCGAGGGGAGCAAATCCCAAAAACCGGTCCCAGTTC

GGACTGCAGGCTGCAACCCGCCTGCACGAAGCCGGAGTTGCTAGTAATCGTGGATCAGAA

TGCCACGGTGAATGCGTTCCCGGGTCTTGTACACACCGCCCGTCACACCATGGAAGTTGG

GGGTGCCCGAAGCCGGCAGGGAGATATGCTGTCTAAGGCAAAACCAAT

HMI_22 Clostridium_thermocellum 16S rDNA sequence (SEQ ID NO: 21)

GGATGAGGAAATGCTTCGGCATGGAGACATCCGATCTAGTGGCGGACGGGTGAGTAACGC
GTGAGCAACCTGTCCTGCACAGGGGGATAACACTGAGAAATCAGTGCTAATACCGCATGA
GACCACAGTATCACATGGTACAGGGGTCAAAGGAGAAATCCGGTGCAGGGTGGGCTCGCG
TCCCATTAGCTAGTTGGTAGGGTAAAGGCCTACCAAGGCGACGATGGGTAGCCGGACTGA
GAGGTTGGCCGGCCACACTGGGACTGAGACACGGCCCAGACTCCTACGGGAGGCAGCAGT
GGGGAATATTGGGCAATGGGCGAAAGCCTGACCCAGCAACGCCGCGTGAAGGAAGAAGGT
CTTTGGATTGTAAACTTTTGTCCTATGGGAAGAAGGAAGTGACGGTACCATGGGAGGAAG
CCCCGGCTAACTACGTGCCAGCAGCCGCGGTAATACGTAGGGGGCGAGCGTTGTCCGGAA
TTACTGGGCGTAAAGGGCGCGCAGGCGGCCGATCAAGTTAGATGTGAAATACCCGGGCTT
AACCTGGGAACTGCATTTAAAACTGGTTGGCTAGGAGTGCAGGAGAGGGAAGCGGAATTC
CTAGTGTAGCGGTGAAATGCGTAGATATTAGGAGGAACACCAGTGGCGAAGGCGGCTTTC
TGGACTGTAACTGACGCTGAGGCGCGAAAGCGTGGGGAGCGAACAGGATTAGATACCCTG
GTAGTCCACGCTGTAAACGATGAATACTAGGTGTAGGGGGTATCGACCCCCCCTGTGCCG
GAGCAAACGCAATAAGTATTCCGCCTGGGGAGTACGGCCGCAAGGTTGAAACTCAAAGGA
ATTGACGGGGCCCGCACAAGCAGCGGAGCATGTGGTTTAATTCGAAGCAACGCGAAGAA
CCTTACCAGGTCTTGACATCCCTCGAAGTGCATAGAGATATGTACGTCCTTCGGGACGAG
GAGACAGGTGGTGCATGGTTGTCGTCAGCTCGTGTCGTGAGATGTTGGGTTAAGTCCCGC
AACGAGCGCAACCCCTACAGTTAGTTACCAGCGGGTAAAGCCGGGGACTCTAACAGGACT
GCCGTGGATAACACGGAGGAAGGTGGGGACGACGTCAAATCATCATGCTCCTTATGACCT
GGGCTACACACGTGCTACAATGGCCGGTACAAAGAGAAGCGAGACCGTAAGGTGGAGCGG
ATCTCAAAAAACCGGTCCCAGTTCGGATTGTGGGCTGCAACCCGCCCACATGAAGTTGGA
GTTGCTAGTAATCGCGAATCAGCATGTCGCGGTGAATGCGTTCCCGGGCCTTGTACACAC
CGCCCGTCACACCATGGGAGTTGGGAGCGCCCGAAGTCGTTGAGGTAACCCGCAAGGGAG
CCAGGCGCCGAAGGTGAGACCGATAACTGGGGTGAAGTCGT

HMI_23 Anaerovorax_odorimutans 16S rDNA sequence (SEQ ID NO: 22)

AGAGTTTGATCCTGGCTCAGGATGAACGCTGGCGGCGTGCCTAACACATGCAAGTCGAGC
GGGAAATCTTGGAACGATACTTCGGTAAAGGGAAGAGATGGATAGCGGCGGACGGGTGAG
TAACGCGTAGGTAACCTGCCTCATGCAGAGGGATAGCCTCGGGAAACTGGGATTAATACC
TCATAATGCGGAGGAGTCACATGGCTCCATCGCCAAAGATTTATCGGCATGAGATGGACC
TGCGTCTGATTAGTTAGTTGGTGAGGTAACGGCTCACCAAGGCAGCGATCAGTAGCCGAC
CTGAGAGGGTAATCGGCCACATTGGAACTGAGACACGGTCCAAACTCCTACGGGAGGCAG
CAGTGGGGAATATTGCACAATGGGCGCAAGCCTGATGCAGCAACGCCGCGTGAGCGATGA
AGGTCTTCGGATCGTAAAGCTCTGTCCTAGGGGAAGAATATATGACGGTACCCTTGGAGG
AAGCCCCGGCTAACTACGTGCCAGCAGCCGCGGTAATACGTAGGGGGCGAGCGTTATCCG
GAATTATTGGGCGTAAAGAGTTCGTAGGTGGTTTTGTAAGCGCGGGGTTTAAGGCAACGG
CTCAACCGTTGTTCGCCTTGCGAACTGCAAGACTTGAGTGCGGGAGAGGAAAGTGGAATT
CCTAGTGTAGCGGTGAAATGCGTAGATATTAGGAGGAACACCAGTGGCGAAGGCGACTTT
CTGGACCGTAACTGACACTGAGGAACGAAAGCGTGGGGAGCAAACAGGATTAGATACCCT
GGTAGTCCACGCCGTAAACGATGAGCACTAGGTGTCGGGCCGCAAGGTTTCGGTGCCGC
AGTTAACGCATTAAGTGCTCCGCCTGGGGAGTACGCACGCAAGTGTGAAACTCAAAGGAA

```
TTGACGGGGACCCGCACAAGCAGCGGAGCATGTGGTTTAATTCGAAGCAACGCGAAGAAC

CTTACCAGGGCTTGACATCCCGATGACCGGCGGGTAACGCCGCCTTCTCTTCGGAGCATC

GGTGACAGGTGGTGCATGGTTGTCGTCAGCTCGTGTCGTGAGATGTTGGGTTAAGTCCCG

CAACGAGCGCAACCCTTGTCATTAGTTGCCAGCAGTTCGGCTGGGCACTCTAGTGAGACT

GCCGGGGACAACTCGGAGGAAGGTGGGGATGACGTCAAATCATCATGCCCCTTATGTTCT

GGGCTACACACGTGCTACAATGGCCGGTACAGAGAGACGCAAGACTGTGAAGTGGAGCAA

AACTCTAAAACCGGTCCCAGTTCGGATTGTAGGCTGCAACTCGCCTACATGAAGTTGGAG

TTGCTAGTAATCGCGAATCAGAATGTCGCGGTGAATGCGTTCCCGGGTCTTGTACACACC

GCCCGTCACACCATGGAAGTTGGGGGCGCCCGAAGTTGGTCAACAAATCGATTACCTAAG

GCGAAACCAATGACTGGGGTGAAGTCGTAACAAGGTAGCCGTATCGGAAGGTGCGGCTGG

ATCACCT
```

HMI_24 *Clostridium_saccharogumia* 16S rDNA sequence                                  (SEQ ID NO: 23)

```
AGCCACCGGCTTCGGGTGTTATCAACTCTCATGGTGTGACGGGCGGTGTGTACAAGGCCC

GAGAACGTATTCACCGCGGCATGCTGATCCGCGATTACTAGCGATTCCATCTTCATGCAG

GCGAGTTGCAGCCTGCAATCCGAACTGAGAACGGGTTTTTGAGTTTCGCTCCAAGTCGCC

TCTTCGCTTCCCTTTGATCCGTCCATTGTAGCACGTGTGTAGCCCAGGTCATAAGGGGCA

TGATGATTTGACGTCATCCCCGCCTTCCTCCGGCTTGTCACCGGCTGTCTCGTTAGAGTC

CCCATCTTACTGCTGGTAACTAACGACAAGGGTTGCGCTCGTTGCGGGACTTAACCCAAC

ATCTCACGACACGAGCTGACGACAACCATGCACCACCTGTCTTGAGTATATCTATCCCTC

TATCTCTAGAGTCTTTACTCTGATGTCAAGACCTGGTAAGGTTCTTCGCGTTGCTTCGAA

TTAAACCACATGCTCCACCGCTTGTGCGGGCCCCCGTCAATTCCTTTGAGTTTCATTCTT

GCGAACGTACTACTCAGGCGGAGTACTTATTGCGTTAACTGCAGCACTGAGGCTTGTCCC

CCCAACACTTAGTACTCATCGTTTACGGCGTGGACTACTAGGGTATCTAATCCTATTTGC

TCCCCACGCTTTCGGGACTGAGCGTCAGTTACAGACCAGATCGTCGCCTTCGCCACTGGT

GTTCCTCCATATATCTACGCATTTCACCGCTACACATGGAATTCCACGATCCTCTTCTGC

ACTCTAGCTATTTGGTTTCCATGGCTTACTGAAGTTAAGCTTCAGCCTTTTACCACAGAC

CTCCATTGCCGCCTGCTCCCTCTTTACGCCCAATAATTCCGGATAACGCTTGCCACCTAC

GTATTACCGCGGCTGCTGGCACGTAGTTAGCCGTGGCTTCCTCACAAAGTACCGTCACTC

TAATACCATTCCCTGTATTAGTCGTTCTTCCTTTATAACAGAAGTTTACAACCCGAAGGC

CTTCTTCCTTCACGCGGCGTTGCTCGGTCAGGGTTCCCCCCATTGCCGAAAATTCCCTAC

TGCTGCCTCCCGTAGGAGTCTGGGCCGTGTCTCAGTCCCAGTGTGGCCGTTCACCCTCTC

AGGCCGGCTATGCATCGTCGCCTTGGTAGGCCGTTACCCCTCCAACTAGCTAATGCACCA

TAAGCCCATCTGTTCCCTATCCCTTAGGATATTTAACTTAGAGAAAATGCTTCCTCTAAG

CCTATGCGGTGTTAGCGCATGTTTCCACGCGTTATCCCCCTGGTACAGCCAGGTTGCTTA

TGTCTTACTCACCCGTTCGCCACTCATCACCGAAGTGATGCGTTCGACTTGCATGTAT
```

HMI_25 *Clostridium_saccharogumia* 16S rDNA sequence                                  (SEQ ID NO: 24)

```
GGCATCTACAGGGGGATAACTGATGGAAACGTCAGCTAAGACCGCATAGGTGTAGAGATC

GCATGAACTCTATATGAAAAGTGCTACGGGACTGGTAGATGATGGACTTATGGCGCATTA

GCTTGTTGGTAGGGTAACGGCCTACCAAGGCGACGATGCGTAGCCGACCTGAGAGGGTGA

CCGGCCACACTGGGACTGAGACACGGCCCAGACTCCTACGGGAGGCAGCAGTAGGGAATT
```

-continued

TTCGGCAATGGGGGAAACCCTGACCGAGCAACGCCGCGTGAAGGAAGAAGTAATTCGTTA

TGTAAACTTCTGTCATAGAGGAAGAACGGTGGATATAGGGAATGATATCCAAGTGACGGT

ACTCTATAAGAAAGCCACGGCTAACTACGTGCCAGCAGCCGCGGTAATACGTAGGTGGCG

AGCGTTATCCGGAATTATTGGGCGTAAAGAGGGAGCAGGCGGCACTAAGGGTCTGTGGTG

AAAGATCGAAGCTTAACTTCGGTAAGCCATGGAAACCGTAGAGCTAGAGTGTGTGAGAGG

ATCGTGGAATTCCATGTGTAGCGGTGAAATGCGTAGATATATGGAGGAACACCAGTGGCG

AAGGCGACGATCTGGCGCATAACTGACGCTCAGTCCCGAAAGCGTGGGGAGCAAATAGGA

TTAGATACCCTAGTAGTCCACGCCGTAAACGATGAGTACTAAGTGTTGGGTGTCAAAGCT

CAGTGCTGCAGTTAACGCAATAAGTACTCCGCCTGAGTAGTACGTTCGCAAGAATGAAAC

TCAAAGGAATTGACGGGGGCCCGCACAAGCGGTGGAGCATGTGGTTTAATTCGAAGCAAC

GCGAAGAACCTTACCAGGTCTTGACATCGATCTAAAGGCTCCAGAGATGGAGAGATAGCT

ATAGAGAAGACAGGTGGTGCATGGTTGTCGTCAGCTCGTGTCGTGAGATGTTGGGTTAAG

TCCCGCAACGAGCGCAACCCCTGTTGCCAGTTGCCAGCATTAAGTTGGGGACTCTGGCGA

GACTGCCGGTGACAAGCCGGAGGAAGGCGGGGATGACGTCAAATCATCATGCCCCTTATG

ACCTGGGCTACACACGTGCTACAATGGACAGAGCAGAGGGAAGCGAAGCCGCGAGGTGGA

GCGAAACCCATAAAACTGTTCTCAGTTCGGACTGCAGTCTGCAACTCGACTGCACGAAGA

TGGAATCGCTAGTAATCGCGAATCAGCATGTCGCGGTGAATACGTTCTCGGGCCTTGTAC

ACACCGCCCGTCACACCATGAGAGTCGGTAACACCCGAAGCCGGTGGCCTAACCGCAAGG

AAGGAGCTGTCTAAGGTGGGACTGATGATTGGGGTGAAGTCGTAACAAGGGTAACC

HMI_26 *Blautia_luti* 16S rDNA sequence (SEQ ID NO: 25)
CGGGAATACTTTATTGAAACTTCGGTGGATTTAATTTATTTCTAGTGGCGGACGGGTGAGTAACGCGTGGGTAAC

CTGCCTTATACTGGGGGATAACAGCCAGAAATGACTGCTAATACCGCATAAGCGCACAGAACCGCATGGTTCCGT

GTGAAAAACTCCGGTGGTATAAGATGGACCCGCGTTGGATTAGCTAGTTGGCAGGGCAGCGGCCTACCAAGGCGA

CGATCCATAGCCGGCCTGAGAGGGTGAACGGCCACATTGGGACTGAGACACGGCCCAGACTCCTACGGGAGGCAG

CAGTGGGGAATATTGCACAATGGGGGAAACCCTGATGCAGCGACGCCGCGTGAAGGAAGAAGTATCTCGGTATGT

AAACTTCTATCAGCAGGGAAGATAATGACGGTACCTGACTAAGAAGCCCCGGCTAACTACGTGCCAGCAGCCGCG

GTAATACGTAGGGGGCAAGCGTTATCCGGATTTACTGGGTGTAAAGGGAGCGTAGACGGCGCAGCAAGTCTGATG

TGAAAGGCAGGGGCTTAACCCCTGGACTGCATTGGAAACTGCTGTGCTTGAGTGCCGGAGGGGTAAGCGGAATTC

CTAGTGTAGCGGTGAAATGCGTAGATATTAGGAGGAACACCAGTGGCGAAGGCGGCTTACTGGACGGTAACTGAC

GTTGAGGCTCGAAAGCGTGGGGAGCAAACAGGATTAGATACCCTGGTAGTCCACGCCGTAAACGATGAATACTAG

GTGTCAGGGAGCACAGCTCTTTGGTGCCGCCGCAAACGCATTAAGTATTCCACCTGGGGAGTACGTTCGCAAGAA

TGAAACTCAAAGGAATTGACGGGACCCGCACAAGCGGTGGAGCATGTGGTTTAATTCGAAGCAACGCGAAGAAC

CTTACCAAATCTTGACATCCCTCTGACCGGGACTTAACCGTCCCTTTCCTTCGGGACAGGGGAGACAGGTGGTGC

ATGGTTGTCGTCAGCTCGTGTCGTGAGATGTTGGGTTAAGTCCCGCAACGAGCGCAACCCCTATCCTTAGTAGCC

AGCACGTAATGGTGGGCACTCTGAGGAGACTGCCAGGGATAACCTGGAGGAAGGCGGGGATGACGTCAAATCATC

ATGCCCCTTATGATTTGGGCTACACACGTGCTACAATGGCGTAAACAAAGGGAAGCGAACCCGCGAGGGTGGGCA

AATCTCAAAAATAACGTCCCAGTTCGGACTGCAGTCTGCAACTCGACTGCACGAAGCTGGAATCGCTAGTAATCG

CGGATCAGAATGCCGCGGTGAATACGTTCCCGGGTCTTGTACACACCGCCCGTCACACCATGGGAGTCAGTAACG

CCCGAAGTCAG

HMI_27 Clostridium_clostridioforme 16S rDNA sequence (SEQ ID NO: 26)
TTGCGGTAGGTCACAGGCTTCGGGCATTTCCAACTCCCATGGTGTGACGGGCGGTGTGTA
CAAGACCCGGGAACGTATTCACCGCGACATGCTGATTCGCGATTACTAGCGATTCCAGCT
TCATGTAGTCGAGTTGCAGACTACAATCCGAACTGAGACGTTATTTCTGGGATTTGCTCA
ACATCACTGTCTCGCTTCCCTTTGTTTACGCCATTGTAGCACGTGTGTAGCCCAAATCAT
AAGGGGCATGATGATTTGACGTCATCCCCGCCTTCCTCCGGGTTATCCCCGGCAGTCTCC
CTAGAGTGCCCAGCTCTACCTGCTGGCTACTAAGGATAAGGGTTGCGCTCGTTGCGGGAC
TTAACCCAACATCTCACGACACGAGCTGACGACAACCATGCACCACCTGTCTCCAATGCT
CCGAAGAGAATGCCCCGTTACGGACACGTCATTGGGATGTCAAGACTTGGTAAGGTTCTT
CGCGTTGCTTCGAATTAAACCACATGCTCCACCGCTTGTGCGGGTCCCCGTCAATTCCTT
TGAGTTTCATTCTTGCGAACGTACTCCCCAGGTGGATTGCTTATTGCGTTAGCTGCGGCA
CCGATGGGTCCATACCCACCTACACCTAGCAATCATCGTTTACCGCGTGGACTACCAGGG
TATCTAATCCTGTTTGCTCCCCACGCTTTCGAGCCTCAACGTCAGTTACAGTCCAGTAAG
CCGCCTTCGCCACTGGTGTTCCTCCTAATATCTACGCATTTCACCGCTACACTAGGAATT
CCGCTTACCTCTCCTGCACTCCAGCCTGGCAGTTCCAAATGCAGTCCCAGGGTTGAGCCC
TGGGTTTTCACATCTGGCTTGTCATGCCGTCTACGCTCCCTTTACACCCAGTAAATCCGG
ATAACGCTTGCCCCCTACGTATTACCGCGGCTGCTGGCACGTAGTTAGCCGGGGCTTCTT
AGTCAGGTACCGTCATTTTCTTCCCTGCTGATAGAGCTTTACATACCGAAATACTTCTTC
ACTCACGCGGCGTCGCTGCATCAGGGTTTCCCCCATTGTGCAATATTCCCCACTGCTGCC
TCCCGTAGGAGTTTGGGCCGTGTCTCAGTCCCAATGTGGCCGTTCACCCTCTCAGGCCGG
CTACTGATCGTCGCTTTGGTAGGCCGTTACCCTGCCAACTGGCTAATCAGACGCGGGACC
ATCCTGTACCACCGGAGTTTTTCACACTGCCTCATGTGAAGCTGTGCGCTTATGCGGTAT
TAGCACCTATTTCTAAGTGTTATCCCCCGGTACAGGGCAGGTTTCCCACGCGTTACTCAC
CCGTCCGCCACTAAGTTACGCCGATTCCATCCGAAAACTTCCTCTGCATAACTCCGTCGA
CTG HMI_28 Blautia_producta 16S rDNA sequence (SEQ ID NO: 27)
CCGGTGGTCG CATCGGCGCT CCTCCTGTAG GTTGGGTCAC TGACTTCGGG
CGTTACTGAC TCCCATGGTG TGACGGGCGG TGTGTACAAG ACCCGGGAAC
GTATTCACCG CGACATTCTG ATTCGCGATT ACTAGCGATT CCAGCTTCGT
GCAGTCGAGT TGCAGACTGC AGTCCGAACT GGGACGTTAT TTTGGGATT
TGCTCAACAT CGCTGTCTCG CTTCCCTTTG TTTACGCCAT TGTAGCACGT
GTGTAGCCCA AATCATAAGG GGCATGATGA TTTGACGTCG TCCCCGCCTT
CCTCCGGGTT ATCCCCGGCA GTCTCCCTAG AGTGCCCAGC TTCACCTGCT
GGCTACTAAG GATAGGGGTT GCGCTCGTTG CGGGACTTAA CCCAACATCT
CACGACACGA GCTGACGACA ACCATGCACC ACCTGTCTCC TCTGCCCCGA
AGGGAAGGCC CCGTTACGGG CCGGTCAGAG GGATGTCAAG ACTTGGTAAG
GTTCTTCGCG TTGCTTCGAA TTAAACCACA TGCTCCACCG CTTGTGCGGG
TCCCCGTCAA TTCCTTTGAG TTTCATTCTT GCGAACGTAC TCCCCAGGTG
GAATACTTAT TGCGTTTGCT GCGGCACCGA ATGGGCTTTG CCACCCGACA
CCTAGTATTC ATCGTTTACG GCGTGGACTA CCAGGGTATC TAATCCTGTT
TGCTCCCCAC GCTTTCGAGC CTCAACGTCA GTTACCGTCC AGAAAGCCGC

```
CTTCGCCACT GGTGTTCCTC CTAATATCTA CGCATTTCAC CGCTACACTA

GGAATTCCGC TTACCTCTCC GGCACTCTAG AAAAACAGTT TCCAATGCAG

TCCTGGGGTT AAGCCCCAGC CTTTCACATC AGACTTGCTC TTCCGTCTAC

GCTCCCTTTA CACCCAGTAA ATCCGGATAA CGCTTGCCCC CTACGTATTA

CCGCGGCTGA TGGCACGTAG TTAGCCGGGG CTTCTTAGTC AGGTACCGTC

ATTTTCTTCC CTGCTGATAG AAGTTTACAT ACCGAGATAC TTCTTCCTTC

ACGCGGCGTC GCTGCATCAG GGTTTCCCCC ATTGTGCAAT ATTCCCCACT

GCTGCCTCCC GTAGGAGTCT GGGCCGTGTC TCAGTCCCAA TGTGGCCGTT

CACCCTCTCA GGCCGGCTAC TGATCGTCGC CTTGGTGGGC CGTTACCCCT

CCAACTAGCT AATCAGACGC GGGTCCATCT CATACCACCG GAGTTTTTCA

CACCAGACCA TGCGGTCCTG TGCGCTTATG CGGTATTAGC AGCCATTTCT

AACTGTTATC CCCCTGTATG AGGCAGGTTA CCCACGCGTT ACTCAGCCCG

TCCGCCGCTC AGTCAAATAA GTTTCAATCC GAAGAGATCC ACTTAAGTGC

TTCGCTCGAC TTGCATGTGT TAAGCACGCC GCCAGCGTTC ATCCT
```

HMI_29 *Blautia glucerasea* 16S rDNA sequence (SEQ ID NO: 28)

```
GCCTTCGGCAGCTCCGTCCTTTCGGTTCGGTCACTGACTTCGGGCGTTACTGACTCCCAT
GGTGTGACGGGCGGTGTGTACAAGACCCGGGAACGTATTCACCGCGGCATTCTGATCCGC
GATTACTAGCGATTCCAGCTTCGTGCAGTCGAGTTGCAGACTGCAGTCCGAACTGGGACG
TTATTTTTGGGATTTGCTTAAGCTCACACTCTCGCTTCCCTTTGTTTACGCCATTGTAGC
ACGTGTGTAGCCCAAATCATAAGGGGCATGATGATTTGACGTCATCCCCGCCTTCCTCCA
GGTTATCCCTGGCAGTCTCCTCAGAGTGCCCGGCCAAACCGCTGGCTACTAAGGATAGGG
GTTGCGCTCGTTGCGGGACTTAACCCAACATCTCACGACACGAGCTGACGACAACCATGC
ACCACCTGTCTCCGATGCTCCGAAGAAAAGGCGACGTTACTCGCCGGTCATAGGGATGTC
AAGACTTGGTAAGGTTCTTCGCGTTGCTTCGAATTAAACCACATGCTCCACCGCTTGTGC
GGGTCCCCGTCAATTCCTTTGAGTTTCATTCTTGCGAACGTACTCCCCAGGTGGAATACT
TACTGCGTTTGCTGCGGCACCGAATGGCTCTGCCACCCGACACCTAGTATTCATCGTTTA
CGGCGTGGACTACCAGGGTATCTAATCCTGTTTGCTCCCCACGCTTTCGAGCCTCAACGT
CAGTTACCGTCCAGTAAGCCGCCTTCGCCACTGGTGTTCCTCCTAATATCTACGCATTTC
ACCGCTACACTAGGAATTCCGCTTACCTCTCCGGTACTCAAGATCAACAGTTTCCAATGC
AGTCCGGGGGTTGAGCCCCGCCTTTCACATCAGACTTGCTGCTCCGTCTACGCTCCCTT
TACACCCAGTAAATCCGGATAACGCTTGCCCCCTACGTATTACCGCGGCTGCTGGCACGT
AGTTAGCCGGGGCTTCTTAGTCAGGTACCGTCATTTTCTTCCCTGCTGATAGAAGTTTAC
ATACCGAGATACTTCTTCCTTCACGCGGCGTCGCTGCATCAGGGTTTCCCCCATTGTGCA
ATATTCCCCACTGCTGCCTCCCGTAGGAGTCTGGGCCGTGTCTCAGTCCCAATGTGGCCG
TCCACCCTCTCAGGCCGGCTATGGATCGTCGCTTTGGTAGGCCGTTACCCTGCCAACTGG
CTAATCCAACGCGGGTCCATCTCACACCACCGGAGTTTTTCACACTGGATCATGCAATCC
CGTGCGCTTATGCGGTATTAGCAGTCATTTCTGACTGTTATCCCCCAGTGTGAGGCAGGT
TACCCACGCGTTACTCACCCGTCCGCCACTAGGATTATAACGACTTCAACCGAAGTCTCT
GTCAAAATAATCCCCGTTCGACTTGCATGTGT
```

HMI_30 *Clostridium_straminisolvens* 16S rDNA sequence (SEQ ID NO: 29)

AGCGGCGGACGGGTGAGTAACGCGTGAGTAACCTGCCTTTAGGAGGGGGACAACATTCCGAAAGGGATGCTAATA

CCGCATAAAATTATTGTATCGCATGGTATAATAATCAAAGATTTATCGCCTAAAGATGGACTCGCGTCCGATTAG

CTAGTTGGTGGGGTAAAAGCCTACCAAGGCGACGATCGGTAGCCGAACTGAGAGGTTGATCGGCCACATTGGGAC

TGAGACACGGCCCAGACTCCTACGGGAGGCAGCAGTGGGGATATTGCGCAATGGGGGAAACCCTGACGCAGCAA

CGCCGCGTGAAGGAAGAAGGCCTTCGGGTTGTAAACTTCTTTAAGTGTGGAAGATAATGACGGTACACACAGAAT

AAGCCACGGCTAACTACGTGCCAGCAGCCGCGGTAATACGTAGGTGGCAAGCGTTGTCCGGATTTACTGGGTGTA

AAGGGCGTGTAGGCGGGTAGACAAGTCAGATGTGAAATACCGGGGCTCAACTCCGGGGCTGCATTTGAAACTGTA

TATCTTGAGTGTCGGAGAGGAAAGCGGAATTCCTAGTGTAGCGGTGAAATGCGTAGATATTAGGAGGAACACCAG

TGGCGAAGGCGGCTTTCTGGACGATAACTGACGCTGAGGCGCGAAAGCGTGGGGAGCAAACAGGATTAGATACCC

TGGTAGTCCACGCCGTAAACGATGGATACTAGGTGTAGGAGGTATCGACCCCTTCTGTGCCGCAGTTAACACAAT

AAGTATCCCACCTGGGGAGTACGGTCGCAAGATTGAAACTCAAAGGAATTGACGGGGGCCCGCACAAGCAGTGGA

GTATGTGGTTTAATTCGAAGCAACGCGAAGAACCTTACCAGGACTTGACATCCCACGCATAGCCTAGAGATAGGT

GAAGTCCTACGGGACGTGGAGACAGGTGGTGCATGGTTGTCGTCAGCTCGTGTCGTGAGATGTTGGGTTAAGTCC

CGCAACGAGCGCAACCCTTACTGTCAGTTACCATCATTAAGTTGGGGACTCTGGCAGGACTGCCGGTGACAAATC

GGAGGAAGGTGGGGACGACGTCAAATCATCATGCCCCTTATGTCCTGGGCTACACACGTACTACAATGGCTGTTA

ACAAAGTGAAGCAAAGCAGTGATGTGGAGCAAAACACAAAAAGCAGTCTCAGTTCAGATTGTAGGCTGAAACTCG

CCTATATGAAGTCGGAATTGCTAGTAATCGCAGATCAGCATGCTGCGGTGAATACGTTCCCGGGCCTTGTACACA

CCGCCCGTCACACCATGAGAGTCGATAACACCCGAAGCCTGT

HMI_31 *Butyricoccus_pullicaecorum* 16S rDNA sequence (SEQ ID NO: 30)

AGTGGCGGACGGGTGAGTAACGCGTGAGCAATCTGCCTTTAAGAGGGGGATAACAGTCGGAAACGGCTGCTAATA

CCGCATAAAGCATCGAAACCGCATGATTTTGATGCCAAAGGAGCAATCCGCTTTTAGATGAGCTCGCGTCTGATT

AGCTGGTTGGCGGGGTAACGGCCCACCAAGGCGACGATCAGTAGCCGGACTGAGAGGTTGAACGGCCACATTGGG

ACTGAGACACGGCCCAGACTCCTACGGGAGGCAGCAGTGGGGAATATTGCGCAATGGGGGAAACCCTGACGCAGC

AACGCCGCGTGATTGAAGAAGGCCTTCGGGTTGTAAAGATCTTTAATCAGGGACGAAACAAATGACGGTACCTGA

AGAATAAGCTCCGGCTAACTACGTGCCAGCAGCCGCGGTAATACGTAGGGAGCAAGCGTTATCCGGATTTACTGG

GTGTAAAGGGCGCGCAGGCGGGCCGGTAAGTTGGAAGTGAAATCTATGGGCTTAACCCATAAACTGCTTTTCAAA

CTGCTGGTCTTGAGTGATGGAGAGGCAGGCGGAATTCCGTGTGTAGCGGTGAAATGCGTAGATATACGGAGGAAC

ACCAGTGGCGAAGGCGGCCTGCTGGACATTAACTGACGCTGAGGCGCGAAAGCGTGGGGAGCAAACAGGATTAGA

TACCCTGGTAGTCCACGCCGTAAACGATGGATACTAGGTGTGGGAGGTATTGACCCCTTCCGTGCCGCAGTTAAC

ACAATAAGTATCCCACCTGGGGAGTACGGCCGCAAGGTTGAAACTCAAAGGAATTGACGGGGGCCCGCACAAGCA

GTGGAGTATGTGGTTTAATTCGAAGCAACGCGAAGAACCTTACCAGGTCTTGACATCCCGATGACCGCCTCAGAG

ATGAGCCTTTTCTTCGGAACATCGGTGACAGGTGGTGCATGGTTGTCGTCAGCTCGTGTCGTGAGATGTTGGGTT

AAGTCCCGCAACGAGCGCAACCCTTACGGTTAGTTGATACGCAAGATCACTCTAGCCGGACTGCCGTTGACAAAA

CGGAGGAAGGTGGGGACGACGTCAAATCATCATGCCCCTTATGACCTGGGCTACACACGTACTACAATGGCAGTC

ATACAGAGGGAAGCAAAACCGCGAGGTGGAGCAAATCCCTAAAAGCTGTCCCAGTTCAGATTGCAGGCTGCAACC

CGCCTGCATGAAGTCGGAATTGCTAGTAATCGCGGATCAGCATGCCGCGGTGAATACGTTCCCGGGCCTTGTACA

CACCGCCCGTCACACCATGAGAGCCGTCAATACCCGAAGTCCGT

HMI_32 *Clostridium_maritium* 16S rDNA sequence (SEQ ID NO: 31)

CTACACTGCA GTCGAGCGAT TTCTTCGGTA AGAGCGGCGG ACGGGTGAGT

AACGCGTGGG TAACCTGCCC TATACACACG GATAACATAC CGAAAGGTAT

```
GCTAATACGA GATAACATAA GAGATTCGCA TGGATTTCTT ATCAAAGCTT
TTGCGGTATA GGATGGACCC GCGTCTGATT AGCTAGTTGG TAAGGTAACG
GCTTACCAAG GCGACGATCA GTAGCCGACC TGAGAGGGTG ATCGGCCACA
TTGGAACTGA GACACGGTCC AAACTCCTAC GGGAGGCAGC AGTGGGGAAT
ATTGCACAAT GGGCGAAAGC CTGATGCAGC AACGCCGCGT GAGCGATGAA
GGCCTTCGGG TCGTAAAGCT CTGTCCTCAA GGAAGATAAT GACGGTACTT
GAGGAGGAAG CCCCGGCTAA CTACGTGCCA GCAGCCGCGG TAATACGTAG
GGGGCTAGCG TTATCCGGAA TTACTGGGCG TAAAGGGTGC GTAGGTGGTT
TCTTAAGTCA GAGGTGAAAG GCTACGGCTC AACCGTAGTA AGCCTTTGAA
ACTGAGAAAC TTGAGTGCAG GAGAGGAGAG TAGAATTCCT AGTGTAGCGG
TGAAATGCGT AGATATTAGG AGGAATACCA GTTGCGAAGG CGGCTCTCTG
GACTGTAACT GACACTGAGG CACGAAAGCG TGGGGAGCAA ACAGGATTAG
ATACCCTGGT AGTCCACGCC GTAAACGATG AGTACTAGCT GTCGGAGGTT
ACCCCCTTCG GTGGCGCAGC TAACGCATTA AGTACTCCGC C
```

HMI_33 *Eubacterium fissicatens* 16S rDNA sequence (SEQ ID NO: 32)

```
AGTGGCGGAC GGGTGAGTAA CGCGTGGGTA ACCTGCCTTG TACAGGGGGA
TAACAGTTAG AAATGACTGC TAATACCGCA TAAGCGCACA GTATCGCATG
GTACAGTGTG AAAAACTCCG GTGGTACAAG ATGGACCCGC GTCTGATTAG
CTAGTTGGTA AGGTAACGGC TTACCAAGGC AACGATCAGT AGCCGACTTG
AGAGAGTGAT CGGCCACATT GGGACTGAGA CACGGCCCAA ACTCCTACGG
GAGGCAGCAG TGGGGAATAT TGCACAATGG GGGAAACCCT GATGCAGCGA
CGCCGCGTGA GTGAAGAAGT ATTTCGGTAT GTAAAACTCT ATCAGCAAGG
AAGATAATGA CGGTACTTGA CTAAGAAGCC CCGGCTAACT ACGTGCCAGC
AGCCGCGGTA ATACGTAGGG GGCAAGCGTT ATCCGGATTT ACTGGGTGTA
AAGGGAGCGT AGACGGTATG GTAAGTCAGA TGTGAAAGCC CGGGGCTTAA
CCCCGGAACT GCATTTGAAA CTATCAAACT AGAGTGTCGG AGAGGTAAGT
GGAATTCCTA GTGTAGCGGT GAAATGCGTA GATATTAGGA GGAACACCAG
TGGCGAAGGC GGCTTACTGG ACGATAACTG ACGTTGAGGC TCGAAAGCGT
GGGGAGCAAA CAGGATTAGA TACCCTGGTA GTCCACGCCG TAAACGATGA
ATACTAGGTG TCAGGGAACA ATAGTTCTTT GGTGCCGCAG CAAACGCATT
AAGTATTCCA CCTGGGGAGT ACGTTCGCAA GAATGAAACT CAAAGGAATT
GACGGGGACC CGCACAAGCG GTGGAGCATG TGGTTTAATT CGAAGCAACG
CGAAGAACCT TACCTGGTCT TGACATCCCA ATGACGCCTC TTTAATCGGA
GGTTTCCTTC GGGACATTGG AGACAGGTGG TGCATGGTTG TCGTCAGCTC
GTGTCGTGAG ATGTTGGGTT AAGTCCCGCA ACGAGCGCAA CCCTTATCTT
TAGTAGCCAG CAGTTCGGCT GGGCACTCTA GAGAGACTGC CAGGGATAAC
CTGGAGGAAG GTGGGGATGA CGTCAAATCA TCATGCCCCT TATGACCAGG
GCTACACACG TGCTACAATG GCGTAAACAA AGGGAAGCAA AACTGTGAGG
TTGAGCAAAT CCCAAAAATA ACGTCTCAGT TCGGATTGTA GTCTGCAACT
CGACTACATG AAGCTGGAAT CGCTAGTAAT CGCAGATCAG AATGCTGCGG
```

```
TGAATACGTT CCCGGGTCTT GTACACACCG CCCGTCACAC CATGGGAGTC

GGATATGCCC GAAGTCAGTG ACCCAACCGT AAGGAGGGAG CTGCCGAAGG

TGGAGCCGAT AACTGGGGTG AAGTCGT
```

HMI_34 *Clostridium_saccharolyticum* 16S rDNA sequence    (SEQ ID NO: 33)

```
AGCGGCGGAC GGGTGAGTAA CGCGTGGGTA ACCTGCCTCA TACAGGGGGA

TAACAGTTAG AAATGACTGC TAATACCGCA TAAGCGCACA GTGCTGCATG

GCACAGTGTG AAAAACTCCG GTGGTATGAG ATGGACCCGC GTTGGATTAG

GCAGTTGGCG GGGTAACGGC CCACCAAACC GACGATCCAT AGCCGGCCTG

AGAGGGTGAA CGGCCACATT GGGACTGAGA CACGGCCCAA ACTCCTACGG

GAGGCAGCAG TGGGGAATAT TGCACAATGG GGGAAACCCT GATGCAGCGA

CGCCGCGTGA GTGAAGAAGT AATTCGTTAT GTAAAGCTCT ATCAGCAGGG

AAGAAAATGA CGGTACCTGA CTAAGAAGCC CCGGCTAACT ACGTGCCAGC

AGCCGCGGTA ATACGTAGGG GGCAAGCGTT ATCCGGATTT ACTGGGTGTA

AAGGGAGCGT AGACGGCCGT GCAAGTCTGA TGTGAAAGGC TGGGGCTCAA

CCCCGGGACT GCATTGGAAA CTGTATGGCT GGAGTGCCGG AGAGGTAAGC

GGAATTCCTA GTGTAGCGGT GAAATGCGTA GATATTAGGA GGAACACCAG

TGGCGAAGGC GGCTTACTGG ACGGTAACTG ACGTTGAGGC TCGAAAGCGT

GGGGAGCAAA CAGGATTAGA TACCCTGGTA GTCCACGCCG TAAACGATGA

TTACTAGGTG TTGGGGGACA TGGTCCTTCG GTGCCGCCGC AAACGCAGTA

AGTAATCCAC CTGGGGAGTA CGTTCGCAAG AATGAAACTC AAAGGAATTG

ACGGGGACCC GCACAAGCGG TGGAGCATGT GGTTTAATTC GAAGCAACGC

GAAGAACCTT ACCAAGTCTT GACATCGAGA GGACAGAGTA TGTAATGTAC

TTTCCCTTCG GGGCCTCGAA GACAGGTGGT GCATGGTTGT CGTCAGCTCG

TGTCGTGAGA TGTTGGGTTA AGTCCCGCAA CGAGCGCAAC CCCTATCTTC

AGTAGCCAGC AATTCGGATG GCACTCTGG AGAGACTGCC GGGATAACC

CGGAGGAAGG CGGGGATGAC GTCAAATCAT CATGCCCCTT ATGACTTGGG

CTACACACGT GCTACAATGG CGTAAACAAA GGGAAGCGAG GGAGTGATCC

GGAGCAAATC CCAAAAATAA CGTCTCAGTT CGGATTGTAG TCTGCAACTC

GACTACATGA AGCTGGAATC GCTAGTAATC GCGAATCAGC ATGTCGCGGT

GAATACGTTC CCGGGTCTTG TACACACCGC CCGTCACACC ATGGGAGTCG

ATAACGCCCG AAGTCAGTGA CCCAACCGAA AGGAGGGAGC TGCCGAAGGC

GGGATTGGTA ACTGGGGTGA AGTCGT
```

HMI_35 *Blautia_luti* 16S rDNA sequence    (SEQ ID NO: 34)

```
AGTGGCGGAC GGGTGAGTAA CGCGTGGGTA ACCTGCCTTA TACTGGGGGA

TAACAGCCAG AAATGGCTGC TAATACCGCA TAAGCGCACG GGGCCGCATG

GTCCTGTGTG AAAAACTCCG GTGGTATAAG ATGGACCCGC GTTGGATTAG

CTAGTTGGCA GGGCAGCGGC CTACCAAGGC GACGATCCAT AGCCGGCCTG

AGAGGGTGAA CGGCCACATT GGGACTGAGA CACGGCCCAG ACTCCTACGG

GAGGCAGCAG TGGGGAATAT TGCACAATGG GGGAAACCCT GATGCAGCGA

CGCCGCGTGA AGGAAGAAGT ATCTCGGTAT GTAAACTTCT ATCAGCAGGG

AAGATAATGA CGGTACCTGA CTAAGAAGCC CCGGCTAACT ACGTGCCAGC
```

-continued

```
AGCCGCGGTA ATACGTAGGG GGCGAGCGTT ATCCGGATTT ACTGGGTGTA

AAGGGAGCGT AGACGGCGTA TCAAGTCTGA TGTGAAAGGC AGGGGCTTAA

CCCCTGGACT GCATTGGAAA CTGGTATGCT TGAGTGCCGG AGGGGTAAGC

GGAATTCCTA GTGTAGCGGT GAAATGCGTA GATATTAGGA GGAACACCAG

TGGCGAAGGC GGCTTACTGG ACGGTAACTG ACGTTGAGGC TCGAAAGCGT

GGGGAGCAAA CAGGATTAGA TACCCTGGTA GTCCACGCCG TAAACGATGA

ATACTAGGTG TCTGGGAGCA CAGCTCTTAG GTGCCGCCGC AAACGCATTA

AGTATTCCAC CTGGGGAGTA CGTTCGCAAG AATGAAACTC AAAGGAATTG

ACGGGGACCC GCACAAGCGG TGGAGCATGT GGTTTAATTC GAAGCAACGC

GAAGAACCTT ACCAAATCTT GACATCCCTC TGACAGAGTA TGTAATGTAC

TTTTCCTTCG GGACAGGGGA GACAGGTGGT GCATGGTTGT CGTCAGCTCG

TGTCGTGAGA TGTTGGGTTA AGTCCCGCAA CGAGCGCAAC CCCTATCCTT

AGTAGCCAGC AAGTAATGTT GGGCACTCTG AGGAGACTGC CAGGGATAAC

CTGGAGGAAG GCGGGGATGA CGTCAAATCA TCATGCCCCT TATGATTTGG

GCTACACACG TGCTACAATG GCGTAAACAA AGGGAAGCGA ACCTGTGAGG

GTGGGCAAAT CTCAAAAATA ACGTCCCAGT TCGGACTGCA GTCTGCAACT

CGACTGCACG AAGCTGGAAT CGCTAGTAAT CGCGGATCAG AATGCCGCGG

TGAATACGTT CCCGGGTCTT GTACACACCG CCCGTCACAC CATGGGAGTC

AGTAACGCCC GAAGTCAGTG ACCTAACCGT AAGGAAGGAG CTGCCGAAGG

CGGGACGGAT GACTGGGGTG AAGTCGT

HMI_36 Clostridium_methylpentosum 16S rDNA sequence                    (SEQ ID NO: 35)
GGTTACCTTGTTACGACTTCACCCCAATCATCAACCCCACCTTCGACGACGTCCCCCTTG

CGGTTAGACTATCGGCTTCGGGTGTTGCCAACTCTCATGGTGTGACGGGCGGTGTGTACA

AGGCCCGGGAACGTATTCACCGCGGCATGCTGATCCGCGATTACTAGCAATTCCGGCTTC

ATGCAGGCGGGTTGCAGCCTGCAATCCGAACTGAGACTATTTTTAGGGGTTTGCTCCATG

TCACCATCTTGCTTCCCTCTGTTAATAGCCATTGTAGTACGTGTGTAGCCCAGGTCATAA

GGGGCATGATGATTTGACGTCATCCCCACCTTCCTCCGTTTTGTCAACGGCAGTCCGTCT

AGAGTGCTCTTGCGTAGCAACTAAACGTAAGGGTTGCGCTCGTTGCGGGACTTAACCCAA

CATCTCACGACACGAGCTGACGACAACCATGCACCACCTGTCTCGGTGCCCCGAAGGGCT

TCACCTATCTCTAGGCTATGCACCGGATGTCAAGACCTGGTAAGGTTCTTCGCGTTGCTT

CGAATTAAACCACATACTCCACTGCTTGTGCGGGCCCCCGTCAATTCCTTTGAGTTTCAA

CCTTGCGGTCGTACTCCCCAGGTGGATTACTTATTGTGTTAACTCCGGCACGGAAGGGGT

CAGTCCCCCCACACCTAGTAATCATCGTTTACAGCGTGGACTACCAGGGTATCTAATCCT

GTTTGCTACCCACGCTTTCGAGCCTCAGCGTCAGTTAAAGCCCAGCAGGCCGCCTTCGCC

ACTGGTGTTCCTCCTAATATTTACGCATTTCACCGCTACACTAGGAATTCCGCCTGCCTC

TACTTCACTCAAGAACTGCAGTTTTGAACGCGGCTATGGGTTGAGCCCATAGATTTAACA

TTCAACTTGCAATCCCGCCTACGCTCCCTTTACACCCAGTAATTCCGGACAACGCTCGCT

ACCTACGTATTACCGCGGCTGCTGGCACGTAGTTAGCCGTAGCTTCCTCCTTGGTTACCG

TCATTATCTTCACCAAGGACAGAGGTTTACAATCCGAAAACCTTCTTCCCTCACTCGGCG

TCGCTGCATCAGGGTTTCCCCCATTGTGCAATATTCCCCACTGCTGCCTCCCGTAGGAGT
```

-continued

```
CTGGGCCGTGTCTCAGTCCCAATGTGGCCGTTCAACCTCTCAGTCCGGCTACCAATCGTC

GCCTTGGTGGGCCGTTACCTCACCAACTAGCTAATTGGACGCGAGTCCATCTTTCAGCGG

ATTGCTCCTTTGATATCAGCTCCATGCGAAACCAATATGTTATGCGGTATTAGCGTCCGT

TTCCAGACGTTATCCCCCTCTGAAAGGCAGGTTACTCACGCGTTACTCACCCGTCCGCCA

CTAAGTTGAATCAAATTCCTTCCGAAGAATTCATTCAAAGCAACTTCGTCGACTTGCATG

TGTAAGGCGCGCCGACAGCGTTCGT
```

HMI_37 *Clostridium_xylanolyticum* 16S rDNA sequence (SEQ ID NO: 36)

```
AGAGTTTGATCCTGGCTCAGGATGAACGCTGGCGGCGTGCCTAACACATGCAAGTCGAAC

GGAATTTACATGAAGCCTAGCGATTGTAAATTTAGTGGCGGACGGGTGAGTAACGCGTGG

GTAACCTGCCTTGTACTGGGGGACAACAGTTGGAAACGACTGCTAATACCGCATAAGCGC

ACAGCTTCGCATGAAGCAGTGTGAAAAACTCCGGTGGTACAAGATGGACCCGCGTCTGAT

TAGCTGGTTGGTGAGGTAACGGCCCACCAAGGCGACGATCAGTAGCCGGCCTGAGAGGGT

GAACGGCCACATTGGGACTGAGACACGGCCCAAACTCCTACGGGAGGCAGCAGTGGGGAA

TATTGCACAATGGGGGAAACCCTGATGCAGCAACGCCGCGTGAGTGAAGAAGTATTTCGG

TATGTAAAGCTCTATCAGCAGGAAAGAAAATGACGGTACCTGACTAAGAAGCCCCGGCTA

ACTACGTGCCAGCAGCCGCGGTAATACGTAGGGGGCAAGCGTTATCCGGATTTACTGGGT

GTAAAGGGAGCGTAGACGGTTTTGCAAGTCTGAAGTGAAAGCCCGGGGCTTAACCCCGGG

ACTGCTTTGGAAACTGTAGGACTAGAGTGCAGGAGAGGTAAGTGGAATTCCTAGTGTAGC

GGTGAAATGCGTAGATATTAGGAGGAACACCAGTGGCGAAGGCGGCTTACTGGACTGTAA

CTGACGTTGAGGCTCGAAAGCGTGGGGAGCAAACAGGATTAGATACCCTGGTAGTCCACG

CCGTAAACGATGATTACTAGGTGTTGGTGGGTACGACCCATCGGTGCCGCAGCAAACGCA

ATAAGTAATCCACCTGGGGAGTACGTTCGCAAGAATGAAACTCAAAGGAATTGACGGGGA

CCCGCACAAGCGGTGGAGCATGTGGTTTAATTCGAAGCAACGCGAAGAACCTTACCTGGT

CTTGACATCCCTATGAATAACGGGCAATGCCGTTAGTACTTCGGTACATAGGAGACAGGT

GGTGCATGGTTGTCGTCAGCTCGTGTCGTGAGATGTTGGGTTAAGTCCCGCAACGAGCGC

AACCCTTATCTTTAGTAGCCAGCAGTAAGATGGGCACTCTAGAGAGACTGCCGGGGATAA

CCCGGAGGAAGGTGGGGATGACGTCAAATCATCATGCCCCTTATGACCAGGGCTACACAC

GTGCTACAATGGCGTAAACAAAGAGAAGCGAAGTCGTGAGGCAGAGCGAATCTCAAAAAT

AACGTCTCAGTTCGGATTGTAGTCTGCAACTCGACTACATGAAGCTGGAATCGCTAGTAA

TCGCAGATCAGAATGCTGCGGTGAATACGTTCCCGGGTCTTGTACACACCGCCCGTCACA

CCATGGGAGTCGGAAATGCCCGAAGTCGGTGACCTAACCGAA
```

HMI_38 *Oscillibacter_valericigenes* 16S rDNA sequence (SEQ ID NO: 37)

```
CTCAGGACGAACGCTGGCGGCGTGCTTAACACATGCAAGTCGAACGGAGCACCCTTGACT

GAGGTTTCGGCCAAATGATAGGAATGCTTAGTGGCGGACTGGTGAGTAACGCGTGAGGAA

CCTACCTTCCAGAGGGGGACAACAGTTGGAAACGACTGCTAATACCGCATGACGCATGAC

CGGGGCATCCCGGGCATGTCAAAGATTTTATCGCTGGAAGATGGCCTCGCGTCTGATTAG

CTAGATGGTGGGGTAACGGCCCACCATGGCGACGATCAGTAGCCGGACTGAGAGGTTGAC

CGGCCACATTGGGACTGAGATACGGCCCAGACTCCTACGGGAGGCAGCAGTGGGGAATAT

TGGGCAATGGACGCAAGTCTGACCCAGCAACGCCGCGTGAAGGAAGAAGGCTTTCGGGTT

GTAAACTTCTTTTGTCAGGGAAGAGTAGAAGACGGTACCTGACGAATAAGCCACGGCTAA

CTACGTGCCAGCAGCCGCGGTAATACGTAGGTGGCAAGCGTTGTCCGGATTTACTGGGTG
```

```
TAAAGGGCGTGCAGCCGGGCCGGCAAGTCAGATGTGAAATCTGGAGGCTTAACCTCCAAA

CTGCATTTGAAACTGTAGGTCTTGAGTACCGGAGAGGTTATCGGAATTCCTTGTGTAGCG

GTGAAATGCGTAGATATAAGGAAGAACACCAGTGGCGAAGGCGGATAACTGGACGGCAAC

TGACGGTGAGGCGCGAAAGCGTGGGGAGCAAACAGGATTAGATACCCTGGTAGTCCACGC

TGTAAACGATGGATACTAGGTGTGCGGGGACTGACCCCCTGCGTGCCGCAGTTAACACAA

TAAGTATCCCACCTGGGGAGTACGATCGCAAGGTTGAAACTCAAAGGAATTGACGGGGGC

CCGCACAAGCGGTGGATTATGTGGTTTAATTCGAAGCAACGCGAAGAACCTTACCAGGGC

TTGACATCCTACTAACGAAGTAGAGATACATCAGGTGCCCTTCGGGGAAAGTAGAGACAG

GTGGTGCATGGTTGTCGTCAGCTCGTGTCGTGAGATGTTGGGTTAAGTCCCGCAACGAGC

GCAACCCCTATTGTTAGTTGCTACGCAAGAGCACTCTAGCGAGACTGCCGTTGACAAAAC

GGAGGAAGGTGGGGACGACGTCAAATCATCATGCCCCTTATGTCCTGGGCTACACACGTA

ATACAATGGCGGTCAACAGAGGGAGGCAAAGCCGCGAGGCAGAGCAAACCCCCAAAAGCC

GTCCCAGTTCGGATCGCAGGCTGCAACCCGCCTGCGTGAAGTCGGAATCGCTAGTAATCG

CGGATCAGCATGCCGCGGTGAATACGTTCCCGGGCCTTGTACACACCGCCCGTCACACCA

TGAGAGTCGGGAACACCCGAAGTCCGTAGCCTAACCGCAAGGAGGGCGCGGCCGAAGGTG

GGTTCGATAATTGGGGTGAAGTCGTAACAAGGTAACCG
```

HMI_39 *Ruminococcus_obeum* 16S rDNA sequence (SEQ ID NO: 38)

```
AGTCGAACGGGAACCTTTTATTGAAGCTTCGGCAGATTTAGCTGGTTTCTAGTGGCGGAC

GGGTGAGTAACGCGTGGGTAACCTGCCCTATACAGGGGGATAACAACCAGAAATGGTTGC

TAATACCGCATAAGCGCACAGGACCGCATGGTCCGGTGTGAAAAACTCCGGTGGTATAGG

ATGGACCCGCGTTGGATTAGCCAGTTGGCAGGGTAACGGCCTACCAAAGCGACGATCCAT

AGCCGGCCTGAGAGGGTGAACGGCCACATTGGGACTGAGACACGGCCCAGACTCCTACGG

GAGGCAGCAGTGGGGAATATTGCACAATGGGGGAAACCCTGATGCAGCGACGCCGCGTGA

AGGAAGAAGTATCTCGGTATGTAAACTTCTATCAGCAGGGAAGATAGTGACGGTACCTGA

CTAAGAAGCCCCGGCTAACTACGTGCCAGCAGCCGCGGTAATACGTAGGGGGCAAGCGTT

ATCCGGATTTACTGGGTGTAAAGGGAGCGTAGACGGATTAGCAAGTCTGATGTGAAAGGC

AGGGGCTCAACCCCTGGACTGCATTGGAAACTGCCAGTCTTGAGTGCCGGAGAGGTAAGC

GGAATTCCTAGTGTAGCGGTGAAATGCGTAGATATTAGGAGGAACACCAGTGGCGAAGGC

GGCTTACTGGACGGCAACTGACGTTGAGGCTCGAAAGCGTGGGGAGCAAACAGGATTAGA

TACCCTGGTAGTCCACGCCGTAAACGATGAATACTAGGTGTTGGGGAGCAAAGCTCTTCG

GTGCCGCCGCAAACGCATTAAGTATTCCACCTGGGGAGTACGTTCGCAAGAATGAAACTC

AAAGGAATTGACGGGACCCGCACAAGCGGTGGAGCATGTGGTTTAATTCGAAGCAACGC

GAAGAACCTTACCAAGTCTTGACATCCCTCTGACGGACTCTTAACCGAGTCTTTCCTTCG

GGACAGAGGAGACAGGTGGTGCATGGTTGTCGTCAGCTCGTGTCGTGAGATGTTGGGTTA

AGTCCCGCAACGAGCGCAACCCCTATCCCCAGTAGCCAGCATTTCGGATGGGCACTCTGA

GGAGACTGCCAGGGATAACCTGGAGGAAGGCGGGGATGACGTCAAATCATCATGCCCCTT

ATGATTTGGGCTACACACGTGCTACAATGGCGTAAACAAAGGGAAGCGAGCCTGCGAGGG

TAAGCAAATCCCAAAAATAACGTCCCAGTTCGGACTGCAGTCTGCAACTCGACTGCACGA

AGCTGGAATCGCTAGTAATCGCGGATCAGAATGCCGCGGTGAATACGTTCCCGGGTCTTG

TACACACCGCCCGTCACACCATGGGAGTCAGTAACGCCCGAAGTCAGTGACCTAACCGCA
```

```
                              -continued
AGGGAGGAGCTGCCGAAGGCGGGACCGATGACTGGGGTGAAGTCGTAACAAGGTAACCGT

GACTACACGAAGCTGGAATCGCTAGTAATCGCGGATCAGAATGCCGCGGTGAATACGTTCC

CGGGTCTTGTACACACCGCCCGTCACACCATGGGAGTCAGTAACGCCCGAAGTCAGTGACC

TAACCGCAAGGAAGGAGCTGCCGAAGGCGGGACCGATGACTGGGGTGAAGTCGTAACA
```

HMI_40 *Megasphaera elsdenii* 16S rDNA sequence (SEQ ID NO: 39)

```
ACGCGTAAGCAACCTGCCCTCCGGATGGGGACAACAGCTGGAAACGGCTGCTAATACCGA

ATACGTTTCCATTGCCGCATGGCAGTGGGAAGAAAGGTGGCCTCTGAATATGCTACCGCC

GGGGGAGGGGCTTGCGTCTGATTAGCTAGTTGGAGGGGTAACGGCCCACCAAGGCGACGA

TCAGTAGCCGGTCTGAGAGGATGAACGGCCACATTGGAACTGAGACACGGTCCAGACTCC

TACGGGAGGCAGCAGTGGGGAATCTTCCGCAATGGGCGAAAGCCTGACGGAGCAACGCCG

CGTGAGCGAAGACGGCCTTCGGGTTGTAAAGCTCTGTTATACGGGACGAACGGCTAGTGT

GCCAATACCACATTAGAATGACGGTACCGTAAGAGAAAGCCACGGCTAACTACGTGCCAG

CAGCCGCGGTAATACGTAGGTGGCAAGCGTTGTCCGGAATTATTGGGCGTAAAGGGCGCG

CAGGCGGTTTCATAAGTCTGTCTTAAAAGTGCGGGGCTTAACCCCGTGAGGGGACGGAAA

CTGTGAGACTGGAGTGTCGGAGAGGAAAGCGGAATTCCTAGTGTAGCGGTGAAATGCGTA

GATATTAGGAGGAACACCAGTGGCGAAAGCGGCTTTCTGGACGACAACTGACGCTGAGGC

GCGAAAGCCAGGGGAGCGAACGGGATTAGATACCCCGGTAGTCCTGGCCGTAAACGATGG

ATACTAGGTGTAGGGGGTATCGACCCCTCCTGTGCCGGAGTTAACGCAATAAGTATCCCG

CCTGGGGAGTACGGCCGCAAGGCTGAAACTCAAAGGAATTGACGGGGGCCCGCACAAGCG

GTGGAGTATGTGGTTTAATTCGACGCAACGCGAAGAACCTTACCAAGCCTTGACATTGAG

TGCTATCCTCAGAGATGAGGAGTTCTTCTTCGGAAGACGCGAAAACAGGTGGTGCACGGC

TGTCGTCAGCTCGTGTCGTGAGATGTTGGGTTAAGTCCCGCAACGAGCGCAACCCCTATC

TTCTGTTGCCAGCGCGTCATGGCGGGGACTCAGGAGAGACTGCCGCAGACAATGCGGAGG

AAGGCGGGGATGACGTCAAGTCATCATGCCCCTTATGGCTTGGGCTACACACGTACTACA

ATGGCTCTTAATAGAGGGAAGCGAAGGAGCGATCCGGAGCAAACCCCAAAAACAGAGTCC

CAGTTCGGATTGCAGGCTGCAACCCGCCTGCATGAAGCAGGAATCGCTAGTAATCGCAGG

TCAGCATACTGCGGTGAATACGTTCCCGGGCCTTGTACACACCGCCCGTCACACCACGAA

AGTCATTCACACCCGAAGCCGGTGAGGTAACCGTAAGGAGCCAGCCGTCGAAGGTGGGGG

CGATGATTGGGGTGAAGTCGTAA
```

HMI_41 *Blautia_luti* 16S rDNA sequence (SEQ ID NO: 40)

```
GGTGAGTAACGCGTGGGTAACCTGCCTTATACAGGGGGATAACAGTCAGAAATGGCTGCT

AATACCGCATAAGCGCACAGGGCCGCATGGCCCGGTGTGAAAAACTGAGGTGGTATAAGA

TGGACCCGCGTTGGATTAGCCAGTTGGCAGGGTAACGGCCTACCAAAGCGACGATCCATA

GCCGGCCTGAGAGGGTGAACGGCCACATTGGGACTGAGACACGGCCCAGACTCCTACGGG

AGGCAGCAGTGGGGAATATTGCACAATGGGGGAAACCCTGATGCAGCGACGCCGCGTGAA

GGAAGAAGTATCTCGGTATGTAAACTTCTATCAGCAGGGAAGAAAATGACGGTACCTGAC

TAAGAAGCCCCGGCTAACTACGTGCCAGCAGCCGCGGTAATACGTAGGGGGCAAGCGTTA

TCCGGATTTACTGGGTGTAAAGGGAGCGTAGACGGCATAACAAGTCTGATGTGAAAGGCT

GGGGCTTAACCCCGGGACTGCATTGGAAACTGTTAAGCTTGAGTGCCGGAGGGGTAAGCG

GAATTCCTAGTGTAGCGGTGAAATGCGTAGATATTAGGAGGAACACCAGTGGCGAAGGCG

GCTTACTGGACGGTAACTGACGTTGAGGCTCGAAAGCGTGGGGAGCAAACAGGATTAGAT
```

-continued

```
ACCCTGGTAGTCCACGCCGTAAACGATGAATACTAGGTGTCGGGGAGCACAGCTCTTCGG

TGCCGCCGCAAACGCATTAAGTATTCCACCTGGGGAGTACGTTCGCAAGAATGAAACTCA

AAGGAATTGACGGGGACCCGCACAAGCGGTGGAGCATGTGGTTTAATTCGAAGCAACGCG

AAGAACCTTACCAAGTCTTGACATCTGCCTGACCGGTGAGTAACGTCACCTTTCCTTCGG

GACAGGCAAGACAGGTGGTGCATGGTTGTCGTCAGCTCGTGTCGTGAGATGTTGGGTTAA

GTCCCGCAACGAGCGCAACCCCTATCCCCAGTAGCCAGCATGTAAAGGTGGGCACTCTGA

GGAGACTGCCAGGGATAACCTGGAGGAAGGTGGGGATGACGTCAAATCATCATGCCCCTT

ATGATTTGGGCTACACACGTGCTACAATGGCGTAAACAGAGGGAAGCGAAAGGGTGACCT

GGAGCAAATCCCAAAAATAACGTCCCAGTTCGGACTGTAGTCTGCAACCCGACTACACGA

AGCTGGAATCGCTAGTAATCGCGGATCAGAATGCCGCGGTGAATACGTTCCCGGGTCTTG

TACACACCGCCCGTCACACCATGGGAGTCAGTAACGCCCGAAGTCAGTGACCTAACCGAA

AGGGAGGAGCTGCCGAAGGCGGGACGGATGACTGGGGTGAAGTCGTAAC
```

HMI_42 *Bacteroides coprocola* 16S rDNA sequence (SEQ ID NO: 41)

```
GTATCCAACCTTCCGTTTACTCAGGGATAGCCTTTCGAAAGAAAGATTAATACCTGATAG

TATGGTAAGATTGCATGATAATACCATTAAAGATTCATCGGTAAACGATGGGGATGCGTT

CCATTAGGTAGTAGGCGGGGTAACGGCCCACCTAGCCGACGATGGATAGGGGTTCTGAGA

GGAAGGTCCCCCACATTGGAACTGAGACACGGTCCAAACTCCTACGGGAGGCAGCAGTGA

GGAATATTGGTCAATGGGCGAGAGCCTGAACCAGCCAAGTAGCGTGAAGGATGAAGGTTC

TATGGATTGTAAACTTCTTTTATAAGGGAATAAAGTGCTTTACGTGTAGAGTTTTGTATG

TACCTTATGAATAAGCATCGGCTAACTCCGTGCCAGCAGCCGCGGTAATACGGAGGATGC

GAGCGTTATCCGGATTTATTGGGTTTAAAGGGAGCGTAGACGGGATGTTAAGTCAGCTGT

GAAAGTTTGGGGCTCAACCTTAAAATTGCAGTTGAAACTGGCGTTCTTGAGTGCGGTAGA

GGCAGGCGGAATTCGTGGTGTAGCGGTGAAATGCTTAGATATCACGAAGAACCCCGATTG

CGAAGGCAGCTTGCTGGAGCGTAACTGACGTTGATGCTCGAAAGTGTGGGTATCAAACAG

GATTAGATACCCTGGTAGTCCACACGGTAAACGATGGATACTCGCTGTTGGCGATATACG

GTCAGCGGCCAAGCGAAAGCATTAAGTATCCCACCTGGGGAGTACGCCGGCAACGGTGAA

ACTCAAAGGAATTGACGGGGGCCCGCACAAGCGGAGGAACATGTGGTTTAATTCGATGAT

ACGCGAGGAACCTTACCCGGGCTTAAATTATGCATGAATGATCTGGAGACAGATCAGCCG

CAAGGCATGTATGAAGGTGCTGCATGGTTGTCGTCAGCTCGTGCCGTGAGGTGTCGGCTT

AAGTGCCATAACGAGCGCAACCCTTTCTGCCAGTTACTAACAGGCAATGCTGAGGACTCT

GGCGGTACTGCCATCGTAAGATGTGAGGAAGGTGGGGATGACGTCAAATCAGCACGGCCC

TTACGTCCGGGGCTACACACGTGTTACAATGGGGGGTACAGAAGGCAGCTTACCGGCGAC

GGTTGGCCAATCCCTAAAGCCCCTCTCAGTTCGGACTGGAGTCTGCAACCCGACTCCACG

AAGCTGGATTCGCTAGTAATCGCGCATCAGCCACGGCGCGGTAATACGTTCCCGGGCCT

TGTACACACCGCCCGTCAAGCCATGAAAGCCGGGAGTACCTGAAGTGCGTAACCGCGAGG

AGCGCCCTAGGGTAACACTGGTAATTGGGGCTAAGTCGT
```

HMI_43 *Bacteroides plebius* 16S rDNA sequence (SEQ ID NO: 42)

```
GGGGCAGCATGAACTTAGCTTGCTAAGTTCGATGGCGACCGGCGCACCGTTGAGTAACGC

GTATCCAACCTTCCGTACACTCAGGAATAGCCTTTCGAAAGAAAGATTAATACCTGATGG

TATGATGGGATTGCATGAAATCATCATTAAAGATTCATCGGTGTACGATGGGGATGCGTT
```

-continued

CCATTAGATAGTAGGCGGGGTAACGGCCCACCTAGTCGACGATGGATAGGGGTTCTGAGA

GGAAGGTCCCCCACATTGGAACTGAGACACGGTCCAAACTCCTACGGGAGGCAGCAGTGA

GGAATATTGGTCAATGGGCGCGAGCCTGAACCAGCCAAGTAGCGTGAAGGATGAAGGTCC

TACGGATTGTAAACTTCTTTTATAAGGGAATAAAGTCACCCACGTGTGGGTGTTTGTATG

TACCTTATGAATAAGCATCGGCTAACTCCGTGCCAGCAGCCGCGGTAATACGGAGGATGC

GAGCGTTATCCGGATTTATTGGGTTTAAAGGGAGCGTAGACGGGTCGTTAAGTCAGCTGT

GAAAGTTCGGGGCTCAACCTTGAAATTGCAGTTGATACTGGCGTCCTTGAGTACGGTTGA

GGCAGGCGGAATTCGTGGTGTAGCGGTGAAATGCTTAGATATCACGAAGAACCCCGATTG

CGAAGGCAGCCTGCTAAACCGCCACTGACGTTGAGGCTCGAAAGTGTGGGTATCAAACAG

GATTAGATACCCTGGTAGTCCACACGGTAAACGATGGATACTCGCTGTTGGCGATAGACT

GTCAGCGGCTTAGCGAAAGCGTTAAGTATCCCACCTGGGGAGTACGCCGGCAACGGTGAA

ACTCAAAGGAATTGACGGGGGCCCGCACAAGCGGAGGAACATGTGGTTTAATTCGATGAT

ACGCGAGGAACCTTACCCGGGCTTGAATTGCAGACGAATTGCTTGGAAACAGGCAAGCCG

CAAGGCGTCTGTGAAGGTGCTGCATGGTTGTCGTCAGCTCGTGCCGTGAGGTGTCGGCTT

AAGTGCCATAACGAGCGCAACCCTCGTGTCCAGTTGCTAGCAGGTAGTGCTGAGGACTCT

GGACAGACTGCCATCGTAAGATGTGAGGAAGGTGGGGATGACGTCAAATCAGCACGGCCC

TTACGTCCGGGGCTACACACGTGTTACAATGGGGGGTACAGCAGGCAGCTACCGGGCGAC

CGGATGCCAATCCCGAAAGCCTCTCTCAGTTCGGACTGGAGTCTGCAACCCGACTCCACG

AAGCTGGATTCGCTAGTAATCGCGCATCAGCCACGGCGCGGTGAATACGTTCCCGGGCCT

TGTACACACCGCCCGTCAAGCCATGAAAGCCGGGGGTACCTGAAGTGCGTAACCGCAAGG

AGCGCCCTAGGGTAAAACTGGTAATT

HMI_44 *Roseburia inulinivorans* 16S rDNA sequence (SEQ ID NO: 43)

GCACTTTTGCCGATTTTCTTCGGAACTGAAGTAATAGTGACTGAGTGGCGGACGGGTGAG

TAACGCGTGGATAACCTGCCTCACACAGGGGGATAACAGTTAGAAATGACTGCTAATACC

GCATAAGCGCACAGTACCGCATGGTACAGTGTGAAAAACTCCGGTGGTGTGAGATGGATC

CGCGTCTGATTAGCCAGTTGGCGGGGTAACGGCCCACCAAAGCGACGATCAGTAGCCGGC

CTGAGAGGGCGACCGGCCACATTGGGACTGAGACACGGCCCAGACTCCTACGGGAGGCAG

CAGTGGGGAATATTGCACAATGGGGGAAACCCTGATGCAGCGACGCCGCGTGAGCGAAGA

AGTATTTCGGTATGTAAAGCTCTATCAGCAGGGAAGAAAATGACGGTACCTGACTAAGAA

GCTCCGGCTAAATACGTGCCAGCAGCCGCGGTAATACGTATGGAGCAAGCGTTATCCGGA

TTTACTGGGTGTAAAGGGAGCGCAGGCGGTATGACAAGTCTGATGTGAAAGGCTGGGGCT

CAACCCCAGGACTGCATTGGAAACTGTCAGACTAGAGTGTCGGAGAGGTAAGTGGAATTC

CTAGTGTAGCGGTGAAATGCGTAGATATTAGGAGGAACACCAGTGGCGAAGGCGGCTTAC

TGGACGACAACTGACGCTGAGGCTCGAAAGCGTGGGGAGCAAACAGGATTAGATACCCTG

GTAGTCCACGCCGTAAACGATGAATACTAGGTGTCGGGAGGCAGAGCCTTTCGGTGCCGC

AGCAAACGCAGTAAGTATTCCACCTGGGGAGTACGTTCGCAAGAATGAAACTCAAAGGAA

TTGACGGGACCCGCACAAGCGGTGGAGCATGTGGTTTAATTCGAAGCAACGCGAAGAAC

CTTACCAGGCCTTGACATCCCCCTGACGGGACAGTAATGTGTCCGTTCCTTCGGGACAGA

GGAGACAGGTGGTGCATGGTTGTCGTCAGCTCGTGTCGTGAGATGTTGGGTTAAGTCCCG

CAACGAGCGCAACCCTTATCCTCAGTAGCCAGCGGATAAAGCCGGGCACTCTGTGGAGAC

TGCCAGGGACAACCTGGAGGAAGGTGGGGATGACGTCAAATCATCATGCCCCTTATGGCC

-continued

TGGGCTACACACGTGCTACAATGGCGTAAACAAAGGGAAGCGAAGCTGTGAAGTGAAGCA

AATCCCAAAAATAACGTCTCAGTTCGGATTGTAGTCTGCAACTCGACTACATGAAGCTGG

AATCGCTAGTAATCGCGAATCAGAATGTCGCGGTGAATACGTTCCCGGGTCTTGTACACA

CCGCCCGTCACACCATGGGAGTCGGGAATGCCCGAAGCCGGTGACCCAACCTTAAGGAGG

GAGCCGTCGAAGGCAGGCCTGATAACTGGGGTGAAGTCGT

HMI_45 *Ruminococcus albus* 16S rDNA sequence (SEQ ID NO: 44)

CTGATCTAGTGGCGGACGGGTGAGTAACACGTGAGCAATCTGCCTTTCAGAGGGGGATAC

CGATTGGAAACGATCGTTAATACCGCATAACATAATTGAACCGCATGATTTGATTATCAA

AGATTTATCGCTGAAAGATGAGCTCGCGTCTGATTAGCTAGTTGGTAAGGTAACGGCTTA

CCAAGGCGACGATCAGTAGCCGGACTGAGAGGTTGATCGGCCACATTGGGACTGAGACAC

GGCCCAGACTCCTACGGGAGGCAGCAGTGGGGAATATTGCACAATGGAGGAAACTCTGAT

GCAGCGATGCCGCGTGAGGGAAGAAGGTTTTAGGATTGTAAACCTCTGTCTTCAGGGACG

AAAAAAGACGGTACCTGAGGAGGAAGCTCCGGCTAACTACGTGCCAGCAGCCGCGGTAAT

ACGTAGGGAGCGAGCGTTGTCCGGAATTACTGGGTGTAAAGGGAGCGTAGGCGGGATCGC

AAGTCAGATGTGAAAACTATGGGCTTAACCCATAAACTGCATTTGAAACTGTGGTTCTTG

AGTGAAGTAGAGGTAAGCGGAATTCCTAGTGTAGCGGTGAAATGCGTAGATATTAGGAGG

AACATCAGTGGCGAAGGCGGCTTACTGGGCTTTAACTGACGCTGAGGCTCGAAAGCGTGG

GGAGCAAACAGGATTAGATACCCTGGTAGTCCACGCCGTAAACGATGATTACTAGGTGTG

GGGGGACTGACCCCTTCCGTGCCGCAGCAAACGCAATAAGTAATCCACCTGGGGAGTACG

ACCGCAAGGTTGAAACTCAAAGGAATTGACGGGGGCCCGCACAAGCAGTGGAGTATGTGG

ATTAATTCGAAGCAACGCGAAGAACCTTACCAGGTCTTGACATCGTATGCATAGCTCAGA

GATGAGTGAAATCTCTTCGGAGACATATAGACAGGTGGTGCATGGTTGTCGTCAGCTCGT

GTCGTGAGATGTTGGGTTAAGTCCCGCAACGAGCGCAACCCTTACTGTTAGTTGCTACGC

AAGAGCACTCTAGCAGGACTGCCGTTGACAAAACGGAGGAAGGTGGGGATGACGTCAAAT

CATCATGCCCCTTATGACCTGGGCCTCACACGTACTACAATGGCTGTTAACAGAGGGATG

CAAAGCCGCGAGGTAGAGCGAACCCCTAAAAGCAGTCTTAGTTCGGATTGTAGGCTGCAA

CCCGCCTACATGAAGTCGGAATTGCTAGTAATCGCAGATCAGCATGCTGCGGTGAATACG

TTCCCGGGCCTTGTACACACCGCCCGTCACGCCATGGGAGTCGGTAACACCCGAAGCCTG

TAGTCTAACCGCAAGGAGGACGCAGTCGAAGGTGGGATTGATGACTGGGGTGAAGTCGTA

ACAGGGTAACCG

HMI_46 *Blautia producta* 16S rDNA sequence (SEQ ID NO: 45)

TGGACAGATTCTTCGGATGAAGTCCTTAGTGACTGAGTGGCGGACGGGTGAGTAACGCGT

GGGTAACCTGCCTCATACAGGGGGATAACAGTTAGAAATGGCTGCTAATACCGCATAAGC

GCACGGTACTGCATGGTACAGTGTGAAAAACTCCGGTGGTATGAGATGGACCCGCGTTGG

ATTAGCTAGTTGGCAGGGTAACGGCCTACCAAGGCGACGATCCATAGCCGGCCTGAGAGG

GTGGACGGCCACATTGGGACTGAGACACGGCCCAGACTCCTACGGGAGGCAGCAGTGGGG

AATATTGCACAATGGGGGAAACCCTGATGCAGCGACGCCGCGTGAGCGAAGAAGTATTTC

GGTATGTAAAGCTCTATCAGCAGGGAAGAAAATGACGGTACCTGACTAAGAAGCCCCGGC

TAACTACGTGCCAGCAGCCGCGGTAATACGTAGGGGGCAAGCGTTATCCGGATTTACTGG

GTGTAAAGGGAGCGTAGACGGAATGGCAAGTCTGATGTGAAAGGCCGGGGCTCAACCCCG

-continued
GGACTGCATTGGAAACTGTCAATCTAGAGTACCGGAGGGGTAAGTGGAATTCCTAGTGTA

GCGGTGAAATGCGTAGATATTAGGAGGAACACCAGTGGCGAAGGCGGCTTACTGGACGGT

AACTGACGTTGAGGCTCGAAAGCGTGGGGAGCAAACAGGATTAGATACCCTGGTAGTCCA

CGCCGTAAACGATGAATACTAGGTGTTGGGGAGCAAAGCTCTTCGGTGCCGCAGCAAACG

CAATAAGTATTCCACCTGGGGAGTACGTTCGCAAGAATGAAACTCAAAGGAATTGACGGG

GACCCGCACAAGCGGTGGAGCATGTGGTTTAATTCGAAGCAACGCGAAGAACCTTACCAA

ATCTTGACATCGATCTGACCGGACTGTAATGAGTCCTTTCCCTTCGGGGACAGAGAAGAC

AGGTGGTGCATGGTTGTCGTCAGCTCGTGTCGTGAGATGTTGGGTTAAGTCCCGCAACGA

GCGCAACCCTTATCCTCAGTAGCCAGCAAGTGAAGTTGGGCACTCTGTGGAGACTGCCAG

GGATAACCTGGAGGAAGGTGGGGATGACGTCAAATCATCATGCCCCTTATGATTTGGGCT

ACACACGTGCTACAATGGCGTAAACAAAGGGAAGCGATCACGCGAGTGTGAGCAAATCTC

AAAAATAACGTCTCAGTTCGGATTGTAGTCTGCAACTCGACTACATGAAGCTGGAATCGC

TAGTAATCGCAGGTCAGCATACTGCGGTGAATACGTTCCCGGGTCTTGTACACACCGCCC

TCGAAGGTGGGACCGATAACTGGGGTGAAGTCGT

HMI_47 *Clostridium nexile* 16S rDNA sequence (SEQ ID NO: 46)

GTTTGTGACTTAGTGGCGGACGGGTGAGTAACGCGTGGGTAACCTGCCTTATACAGGGGG

ATAACAGTTAGAAATGACTGCTAATACCGCATAAGCGCACAGTCTCGCATGGGACAGTGT

GAAAAACTAAGGTGGTATAAGATGGACCCGCGTCTGATTAGCTAGTTGGTGGGGTAAAGG

CCTACCAAGGCGACGATCAGTAGCCGACCTGAGAGGGTGATCGGCCACATTGGGACTGAG

ACACGGCCCAAACTCCTACGGGAGGCAGCAGTGGGGAATATTGCACAATGGGGGAAACCC

TGATGCAGCAACGCCGCGTGAAGGAAGAAGTATCTCGGTATGTAAACTTCTATCAGCAGG

GAAGAAAATGACGGTACCTGACTAAGAAGCTCCGGCTAAATACGTGCCAGCAGCCGCGGT

AATACGTATGGAGCAAGCGTTATCCGGATTTACTGGGTGTAAAGGGAGCGTAGGCGGTTA

TGCAAGTCAGATGTGAAAGCCCGGGGCTTAACCCCGGGACTGCATTTGAAACTGTGTAAC

TAGAGTGTCGGAGAGGTAAGTGGAATTCCTAGTGTAGCGGTGAAATGCGTAGATATTAGG

AGGAACACCAGTGGCGAAGGCGGCTTACTGGACGATAACTGACGCTGAGGCTCGAAAGCG

TGGGGAGCAAACAGGATTAGATACCCTGGTAGTCCACGCCGTAAACGATGAATACTAGGT

GTTGGGGAGCAAAGCTCTTCGGTGCCGCAGCAAACGCAATAAGTATTCCACCTGGGGAGT

ACGTTCGCAAGAATGAAACTCAAAGGAATTGACGGGGACCCGCACAAGCGGTGGAGCATG

TGGTTTAATTCGAAGCAACGCGAAGAACCTTACCAAGTCTTGACATCTGGATGACCGGAC

CGTAATGGGTCCTTTCCTTCGGGACATCCAAGACAGGTGGTGCATGGTTGTCGTCAGCTC

GTGTCGTGAGATGTTGGGTTAAGTCCCGCAACGAGCGCAACCCTTATCCTTAGTAGCCAG

CAGTAAGATGGGCACTCTAGGGAGACTGCCGGAGACAATCCGGAGGAAGGTGGGGATGAC

GTCAAATCATCATGCCCCTTATGACTTGGGCTACACACGTGCTACAATGGCGTAAACAAA

GGGAAGCGAGACCGCGAGGTTAAGCAAATCTCAAAAATAACGTCTCAGTTCGGATTGTAG

TCTGCAACTCGACTACATGAAGCTGGAATCGCTAGTAATCGCGAATCAGCATGTCGCGGT

GAATACGTTCCCGGGTCTTGTACACACCGCCCGTCACACCATGGGAGTCGATAACGCCCG

AAGCCGGTGACTCAACCGAAAGGAGAGAGCCGTCGAAGGCGGGATGGATAACTGGGGTGA

AGTCGTAAC

-continued

HMI_48 *Butyricicoccus pullicaecorum* 16S rDNA sequence
(SEQ ID NO: 47)

ATCTCTTCGGAGATGGAATTCTTAACCTAGTGGCGGACGGGTGAGTAACGCGTGAGCAAT

CTGCCTTTAGGAGGGGGATAACAGTCGGAAACGGCTGCTAATACCGCATAATACGTTTGG

GAGGCATCTCTTGAACGTCAAAGATTTTATCGCCTTTAGATGAGCTCGCGTCTGATTAGC

TGGTTGGCGGGGTAACGGCCCACCAAGGCGACGATCAGTAGCCGGACTGAGAGGTTGAAC

GGCCACATTGGGACTGAGACACGGCCCAGACTCCTACGGGAGGCAGCAGTGGGGAATATT

GCGCAATGGGGGAAACCCTGACGCAGCAACGCCGCGTGATTGAAGAAGGCCTTCGGGTTG

TAAAGATCTTTAATCAGGGACGAAAAATGACGGTACCTGAAGAATAAGCTCCGGCTAACT

ACGTGCCAGCAGCCGCGGTAATACGTAGGGAGCAAGCGTTATCCGGATTTACTGGGTGTA

AAGGGCGCGCAGGCGGGCCGGCAAGTTGGGAGTGAAATCCCGGGGCTTAACCCCGGAACT

GCTTTCAAAACTGCTGGTCTTGAGTGATGGAGAGGCAGGCGGAATTCCGTGTGTAGCGGT

GAAATGCGTAGATATACGGAGGAACACCAGTGGCGAAGGCGGCCTGCTGGACATTAACTG

ACGCTGAGGCGCGAAAGCGTGGGGAGCAAACAGGATTAGATACCCTGGTAGTCCACGCCG

TAAACGATGGATACTAGGTGTGGGAGGTATTGACCCCTTCCGTGCCGCAGTTAACACAAT

AAGTATCCCACCTGGGGAGTACGGCCGCAAGGTTGAAACTCAAAGGAATTGACGGGGGCC

CGCACAAGCAGTGGAGTATGTGGTTTAATTCGAAGCAACGCGAAGAACCTTACCAGGTCT

TGACATCCCGATGACCGGCGTAGAGATACGCCCTCTCTTCGGAGCATCGGTGACAGGTGG

TGCATGGTTGTCGTCAGCTCGTGTCGTGAGATGTTGGGTTAAGTCCCGCAACGAGCGCAA

CCCTTACGGTTAGTTGATACGCAAGATCACTCTAGCCGGACTGCCGTTGACAAAACGGAG

GAAGGTGGGGACGACGTCAAATCATCATGCCCCTTATGACCTGGGCTACACACGTACTAC

AATGGCAGTCATACAGAGGGAAGCAATACCGCGAGGTGGAGCAAATCCCTAAAAGCTGTC

CCAGTTCAGATTGCAGGCTGCAACCCGCCTGCATGAAGTCGGAATTGCTAGTAATCGCGG

ATCAGCATGCCGCGGTGAATACGTTCCCGGGCCTTGTACACACCGCCCGTCACACCATGA

GAGCCGTCAATACCCGAAGTCCGTAGCCTAACCGCAAGGGGGCGCGGCCGAAGGTAGGG

GTGGTAATTAGGGTGAAGTCGTAC

HMI_49 *Ruminococcus flavefaciens* 16S rDNA sequence
(SEQ ID NO: 48)

AGTCGACGGACGAGGAGGAGCTTGCTTCTCCGAGTTAGTGGCGGACGGGTGAGTAACACG

TGAGCAACCTACCCTTGAGAGGGGGATAGCTTCTGGAAACGGATGGTAATACCCCATAAC

ATATATTTTAGGCATCTAAGATATATCAAAGAAATTCGCTCAAGGATGGGCTCGCGTCTG

ATTAGATAGTTGGTGAGGTAACGGCCCACCAAGTCGACGATCAGTAGCCGGACTGAGAGG

TTGAACGGCCACATTGGGACTGAGACACGGCCCAGACTCCTACGGGAGGCAGCAGTGGGG

AATATTGCACAATGGGGGAACCCTGATGCAGCGATGCCGCGTGGAGGAAGAAGGTTTTC

GGATTGTAAACTCCTTTTAACAGGGACGATAATGACGGTACCTGAAGAAAAAGCTCCGGC

TAACTACGTGCCAGCAGCCGCGGTAATACGTAGGGAGCGAGCGTTGTCCGGAATTACTGG

GTGTAAAGGGAGCGTAGGCGGACGGTAAGTCAGGTGTGAAATATACGTGCTCAACATGT

AGACTGCACTTGAAACTGCTGTTCTTGAGTGAAGTAGAGGTAAGCGGAATTCCTAGTGTA

GCGGTGAAATGCGTAGATATTAGGAGGAACATCGGTGGCGAAGGCGGCTTACTGGGCTTT

TACTGACGCTGAGGCTCGAAAGCGTGGGGAGCAAACAGGATTAGATACCCTGGTAGTCCA

CGCTGTAAACGATGATTACTAGGTGTGGGGGGACTGACCCCTTCCGTGCCGCAGTTAACA

CAATAAGTAATCCACCTGGGGAGTACGACCGCAAGGTTGAAACTCAAAGGAATTGACGGG

GGCCCGCACAAGCAGTGGAGTATGTGGTTTAATTCGAAGCAACGCGAAGAACCTTACCAG

-continued

```
GTCTTGACATCGTATGCATAGTCTAGAGATAGATGAAATCCCTTCGGGGACATATAGACA

GGTGGTGCATGGTTGTCGTCAGCTCGTGTCGTGAGATGTTGGGTTAAGTCCCGCAACGAG

CGCAACCCTTACCTTTAGTTGCTACGCAAGAGCACTCTAGAGGGACTGCCGTTGACAAAA

CGGAGGAAGGTGGGGATGACGTCAAATCATCATGCCCCTTATGACCTGGGCTACACACGT

ACTACAATGGCAATTAACAGAGGGAAGCAAAACAGCGATGTGGAGCAAATCCCGAAAAAT

TGTCCCAGTTCAGATTGCAGGCTGCAACTCGCCTGCATGAAGTCGGAATTGCTAGTAATC

GCAGATCAGAATGCTGCGGTGAATACGTTCCCGGGCCTTGTACACACCGCCCGTCACACC

ATGGGAGTCGGTAACACCCGAAGCCTGTAGTCTAACCTTATAGGAGGACGCAGTCGAAGG

TGGGATTGATGACTGGGGTGAAGTCGT
```

HMI_50 *Clostridium orbiscindens* 16S rDNA sequence (SEQ ID NO: 49)

```
AAAGGGAATGCTTAGTGGCGGACGGGTGAGTAACGCGTGAGTAACCTGCCTTGGAGTGGG

GAATAACAGCCGGAAACGGCTGCTAATACCGCATGATGTATCTGGATCGCATGGTTCTGG

ATACCAAAGATTTATCGCTCTGAGATGGACTCGCGTCTGATTAGCTAGTTGGTGAGGTAA

CGGCTCACCAAGGCGACGATCAGTAGCCGGACTGAGAGGTTGGCCGGCCACATTGGGACT

GAGACACGGCCCAGACTCCTACGGGAGGCAGCAGTGGGGAATATTGGGCAATGGGCGAAA

GCCTGACCCAGCAACGCCGCGTGAAGGAAGAAGGCCCTCGGGTTGTAAACTTCTTTTGTC

AGGGACGAAGCAAGTGACGGTACCTGACGAATAAGCCACGGCTAACTACGTGCCAGCAGC

CGCGGTAATACGTAGGTGGCAAGCGTTATCCGGATTTACTGGGTGTAAAGGGCGTGTAGG

CGGGAGTGCAAGTCAGATGTGAAAACTATGGGCTCAACCCATAGCCTGCATTTGAAACTG

TACTTCTTGAGTGATGGAGAGGCAGGCGGAATTCCCTGTGTAGCGGTGAAATGCGTAGAT

ATAGGGAGGAACACCAGTGGCGAAGGCGGCCTGCTGGACATTAACTGACGCTGAGGCGCG

AAAGCGTGGGGAGCAAACAGGATTAGATACCCTGGTAGTCCACGCCGTAAACGATGGATA

CTAGGTGTGGGGGGTCTGACCCCCTCCGTGCCGCAGTTAACACAATAAGTATCCCACCTG

GGGAGTACGATCGCAAGGTTGAAACTCAAAGGAATTGACGGGGGCCCGCACAAGCGGTGG

AGTATGTGGTTTAATTCGAAGCAACGCGAAGAACCTTACCAGGACTTGACATCCTACTAA

CGAAGCAGAGATGCATAAGGTGCCCTTCGGGGAAAGTAGAGACAGGTGGTGCATGGTTGT

CGTCAGCTCGTGTCGTGAGATGTTGGGTTAAGTCCCGCAACGAGCGCAACCCTTATTGTT

AGTTGCTACGCAAGAGCACTCTAGCGAGACTGCCGTTGACAAAACGGAGGAAGGTGGGGA

CGACGTCAAATCATCATGCCCCTTATGTCCTGGGCCACACACGTACTACAATGGCGGTCA

ACAGAGGGAAGCAAAGCCGCGAGGTGGAGCAAATCCCTAAAAGCCGTCCCAGTTCGGATT

GCAGGCTGAAACTCGCCTGTATGAAGTCGGAATCGCTAGTAATCGCGGATCAGCATGCCG

CGGTGAATACGTTCCCGGGCCTTGTACACACCGCCCGTCACACCATGAGAGTCGGGAACA

CCCGAAGTCCGTAGCCTAACAGCAATGGG
```

HMI_51 *Ruminococcus_bromii* 16S rDNA sequence (SEQ ID NO: 50)

```
ACGAAGCTTTGAGGAGCTTGCTTTTTAAGCTTAGTGGCGGACGGGTGAGTAACGCGTGAG

CAACCTGCCTCTCAGAGGGGAATAACGTTTTGAAAAGAACGCTAATACCGCATAACATAT

CGGAACCGCATGATTCTGATATCAAAGGAGCAATCCGCTGAGAGATGGGCTCGCGTCCGA

TTAGTTAGTTGGTGAGGTAACGGCTCACCAAGACTACGATCGGTAGCCGGACTGAGAGGT

TGATCGGCCACATTGGGACTGAGACACGGCCCAGACTCCTACGGGAGGCAGCAGTGGGGG

ATATTGCGCAATGGGGGAAACCCTGACGCAGCAACGCCGCGTGAAGGAAGAAGGTCTTCG
```

```
GATTGTAAACTTCTTTTGTCAGGGACGAAGAAAGTGACGGTACCTGACGAATAAGCTCCG

GCTAACTACGTGCCAGCAGCCGCGGTAATACGTAGGGAGCGAGCGTTGTCCGGATTTACT

GGGTGTAAAGGGTGCGTAGGCGGCCGAGCAAGTCAGTTGTGAAAACTATGGGCTTAACCC

ATAACGTGCAATTGAAACTGTCCGGCTTGAGTGAAGTAGAGGTAGGCGGAATTCCCGGTG

TAGCGGTGAAATGCGTAGAGATCGGGAGGAACACCAGTGGCGAAGGCGGCCTACTGGGCT

TTAACTGACGCTGAGGCACGAAAGCATGGGTAGCAAACAGGATTAGATACCCTGGTAGTC

CATGCCGTAAACGATGATTACTAGGTGTGGGGGGACTGACCCCTTCCGTGCCGCAGTTAA

CACAATAAGTAATCCACCTGGGGAGTACGGCCGCAAGGTTGAAACTCAAAGGAATTGACG

GGGGCCCGCACAAGCAGTGGAGTATGTGGTTTAATTCGAAGCAACGCGAAGAACCTTACC

AGGTCTTGACATCCTGAGAATCCTTAAGAGATTAGGGAGTGCCTTCGGGAACTCAGAGAC

AGGTGGTGCATGGTTGTCGTCAGCTCGTGTCGTGAGATGTTGGGTTAAGTCCCGCAACGA

GCGCAACCCTTGCTATTAGTTGCTACGCAAGAGCACTCTAATAGGACTGCCGTTGACAAA

ACGGAGGAAGGTGGGGACGACGTCAAATCATCATGCCCCTTATGACCTGGGCTACACACG

TACTACAATGGCCATTAACAGAGGGAAGCAAAACCGCGAGGCAGAGCAAACCCCTAAAAA

TGGTCCCAGTTCGGATTGTAGGCTGCAACCCGCCTACATGAAGTTGGAATTGCTAGTAAT

CGCGGATCAGCATGCCGCGGTGAATACGTTCCCGGGCCTTGTACACACCGCCCGTCACAC

CATGGGAGCCGGTAATACCCGAAGTCAGTAGTCTAACAGCAATGAGGACGCTGCCGAAGG

TAGGATTGGCGACTGGGGTGAAGTCGTAACAAGGTAACCG

HMI_52 Ruminococcus albus 926R 16S rDNA sequence              (SEQ ID NO: 51)

AGAGTTTGATCCTGGCTCAGGACGAACGCTGGCGGCACGCTTAACACATGCAAGTCGAAC

GAGAGAAGAGAAGCTTGCTTTTCTGATCTAGTGGCGGACGGGTGAGTAACACGTGAGCAA

TCTGCCTTTCAGAGGGGGATACCGATTGGAAACGATCGTTAATACCGCATAACATAATTG

AACCGCATGATTTGATTATCAAAGATTTATCGCTGAAAGATGAGCTCGCGTCTGATTAGC

TAGTTGGTAAGGTAACGGCTTACCAAGGCGACGATCAGTAGCCGGACTGAGAGGTTGATC

GGCCACATTGGGACTGAGACACGGCCCAGACTCCTACGGGAGGCAGCAGTGGGGAATATT

GCACAATGGAGGAAACTCTGATGCAGCGATGCCGCGTGAGGGAAGAAGGTTTTAGGATTG

TAAACCTCTGTCTTCAGGGACGAAAAAAAAGACGGTACCTGAGGAGGAAGCTCCGGCTAA

CTACGTGCCAGCAGCCGCGGTAATACGTAGGGAGCGAGCGTTGTCCGGAATTACTGGGTG

TAAAGGGAGCGTAGGCGGGATCGCAAGTCAGATGTGAAAACTATGGGCTTAACCCATAAA

CTGCATTTGAAACTGTGGTTCTTGAGTGAAGTAGAGGTAAGCGGAATTCCTAGTGTAGCG

GTGAAATGCGTAGATATTAGGAGGAACATCAGTGGCGAAGGCGGCTTACTGGGCTTTAAC

TGACGCTGAGGCTCGAAAGCGTGGGGAGCAAACAGGATTAGATACCCTGGTAGTCCACGC

CGTAAACGATGATTACTAGGTGTGGGGGGACTGACCCCTTCCGTGCCGCAGCAAACGCAA

TAAGTAATCCACCTGGGGAGTACGACCGCAAGGTTGAAACTCAAAGGAATTGACGGGGGC

CCGCACAAGCAGTGGAGTATGTGGATTAATTCGAAGCAACGCGAAGAACCTTACCAGGTC

TTGACATCGTATGCATAGCTCAGAGATGAGTGAAATCTCTTCGGAGACATATAGACAGGT

GGTGCATGGTTGTCGTCAGCTCGTGTCGTGAGATGTTGGGTTAAGTCCCGCAACGAGCGC

AACCCTTACTGTTAGTTGCTACGCAAGAGCACTCTAGCAGGACTGCCGTTGACAAAACGG

AGGAAGGTGGGGATGACGTCAAATCATCATGCCCCTTATGACCTGGGCCTCACACGTACT

ACAATGGCTGTCAACAGAGGGATGCAAAGCCGCGAGGTGGAGCGAACCCCTAAAAGCAGT

CTTAGTTCGGATTGTAGGCTGCAACCCGCCTACATGAAGTCGGAATTGCTAGTAATCGCA
```

-continued

```
GATCAGCATGCTGCGGTGAATACGTTCCCGGGCCTTGTACACACCGCCCGTCACGCCATG

GGAGTCGGTAACACCCGAAGCCTGTAGTCTAACCGCAAGGAGGACGCAGTCGAAGGTGGG

ATTGATGACTGGGGTGAAGTCGTAACAAGGTAGCCGTATCGGAAGGTGCG
```

REFERENCES

All documents mentioned in this specification are incorporated herein by reference in their entirety.

Abecasis, A. B., M. Serrano, R. Alves, L. Quintais, J. B. Pereira-Leal and A. O. Henriques (2013). "A genomic signature and the identification of new sporulation genes." J Bacteriol 195(9): 2101-2115.

Abujamel, T et al. (2013). "Defining the Vulnerable Period for Re-Establishment of *Clostridium difficile* Colonization after Treatment of *C. difficile* Infection with Oral Vancomycin or Metronidazole." PLoS ONE 8(10): e76269.

Altschul, S. F., W. Gish, W. Miller, E. W. Myers and D. J. Lipman (1990). "Basic local alignment search tool." Journal of Molecular Biology 215(3): 403-410.

Altschul, S. F., W. Gish, W. Miller, E. W. Myers and D. J. Lipman (1990). "Basic local alignment search tool." J Mol Biol 215(3): 403-410.

Angriman, I., M. Scarpa and I. Castagliuolo (2014). "Relationship between pouch microbiota and pouchitis following restorative proctocolectomy for ulcerative colitis." World J Gastroenterol 20(29): 9665-9674.

Atarashi, K., T. Tanoue, K. Oshima, W. Suda, Y. Nagano, H. Nishikawa, S. Fukuda, T. Saito, S. Narushima, K. Hase, S. Kim, J. V. Fritz, P. Wilmes, S. Ueha, K. Matsushima, H. Ohno, B. OIle, S. Sakaguchi, T. Taniguchi, H. Morita, M. Hattori and K. Honda (2013). "Treg induction by a rationally selected mixture of Clostridia strains from the human microbiota". Nature 500(7461): 232-236.

Blanton, L. V., M. R. Charbonneau, T. Salih, M. J. Barratt, S. Venkatesh, O. Ilkaveya, S. Subramanian, M. J. Manary, I. Trehan, J. M. Jorgensen, Y. M. Fan, B. Henrissat, S. A. Leyn, D. A. Rodionov, A. L. Osterman, K. M. Maleta, C. B. Newgard, P. Ashorn, K. G. Dewey and J. I. Gordon (2016). "Gut bacteria that prevent growth impairments transmitted by microbiota from malnourished children." Science 351(6275).

Bajaj, J. S. (2014). "The role of microbiota in hepatic encephalopathy." Gut Microbes 5(3): 397-403.

Bajaj, J. S., P. B. Hylemon and Z. Younossi (2012). "The intestinal microbiota and liver disease." Am J Gastroenterol. Suppl. 1:9-14

Bosshard, P. P., S. Abels, R. Zbinden, E. C. Bottger and M. Altwegg (2003). "Ribosomal DNA sequencing for identification of aerobic gram-positive rods in the clinical laboratory (an 18-month evaluation)." J Clin Microbiol 41(9): 4134-4140.

Britton, R. A. and V. B. Young (2014). "Role of the intestinal microbiota in resistance to colonization by *Clostridium difficile*." Gastroenterology 146(6): 1547-1553.

Buffie, C. G., et al. (2015). "Precision microbiome reconstitution restores bile acid mediated resistance to *Clostridium difficile*." Nature 517(7533): 205-208.

Chakraborty, A., S. Ghosh, G. Chowdhary, U. Maulik and S. Chakrabarti (2012). "DBETH: a Database of Bacterial Exotoxins for Human." Nucleic Acids Res 40(Database issue): D615-620.

Clarridge, J. E., 3rd (2004). "Impact of 16S rRNA gene sequence analysis for identification of bacteria on clinical microbiology and infectious diseases." Clin Microbiol Rev 17(4): 840-862, table of contents.

Cole, J. R., et al. (2014). "Ribosomal Database Project: data and tools for high throughput rRNA analysis." Nucleic Acids Research 42(D1): D633-D642.

Collins, S. M. (2014). "A role for the gut microbiota in IBS." Nat Rev Gastroenterol Hepatol 11(8): 497-505.

Comely, O. A., M. A. Miller, T. J. Louie, D. W. Crook and S. L. Gorbach (2012). "Treatment of First Recurrence of *Clostridium difficile* Infection: Fidaxomicin Versus Vancomycin." Clinical Infectious Diseases: An Official Publication of the Infectious Diseases Society of America 55(Suppl 2): S154-5161.

Dominguez-Bello, M. G., E. K. Costello, M. Contreras, M. Magris, G. Hidalgo, N. Fierer and R. Knight (2010). "Delivery mode shapes the acquisition and structure of the initial microbiota across multiple body habitats in newborns." Proc Natl Acad Sci USA 107(26): 11971-11975.

Duncan, S. H., G. L. Hold, H. J. Harmsen, C. S. Stewart and H. J. Flint (2002). "Growth requirements and fermentation products of *Fusobacterium prausnitzii*, and a proposal to reclassify it as *Faecalibacterium prausnitzii* gen. nov., comb. nov." Int J Syst Evol Microbiol 52(Pt 6): 2141-2146.

Eckburg, P. B., E. M. Bik, C. N. Bernstein, E. Purdom, L. Dethlefsen, M. Sargent, S. R. Gill, K. E. Nelson and D. A. Reiman (2005). "Diversity of the human intestinal microbial flora." Science 308(5728): 1635-1638.

Fodor, A. A., T. Z. DeSantis, K. M. Wylie, J. H. Badger, Y. Ye, T. Hepburn, P. Hu, E. Sodergren, K. Liolios, H. Huot-Creasy, B. W. Birren and A. M. Earl (2012). "The "most wanted" taxa from the human microbiome for whole genome sequencing." PLoS One 7(7): e41294.

Forster, S. C., H. P. Browne, N. Kumar, M. Hunt, H. Denise, A. Mitchell, R. D. Finn and T. D. Lawley (2015). "HPMCD: the database of human microbial communities from metagenomic datasets and microbial reference genomes." Nucleic Acids Res.

Francis, M. B., C. A. Allen, R. Shrestha and J. A. Sorg (2013). "Bile acid recognition by the *Clostridium difficile* germinant receptor, CspC, is important for establishing infection." PLoS Pathog 9(5): e1003356.

Galperin, M. Y., S. L. Mekhedov, P. Puigbo, S. Smirnov, Y. I. Wolf and D. J. Rigden (2012). "Genomic determinants of sporulation in Bacilli and Clostridia: towards the minimal set of sporulation-specific genes." Environ Microbiol 14(11): 2870-2890.

Goodman, A. L., G. Kalistrom, J. J. Faith, A. Reyes, A. Moore, G. Dantas and J. I. Gordon (2011). "Extensive personal human gut microbiota culture collections characterized and manipulated in gnotobiotic mice." Proc Natl Acad Sci USA 108(15): 6252-6257.

Hattori, M. and T. D. Taylor (2009). "The human intestinal microbiome: a new frontier of human biology." DNA Res 16(1): 1-12.

Hold, G. L., M. Smith, C. Grange, E. R. Watt, E. M. El-Omar and I. Mukhopadhya (2014). "Role of the gut microbiota in inflammatory bowel disease pathogenesis: what have we learnt in the past 10 years?" World J Gastroenterol 20(5): 1192-1210.

Hooper, L. V., D. R. Littman and A. J. Macpherson (2012). "Interactions between the microbiota and the immune system." Science 336(6086): 1268-1273.

Hooper, L. V., M. H. Wong, A. Thelin, L. Hansson, P. G. Falk and J. I. Gordon (2001). "Molecular analysis of commensal host-microbial relationships in the intestine." Science 291(5505): 881-884.

Huse, S. M., L. Dethlefsen, J. A. Huber, D. M. Welch, D. A. Reiman and M. L. Sogin (2008). "Exploring Microbial Diversity and Taxonomy Using SSU rRNA Hypervariable Tag Sequencing." PLoS Genet 4(11): e1000255.

Janoir, C., C. Deneve, S. Bouttier, F. Barbut, S. Hoys, L. Caleechum, D. Chapeton-Montes, F. C. Pereira, A. O. Henriques, A. Collignon, M. Monot and B. Dupuy (2013). "Adaptive strategies and pathogenesis of *Clostridium difficile* from in vivo transcriptomics." Infect Immun 81(10): 3757-3769.

Johnson, M., I. Zaretskaya, Y. Raytselis, Y. Merezhuk, S. McGinnis and T. L. Madden (2008). "NCBI BLAST: a better web interface." Nucleic Acids Research 36(Web Server issue): W5-W9.

Jostins, L., et al. (2012). "Host-microbe interactions have shaped the genetic architecture of inflammatory bowel disease." Nature 491(7422): 119-124.

Koenig, J. E., et al. (2011). "Succession of microbial consortia in the developing infant gut microbiome." Proc Natl Acad Sci USA 108 Suppl 1: 4578-4585.

Kozich, J. J., S. L. Westcott, N. T. Baxter, S. K. Highlander and P. D. Schloss (2013). "Development of a dual-index sequencing strategy and curation pipeline for analyzing amplicon sequence data on the MiSeq Illumina sequencing platform." Appl Environ Microbiol 79(17): 5112-5120.

Lagier, J. C., P. Hugon, S. Khelaifia, P. E. Fournier, B. La Scola and D. Raoult (2015). "The Rebirth of Culture in Microbiology through the Example of Culturomics To Study Human Gut Microbiota." Clin Microbiol Rev 28(1): 237-264.

Landy, J., H. O. Al-Hassi, S. D. McLaughlin, A. W. Walker, P. J. Ciclitira, R. J. Nicholls, S. K. Clark and A. L. Hart (2011). "Review article: faecal transplantation therapy for gastrointestinal disease." Alimentary Pharmacology & Therapeutics 34(4): 409-415.

Lawley, T. D., et al. (2009). "Antibiotic treatment of *Clostridium difficile* carrier mice triggers a supershedder state, spore-mediated transmission, and severe disease in immunocompromised hosts." Infect Immun 77(9): 3661-3669.

Lawley, T. D., et al. (2012). "Targeted restoration of the intestinal microbiota with a simple, defined bacteriotherapy resolves relapsing *Clostridium difficile* disease in mice." PLoS Pathog 8(10): e1002995.

Lawley, T. D. and A. W. Walker (2013). "Intestinal colonization resistance." Immunology 138(1): 1-11.

Letunic, I. and P. Bork (2011). "Interactive Tree Of Life v2: online annotation and display of phylogenetic trees made easy." Nucleic Acids Res 39(Web Server issue): W475-478.

Louis, P and H. J. Flint (2009). "Diversity, metabolism and microbial ecology of butyrate-producing bacteria from the human large intestine." FEMS Microbiol. Lett. 294 (1): 1-8.

Lozupone, C. and R. Knight (2005). "UniFrac: a New Phylogenetic Method for Comparing Microbial Communities." Applied and Environmental Microbiology 71(12): 8228-8235.

Ludwig, W., et al. (2004). "ARB: a software environment for sequence data." Nucleic Acids Res 32(4): 1363-1371.

McArthur, A. G. et al. (2013). "The comprehensive antibiotic resistance database." Antimicrob Agents Chemother 57(7): 3348-3357.

Meehan, C. J. and R. G. Beiko (2014). "A phylogenomic view of ecological specialization in the Lachnospiraceae, a family of digestive tract-associated bacteria." Genome Biol Evol 6(3): 703-713.

Nielsen, H. B., et al. (2014). "Identification and assembly of genomes and genetic elements in complex metagenomic samples without using reference genomes." Nat Biotechnol 32(8): 822-828.

Oilman, N., H. Smidt, W. M. de Vos and C. Belzer (2012). "The function of our microbiota: who is out there and what do they do?" Front Cell Infect Microbiol 2: 104.

Perez Martinez, G., C. Bauerl and M. C. Collado (2014). "Understanding gut microbiota in elderly's health will enable intervention through probiotics." Benef Microbes 5(3): 235-246. Petrof, E. O., G. B. Gloor, S. J. Vanner, S. J. Weese, D. Carter, M. C. Daigneault, E. M. Brown, K. Schroeter and E. Allen-Vercoe (2013). "Stool substitute transplant therapy for the eradication of *Clostridium difficile* infection: 'RePOOPulating' the gut." Microbiome 1(1): 3.

Price, M. N., P. S. Dehal and A. P. Arkin (2010). "FastTree 2—approximately maximum-likelihood trees for large alignments." PLoS One 5(3): e9490.

Pruesse, E., C. Quast, K. Knittel, B. M. Fuchs, W. Ludwig, J. Peplies and F. O. Glockner (2007). "SILVA: a comprehensive online resource for quality checked and aligned ribosomal RNA sequence data compatible with ARB." Nucleic acids research 35(21): 7188-7196.

Qin, J., et al. (2010). "A human gut microbial gene catalogue established by metagenomic sequencing." Nature 464 (7285): 59-65.

Quince, C., A. Lanzen, R. Davenport and P. Turnbaugh (2011). "Removing Noise From Pyrosequenced Amplicons." BMC Bioinformatics 12(1): 38.

Rajilic-Stojanovic, M. and W. M. de Vos (2014). "The first 1000 cultured species of the human gastrointestinal microbiota." FEMS Microbiol Rev 38(5): 996-1047.

Riley, T. V., J. S. Brazier, H. Hassan, K. Williams and K. D. Phillips (1987). "Comparison of alcohol shock enrichment and selective enrichment for the isolation of *Clostridium difficile*." Epidemiol Infect 99(2): 355-359.

Scheperjans, F., et al. (2015). "Gut microbiota are related to Parkinson's disease and clinical phenotype." Mov Disord 30(3): 350-358.

Schloss, P. D., D. Gevers and S. L. Westcott (2011). "Reducing the Effects of PCR Amplification and Sequencing Artifacts on 16S rRNA-Based Studies." PLoS ONE 6(12): e27310.

Schloss, P. D., et al. (2009). "Introducing mothur: Open-Source, Platform-Independent, Community-Supported Software for Describing and Comparing Microbial Communities." Applied and Environmental Microbiology 75(23): 7537-7541.

Schloss, P. D., et al. (2009). "Introducing mothur: open-source, platform-independent, community-supported software for describing and comparing microbial communities." Appl Environ Microbiol 75(23): 7537-7541.

Sekirov, I., S. L. Russell, L. C. Antunes and B. B. Finlay (2010). "Gut microbiota in health and disease." Physiol Rev 90(3): 859-904.

Snyder, A (2014). "Genetic basis for clinical response to CTLA-4 blockade in melanoma". N Engl J Med. 371(23): 2189-99.

Stewart, E. J. (2012). "Growing unculturable bacteria." J Bacteriol 194(16): 4151-4160. van Nood, E., A. Vrieze, M. Nieuwdorp, S. Fuentes, E. G. Zoetendal, W. M. de Vos, C. E. Visser, E. J. Kuijper, J. F. Bartelsman, J. G. Tijssen, P. Speelman, M. G. Dijkgraaf and J. J. Keller (2013). "Duodenal infusion of donor feces for recurrent Clostridium difficile." N Engl J Med 368(5): 407-415.

Wang, Q., G. M. Garrity, J. M. Tiedje and J. R. Cole (2007). "Naive Bayesian classifier for rapid assignment of rRNA sequences into the new bacterial taxonomy." Appl Environ Microbiol 73(16): 5261-5267.

Xu et al. (2015). "Fecal microbiota transplantation broadening its application beyond intestinal disorders". World J Gastroenterol. 21(1): 102-111.

Ze, X., F. Le Mougen, S. H. Duncan, P. Louis and H. J. Flint (2013). "Some are more equal than others: the role of "keystone" species in the degradation of recalcitrant substrates." Gut Microbes 4(3): 236-240.

The invention claimed is:

1. A therapeutic composition comprising at least one isolated bacterium and a pharmaceutically acceptable excipient, wherein the bacterium comprises a gene encoding a 16S ribosomal RNA (rRNA) and said gene comprises a sequence with at least 93% sequence identity of SEQ ID NO: 40 or at least 98% sequence identity of SEQ ID NO: 27, wherein the composition is formulated for oral administration or rectal administration.

2. The therapeutic composition according to claim 1, wherein the isolated bacterium is a bacterium as deposited at the Leibniz-Institut DSMZ under accession number DSM32179 or DSM32226.

3. The therapeutic composition according to claim 1, wherein the composition comprises at least two distinct isolated bacteria, and wherein the bacteria are as defined in claim 1.

4. A method of treating a dysbiosis of the gastrointestinal tract in an individual in need thereof, the method comprising administering to the individual a therapeutically effective amount of the therapeutic composition according to claim 1.

5. The method according to claim 4, wherein the dysbiosis is associated with an enteric bacterial infection.

6. The method according to claim 5, wherein the enteric bacterial infection is an infection with a pathogenic bacterium selected from the group consisting of a pathogenic bacterium of the genus *Clostridium, Escherichia, Enterococcus, Klebsiella, Enterobacter, Proteus, Salmonella, Shigella, Staphylococcus, Vibrio, Aeromonas, Campylobacter, Bacillus, Helicobacter, Listeria, Plesiomonas*, and *Yersinia*.

7. The method according to claim 6, wherein the pathogenic bacterium is resistant to treatment with one or more antibiotic.

8. The method according to claim 5, wherein the enteric bacterial infection is an infection with *Clostridium difficile* or *Escherichia coli*.

9. The method according to claim 4, wherein the dysbiosis is associated with inflammatory bowel disease (IBD), pouchitis, irritable bowel syndrome (IBS), a metabolic disease, a neuropsychiatric disorder, an autoimmune disease, an allergic disorder, a cancer, or hepatic encephalopathy.

10. The method according to claim 9, wherein the IBD is ulcerative colitis (UC) or Crohn's disease.

11. The therapeutic composition according to claim 1, wherein at least one of the bacteria in the composition is antagonistic towards a pathogenic intestinal bacterium, inhibits or prevents the growth of a pathogenic intestinal bacterium, or neutralizes or protects against a toxin produced by an intestinal bacterium.

12. The therapeutic composition according to claim 1, wherein at least one of the bacteria in the composition has immunomodulatory activity.

13. The therapeutic composition according to claim 1, wherein the composition further comprises a carrier.

14. The therapeutic composition according to claim 1, wherein the composition is formulated for oral administration and is lyophilised.

15. The therapeutic composition according to claim 14, wherein the composition further comprises a stabiliser and/or a cryoprotectant.

16. The therapeutic composition according to claim 1, wherein the composition is the form of a capsule, a tablet, or an enema.

17. A method of preparing the therapeutic composition according to claim 1, wherein the method comprises the steps of:
    (i) culturing the isolated bacterium as set out in claim 1; and
    (ii) mixing the bacteria obtained in (i) with a pharmaceutically acceptable excipient.

18. A method of preparing the therapeutic composition according to claim 1, wherein the method comprises the steps of:
    (i) culturing a first isolated bacterium as set out in claim 1;
    (ii) culturing a second isolated bacterium as set out in claim 1; and (ii) mixing the bacteria obtained in (i) and (ii) with a pharmaceutically acceptable excipient, wherein the bacteria cultured in steps (i) and (ii) have distinct 16S rRNA sequences, and wherein steps (i) and (ii) are performed independently.

19. The therapeutic composition according to claim 2, wherein the composition comprises at least two distinct isolated bacteria, and wherein the bacteria are as defined in claim 2.

* * * * *

SEQUENCE LISTING

```
<160> NUMBER OF SEQ ID NOS: 57

<210> SEQ ID NO 1
<211> LENGTH: 1467
<212> TYPE: DNA
<213> ORGANISM: Clostridium thermocellum

<400> SEQUENCE: 1
caggacgaac gctggcggcg tgcctaacac atgcaagtcg aacgagaatc tttgaacaga      60
tcttttcgga gtgacgttca aagaggaaag tggcggacgg gcgagtaacg cgtgagtaac     120
ctgcccataa gaggggata atccatggaa acgtggacta ataccgcata ttgtagtcaa     180
gtcgcatgac tagattatga aagatttatc gcttatggat ggactcgcgt cagattagat     240
agttggtgag gtaacggctc accaagtcaa cgatctgtag ccgaactgag aggttgatcg     300
gccgcattgg gactgagaca cggcccagac tcctacggga ggcagcagtg gggaatattg     360
cgcaatgggg gcaaccctga cgcagcaacg ccgcgtgcag gaagaaggtc ttcggattgt     420
aaactgttgt cgcaagggaa gaagacagtg acggtacctt gtgagaaagt cacggctaac     480
tacgtgccag cagccgcggt aatacgtagg tgacaagcgt tgtccggatt tactgggtgt     540
aaagggcgcg taggcggact gtcaagtcag tcgtgaaata ccggggctta accccggggc     600
tgcgattgaa actgacagcc ttgagtatcg gagaggaaag cggaattcct agtgtagcgg     660
tgaaatgcgt agatattagg aggaacacca gtggcgaagg cggctttctg gacgacaact     720
gacgctgagg cgcgaaagtg tggggagcaa acaggattag ataccctggt agtccacacc     780
gtaaacgatg gatactaggt gtaggaggta tcgaccccttt ctgtgccgca gttaacacaa     840
taagtatccc acctggggag tacgaccgca aggttgaaac tcaaaggaat tgacgggggc     900
ccgcacaagc agtggagtat gtggtttaat tcgaagcaac gcgaagaacc ttacctgggc     960
ttgacatccc tggaatcgag tagagatact tgagtgcctt cgggaatcag gtgacaggtg    1020
gtgcatggtt gtcgtcagct cgtgtcgtga gatgttgggt taagtcccgc aacgagcgca    1080
acccctattg tcagttgcca tcattaagtt gggcactctg gcgagactgc cggtgacaaa    1140
tcggaggaag gtggggacga cgtcaaatca tcatgcccct tatgcccagg gctacacacg    1200
tactacaatg gccgataaca aagtgcagcg aaaccgtgag gtggagcgaa tcacaaaact    1260
cggtctcagt tcagattgca ggctgcaact cgcctgcatg aagttggaat tgctagtaat    1320
cgcggatcag aatgccgcgg tgaatacgtt cccgggcctt gtacacaccg cccgtcacac    1380
```
catgagagtc gataacaccc gaagcctgtg agctaaccta ttaggaggca gcagtcgaag    1440
gtggggttga tgattggggt gaagtcg                                        1467

<210> SEQ ID NO 2
<211> LENGTH: 1419
<212> TYPE: DNA
<213> ORGANISM: Flavonifractor pautii

<400> SEQUENCE: 2
gagtgctcat gacagaggat tcgtccaatg gagtgagtta cttagtggcg gacgggtgag      60
taacgcgtga gtaacctgcc ttggagtggg gaataacagg tggaaacatc tgctaatacc     120
gcatgatgca gttgggtcgc atggctctga ctgccaaaga tttatcgctc tgagatggac     180
tcgcgtctga ttagctggtt ggcggggtaa cggcccacca aggcgacgat cagtagccgg     240
actgagaggt tggccggcca cattgggact gagacacggc ccagactcct acgggaggca     300
gcagtgggga atattgggca atgggcgcaa gcctgaccca gcaacgccgc gtgaaggaag     360
aaggctttcg ggttgtaaac ttcttttctc agggacgaag caagtgacgg tacctgagga     420
ataagccacg gctaactacg tgccagcagc cgcggtaata cgtaggtggc gagcgttatc     480
cggatttact gggtgtaaag ggcgtgtagg cgggactgca agtcagatgt gaaaaccatg     540
ggctcaacct gtggcctgca tttgaaactg tagttcttga gtactggaga ggcagacgga     600
attcctagtg tagcggtgaa atgcgtagat attaggagga acaccagtgg cgaaggcggt     660
ctgctggaca gcaactgacg ctgaggcgcg aaagcgtggg gagcaaacag gattagatac     720
cctggtagtc cacgctgtaa acgatggata ctaggtgtgg gggtctgac ccctccgtg      780 ccgcagttaa cacaataagt atcccacctg gggagtacga tcgcaaggtt gaaactcaaa     840
ggaattgacg gggcccgca caagcggtgg agtatgtggt ttaattcgaa gcaacgcgaa      900
gaaccttacc agggcttgac atcccggtga ccggtgtaga gatacacctt cttcttcgga     960
agcgccggtg acaggtggtg catggttgtc gtcagctcgt gtcgtgagat gttgggttaa    1020
gtcccgcaac gagcgcaacc cttattgtta gttgctacgc aagagcactc tagcgagact    1080
gccgttgaca aaacggagga aggtggggac gacgtcaaat catcatgccc cttatgtcct    1140
gggccacaca cgtactacaa tggtggtcaa cagagggaag caagaccgcg aggtggagca    1200 aaccccctaaa agccatccca gttcggattg caggctgcaa ctcgcctgta tgaagttgga    1260
atcgctagta atcgcggatc agcatgccgc ggtgaatacg ttcccgggcc ttgtacacac    1320
cgcccgtcac accatgagag tcgggaacac ccgaagtccg tagcctaacc gcaagggggg    1380
cgcggccgaa ggtgggttcg ataattgggg tgaagtcgt                          1419

<210> SEQ ID NO 3
<211> LENGTH: 1398
<212> TYPE: DNA
<213> ORGANISM: Flavonifractor plautii

<400> SEQUENCE: 3
tggctgttta gtggcggacg ggtgagtaac gcgtgagtaa cctgccttgg agtggggaat      60
aacacagtga aaactgtgct aataccgcat gacatattgg tgtcgcatgg cactgatatc     120
aaagatttat cgctctgaga tggactcgcg tctgattaga tagttggcgg ggtaacggcc     180
caccaagtcg acgatcagta gccggactga gaggttggcc ggccacattg ggactgagac     240
acggcccaga ctcctacggg aggcagcagt ggggaatatt ggcaatggg cgcaagcctg      300 acccagcaac gccgcgtgaa ggaagaaggc tttcgggttg taaacttctt ttaacaggga     360

```
cgaagtaagt gacggtacct gttgaataag ccacggctaa ctacgtgcca gcagccgcgg    420
taatacgtag gtggcaagcg ttatccggat ttactgggtg taaagggcgt gtaggcggga    480
ctgcaagtca gatgtgaaaa ctatgggctc aacccatagc ctgcatttga aactgtagtt    540
cttgagtgtc ggagaggcaa tcggaattcc gtgtgtagcg gtgaaatgcg tagatatacg    600
gaggaacacc agtggcgaag gcggattgct ggacgataac tgacgctgag gcgcgaaagc    660
gtggggagca aacaggatta gatacctgg tagtccacgc cgtaaacgat ggatactagg    720 tgtgggggt ctgaccccct ccgtgccgca gctaacgcaa taagtatccc acctggggag    780
tacgatcgca aggttgaaac tcaaaggaat tgacggggc ccgcacaagc ggtggagtat    840
gtggtttaat tcgaagcaac gcgaagaacc ttaccagggc ttgacatcct actaacgaac    900
cagagatgga ttaggtgccc ttcggggaaa gtagagacag tggtgcatg gttgtcgtca    960 gctcgtgtcg tgagatgttg ggttaagtcc cgcaacgagc gcaacccttta ttgttagttg   1020 ctacgcaaga gcactctagc gagactgccg ttgacaaaac ggaggaaggt ggggacgacg   1080
tcaaatcatc atgccccttta tgtcctgggc cacacacgta ctacaatggc ggttaacaga   1140
gggaggcaaa gccgcgaggc agagcaaacc cctaaaagcc gtcccagttc ggattgcagg   1200
ctgaaacccg cctgtatgaa gtcggaatcg ctagtaatcg cggatcagca tgccgcggtg   1260
aatacgttcc cgggccttgt acacaccgcc cgtcacacca tgagagtcgg gaacacccga   1320
agtccgtagc ctaactgcaa aggggggcgcg gccgaaggtg ggttcgataa ttggggtgaa   1380
gtcgtaacag ggtaaccg                                                  1398

<210> SEQ ID NO 4
<211> LENGTH: 1386
<212> TYPE: DNA
<213> ORGANISM: Clostridium orbiscindens

<400> SEQUENCE: 4
tggcggacgg gtgagtaacg cgtgaggaac ctgcctcgga gtggggaata acagaccgaa     60
aggcctgcta ataccgcatg atgcagttgg accgcatggt cctgactgcc aaagatttat    120
cgctctgaga tggcctcgcg tctgattagc ttgttggcgg ggtaatggcc caccaaggcg    180
acgatcagta gccggactga gaggttggcc ggccacattg ggactgagac acggcccaga    240
ctcctacggg aggcagcagt ggggaatatt ggcaatggg cgcaagcctg acccagcaac    300
gccgcgtgaa ggaagaaggc tttcgggttg taaacttctt ttctcaggga cgaacaaatg    360
acggtacctg aggaataagc cacggctaac tacgtgccag cagccgcggt aatacgtagg    420
tggcaagcgt tatccggatt tactgggtgt aaagggcgtg taggcgggaa ggcaagtcag    480
atgtgaaaac tatgggctca acccatagcc tgcatttgaa actgtttttc ttgagtgctg    540
gagaggcaat cggaattccg tgtgtagcgg tgaaatgcgt agatatacgg aggaacacca    600
gtggcgaagg cggattgctg gacagtaact gacgctgagg cgcgaaagcg tggggagcaa    660
acaggattag ataccctggt agtccacgct gtaaacgatg gatactaggt gtgggggtc    720 tgaccccctc cgtgccgcag ttaacacaat aagtatccca cctggggagt acgatcgcaa    780
ggttgaaact caaaggaatt gacggggcc cgcacaagcg gtggagtatg tggtttaatt    840
cgaagcaacg cgaagaacct taccagggct tgacatccta ctaacgaagc agagatgcat    900
taggtgccct tcggggaaag tagagacagg tggtgcatgg ttgtcgtcag ctcgtgtcgt    960
gagatgttgg gttaagtccc gcaacgagcg caacccttat tgttagttgc tacgcaagag   1020
```

```
cactctagcg agactgccgt tgacaaaacg gaggaaggcg gggacgacgt caaatcatca    1080
tgccccttat gtcctgggct acacacgtac tacaatggtg gtaaacagag ggaagcaaga    1140
ccgcgaggtg gagcaaatcc ctaaaagcca tcccagttcg gattgcaggc tgaaacccgc    1200
ctgtatgaag ttggaatcgc tagtaatcgc ggatcagcat gccgcggtga atacgttccc    1260
gggccttgta cacaccgccc gtcacaccat gagagtcggg aacacccgaa gtccgtagtc    1320
taaccgcaag ggggacgcgg ccgaaggtgg gttcgataat tggggtgaag tcgtaacagg    1380
gtaacc                                                               1386
```

<210> SEQ ID NO 5
<211> LENGTH: 1324
<212> TYPE: DNA
<213> ORGANISM: Ruminococcus flavefaciens

<400> SEQUENCE: 5

```
cggatcagtg gcggacgggt gagtaacacg tgagcaacct gcctttaaga gggggataac     60
gtttggaaac gaacgctaat accgcataac atagaagatt cacatgtttc ttctatcaaa    120
gatttatcgc ttaaagatgg gctcgcgtct gattagctag ttggtgaggt aacggctcac    180
caaggcgacg atcagtagcc gtactgagag gtagaacggc cacattggga ctgagacacg    240
gcccagactc ctacgggagg cagcagtggg gaatattgca caatggagga aactctgatg    300
cagcgatgcc gcgtgaggga agaaggtttt cggattgtaa acctctgtct tcagggacga    360
taatgacggt acctgaggag gaagctccgg ctaactacgt gccagcagcc gcggtaatac    420
gtagggagcg agcgttgtcc ggaattactg ggtgtaaagg gagcgtaggc gggatcttaa    480
gtcaggtgtg aaaactatgg gctcaaccca tagactgcac ttgaaactga ggttcttgag    540
tgaagtagag gcaggcggaa ttcctagtgt agcggtgaaa tgcgtagata ttaggaggaa    600
catcagtggc gaaggcggcc tgctgggctt ttactgacgc tgaggctcga agcgtgggg    660 agcaaacagg attagatacc ctggtagtcc acgctgtaaa cgatgattac taggtgtggg    720
gggactgacc ccttccgtgc cgcagttaac acaataagta atccacctgg ggagtacggc    780
cgcaaggttg aaactcaaag gaattgacgg gggcccgcac aagcagtgga gtatgtggtt    840
taattcgaag cacgcgaaga accttaccgg gtcttgacat ctacagaatc ctttagagat    900
aagggagtgc ccttcgggga actgtaagac aggtggtgca tggttgtcgt cagctcgtgt    960
cgtgagatgt tgggttaagt cccgcaacga gcgcaacccc tatcattagt tgctacgcaa    1020
gagcactcta atgagactgc cgttgacaaa acggaggaag gtgggggatga cgtcaaatca    1080 tcatgcccct tatgacccgg gctacacacg tactacaatg gcgtaacaga gggaagcaac    1140
atcgcgaggt gaagcaaatc tctaaaaaac gtcccagttc agattgcagg ctgcaactcg    1200
cctgcatgaa gacggaattg ctagtaatcg cagatcagca tgctgcggtg aatacgttcc    1260
cgggccttgt acacaccgcc cgtcacacca tgggagtcgg taacacccga agtcgcttgt    1320
ctaa                                                                1324
```

<210> SEQ ID NO 6
<211> LENGTH: 1426
<212> TYPE: DNA
<213> ORGANISM: Anaerotruncus colihominis

<400> SEQUENCE: 6

```
agtcgacgga cacatccgac ggaatagctt gctaggaaga tggatgttgt tagtggcgga     60
cgggtgagta acacgtgagc aacctacctc agagtggggg acaacagttg gaaacgactg    120
```

```
ctaataccgc ataagatggc agggtcgcat ggcctggtca taaaaggagc aattcgctct      180
gagatgggct cgcgtctgat tagctagttg gtgaggtaac ggctcaccaa ggcaacgatc      240
agtagccgga ctgagaggtt gaacggccac attgggactg agacacggcc cagactccta      300
cgggaggcag cagtggggaa tattgcacaa tgggggaaac cctgatgcag cgacgccgcg      360
tgagggaaga cggttttcgg attgtaaacc tctgtcttgt gggacgatag tgacggtacc      420
acaggaggaa gccatggcta actacgtgcc agcagccgcg gtaatacgta gatgcgagc       480 gttgtccgga attactgggt gtaaagggag tgtaggcggg ctggtaagtt gaatgtgaaa      540
ccttcgggct caacccggag cgtgcgttca aaactgctgg tcttgagtga agtagaggca      600
ggcggaattc ccggtgtagc ggtggaatgc gtagatatcg gaggaacac cagtggcgaa       660 ggcggcctgc tgggctttta ctgacgctga ggctcgaaag catgggtagc aaacaggatt      720
agataccctg gtagtccatg ccgtaaacga tgattactag gtgtgggggg attgaccccc      780
tccgtgccgg agttaacaca ataagtaatc cacctgggga gtacgaccgc aaggttgaaa     840
ctcaaaggaa ttgacggggg cccgcacaag cagtggagta tgtggtttaa ttcgaagcaa     900
cgcgaaaaac cttaccaggt cttgacatcc atcgccaggc taagagatta gctgttccct     960
ccggggacga tgagacaggt ggtgcatggt tgtcgtcagc tcgtgtcgtg agatgttggg    1020
ttaagtcccg caacgagcgc aacccttact attagttgct acgcaagagc actctaatgg    1080
gactgccgtt gacaaaacgg aggaaggtgg ggatgacgtc aaatcatcat gccccttatg    1140
acctgggcta cacacgtact acaatggccg ttaacagaga gcagcgatac cgcgaggtgg    1200
agcgaatcta gaaaaacggt ctcagttcgg attgcaggct gaaactcgcc tgcatgaagt    1260
cggaattgct agtaatcgcg gatcagcatg ccgcggtgaa tacgttcccg ggccttgtac    1320
acaccgcccg tcacaccatg agagccggta acacccgaag tcagtagcct aaccgcaagg    1380
agggcgctgc cgaaggtggg gctggtaatt ggggtgaagt cgtaac                    1426
```

<210> SEQ ID NO 7
<211> LENGTH: 1373
<212> TYPE: DNA
<213> ORGANISM: Clostridium xylanolyticum

<400> SEQUENCE: 7

```
gtaacgcgtg ggtaacctgc ctcatacagg gggataacag ttagaaatga ctgctaatac      60
cgcataagcg cacagggtcg catgacctag tgtgaaaaac tccggtggta tgagatggac     120
ccgcgtctga ttagctagtt ggtgaggtaa cggctcacca aggcgacgat cagtagccga     180
cctgagaggg tgatcggcca cattgggact gagacacggc ccaaactcct acgggaggca     240
gcagtgggga atattgcaca atgggggaaa ccctgatgca gcgacgccgc gtgaaggaag     300
aagtatttcg gtatgtaaac ttctatcagc agggaagaaa atgacggtac ctgactaaga     360
agccccggct aactacgtgc cagcagccgc ggtaatacgt aggggcaag cgttatccgg      420 atttactggg tgtaaaggga gcgtaggcgg tctgacaagt cagaagtgaa agcccggggc     480
tcaactccgg gactgctttt gaaactgccg gactagattg caggagaggt aagtggaatt     540
cctagtgtag cggtgaaatg cgtagatatt aggaggaaca ccagtggcga aggcggctta     600
ctggactgta aatgacgctg aggctcgaaa gcgtgggag caaacaggat tagatacccct     660 ggtagtccac gccgtaaacg atgaatacta ggtgttgggg agcacagctc ttcggtgccg     720
cagcaaacgc aataagtatt ccacctgggg agtacgttcg caagaatgaa actcaaagga    780
```

```
attgacgggg acccgcacaa gcggtggagc atgtggttta attcgaagca acgcgaagaa        840
ccttaccaag tcttgacatc ccgatgaccg tcccgtaacg ggggcttctc ttcggagcat        900
cggtgacagg tggtgcatgg ttgtcgtcag ctcgtgtcgt gagatgttgg gttaagtccc        960
gcaacgagcg caaccettat ctttagtagc cagcggtacg gccgggcact ctagagagac       1020
tgccagggat aacctggagg aaggtgggga tgacgtcaaa tcatcatgcc ccttatgatt       1080
tgggctacac acgtgctaca atggcgtaaa caaagggaag cgaaactgtg aagtctagca       1140
aatctcaaaa ataacgtctc agttcggatt gtagtctgca actcgactac atgaagctgg       1200
aatcgctagt aatcgcgaat cagcatgtcg cggtgaatac gttcccgggt cttgtacaca       1260
ccgcccgtca caccatggga gttggaaacg cccgaagtca gtgacccaac cgtaaggagg       1320
gagctgccga aggcgggtct gataactggg gtgaagtcgt aacaaggtaa ccg              1373
```

<210> SEQ ID NO 8
<211> LENGTH: 1416
<212> TYPE: DNA
<213> ORGANISM: Clostridium oroticum

<400> SEQUENCE: 8

```
ttttgattga tttcttcgga aagagagaga ctgtgactga gtggcggacg ggtgagtaac        60
gcgtgggtaa cctgcctcat acagggggat aacagttaga aatgactgct aataccgcat       120
aagcacacag cttcgcatga agcagtgtga aaaactccgg tggtatgaga tggacccgcg       180
tctgattagg tagttggtgg ggtaacggcc caccaagccg acgatcagta gccgacctga       240
gagggtgacc ggccacattg ggactgagac acggcccaaa ctcctacggg aggcagcagt       300
ggggaatatt gcacaatggg ggaaaccctg atgcagcgac gccgcgtgaa ggatgaagta       360
tttcggtatg taaacttcta tcagcaggga agaaaatgac ggtacctgac taagaagccc       420
cggctaacta cgtgccagca gccgcggtaa tacgtagggg gcaagcgtta tccggattta       480
ctgggtgtaa agggagcgta gacggtaatg caagtctgga gtgaaaaccc ggggctcaac       540
cccgggactg ctttggaaac tgtgtaacta gagtgtcgga gaggcaagtg gaattcctag       600
tgtagcggtg aaatgcgtag atattaggag gaacaccagt ggcgaaggcg gcttgctgga       660
cgatgactga cgttgaggct cgaaagcgtg gggagcaaac aggattagat accctggtag       720
tccacgccgt aaacgatgac tactaggtgt cggtaagcaa agcttatcgg tgccgcagca       780
aacgcaataa gtagtccacc tggggagtac gttcgcaaga atgaaactca aaggaattga       840
cggggacccg cacaagcggt ggagcatgtg gtttaattcg aagcaacgcg aagaacctta       900
cctggtcttg acatccctct gacagctgag taatgtcggt tttctttcgg acagaggag       960
acaggtggtg catggttgtc gtcagctcgt gtcgtgagat gttgggttaa gtcccgcaac      1020
gagcgcaacc cctatcttca gtagccagca tatgagatgg cactctgga gagactgcca      1080
gggataaccct ggaggaaggt ggggatgacg tcaaatcatc atgccccta tgatcagggc      1140
tacacacgtg ctacaatggc gtaaacaaag gaagcgagc ctgcgagggg gagcaaatcc      1200
caaaaataac gtctcagttc ggattgtagt ctgcaactcg actacatgaa gctggaatcg      1260
ctagtaatcg cgaatcagaa tgtcgcggtg aatacgttcc cggtcttgt acacaccgcc      1320
cgtcacacca tgggagtcag taacgcccga agtcagtgac ccaaccttttc aggagggagc      1380
tgccgaaggc gggaccgata actggggtga agtcgt                                1416
```

<210> SEQ ID NO 9
<211> LENGTH: 1427

<212> TYPE: DNA
<213> ORGANISM: Eubacterium contortum

<400> SEQUENCE: 9

```
cttaagtttg attcttcgga tgaagacttt tgtgactgag tggcggacgg gtgagtaacg      60
cgtgggtaac ctgcctcata caggtggata acagttagaa atgactgcta ataccgcata     120
agaccacagc accgcatggt gcaggggtaa aaactccggt ggtatgagat ggacccgcgt     180
ctgattagct agttggtggg gtaacggcct accaaggcga cgatcagtag ccgacctgag     240
agggtgaccg gccacattgg gactgagaca cggcccaaac tcctacggga ggcagcagtg     300
gggaatattg cacaatgggg gaaaccctga tgcagcgacg ccgcgtgaag gatgaagtat     360
ttcggtatgt aaacttctat cagcagggaa gaaaatgacg gtacctgact aagaagcccc     420
ggctaactac gtgccagcag ccgcggtaat acgtaggggg caagcgttat ccggatttac     480
tgggtgtaaa gggagcgtag acggtatggc aagtctgatg tgaaaggcca gggctcaacc     540
ctgggactgc attggaaact gtcgaactag agtgtcggag aggcaagtgg aattcctagt     600
gtagcggtga aatgcgtaga tattaggagg aacaccagtg gcgaaggcgg cttgctggac     660
gatgactgac gttgaggctc gaaagcgtgg ggagcaaaca ggattagata ccctggtagt     720
ccacgccgta aacgatgact actaggtgtc gggtagcaga gctattcggt gccgcagcca     780
acgcaataag tagtccacct ggggagtacg ttcgcaagaa tgaaactcaa aggaattgac     840
ggggacccgc acaagcggtg gagcatgtgg tttaattcga gcaacgcga agaaccttac     900
ctgctcttga catctccctg accggcaagt aatgttgcct ttccttcggg acagggatga     960
caggtggtgc atggttgtcg tcagctcgtg tcgtgagatg ttgggttaag tcccgcaacg    1020
agcgcaaccc ctatctttag tagccagcgg tttggccggg cactctagag agactgccag    1080
ggataacctg gaggaaggtg gggatgacgt caaatcatca tgccccttat gagcagggct    1140
acacacgtgc tacaatggcg taaacaaagg gaagcgagcc tgcgagggta agcaaatctc    1200
aaaaataacg tctcagttcg gattgtagtc tgcaactcga ctacatgaag ctggaatcgc    1260
tagtaatcgc gaatcagaat gtcgcggtga atacgttccc gggtcttgta cacaccgccc    1320
gtcacaccat gggagttggt aacgcccgaa gtcagtgacc caaccgcaag gagggagctg    1380
ccgaaggtgg gaccgataac tggggtgaag tcgtaacaag gtaaccg                  1427
```

<210> SEQ ID NO 10
<211> LENGTH: 1447
<212> TYPE: DNA
<213> ORGANISM: Clostridium oroticum

<400> SEQUENCE: 10

```
acatgcaagt cgagcgagcg ctttagtgga attctacgga aggaaagtga agtgactgag      60
cggcggacgg gtgagtaacg cgtgggtaac ctgcctcata caggggata acagttagaa     120
atgactgcta ataccgcata agaccccagt accgcatggt acagaggtaa aaactgaggt     180
ggtatgagat ggacccgcgt ctgattagct agttggtgag gtagaggctc accaaggcga     240
cgatcagtag ccgacctgag agggtgaccg gccacattgg gactgagaca cggcccaaac     300
tcctacggga ggcagcagtg gggaatattg cacaatgggg gaaaccctga tgcagcgacg     360
ccgcgtgagc gaagaagtat ttcggtatgt aaagctctat cagcagggaa gaaaatgacg     420
gtacctgact aagaagcacc ggctaaatac gtgccagcag ccgcggtaat acgtatggtg     480
caagcgttat ccggatttac tgggtgtaaa gggagcgtag acggagcagc aagtctgatg     540
```

```
tgaaaacccg gggctcaacc ccgggagtgc attggaaact gttgatctag agtgctggag    600
aggtaagtgg aattcctagt gtagcggtga aatgcgtaga tattaggagg aacaccagtg    660
gcgaaggcgg cttactggac agtgactgac gttgaggctc gaaagcgtgg ggagcaaaca    720
ggattagata ccctggtagt ccacgccgta acgatgact actaggtgtc gggtagcaaa    780
gctattcggt gccgcagcca acgcaataag tagtccacct ggggagtacg ttcgcaagaa    840
tgaaactcaa aggaattgac ggggacccgc acaagcggtg gagcatgtgg tttaattcga    900
agcaacgcga agaaccttac ctgcccttga catccgggtg accggcgagt aatgtcgcct    960
tctcttcgga gcagccgaga caggtggtgc atggttgtcg tcagctcgtg tcgtgagatg   1020
ttgggttaag tcccgcaacg agcgcaaccc ttatctttag tagccagcgg ataagccggg   1080
gactctagag agactgccag ggataacctg gaggaaggtg gggatgacgt caaatcatca   1140
tgccccttat gggcagggct acacacgtgc tacaatggcg taaacaaagg gaagcgaagc   1200
tgtgaagcgg agcgaatctc aaaaataacg tctcagttcg gattgtagtc tgcaactcga   1260
ctacatgaag ctggaatcgc tagtaatcgc gaatcagaat gtcgcggtga atacgttccc   1320
gggtcttgta caccgcccc gtcacaccat gggagtcagt aacgcccgaa gtcagtgacc   1380
caaccgtaag gagggagctg ccgaaggcgg gacggataac tggggtgaag tcgtaacaag   1440
gtaaccg                                                               1447
```

<210> SEQ ID NO 11
<211> LENGTH: 1379
<212> TYPE: DNA
<213> ORGANISM: Lachnospira pectinoschiza

<400> SEQUENCE: 11

```
agtggcggac gggtgagtaa cgcgtgggta acctgccctg tacaggggga caacagctgg     60
aaacggctgc taataccgca taagccctta gcactgcatg gtgcataggg aaaaggagca    120
atccggtaca ggatggaccc gcgtctgatt agccagttgg cagggtaacg gcctaccaaa    180
gcgacgatca gtagccgatc tgagaggatg tacggccaca ttgggactga gacacggccc    240
agactcctac gggaggcagc agtggggaat attgcacaat ggaggaaact ctgatgcagc    300
gacgccgcgt gagtgaagaa gtatttcggt atgtaaagct ctatcagcag gaagaaaat    360
gacggtacct gactaagaag caccggctaa atacgtgcca gcagccgcgg taatacgtat    420
ggtgcaagcg ttatccggat ttactgggtg taaagggagc gtaggtggca aggcaagcca    480
gaagtgaaaa cccggggctc aaccgcggga ttgcttttgg aactgtcatg ctagagtgca    540
ggaggggtga gcggaattcc tagtgtagcg gtgaaatgcg tagatattag gaggaacacc    600
ggaggcgaag gcggctcact ggactgtaac tgacactgag gctcgaaagc gtggggagca    660
aacaggatta gataccctgg tagtccacgc ggtaaacgat gaatactaga tgtcgggtag    720
caaagctact cggtgtcgtc gcaaacgcaa taagtattcc acctggggag tacgttcgca    780
agaatgaaac tcaaaggaat tgacggggac ccgcacaagc ggtggagcat gtggtttaat    840
tcgaagcaac gcgaagaacc ttacctgctc ttgacatccc attcgataga gggtaatgct    900
tctagccctt cggggaatg gagacaggtg gtgcatggtt gtcgtcagct cgtgtcgtga    960
gatgttgggt taagtcccgc aacgagcgca acccttattg tcagtagcca gcaggtgaag   1020
ctgggcactc tgatgagact gccggggata acccggagga aggtgggat gacgtcaaat   1080
catcatgccc cttatgagca gggctacaca cgtgctacaa tggcgtaaac agagggaagc   1140
gaaggagtga tctggagcaa atctcaaaaa taacgtctca gttcggattg tagtctgcaa   1200
```

```
ctcgactaca tgaagctgga atcgctagta atcgcagatc aaaatgctgc ggtgaatacg    1260
ttcccgggtc ttgtacacac cgcccgtcac accatgggag tcggtaatgc ccgaagtcag    1320
tgactcaacc gaaaggaaaa agctgccgaa ggcaggactg gtaactgggg tgaagtcgt     1379
```

<210> SEQ ID NO 12
<211> LENGTH: 1444
<212> TYPE: DNA
<213> ORGANISM: Roseburia faecis

<400> SEQUENCE: 12

```
agtcgaacga agcactttat tacgatttct tcggaatgac gatttagtga ctgagtggcg     60
gacgggtgag taacgcgtgg gtaacctgcc ttatacaggg ggataacagt tagaaatgac    120
tgctaatacc gcataagcgc acaggattgc atgatctggt gtgaaaaact ccggtggtat    180
aagatggacc cgcgtctgat tagctggttg gtgaggtaac ggcccaccaa ggcgacgatc    240
agtagccgac ctgagagggt gaccggccac attgggactg agacacggcc caaactccta    300
cgggaggcag cagtggggaa tattgcacaa tgggggaaac cctgatgcag cgacgccgcg    360
tgagcgaaga agtatttcgg tatgtaaagc tctatcagca gggaagaaaa aaatgacggt    420
acctgactaa gaagccccgg ctaactacgt gccagcagcc gcggtaatac gtaggggca    480 agcgttatcc ggatttactg ggtgtaaagg gagcgcaggc ggtgcggcaa gtctgatgtg    540
aaagcccggg gctcaacccc gggactgcat tggaaactgt cgtacttgag tatcggagag    600
gtaagtggaa ttcctagtgt agcggtgaaa tgcgtagata ttaggaggaa caccagtggc    660
gaaggcggct tactggacga taactgacgc tgaggctcga aagcgtgggg agcaaacagg    720
attagatacc ctggtagtcc acgccgtaaa cgatgaatac taggtgtcgg gggacatagt    780
ccttcggtgc cgcagcaaac gcaataagta ttccacctgg ggagtacgtt cgcaagaatg    840
aaactcaaag gaattgacgg ggacccgcac aagcggtgga gcatgtggtt taattcgaag    900
caacgcgaag aaccttacca gtcttgaca tcccggtgac aaagtatgta atgtactctt    960
tcttcggaac accggtgaca ggtggtgcat ggttgtcgtc agctcgtgtc gtgagatgtt   1020
gggttaagtc ccgcaacgag cgcaacccct gttcttagta gccagcggtt cggccgggca   1080
ctctagggag actgccaggg ataacctgga ggaaggcggg gatgacgtca atcatcatg    1140 ccccttatga cttgggctac acacgtgcta caatggcgta aacaaaggga agcgaaaagg   1200
tgacttctag caaatcccaa aaataacgtc ccagttcgga ctgtagtctg caactcgact   1260
acacgaagct ggaatcgcta gtaatcgcga atcagaatgt cgcggtgaat acgttcccgg   1320
gtcttgtaca caccgcccgt cacaccatgg gagtcgggaa tgcccgaagc cggtgactca   1380
accgaaagga gagagccgtc gaaggcaggt ctgataactg gggtgaagtc gtaacaaggt   1440
aacc                                                               1444
```

<210> SEQ ID NO 13
<211> LENGTH: 1452
<212> TYPE: DNA
<213> ORGANISM: Clostridium hathewayi

<400> SEQUENCE: 13

```
agtcgacgga gatgcgatgt gagcgagagg tgcttgcact gatcaatctt ttcgtatctt     60
agtggcggac gggtgagtaa cgcgtgggta acctgcctta taccggggga taacacttag    120
aaataggtgc taataccgca taagcgcacg gtgtcgcatg acacagtgtg aaaaactccg    180
```

```
gtggtataag atggacccgc gtctgattag ccagttggca gggtaacggc ctaccaaagc    240
gacgatcagt agccggcctg agagggtgaa cggccacatt gggactgaga cacggcccaa    300
actcctacgg gaggcagcag tggggaatat tgcacaatgg gggaaaccct gatgcagcga    360
cgccgcgtga gtgaagaagt atttcggtat gtaaagctct atcagcaggg aagaagaaat    420
gacggtacct gactaagaag ccccggctaa ctacgtgcca gcagccgcgg taatacgtag    480
ggggcaagcg ttatccggat ttactgggtg taaagggagc gtagacgtg aagcaagtct     540 gaagtgaaag gttgggctc aacccccgaaa ctgctttgga aactgtttaa ctggagtaca    600
ggagaggtaa gtggaattcc tagtgtagcg gtgaaatgcg tagatattag gaggaacacc    660
agtggcgaag gcggcttact ggactgtaac tgacgttgag gctcgaaagc gtggggagca    720
aacaggatta gataccctgg tagtccacgc cgtaaacgat gattactagg tgttggtgga    780
tatggatcca tcggtgccgc agcaaacgca ataagtaatc cacctgggga gtacgttcgc    840
aagaatgaaa ctcaaaggaa ttgacgggga cccgcacaag cggtggagca tgtggtttaa    900
ttcgaagcaa cgcgaagaac cttacctgat cttgacatcc ctatgaatac agggtaatgc    960
ctgtagtact tcggtacata ggagacaggt ggtgcatggt tgtcgtcagc tcgtgtcgtg   1020
agatgttggg ttaagtcccg caacgagcgc aacccctatc tttagtagcc agcagtaaga   1080
tgggcactct agagagactg ccggggataa cccggaggaa ggtggggatg acgtcaaatc   1140
atcatgcccc ttatgaccag ggctacacac gtgctacaat ggcgtaaaca gagggaagcg   1200
aagtggtgac atggagcaaa tcccaaaaat aacgtcccag ttcggattgc aggctgcaac   1260
tcgcctgcat gaagctggaa tcgctagtaa tcgcagatca gaatgctgcg gtgaatacgt   1320
tcccgggtct tgtacacacc gcccgtcaca ccatgggagt aggtaatgcc gaagtcggt    1380 gacctaaccg caaggaagga gccgccgaag gcaggactta taactggggt gaagtcgtaa   1440
caaggtaacc gt                                                       1452
```

<210> SEQ ID NO 14
<211> LENGTH: 1400
<212> TYPE: DNA
<213> ORGANISM: Fusicatenibacter saccharivorans

<400> SEQUENCE: 14

```
cggatggaat cggtataact tagtggcgga cgggtgagta acgcgtggga aacctgccct     60
gtaccggggg ataacactta gaaataggtg ctaataccgc ataagcgcac ggaactgcat    120
ggttctgtgt gaaaaactcc ggtggtacag gatggtcccg cgtctgatta gccagttggc    180
agggtaacgg cctaccaaag cgacgatcag tagccggcct gagagggtga acggccacat    240
tgggactgag acacggccca aactcctacg ggaggcagca gtggggaata ttgcacaatg    300
ggggaaaccc tgatgcagcg acgccgcgtg agtgaagaag tatttcggta tgtaaagctc    360
tatcagcagg gaagaaaatg acggtacctg actaagaagc cccggctaac tacgtgccag    420
cagccgcggt aatacgtagg gggcaagcgt tatccggatt tactgggtgt aaagggagcg    480
tagacggcat ggcaagccag atgtgaaaac ccagggctca accttgggat tgcatttgga    540
actgccaggc tggagtgcag gagaggtaag cggaattcct agtgtagcgg tgaaatgcgt    600
agatattagg aggaacacca gtggcgaagg cggcttactg gactgtaact gacgttgagg    660
ctcgaaagcg tggggagcaa acaggattag ataccctggt agtccacgcg gtaaacgatg    720
attgctaggt gtaggtgggt atggacccat cggtgccgca gctaacgcaa taagcaatcc    780
acctggggag tacgttcgca agaatgaaac tcaaaggaat tgacggggac ccgcacaagc    840
```

```
ggtggagcat gtggtttaat tcgaagcaac gcgaagaacc ttaccaagtc ttgacatccc      900
aatgacgcac ctgtaaagag gtgttccctt cggggcattg agacaggtg gtgcatggtt       960 gtcgtcagct cgtgtcgtga gatgttgggt taagtcccgc aacgagcgca acccttattc     1020
ttagtagcca gcaggtgaag ctgggcactc taaggagact gccggggata cccggagga     1080 aggcggggat gacgtcaaat catcatgccc cttatgattt gggctacaca cgtgctacaa     1140
tggcgtaaac aaagggaagc gagacagtga tgtggagcaa atcccagaaa taacgtctca     1200
gttcggattg tagtctgcaa ctcgactaca tgaagctgga atcgctagta atcgcgaatc     1260
agcatgtcgc ggtgaatacg ttcccgggtc ttgtacacac cgcccgtcac accatgggag     1320
ttggaaatgc ccgaagtctg tgacctaacc gaaagggagg agcagccgaa ggcaggtctg     1380
ataactgggg tgaagtcgta                                                 1400

<210> SEQ ID NO 15
<211> LENGTH: 1416
<212> TYPE: DNA
<213> ORGANISM: Clostridium clostridioforme

<400> SEQUENCE: 15
ctgctttgat gaagttttcg gatggattta aaacagctta gtggcggacg ggtgagtaac       60
gcgtgggtaa cctgcctcac actgggggat aacagttaga aatagctgct aataccgcat      120
aagcgcacgg ttccgcatgg aacagtgtga aaaactccgg tggtgtgaga tggacccgcg      180
tctgattagc cagttggcgg ggtaacggcc caccaaagcg acgatcagta gccggcctga      240
gagggtgaac ggccacattg ggactgagac acggcccaaa ctcctacggg aggcagcagt      300
ggggaatatt gcacaatggg ggaaaccctg atgcagcgac gccgcgtgag tgaagaagta      360
tttcggtatg taaagctcta tcagcaggga agaaagtgac ggtacctgaa taagaagccc      420
cggctaacta cgtgccagca gccgcggtaa tacgtagggg gcaagcgtta tccggattta      480
ctgggtgtaa agggagcgta gacggcaagg caagtctgaa gtgaaagccc ggtgcttaac      540
gccgggactg ctttggaaac tgtttagctg gagtgccgga gaggtaagcg gaattcctag      600
tgtagcggtg aaatgcgtag atattaggaa gaacaccagt ggcgaaggcg gcttactgga      660
cggtaactga cgttgaggct cgaaagcgtg gggagcaaac aggattagat accctggtag      720
tccacgccgt aaacgatgat tgctaggtgt aggtgggtat ggacccatcg gtgccgcagc      780
taacgcaata agcaatccac ctggggagta cgttcgcaag aatgaaactc aaaggaattg      840
acggggaccc gcacaagcgg tggagcatgt ggtttaattc gaagcaacgc gaagaacctt      900
accaggtctt gacatcccga tgaaaaccc gtaacggggt ccctcttcg gagcatcgga      960 gacaggtggt gcatggttgt cgtcagctcg tgtcgtgaga tgttgggtta agtcccgcaa     1020
cgagcgcaac ccttattctt agtagccagc aggtaaggct gggcactcta aggagactgc     1080
cggggataac ccgaggaag gtggggatga cgtcaaatca tcatgcccct tatgatctgg     1140
gctacacacg tgctacaatg gcgtaacaaa gggaagcgag cctgcgaggg tgagcaaatc     1200
ccaaaaataa cgtcccagtt cggactgtag tctgcaaccc gactacacga agctggaatc     1260
gctagtaatc gcgaatcaga atgtcgcggt gaatacgttc ccgggtcttg tacacaccgc     1320
ccgtcacacc atgggagtcg gaaatgcccg aagtctgtga ctcaaccgca aggagagagc     1380
agccgaaggc aggtctgata actggggtga agtcgt                                1416

<210> SEQ ID NO 16
```

```
<211> LENGTH: 1211
<212> TYPE: DNA
<213> ORGANISM: Rumincoccus torques

<400> SEQUENCE: 16
cggtatgaga tggacccgcg tctgattagc tagttggtgg ggtaacggcc taccaaggcg      60
acgatcagta gccgacctga gagggtgacc ggccacattg ggactgagac acggcccaaa     120
ctcctacggg aggcagcagt ggggaatatt gcacaatggg ggaaaccctg atgcagcgac     180
gccgcgtgag cgaagaagta tttcggtatg taaagctcta tcagcaggga agaaaatgac     240
ggtacctgac taagaagccc cggctaacta cgtgccagca gccgcggtaa tacgtagggg     300
gcaagcgtta tccggattta ctgggtgtaa agggagcgta gacggcgagg caagtctgat     360
gtgaaaaccc ggggctcaac cccgtgactg cattggaaac tgttttgctt gagtgccgga     420
gaggtaagcg gaattcctag tgtagcggtg aaatgcgtag atattaggag gaacaccagt     480
ggcgaaggcg gcttactgga cggcaactga cgttgaggct cgaaagcgtg gggagcaaac     540
aggattagat accctggtag tccacgccgt aaacgatgaa tactaggtgt cggggagcaa     600
agctcttcgg tgccgccgca aacgcaataa gtattccacc tggggagtac gttcgcaaga     660
atgaaactca aaggaattga cggggacccg cacaagcggt ggagcatgtg gtttaattcg     720
aagcaacgcg aagaacctta ccaagccttg acatcccatt gacagagcat gtaatgtgct     780
ttcccttcgg ggcagtggtg acaggtggtg catggttgtc gtcagctcgt gtcgtgagat     840
gttgggttaa gtcccgcaac gagcgcaacc ctatcttca gtagccagcg gtttggccgg     900
gcactctgga gagactgcca gggataacct ggaggaaggt ggggatgacg tcaaatcatc     960
atgcccctta tggcttgggc tacacacgtg ctacaatggc gtaaacaaag ggaagcgagc    1020
ctgcgagggg gagcaaatcc caaaaataac gtctcagttc ggattgtagt ctgcaactcg    1080
actacatgaa gctggaatcg ctagtaatcg cgaatcagaa tgtcgcggtg aatacgttcc    1140
cgggtcttgt acacaccgcc cgtcacacca tgggagtcgg caacgcccga agccagtgac    1200
ccaaccgaaa g                                                         1211

<210> SEQ ID NO 17
<211> LENGTH: 1425
<212> TYPE: DNA
<213> ORGANISM: Closstridium celerecrescens

<400> SEQUENCE: 17
agtcgacgag gtaatgagat gaagttttcg gatggattct tatttccgag tggcggacgg      60
gtgagtaacg cgtgggtaac ctgcctcata caggggata acgattggaa acgattgcta     120
ataccgcata agcgcacagt accacatggt acagtgtgaa aaactccggt ggtatgagat     180
ggacccgcgt ctgattagct agttggtgag gtaacggccc accaaggcaa cgatcagtag     240
ccgacctgag agggtgaccg gccacattgg gactgagaca cggcccagac tcctacggga     300
ggcagcagtg ggggatattg cacaatggag gaaactctga tgcagcgacg ccgcgtgagt     360
gaagaagtat ttcggtatgt aaagctctat cagcaggaa gaaaatgacg gtacctgact     420
aagaagcccc ggctaactac gtgccagcag ccgcggtaat acgtaggggg caagcgttat     480
ccggatttac tgggtgtaaa gggagcgtag acggcgatgc aagtctgaag tgaaataccc     540
gggctcaacc tggaactgc tttgaaaact gtatggctag agtgctggag aggtaagcgg     600
aattcctagt gtagcggtga atgcgtaga tattaggaag aacaccagtg gcgaaggcgg     660
cttactggac agtaactgac gttcaggctc gaaagcgtgg ggagcaaaca ggattagata     720
```

```
ccctggtagt ccacgccgta aacgatgaat actaggtgtc gggggacaaa gtctttcggt      780
gccgccgcaa acgcaataag tattccacct ggggagtacg ttcgcaagaa tgaaactcaa      840
aggaattgac ggggacccgc acaagcggtg gagcatgtgg tttaattcga agcaacgcga      900
agaaccttac caaatcttga catccctctg aaaagccttt aatcgagctc ctccttcggg      960
acagaggtga caggtggtgc atggttgtcg tcagctcgtg tcgtgagatg ttgggttaag     1020
tcccgcaacg agcgcaaccc ctattgtcag tagccagcag gtaaagctgg gcactctgat     1080
gagactgcca gggataacct ggaggaaggt ggggatgacg tcaaatcatc atgccccta      1140 tgatttgggc tacacacgtg ctacaatggc gtaaacaaag agaggcgaag ctgtgaggca     1200
gagcaaatct caaaaataac gtctcagttc ggattgtagt ctgcaactcg actacatgaa     1260
gctggaatcg ctagtaatcg cggatcagaa tgccgcggtg aatacgttcc cgggtcttgt     1320
acacaccgcc cgtcacacca tgggagtcgg aaatgcccga agccagtgac ccaagcgaaa     1380
gcagggagct gtcgaaggca ggtctgataa ctggggtgaa gtcgt                    1425
```

<210> SEQ ID NO 18
<211> LENGTH: 1437
<212> TYPE: DNA
<213> ORGANISM: Clostridium celerescens

<400> SEQUENCE: 18

```
tcgacgaggt attttgattg aagttttcgg atggatttca gataccgagt ggcggacggg       60
tgagtaacgc gtgggtaacc tgcctcatac aggggggataa cggttagaaa tgactgctaa      120
taccgcataa gcgcacagta ccgcatggta cggtgtgaaa actccggtg gtatgagatg       180 gacccgcgtc tgattagcta gttggtgggg taacggccca ccaaggcgac gatcagtagc      240
cgacctgaga gggtgaccgg ccacattggg actgagacac ggcccagact cctacgggag      300
gcagcagtgg gggatattgc acaatggagg aaactctgat gcagcgacgc cgcgtgagtg      360
aagaagtatt tcggtatgta aagctctatc agcagggaag aaaatgacgg tacctgacta      420
agaagccccg gctaactacg tgccagcagc cgcggtaata cgtaggggc aagcgttatc       480 cggatttact gggtgtaaag ggagcgtaga cggcgacgca agtctgaagt gaaatacccg      540
ggctcaacct gggaactgct ttggaaactg tgttgctaga gtgctggaga ggtaagcgga      600
attcctagtg tagcggtgaa atgcgtagat attaggaaga acaccagtgg cgaaggcggc      660
ttactggaca gtaactgacg ttgaggctcg aaagcgtggg gagcaaacag gattagatac      720
cctggtagtc cacgccgtaa acgatgaata ctaggtgttg gtgagcaaag ctcatcggtg      780
ccgccgcaaa cgcaataagt attccacctg gggagtacgt tcgcaagaat gaaactcaaa      840
ggaattgacg gggacccgca caagcggtgg agcatgtggt ttaattcgaa gcaacgcgaa      900
gaaccttacc aaatcttgac atccctctga aacgccctta atcgggctcc tccttcggga      960
cagaggtgac aggtggtgca tggttgtcgt cagctcgtgt cgtgagatgt tgggttaagt     1020
cccgcaacga gcgcaacccc tattgtcagt agccagcagg taaagctggg cactctgatg     1080
agactgccag ggataacctg gaggaaggtg gggatgacgt caaatcatca tgccccttat     1140
gatttgggct acacacgtgc tacaatggcg taaacaaaga gaagcgagcc tgcgagggga     1200
agcaaatctc aaaaataacg tctcagttcg gattgtagtc tgcaactcga ctacatgaag     1260
ctggaatcgc tagtaatcgc agatcagaat gctgcggtga atacgttccc gggtcttgta     1320
cacaccgccc gtcacaccat gggagtcgga aatgcccgaa gccagtgacc caagcgaaag     1380
```
cagggagctg tcgaaggcag gtctgataac tggggtgaag tcgtaacagg gtaaccg    1437

<210> SEQ ID NO 19
<211> LENGTH: 1401
<212> TYPE: DNA
<213> ORGANISM: Eubacterium infirmum

<400> SEQUENCE: 19
gagctcatca cagatgcttc ggttgaagtg atgagtggaa agcggcggac gggtgagtaa     60
cgcgtaggca acctgcccct tgcagaggga tagcctcggg aaaccgggat taaaacctca    120
tgacacctct taaagacatc tttgagaggt caaagattta tcggcagagg atgggcctgc    180
gtctgattag ctagttggtg gggtaacggc ctaccaaggc gacgatcagt agccgacctg    240
agagggtgat cggccacatt ggaactgaga cacggtccaa actcctacgg gaggcagcag    300
tggggaatat tgcacaatgg gggaaaccct gatgcagcaa cgccgcgtga aggaagaagg    360
cctttgggtc gtaaacttct gttctaaggg aagataatga cggtaccttg ggagcaagtc    420
ccggctaact acgtgccagc agccgcggta atacgtaggg ggcaagcgtt atccggaatt    480
attgggcgta aagagtacgt aggtggttac ctaagcacga ggtataaggc aatggcttaa    540
ccattgttcg ccttgtgaac tgggctactt gagtgcagga gaggaaagcg gaattcctag    600
tgtagcggtg aaatgcgtag atattaggag gaacaccagt ggcgaaggcg gctttctgga    660
ctgtaactga cactgaggta cgaaagcgtg gggagcaaac aggattagat accctggtag    720
tccacgccgt aaacgatgag cactaggtgt cggggtcgca agacttcggt gccgcagtta    780
acgcaataag tgctccgcct ggggagtacg ttcgcaagaa tgaaactcaa aggaattgac    840
ggggacccgc acaagcagcg gagcatgtgg tttaattcga agcaacgcga agaaccttac    900
caggacttga catccctctg acagcctttt aatcgaggtt ttctacggac agaggagaca    960
ggtggtgcat ggttgtcgtc agctcgtgtc gtgagatgtt gggttaagtc ccgcaacgag   1020
cgcaacccct tgtcattagt tgccagcagta agatgggcac tctagtgaga ctgccgggga   1080
taactcggag gaaggtgggg atgacgtcaa atcatcatgc cccttatgtt ctgggctaca   1140
cacgtgctac aatggccggt acagagagaa agcgagactg cgaagtggag cgaaactcaa   1200
aagccggtcc cagttcggat tgcaggctgc aactcgcctg catgaagtcg gagttgctag   1260
taatcgcaga tcagaatgct gcggtgaatg cgttcccggg tcttgtacac accgcccgtc   1320
acaccatgga agttggggc gcccgaagtt ggcagataaa tatgttacct aaggcgaaat   1380
caatgactgg ggtgaagtcg t                                             1401

<210> SEQ ID NO 20
<211> LENGTH: 1368
<212> TYPE: DNA
<213> ORGANISM: Eubacterium infirmum

<400> SEQUENCE: 20
tcggtaaagg gatatggcgg aaagcggcgg acgggtgagt aacgcgtagg caacctgccc     60
cttacagagg gatagccatt ggaaacgatg attaagacct cataacgcct ccctcccaca    120
tgaggggag gccaaagatt catccggtaag ggatgggcct cgtctgatt agcttgttgg    180
cggggtaacg gcccaccaag gcgacgatca gtagccgacc tgagagggtg atcggccaca    240
ttggaactga gacacggtcc aaactcctac ggggaggcagc agtggggaat attgcacaat    300
gggcggaagc ctgatgcagc aacgccgcgt gagggatgaa ggccttcggg tcgtaaacct    360
ctgtccttgg ggaagaaaca aatgacggta cccatggagg aagccccggc taactacgtg    420

```
ccagcagccg cggtaatacg taggggggcga gcgttatccg gaattattgg gcgtaaagag      480
tgcgtaggtg gttacctaag cgcagggtct aaggcaatgg ctcaaccatt gttcgccctg      540
cgaactgggc tacttgagtg caggagagga aagcggaatt cctagtgtag cggtgaaatg      600
cgtagatatt aggaggaaca ccagtggcga aggcggcttt ctggactgtt actgacactg      660
aggcacgaaa gcgtggggag caaacaggat tagatacccct ggtagtccac gccgtaaacg      720
atgagcacta ggtgtcgggg ccgcaaggct tcggtgccgc agttaacgca ttaagtgctc      780
cgcctgggga gtacgcacgc aagtgtgaaa ctcaaaggaa ttgacgggga cccgcacaag      840
cagcggagca tgtggtttaa ttcgaagcaa cgcgaagaac cttaccagga cttgacatcc      900
ccctgacaga tccttaaccg gatccttctt cggacagggg agacaggtgg tgcatggttg      960
tcgtcagctc gtgtcgtgag atgttgggtt aagtcccgca acgagcgcaa cccttgccat     1020
tagttgccat cattcagttg ggcactctaa tgggactgcc ggggacaact cggaggaagg     1080
tggggatgac gtcaaatcat catgccccctt atgttctggg ctacacacgt gctacaatgg     1140
ccggtacagc aggaagcgat cccgcgaggg ggagcaaatc ccaaaaaccg gtcccagttc     1200
ggactgcagg ctgcaacccg cctgcacgaa gccggagttg ctagtaatcg tggatcagaa     1260
tgccacggtg aatgcgttcc cgggtcttgt acacaccgcc cgtcacacca tggaagttgg     1320
gggtgcccga agccggcagg gagatatgct gtctaaggca aaaccaat                  1368
```

<210> SEQ ID NO 21
<211> LENGTH: 1421
<212> TYPE: DNA
<213> ORGANISM: Clostridium thermocellum

<400> SEQUENCE: 21

```
ggatgaggaa atgcttcggc atggagacat ccgatctagt ggcggacggg tgagtaacgc       60
gtgagcaacc tgtcctgcac aggggggataa cactgagaaa tcagtgctaa taccgcatga      120
gaccacagta tcacatggta cagggggtcaa aggagaaatc cggtgcaggg tgggctcgcg      180
tcccattagc tagttggtag ggtaaaggcc taccaaggcg acgatgggta gccggactga      240
gaggttggcc ggccacactg gactgagac acggcccaga ctcctacggg aggcagcagt       300
ggggaatatt gggcaatggg cgaaagcctg acccagcaac gccgcgtgaa ggaagaaggt      360
ctttggattg taaactttg tcctatggga agaaggaagt gacggtacca tgggaggaag      420
ccccggctaa ctacgtgcca gcagccgcgg taatacgtag ggggcgagcg ttgtccggaa      480
ttactgggcg taaagggcgc gcaggcggcc gatcaagtta gatgtgaaat acccgggctt      540
aacctgggaa ctgcatttaa aactggttgg ctaggagtgc aggagaggga agcggaattc      600
ctagtgtagc ggtgaaatgc gtagatatta ggaggaacac cagtggcgaa ggcggctttc      660
tggactgtaa ctgacgctga gcgcgaaag cgtggggagc gaacaggatt agataccctg      720
gtagtccacg ctgtaaacga tgaatactag gtgtaggggg tatcgacccc cctgtgccg      780 gagcaaacgc aataagtatt ccgcctgggg agtacggccg caaggttgaa actcaaagga      840
attgacgggg gcccgcacaa gcagcggagc atgtggttta attcgaagca acgcgaagaa      900
ccttaccagg tcttgacatc cctcgaagtg catagagata tgtacgtcct tcgggacgag      960
gagacaggtg gtgcatggtt gtcgtcagct cgtgtcgtga gatgttgggt taagtcccgc     1020
aacgagcgca acccctacag ttagttacca gcgggtaaag ccggggactc taacaggact     1080
gccgtggata acacggagga aggtggggac gacgtcaaat catcatgctc cttatgacct     1140
```

```
gggctacaca cgtgctacaa tggccggtac aaagagaagc gagaccgtaa ggtggagcgg    1200
atctcaaaaa accggtccca gttcggattg tgggctgcaa cccgcccaca tgaagttgga    1260
gttgctagta atcgcgaatc agcatgtcgc ggtgaatgcg ttcccgggcc ttgtacacac    1320
cgcccgtcac accatgggag ttgggagcgc ccgaagtcgt tgaggtaacc cgcaagggag    1380
ccaggcgccg aaggtgagac cgataactgg ggtgaagtcg t                       1421
```

<210> SEQ ID NO 22
<211> LENGTH: 1507
<212> TYPE: DNA
<213> ORGANISM: Anaerovorax odorimutans

<400> SEQUENCE: 22

```
agagtttgat cctggctcag gatgaacgct ggcggcgtgc ctaacacatg caagtcgagc      60
gggaaatctt ggaacgatac ttcggtaaag ggaagagatg gatagcggcg gacgggtgag    120
taacgcgtag gtaacctgcc tcatgcagag ggatagcctc gggaaactgg gattaatacc    180
tcataatgcg gaggagtcac atggctccat cgccaaagat ttatcggcat gagatggacc    240
tgcgtctgat tagttagttg gtgaggtaac ggctcaccaa ggcagcgatc agtagccgac    300
ctgagagggt aatcggccac attggaactg agacacggtc caaactccta cgggaggcag    360
cagtggggaa tattgcacaa tgggcgcaag cctgatgcag caacgccgcg tgagcgatga    420
aggtcttcgg atcgtaaagc tctgtcctag ggaagaata tatgacggta cccttggagg    480
aagccccggc taactacgtg ccagcagccg cggtaatacg taggggcga gcgttatccg    540 gaattattgg gcgtaaagag ttcgtaggtg gttttgtaag cgcggggttt aaggcaacgg    600
ctcaaccgtt gttcgccttg cgaactgcaa gacttgagtg cgggagagga aagtggaatt    660
cctagtgtag cggtgaaatg cgtagatatt aggaggaaca ccagtggcga aggcgacttt    720
ctggaccgta actgacactg aggaacgaaa gcgtggggag caaacaggat tagataccct    780
ggtagtccac gccgtaaacg atgagcacta ggtgtcgggg ccgcaaggtt tcggtgccgc    840
agttaacgca ttaagtgctc cgcctgggga gtacgcacgc aagtgtgaaa ctcaaaggaa    900
ttgacgggga cccgcacaag cagcggagca tgtggtttaa ttcgaagcaa cgcgaagaac    960
cttaccaggg cttgacatcc cgatgaccgg cgggtaacgc cgccttctct tcggagcatc   1020
ggtgacaggt ggtgcatggt tgtcgtcagc tcgtgtcgtg agatgttggg ttaagtcccg   1080
caacgagcgc aacccttgtc attagttgcc agcagttcgg ctgggcactc tagtgagact   1140
gccggggaca actcggagga aggtggggat gacgtcaaat catcatgccc cttatgttct   1200
gggctacaca cgtgctacaa tggccggtac agagagacgc aagactgtga agtggagcaa   1260
aactctaaaa ccggtcccag ttcggattgt aggctgcaac tcgcctacat gaagttggag   1320
ttgctagtaa tcgcgaatca gaatgtcgcg gtgaatgcgt tcccgggtct tgtacacacc   1380
gcccgtcaca ccatggaagt tggggcgccc gaagttggt caacaaatcg attacctaag   1440
gcgaaaccaa tgactggggt gaagtcgtaa caaggtagcc gtatcggaag gtgcggctgg   1500
atcacct                                                             1507
```

<210> SEQ ID NO 23
<211> LENGTH: 1378
<212> TYPE: DNA
<213> ORGANISM: Clostridium saccharogumia

<400> SEQUENCE: 23

```
agccaccggc ttcgggtgtt atcaactctc atggtgtgac gggcggtgtg tacaaggccc     60
```

```
gagaacgtat tcaccgcggc atgctgatcc gcgattacta gcgattccat cttcatgcag    120
gcgagttgca gcctgcaatc cgaactgaga acgggttttt gagtttcgct ccaagtcgcc    180
tcttcgcttc cctttgatcc gtccattgta gcacgtgtgt agcccaggtc ataaggggca    240
tgatgatttg acgtcatccc cgccttcctc cggcttgtca ccggctgtct cgttagagtc    300
cccatcttac tgctggtaac taacgacaag ggttgcgctc gttgcgggac ttaacccaac    360
atctcacgac acgagctgac gacaaccatg caccacctgt cttgagtata tctatccctc    420
tatctctaga gtctttactc tgatgtcaag acctggtaag gttcttcgcg ttgcttcgaa    480
ttaaaccaca tgctccaccg cttgtgcggg cccccgtcaa ttcctttgag tttcattctt    540
gcgaacgtac tactcaggcg gagtacttat tgcgttaact gcagcactga ggcttgtccc    600
cccaacactt agtactcatc gtttacggcg tggactacta gggtatctaa tcctatttgc    660
tccccacgct ttcgggactg agcgtcagtt acagaccaga tcgtcgcctt cgccactggt    720
gttcctccat atatctacgc atttcaccgc tacacatgga attccacgat cctcttctgc    780
actctagcta tttggtttcc atggcttact gaagttaagc ttcagccttt taccacagac    840
ctccattgcc gcctgctccc tctttacgcc caataattcc ggataacgct tgccacctac    900
gtattaccgc ggctgctggc acgtagttag ccgtggcttc ctcacaaagt accgtcactc    960
taataccatt ccctgtatta gtcgttcttc ctttataaca gaagtttaca acccgaaggc   1020
cttcttcctt cacgcggcgt tgctcggtca gggttccccc cattgccgaa aattccctac   1080
tgctgcctcc cgtaggagtc tgggccgtgt ctcagtccca gtgtggccgt tcaccctctc   1140
aggccggcta tgcatcgtcg ccttggtagg ccgttacccc tccaactagc taatgcacca   1200
taagcccatc tgttccctat cccttaggat atttaactta gagaaaatgc ttcctctaag   1260
cctatgcggt gttagcgcat gtttccacgc gttatccccc tggtacagcc aggttgctta   1320
tgtcttactc acccgttcgc cactcatcac cgaagtgatg cgttcgactt gcatgtat     1378
```

```

<210> SEQ ID NO 24
<211> LENGTH: 1376
<212> TYPE: DNA
<213> ORGANISM: Clostridium saccharogumia

<400> SEQUENCE: 24
ggcatctaca gggggataac tgatggaaac gtcagctaag accgcatagg tgtagagatc     60
gcatgaactc tatatgaaaa gtgctacggg actggtagat gatggactta tggcgcatta    120
gcttgttggt agggtaacgg cctaccaagg cgacgatgcg tagccgacct gagagggtga    180
ccggccacac tgggactgag acacggccca gactcctacg ggaggcagca gtagggaatt    240
ttcggcaatg gggggaaccc tgaccgagca acgccgcgtg aaggaagaag taattcgtta    300
tgtaaacttc tgtcatagag gaagaacggt ggatataggg aatgatatcc aagtgacggt    360
actctataag aaagccacgg ctaactacgt gccagcagcc gcggtaatac gtaggtggcg    420
agcgttatcc ggaattattg ggcgtaaaga gggagcaggc ggcactaagg gtctgtggtg    480
aaagatcgaa gcttaacttc ggtaagccat ggaaaccgta gagctagagt gtgtgagagg    540
atcgtggaat tccatgtgta gcggtgaaat gcgtagatat atggaggaac accagtggcg    600
aaggcgacga tctggcgcat aactgacgct cagtcccgaa agcgtgggga gcaaatagga    660
ttagataccc tagtagtcca cgccgtaaac gatgagtact aagtgttggg tgtcaaagct    720
cagtgctgca gttaacgcaa taagtactcc gcctgagtag tacgttcgca agaatgaaac    780
```

| | | |
|---|---|---|
| tcaaaggaat tgacggggc cgcacaagc ggtggagcat gtggtttaat tcgaagcaac | 840 | |
| gcgaagaacc ttaccaggtc ttgacatcga tctaaaggct ccagagatgg agagatagct | 900 | |
| atagagaaga caggtggtgc atggttgtcg tcagctcgtg tcgtgagatg ttgggttaag | 960 | |
| tcccgcaacg agcgcaaccc ctgttgccag ttgccagcat taagttgggg actctggcga | 1020 | |
| gactgccggt gacaagccgg aggaaggcgg ggatgacgtc aaatcatcat gccccttatg | 1080 | |
| acctgggcta cacacgtgct acaatggaca gagcagaggg aagcgaagcc gcgaggtgga | 1140 | |
| gcgaaaccca taaaactgtt ctcagttcgg actgcagtct gcaactcgac tgcacgaaga | 1200 | |
| tggaatcgct agtaatcgcg aatcagcatg tcgcggtgaa tacgttctcg ggccttgtac | 1260 | |
| acaccgcccg tcacaccatg agagtcggta cacccgaag ccggtggcct aaccgcaagg | 1320 | |
| aaggagctgt ctaaggtggg actgatgatt ggggtgaagt cgtaacaagg gtaacc | 1376 | |

<210> SEQ ID NO 25
<211> LENGTH: 1361
<212> TYPE: DNA
<213> ORGANISM: Blautia luti

<400> SEQUENCE: 25

| | | |
|---|---|---|
| cgggaatact ttattgaaac ttcggtggat ttaatttatt tctagtggcg gacgggtgag | 60 | |
| taacgcgtgg gtaacctgcc ttatactggg ggataacagc cagaaatgac tgctaatacc | 120 | |
| gcataagcgc acagaaccgc atggttccgt gtgaaaaact ccggtggtat aagatggacc | 180 | |
| cgcgttggat tagctagttg gcagggcagc ggcctaccaa ggcgacgatc catagccggc | 240 | |
| ctgagagggt gaacggccac attgggactg agacacggcc cagactccta cgggaggcag | 300 | |
| cagtggggaa tattgcacaa tgggggaaac cctgatgcag cgacgccgcg tgaaggaaga | 360 | |
| agtatctcgg tatgtaaact tctatcagca gggaagataa tgacggtacc tgactaagaa | 420 | |
| gccccggcta actacgtgcc agcagccgcg gtaatacgta gggggcaagc gttatccgga | 480 | |
| tttactgggt gtaaagggag cgtagacggc gcagcaagtc tgatgtgaaa ggcagggct | 540 | |
| taaccctgg actgcattgg aaactgctgt gcttgagtgc cggaggggta agcggaattc | 600 | |
| ctagtgtagc ggtgaaatgc gtagatatta ggaggaacac cagtggcgaa ggcggcttac | 660 | |
| tggacggtaa ctgacgttga ggctcgaaag cgtggggagc aaacaggatt agataccctg | 720 | |
| gtagtccacg ccgtaaacga tgaatactag gtgtcaggga gcacagctct ttggtgccgc | 780 | |
| cgcaaacgca ttaagtattc cacctgggga gtacgttcgc aagaatgaaa ctcaaaggaa | 840 | |
| ttgacgggga cccgcacaag cggtggagca tgtggtttaa ttcgaagcaa cgcgaagaac | 900 | |
| cttaccaaat cttgacatcc ctctgaccgg gacttaaccg tccctttcct tcgggacagg | 960 | |
| ggagacaggt ggtgcatggt tgtcgtcagc tcgtgtcgtg agatgttggg ttaagtcccg | 1020 | |
| caacgagcgc aaccctatc cttagtagcc agcacgtaat ggtgggcact ctgaggagac | 1080 | |
| tgccagggat aacctggagg aaggcgggga tgacgtcaaa tcatcatgcc cttatgatt | 1140 | |
| tgggctacac acgtgctaca atggcgtaaa caaagggaag cgaacccgcg agggtgggca | 1200 | |
| aatctcaaaa ataacgtccc agttcggact gcagtctgca actcgactgc acgaagctgg | 1260 | |
| aatcgctagt aatcgcggat cagaatgccg cggtgaatac gttcccgggt cttgtacaca | 1320 | |
| ccgcccgtca caccatggga gtcagtaacg cccgaagtca g | 1361 | |

<210> SEQ ID NO 26
<211> LENGTH: 1383
<212> TYPE: DNA
<213> ORGANISM: Clostridium clostridioforme

<400> SEQUENCE: 26

```
ttgcggtagg tcacaggctt cgggcatttc caactcccat ggtgtgacgg gcggtgtgta        60
caagacccgg gaacgtattc accgcgacat gctgattcgc gattactagc gattccagct       120
tcatgtagtc gagttgcaga ctacaatccg aactgagacg ttatttctgg gatttgctca       180
acatcactgt ctcgcttccc tttgtttacg ccattgtagc acgtgtgtag cccaaatcat       240
aaggggcatg atgatttgac gtcatccccg ccttcctccg ggttatcccc ggcagtctcc       300
ctagagtgcc cagctctacc tgctggctac taaggataag ggttgcgctc gttgcgggac       360
ttaacccaac atctcacgac acgagctgac gacaaccatg caccacctgt ctccaatgct       420
ccgaagagaa tgccccgtta cggacacgtc attgggatgt caagacttgg taaggttctt       480
cgcgttgctt cgaattaaac cacatgctcc accgcttgtg cgggtccccg tcaattcctt       540
tgagtttcat tcttgcgaac gtactcccca ggtggattgc ttattgcgtt agctgcggca       600
ccgatgggtc catacccacc tacacctagc aatcatcgtt taccgcgtgg actaccaggg       660
tatctaatcc tgtttgctcc ccacgctttc gagcctcaac gtcagttaca gtccagtaag       720
ccgccttcgc cactggtgtt cctcctaata tctacgcatt tcaccgctac actaggaatt       780
ccgcttacct ctcctgcact ccagcctggc agttccaaat gcagtcccag ggttgagccc       840
tgggttttca catctggctt gtcatgccgt ctacgctccc tttacaccca gtaaatccgg       900
ataacgcttg cccctacgt attaccgcgg ctgctggcac gtagttagcc ggggcttctt       960
agtcaggtac cgtcattttc ttccctgctg atagagcttt acataccgaa atacttcttc      1020
actcacgcgg cgtcgctgca tcagggtttc ccccattgtg caatattccc cactgctgcc      1080
tcccgtagga gtttgggccg tgtctcagtc ccaatgtggc cgttcaccct ctcaggccgg      1140
ctactgatcg tcgctttggt aggccgttac cctgccaact ggctaatcag acgcgggacc      1200
atcctgtacc accggagttt ttcacactgc ctcatgtgaa gctgtgcgct tatgcggtat      1260
tagcacctat ttctaagtgt tatccccggg tacagggcag gtttcccacg cgttactcac      1320
ccgtccgcca ctaagttacg ccgattccat ccgaaaactt cctctgcata actccgtcga      1380
ctg                                                                   1383
```

<210> SEQ ID NO 27
<211> LENGTH: 1445
<212> TYPE: DNA
<213> ORGANISM: Blautia producta

<400> SEQUENCE: 27

```
ccggtggtcg catcggcgct cctcctgtag gttgggtcac tgacttcggg cgttactgac        60
tcccatggtg tgacgggcgg tgtgtacaag acccgggaac gtattcaccg cgacattctg       120
attcgcgatt actagcgatt ccagcttcgt gcagtcgagt tgcagactgc agtccgaact       180
gggacgttat ttttgggatt tgctcaacat cgctgtctcg cttccctttg tttacgccat       240
tgtagcacgt gtgtagccca atcataagg ggcatgatga tttgacgtcg tccccgcctt       300
cctccgggtt atccccggca gtctcccctag agtgcccagc ttcacctgct ggctactaag       360
gatagggggtt gcgctcgttg cggacttaa cccaacatct cacgacacga gctgacgaca       420
accatgcacc acctgtctcc tctgccccga agggaaggcc ccgttacggg ccggtcagag       480
ggatgtcaag acttggtaag gttcttcgcg ttgcttcgaa ttaaaccaca tgctccaccg       540
cttgtgcggg tccccgtcaa ttcctttgag tttcattctt gcgaacgtac tccccaggtg       600
```

```
gaatacttat tgcgtttgct gcggcaccga atgggctttg ccacccgaca cctagtattc      660
atcgtttacg gcgtggacta ccagggtatc taatcctgtt tgctcccac gctttcgagc       720 ctcaacgtca gttaccgtcc agaaagccgc cttcgccact ggtgttcctc ctaatatcta      780
cgcatttcac cgctacacta ggaattccgc ttacctctcc ggcactctag aaaaacagtt     840
tccaatgcag tcctggggtt aagccccagc cttcacatc agacttgctc ttccgtctac      900 gctccctta cacccagtaa atccggataa cgcttgcccc ctacgtatta ccgcggctga      960
tggcacgtag ttagccgggg cttcttagtc aggtaccgtc atttcttcc ctgctgatag      1020 aagtttacat accgagatac ttcttccttc acgcggcgtc gctgcatcag ggtttccccc    1080
attgtgcaat attccccact gctgcctccc gtaggagtct gggccgtgtc tcagtcccaa    1140
tgtggccgtt caccctctca ggccggctac tgatcgtcgc cttggtgggc cgttaccct    1200 ccaactagct aatcagacgc gggtccatct cataccaccg agttttttca caccagacca   1260
tgcggtcctg tgcgcttatg cggtattagc agccatttct aactgttatc ccctgtatg    1320 aggcaggtta cccacgcgtt actcagcccg tccgccgctc agtcaaataa gtttcaatcc   1380
gaagagatcc acttaagtgc ttcgctcgac ttgcatgtgt taagcacgcc gccagcgttc   1440
atcct                                                               1445

<210> SEQ ID NO 28
<211> LENGTH: 1412
<212> TYPE: DNA
<213> ORGANISM: Blautia glucerasea

<400> SEQUENCE: 28
gccttcggca gctccgtcct ttcggttcgg tcactgactt cgggcgttac tgactcccat      60
ggtgtgacgg gcggtgtgta caagacccgg gaacgtattc accgcggcat tctgatccgc    120
gattactagc gattccagct tcgtgcagtc gagttgcaga ctgcagtccg aactgggacg    180
ttatttttgg gatttgctta agctcacact ctcgcttccc tttgtttacg ccattgtagc    240
acgtgtgtag cccaaatcat aagggcatg atgatttgac gtcatccccg ccttcctcca    300
ggttatccct ggcagtctcc tcagagtgcc cggccaaacc gctggctact aaggataggg   360
gttgcgctcg ttgcgggact taacccaaca tctcacgaca cgagctgacg acaaccatgc    420
accacctgtc tccgatgctc cgaagaaaag gcgacgttac tcgccggtca tagggatgtc    480
aagacttggt aaggttcttc gcgttgcttc gaattaaacc acatgctcca ccgcttgtgc   540
gggtccccgt caattccttt gagtttcatt cttgcgaacg tactccccag gtggaatact   600
tactgcgttt gctgcggcac cgaatggctc tgccacccga cacctagtat tcatcgttta   660
cggcgtggac taccagggta tctaatcctg tttgctcccc acgctttcga gcctcaacgt   720
cagttaccgt ccagtaagcc gccttcgcca ctggtgttcc tcctaatatc tacgcatttc   780
accgctacac taggaattcc gcttacctct ccggtactca agatcaacag tttccaatgc    840
agtccggggg ttgagccccc gcctttcaca tcagacttgc tgctccgtct acgctccctt   900
tacacccagt aaatccggat aacgcttgcc cctacgtat accgcggct gctggcacgt   960 agttagccgg ggcttcttag tcaggtaccg tcatttcttc cctgctgat agaagtttac  1020 ataccgagat acttcttcct tcacgcggcg tcgctgcatc agggtttccc ccattgtgca   1080
atattcccca ctgctgcctc ccgtaggagt ctgggccgtg tctcagtccc aatgtggccg   1140
tccaccctct caggccggct atggatcgtc gctttggtag gccgttaccc tgccaactgg   1200
ctaatccaac gcgggtccat ctcacaccac cggagttttt cacactggat catgcaatcc   1260
```

| | |
|---|---|
| cgtgcgctta tgcggtatta gcagtcattt ctgactgtta tcccccagtg tgaggcaggt | 1320 |
| tacccacgcg ttactcaccc gtccgccact aggattataa cgacttcaac cgaagtctct | 1380 |
| gtcaaaataa tccccgttcg acttgcatgt gt | 1412 |

<210> SEQ ID NO 29
<211> LENGTH: 1317
<212> TYPE: DNA
<213> ORGANISM: Clostridium straminisolvens

<400> SEQUENCE: 29

| | |
|---|---|
| agcggcggac gggtgagtaa cgcgtgagta acctgccttt aggaggggga caacattccg | 60 |
| aaagggatgc taataccgca taaaattatt gtatcgcatg gtataataat caaagattta | 120 |
| tcgcctaaag atggactcgc gtccgattag ctagttggtg gggtaaaagc ctaccaaggc | 180 |
| gacgatcggt agccgaactg agaggttgat cggccacatt gggactgaga cacggcccag | 240 |
| actcctacgg gaggcagcag tggggggatat tgcgcaatgg gggaaaccct gacgcagcaa | 300 |
| cgccgcgtga aggaagaagg ccttcgggtt gtaaacttct ttaagtgtgg aagataatga | 360 |
| cggtacacac agaataagcc acggctaact acgtgccagc agccgcggta atacgtaggt | 420 |
| ggcaagcgtt gtccggattt actgggtgta aagggcgtgt aggcgggtag acaagtcaga | 480 |
| tgtgaaatac cggggctcaa ctccggggct gcatttgaaa ctgtatatct tgagtgtcgg | 540 |
| agaggaaagc ggaattccta gtgtagcggt gaaatgcgta gatattagga ggaacaccag | 600 |
| tggcgaaggc ggctttctgg acgataactg acgctgaggc gcgaaagcgt ggggagcaaa | 660 |
| caggattaga taccctggta gtccacgccg taaacgatgg atactaggtg taggaggtat | 720 |
| cgaccccttc tgtgccgcag ttaacacaat aagtatccca cctggggagt acggtcgcaa | 780 |
| gattgaaact caaaggaatt gacggggggcc cgcacaagca gtggagtatg tggtttaatt | 840 |
| cgaagcaacg cgaagaacct taccaggact tgacatccca cgcatagcct agagataggt | 900 |
| gaagtcctac gggacgtgga gacaggtggt gcatggttgt cgtcagctcg tgtcgtgaga | 960 |
| tgttgggtta agtcccgcaa cgagcgcaac ccttactgtc agttaccatc attaagttgg | 1020 |
| ggactctggc aggactgccg gtgacaaatc ggaggaaggt ggggacgacg tcaaatcatc | 1080 |
| atgcccctta tgtcctgggc tacacacgta ctacaatggc tgttaacaaa gtgaagcaaa | 1140 |
| gcagtgatgt ggagcaaaac acaaaaagca gtctcagttc agattgtagg ctgaaactcg | 1200 |
| cctatatgaa gtcggaattg ctagtaatcg cagatcagca tgctgcggtg aatacgttcc | 1260 |
| cgggccttgt acacaccgcc cgtcacacca tgagagtcga taacacccga agcctgt | 1317 |

<210> SEQ ID NO 30
<211> LENGTH: 1319
<212> TYPE: DNA
<213> ORGANISM: Butyricoccus pullicaecorum

<400> SEQUENCE: 30

| | |
|---|---|
| agtggcggac gggtgagtaa cgcgtgagca atctgccttt aagaggggga taacagtcgg | 60 |
| aaacggctgc taataccgca taaagcatcg aaaccgcatg attttgatgc caaggagcaa | 120 |
| atccgctttt agatgagctc gcgtctgatt agctggttgg cggggtaacg gcccaccaag | 180 |
| gcgacgatca gtagccggac tgagaggttg aacggccaca ttgggactga gacacggccc | 240 |
| agactcctac gggaggcagc agtggggaat attgcgcaat gggggaaacc ctgacgcagc | 300 |
| aacgccgcgt gattgaagaa ggccttcggg ttgtaaagat ctttaatcag ggacgaaaca | 360 |

```
aatgacggta cctgaagaat aagctccggc taactacgtg ccagcagccg cggtaatacg    420
tagggagcaa gcgttatccg gatttactgg gtgtaaaggg cgcgcaggcg ggccggtaag    480
ttggaagtga aatctatggg cttaacccat aaactgcttt tcaaactgct ggtcttgagt    540
gatggagagg caggcggaat tccgtgtgta gcggtgaaat gcgtagatat acggaggaac    600
accagtggcg aaggcggcct gctggacatt aactgacgct gaggcgcgaa agcgtgggga    660
gcaaacagga ttagataccc tggtagtcca cgccgtaaac gatggatact aggtgtggga    720
ggtattgacc ccttccgtgc cgcagttaac acaataagta tcccacctgg ggagtacggc    780
cgcaaggttg aaactcaaag gaattgacgg gggcccgcac aagcagtgga gtatgtggtt    840
taattcgaag caacgcgaag aaccttacca ggtcttgaca tcccgatgac cgcctcagag    900
atgagccttt tcttcggaac atcggtgaca ggtggtgcat ggttgtcgtc agctcgtgtc    960
gtgagatgtt gggttaagtc ccgcaacgag cgcaaccctt acggttagtt gatacgcaag   1020
atcactctag ccggactgcc gttgacaaaa cggaggaagg tggggacgac gtcaaatcat   1080
catgcccctt atgacctggg ctacacacgt actacaatgg cagtcataca gagggaagca   1140
aaaccgcgag gtggagcaaa tccctaaaag ctgtcccagt tcagattgca ggctgcaacc   1200
cgcctgcatg aagtcggaat tgctagtaat cgcggatcag catgccgcgg tgaatacgtt   1260
cccgggcctt gtacacaccg cccgtcacac catgagagcc gtcaataccc gaagtccgt    1319
```

<210> SEQ ID NO 31
<211> LENGTH: 791
<212> TYPE: DNA
<213> ORGANISM: Clostridium maritium

<400> SEQUENCE: 31

```
ctacactgca gtcgagcgat ttcttcggta agagcggcgg acgggtgagt aacgcgtggg     60
taacctgccc tatacacacg gataacatac cgaaaggtat gctaatacga gataacataa    120
gagattcgca tggatttctt atcaaagctt ttgcggtata ggatggaccc gcgtctgatt    180
agctagttgg taaggtaacg gcttaccaag gcgacgatca gtagccgacc tgagagggtg    240
atcggccaca ttggaactga gacacggtcc aaactcctac gggaggcagc agtggggaat    300
attgcacaat gggcgaaagc ctgatgcagc aacgccgcgt gagcgatgaa ggccttcggg    360
tcgtaaagct ctgtcctcaa ggaagataat gacggtactt gaggaggaag ccccggctaa    420
ctacgtgcca gcagccgcgg taatacgtag gggctagcg ttatccggaa ttactgggcg    480
taaagggtgc gtaggtggtt tcttaagtca gaggtgaaag gctacggctc aaccgtagta    540
agcctttgaa actgagaaac ttgagtgcag gagaggagag tagaattcct agtgtagcgg    600
tgaaatgcgt agatattagg aggaatacca gttgcgaagg cggctctctg gactgtaact    660
gacactgagg cacgaaagcg tggggagcaa acaggattag ataccctggt agtccacgcc    720
gtaaacgatg agtactagct gtcggaggtt acccccttcg gtggcgcagc taacgcatta    780
agtactccgc c                                                         791
```

<210> SEQ ID NO 32
<211> LENGTH: 1377
<212> TYPE: DNA
<213> ORGANISM: Eubacterium fissicatens

<400> SEQUENCE: 32

```
agtggcggac gggtgagtaa cgcgtgggta acctgccttg tacaggggga taacagttag     60
aaatgactgc taataccgca taagcgcaca gtatcgcatg gtacagtgtg aaaaactccg    120
```

```
gtggtacaag atggacccgc gtctgattag ctagttggta aggtaacggc ttaccaaggc      180
aacgatcagt agccgacttg agagagtgat cggccacatt gggactgaga cacggcccaa      240
actcctacgg gaggcagcag tggggaatat tgcacaatgg gggaaaccct gatgcagcga      300
cgccgcgtga gtgaagaagt atttcggtat gtaaaactct atcagcaagg aagataatga      360
cggtacttga ctaagaagcc ccggctaact acgtgccagc agccgcggta atacgtaggg      420
ggcaagcgtt atccggattt actgggtgta aagggagcgt agacggtatg gtaagtcaga      480
tgtgaaagcc cggggcttaa ccccggaact gcatttgaaa ctatcaaact agagtgtcgg      540
agaggtaagt ggaattccta gtgtagcggt gaaatgcgta gatattagga ggaacaccag      600
tggcgaaggc ggcttactgg acgataactg acgttgaggc tcgaaagcgt ggggagcaaa      660
caggattaga taccctggta gtccacgccg taaacgatga atactaggtg tcagggaaca      720
atagttcttt ggtgccgcag caaacgcatt aagtattcca cctggggagt acgttcgcaa      780
gaatgaaact caaaggaatt gacggggacc cgcacaagcg gtggagcatg tggtttaatt      840
cgaagcaacg cgaagaacct tacctggtct tgacatccca atgacgcctc tttaatcgga      900
ggtttccttc gggacattgg agacaggtgg tgcatggttg tcgtcagctc gtgtcgtgag      960
atgttgggtt aagtcccgca acgagcgcaa cccttatctt tagtagccag cagttcggct      1020
gggcactcta gagagactgc cagggataac ctggaggaag gtgggatgac gtcaaatca      1080 tcatgcccct tatgaccagg gctacacacg tgctacaatg gcgtaaacaa agggaagcaa      1140
aactgtgagg ttgagcaaat cccaaaaata acgtctcagt tcggattgta gtctgcaact      1200
cgactacatg aagctggaat cgctagtaat cgcagatcag aatgctgcgg tgaatacgtt      1260
cccgggtctt gtacacaccg cccgtcacac catgggagtc ggatatgccc gaagtcagtg      1320
acccaaccgt aaggagggag ctgccgaagg tggagccgat aactggggtg aagtcgt      1377

<210> SEQ ID NO 33
<211> LENGTH: 1376
<212> TYPE: DNA
<213> ORGANISM: Clostridium saccharolyticum

<400> SEQUENCE: 33
agcggcggac gggtgagtaa cgcgtgggta acctgcctca tacaggggga taacagttag       60
aaatgactgc taataccgca taagcgcaca gtgctgcatg gcacagtgtg aaaaactccg      120
gtggtatgag atggacccgc gttggattag gcagttggcg gggtaacggc ccaccaaacc      180
gacgatccat agccggcctg agagggtgaa cggccacatt gggactgaga cacggcccaa      240
actcctacgg gaggcagcag tggggaatat tgcacaatgg gggaaaccct gatgcagcga      300
cgccgcgtga gtgaagaagt aattcgttat gtaaagctct atcagcaggg aagaaaatga      360
cggtacctga ctaagaagcc ccggctaact acgtgccagc agccgcggta atacgtaggg      420
ggcaagcgtt atccggattt actgggtgta aagggagcgt agacggccgt gcaagtctga      480
tgtgaaaggc tggggctcaa ccccgggact gcattggaaa ctgtatggct ggagtgccgg      540
agaggtaagc ggaattccta gtgtagcggt gaaatgcgta gatattagga ggaacaccag      600
tggcgaaggc ggcttactgg acggtaactg acgttgaggc tcgaaagcgt ggggagcaaa      660
caggattaga taccctggta gtccacgccg taaacgatga ttactaggtg ttggggaca      720 tggtccttcg gtgccgccgc aaacgcagta agtaatccac ctggggagta cgttcgcaag      780
aatgaaactc aaaggaattg acggggaccc gcacaagcgg tggagcatgt ggtttaattc      840
```

```
gaagcaacgc gaagaacctt accaagtctt gacatcgaga ggacagagta tgtaatgtac      900
tttcccttcg gggcctcgaa gacaggtggt gcatggttgt cgtcagctcg tgtcgtgaga      960
tgttgggtta agtcccgcaa cgagcgcaac ccctatcttc agtagccagc aattcggatg     1020
ggcactctgg agagactgcc ggggataacc cggaggaagg cggggatgac gtcaaatcat     1080
catgcccctt atgacttggg ctacacacgt gctacaatgg cgtaaacaaa gggaagcgag     1140
ggagtgatcc ggagcaaatc ccaaaaataa cgtctcagtt cggattgtag tctgcaactc     1200
gactacatga agctggaatc gctagtaatc gcgaatcagc atgtcgcggt gaatacgttc     1260
ccgggtcttg tacacaccgc ccgtcacacc atgggagtcg ataacgcccg aagtcagtga     1320
cccaaccgaa aggagggagc tgccgaaggc gggattggta actggggtga agtcgt         1376
```

<210> SEQ ID NO 34
<211> LENGTH: 1377
<212> TYPE: DNA
<213> ORGANISM: Blautia luti

<400> SEQUENCE: 34

```
agtggcggac gggtgagtaa cgcgtgggta acctgcctta tactggggga taacagccag       60
aaatggctgc taataccgca taagcgcacg gggccgcatg gtcctgtgtg aaaaactccg      120
gtggtataag atggacccgc gttggattag ctagttggca gggcagcggc ctaccaaggc      180
gacgatccat agccggcctg agagggtgaa cggccacatt gggactgaga cacggcccag      240
actcctacgg gaggcagcag tggggaatat tgcacaatgg gggaaaccct gatgcagcga      300
cgccgcgtga aggaagaagt atctcggtat gtaaacttct atcagcaggg aagataatga      360
cggtacctga ctaagaagcc ccggctaact acgtgccagc agccgcggta atacgtaggg      420
ggcgagcgtt atccggattt actgggtgta aagggagcgt agacggcgta tcaagtctga      480
tgtgaaaggc aggggcttaa cccctggact gcattggaaa ctggtatgct tgagtgccgg      540
aggggtaagc ggaattccta gtgtagcggt gaaatgcgta gatattagga ggaacaccag      600
tggcgaaggc ggcttactgg acggtaactg acgttgaggc tcgaaagcgt ggggagcaaa      660
caggattaga taccctggta gtccacgccg taaacgatga atactaggtg tctgggagca      720
cagctcttag gtgccgccgc aaacgcatta agtattccac ctggggagta cgttcgcaag      780
aatgaaactc aaaggaattg acggggaccc gcacaagcgg tggagcatgt ggtttaattc      840
gaagcaacgc gaagaacctt accaaatctt gacatccctc tgacagagta tgtaatgtac      900
ttttccttcg ggacagggga cagotgtggt gcatggttgt cgtcagctcg tgtcgtgaga      960
tgttgggtta agtcccgcaa cgagcgcaac ccctatcctt agtagccagc aagtaatgtt     1020
gggcactctg aggagactgc cagggataac ctggaggaag gcgggatgac gtcaaatca     1080
tcatgcccct tatgatttgg gctacacacg tgctacaatg gcgtaaacaa agggaagcga     1140
acctgtgagg gtgggcaaat ctcaaaaata cgtcccagt tcggactgca gtctgcaact     1200
cgactgcacg aagctggaat cgctagtaat cgcggatcag aatgccgcgg tgaatacgtt     1260
cccgggtctt gtacacaccg cccgtcacac catgggagtc agtaacgccc gaagtcagtg     1320
acctaaccgt aaggaaggag ctgccgaagg cgggacggat gactggggtg aagtcgt        1377
```

<210> SEQ ID NO 35
<211> LENGTH: 1465
<212> TYPE: DNA
<213> ORGANISM: Clostridium metylpentosum

<400> SEQUENCE: 35

```
ggttaccttg ttacgacttc accccaatca tcaaccccac cttcgacgac gtccccttg     60
cggttagact atcggcttcg ggtgttgcca actctcatgg tgtgacgggc ggtgtgtaca   120
aggcccggga acgtattcac cgcggcatgc tgatccgcga ttactagcaa ttccggcttc   180
atgcaggcgg gttgcagcct gcaatccgaa ctgagactat tttaggggt ttgctccatg    240
tcaccatctt gcttccctct gttaatagcc attgtagtac gtgtgtagcc caggtcataa   300
ggggcatgat gatttgacgt catccccacc ttcctccgtt ttgtcaacgg cagtccgtct   360
agagtgctct tgcgtagcaa ctaaacgtaa gggttgcgct cgttgcggga cttaacccaa   420
catctcacga cacgagctga cgacaaccat gcaccacctg tctcggtgcc ccgaagggct   480
tcacctatct ctaggctatg caccggatgt caagacctgg taaggttctt cgcgttgctt   540
cgaattaaac cacatactcc actgcttgtg cgggcccccg tcaattcctt tgagtttcaa   600
ccttgcggtc gtactcccca ggtggattac ttattgtgtt aactccggca cggaaggggt   660
cagtcccccc acacctagta atcatcgttt acagcgtgga ctaccagggt atctaatcct   720
gtttgctacc cacgctttcg agcctcagcg tcagttaaag cccagcaggc cgccttcgcc   780
actggtgttc ctcctaatat ttacgcattt caccgctaca ctaggaattc cgcctgcctc   840
tacttcactc aagaactgca gttttgaacg cggctatggg ttgagcccat agatttaaca   900
ttcaacttgc aatcccgcct acgctccctt tacacccagt aattccggac aacgctcgct   960
acctacgtat taccgcggct gctggcacgt agttagccgt agcttcctcc ttggttaccg  1020
tcattatctt caccaaggac agaggtttac aatccgaaaa ccttcttccc tcactcggcg  1080
tcgctgcatc agggtttccc ccattgtgca atattcccca ctgctgcctc ccgtaggagt  1140
ctgggccgtg tctcagtccc aatgtggccg ttcaacctct cagtccggct accaatcgtc  1200
gccttggtgg gccgttacct caccaactag ctaattggac gcgagtccat ctttcagcgg  1260
attgctcctt tgatatcagc tccatgcgaa accaatatgt tatgcggtat tagcgtccgt  1320
ttccagacgt tatccccctc tgaaaggcag gttactcacg cgttactcac ccgtccgcca  1380
ctaagttgaa tcaaattcct tccgaagaat tcattcaaag caacttcgtc gacttgcatg  1440
tgtaaggcgc gccgacagcg ttcgt                                         1465
```

<210> SEQ ID NO 36
<211> LENGTH: 1422
<212> TYPE: DNA
<213> ORGANISM: Clostridium xylanolyticum

<400> SEQUENCE: 36

```
agagtttgat cctggctcag gatgaacgct ggcggcgtgc ctaacacatg caagtcgaac    60
ggaatttaca tgaagcctag cgattgtaaa tttagtggcg gacgggtgag taacgcgtgg   120
gtaacctgcc ttgtactggg ggacaacagt tggaaacgac tgctaatacc gcataagcgc   180
acagcttcgc atgaagcagt gtgaaaaact ccggtggtac aagatggacc cgcgtctgat   240
tagctggttg gtgaggtaac ggcccaccaa ggcgacgatc agtagccggc ctgagagggt   300
gaacggccac attgggactg agacacggcc caaactccta cgggaggcag cagtggggaa   360
tattgcacaa tgggggaaac cctgatgcag caacgccgcg tgagtgaaga agtatttcgg   420
tatgtaaagc tctatcagca ggaaagaaaa tgacggtacc tgactaagaa gccccggcta   480
actacgtgcc agcagccgcg gtaatacgta gggggcaagc gttatccgga tttactgggt   540
gtaaagggag cgtagacggt tttgcaagtc tgaagtgaaa gcccggggct taaccccggg   600
```

| | |
|---|---:|
| actgctttgg aaactgtagg actagagtgc aggagaggta agtggaattc ctagtgtagc | 660 |
| ggtgaaatgc gtagatatta ggaggaacac cagtggcgaa ggcggcttac tggactgtaa | 720 |
| ctgacgttga ggctcgaaag cgtggggagc aaacaggatt agataccctg gtagtccacg | 780 |
| ccgtaaacga tgattactag gtgttggtgg gtacgaccca tcggtgccgc agcaaacgca | 840 |
| ataagtaatc cacctgggga gtacgttcgc aagaatgaaa ctcaaaggaa ttgacgggga | 900 |
| cccgcacaag cggtggagca tgtggtttaa ttcgaagcaa cgcgaagaac cttacctggt | 960 |
| cttgacatcc ctatgaataa cgggcaatgc cgttagtact tcggtacata ggagacaggt | 1020 |
| ggtgcatggt tgtcgtcagc tcgtgtcgtg agatgttggg ttaagtcccg caacgagcgc | 1080 |
| aacccttatc tttagtagcc agcagtaaga tgggcactct agagagactg ccggggataa | 1140 |
| cccggaggaa ggtggggatg acgtcaaatc atcatgcccc ttatgaccag gctacacac | 1200 |
| gtgctacaat ggcgtaaaca agagaagcg aagtcgtgag gcagagcgaa tctcaaaaat | 1260 |
| aacgtctcag ttcggattgt agtctgcaac tcgactacat gaagctggaa tcgctagtaa | 1320 |
| tcgcagatca gaatgctgcg gtgaatacgt tcccgggtct tgtacacacc gcccgtcaca | 1380 |
| ccatgggagt cggaaatgcc cgaagtcggt gacctaaccg aa | 1422 |

<210> SEQ ID NO 37
<211> LENGTH: 1478
<212> TYPE: DNA
<213> ORGANISM: Oscillibacter valericigenes

<400> SEQUENCE: 37

| | |
|---|---:|
| ctcaggacga acgctggcgg cgtgcttaac acatgcaagt cgaacggagc acccttgact | 60 |
| gaggtttcgg ccaaatgata ggaatgctta gtggcggact ggtgagtaac gcgtgaggaa | 120 |
| cctaccttcc agaggggac aacagttgga aacgactgct aataccgcat gacgcatgac | 180 |
| cggggcatcc cggcatgtc aaagatttta tcgctggaag atggcctcgc gtctgattag | 240 |
| ctagatggtg gggtaacggc ccaccatggc gacgatcagt agccggactg agaggttgac | 300 |
| cggccacatt gggactgaga tacggcccag actcctacgg gaggcagcag tggggaatat | 360 |
| tgggcaatgg acgcaagtct gacccagcaa cgccgcgtga aggaagaagg ctttcgggtt | 420 |
| gtaaacttct tttgtcaggg aagagtagaa gacggtacct gacgaataag ccacggctaa | 480 |
| ctacgtgcca gcagccgcgg taatacgtag gtggcaagcg ttgtccggat ttactgggtg | 540 |
| taaagggcgt gcagccgggc cggcaagtca gatgtgaaat ctgaggctt aacctccaaa | 600 |
| ctgcatttga aactgtaggt cttgagtacc ggagaggtta tcggaattcc ttgtgtagcg | 660 |
| gtgaaatgcg tagatataag gaagaacacc agtggcgaag gcggataact ggacggcaac | 720 |
| tgacggtgag gcgcgaaagc gtggggagca aacaggatta gataccctgg tagtccacgc | 780 |
| tgtaaacgat ggatactagg tgtgcgggga ctgacccct gcgtgccgca gttaacacaa | 840 |
| taagtatccc acctggggag tacgatcgca aggttgaaac tcaaaggaat tgacgggggc | 900 |
| ccgcacaagc ggtggattat gtggtttaat tcgaagcaac gcgaagaacc ttaccagggc | 960 |
| ttgacatcct actaacgaag tagagataca tcaggtgccc ttcggggaaa gtagagacag | 1020 |
| gtggtgcatg gttgtcgtca gctcgtgtcg tgagatgttg ggttaagtcc cgcaacgagc | 1080 |
| gcaaccccta ttgttagttg ctacgcaaga gcactctagc gagactgccg ttgacaaaac | 1140 |
| ggaggaaggt ggggacgacg tcaaatcatc atgcccctta tgtcctgggc tacacacgta | 1200 |
| atacaatggc ggtcaacaga gggaggcaaa gccgcgaggc agagcaaacc cccaaaagcc | 1260 |
| gtcccagttc ggatcgcagg ctgcaacccg cctgcgtgaa gtcggaatcg ctagtaatcg | 1320 |

```
cggatcagca tgccgcggtg aatacgttcc cgggccttgt acacaccgcc cgtcacacca    1380
tgagagtcgg aacacccga agtccgtagc ctaaccgcaa ggagggcgcg gccgaaggtg    1440
ggttcgataa ttggggtgaa gtcgtaacaa ggtaaccg                           1478

<210> SEQ ID NO 38
<211> LENGTH: 1620
<212> TYPE: DNA
<213> ORGANISM: Ruminococcus obeum

<400> SEQUENCE: 38
agtcgaacgg gaaccttttta ttgaagcttc ggcagattta gctggtttct agtggcggac     60
gggtgagtaa cgcgtgggta acctgcccta tacaggggga taacaaccag aaatggttgc    120
taataccgca taagcgcaca ggaccgcatg gtccggtgtg aaaaactccg gtggtatagg    180
atggacccgc gttggattag ccagttggca gggtaacggc ctaccaaagc gacgatccat    240
agccggcctg agagggtgaa cggccacatt gggactgaga cacggcccag actcctacgg    300
gaggcagcag tggggaatat tgcacaatgg gggaaaccct gatgcagcga cgccgcgtga    360
aggaagaagt atctcggtat gtaaacttct atcagcaggg aagatagtga cggtacctga    420
ctaagaagcc ccggctaact acgtgccagc agccgcggta atacgtaggg ggcaagcgtt    480
atccggattt actgggtgta aagggagcgt agacggatta gcaagtctga tgtgaaaggc    540
aggggctcaa cccctggact gcattggaaa ctgccagtct tgagtgccgg agaggtaagc    600
ggaattccta gtgtagcggt gaaatgcgta gatattagga ggaacaccag tggcgaaggc    660
ggcttactgg acggcaactg acgttgaggc tcgaaagcgt ggggagcaaa caggattaga    720
taccctggta gtccacgccg taaacgatga atactaggtg ttggggagca agctcttcg     780 gtgccgccgc aaacgcatta agtattccac ctggggagta cgttcgcaag aatgaaactc    840
aaaggaattg acggggaccc gcacaagcgg tggagcatgt ggtttaattc gaagcaacgc    900
gaagaacctt accaagtctt gacatccctc tgacggactc ttaaccgagt ctttccttcg    960
ggacagagga gacaggtggt gcatggttgt cgtcagctcg tgtcgtgaga tgttgggtta   1020
agtcccgcaa cgagcgcaac ccctatcccc agtagccagc atttcggatg ggcactctga   1080
ggagactgcc agggataacc tggaggaagg cggggatgac gtcaaatcat catgcccctt   1140
atgatttggg ctacacacgt gctacaatgg cgtaaacaaa gggaagcgag cctgcgaggg   1200
taagcaaatc ccaaaaataa cgtcccagtt cggactgcag tctgcaactc gactgcacga   1260
agctggaatc gctagtaatc gcggatcaga atgccgcggt gaatacgttc ccgggtcttg   1320
tacacaccgc ccgtcacacc atgggagtca gtaacgcccg aagtcagtga cctaaccgca   1380
agggaggagc tgccgaaggc gggaccgatg actggggtga agtcgtaaca aggtaaccgt   1440
gactacacga agctggaatc gctagtaatc gcggatcaga atgccgcggt gaatacgttc   1500
ccgggtcttg tacacaccgc ccgtcacacc atgggagtca gtaacgcccg aagtcagtga   1560
cctaaccgca aggaaggagc tgccgaaggc gggaccgatg actggggtga agtcgtaaca   1620

<210> SEQ ID NO 39
<211> LENGTH: 1403
<212> TYPE: DNA
<213> ORGANISM: Megasphaera elsdenii

<400> SEQUENCE: 39
acgcgtaagc aacctgccct ccggatgggg acaacagctg gaaacggctg ctaataccga     60
```

| | |
|---|---|
| atacgtttcc attgccgcat ggcagtggga agaaaggtgg cctctgaata tgctaccgcc | 120 |
| gggggagggg cttgcgtctg attagctagt tggaggggta acggcccacc aaggcgacga | 180 |
| tcagtagccg gtctgagagg atgaacggcc acattggaac tgagacacgg tccagactcc | 240 |
| tacgggaggc agcagtgggg aatcttccgc aatgggcgaa agcctgacgg agcaacgccg | 300 |
| cgtgagcgaa gacggccttc gggttgtaaa gctctgttat acgggacgaa cggctagtgt | 360 |
| gccaatacca cattagaatg acggtaccgt aagagaaagc cacggctaac tacgtgccag | 420 |
| cagccgcggt aatacgtagg tggcaagcgt tgtccggaat tattgggcgt aaagggcgcg | 480 |
| caggcggttt cataagtctg tcttaaaagt gcgggctta accccgtgag gggacggaaa | 540 |
| ctgtgagact ggagtgtcgg agaggaaagc ggaattccta gtgtagcggt gaaatgcgta | 600 |
| gatattagga ggaacaccag tggcgaaagc ggctttctgg acgacaactg acgctgaggc | 660 |
| gcgaaagcca ggggagcgaa cgggattaga taccccggta gtcctggccg taaacgatgg | 720 |
| atactaggtg tagggggtat cgaccccctcc tgtgccggag ttaacgcaat aagtatcccg | 780 |
| cctggggagt acggccgcaa ggctgaaact caaaggaatt gacgggggcc cgcacaagcg | 840 |
| gtggagtatg tggtttaatt cgacgcaacg cgaagaacct taccaagcct tgacattgag | 900 |
| tgctatcctc agagatgagg agttcttctt cggaagacgc gaaaacaggt ggtgcacggc | 960 |
| tgtcgtcagc tcgtgtcgtg agatgttggg ttaagtcccg caacgagcgc aaccccctatc | 1020 |
| ttctgttgcc agcgcgtcat ggcgggact caggagagac tgccgcagac aatgcggagg | 1080 |
| aaggcgggga tgacgtcaag tcatcatgcc ccttatggct gggctacac acgtactaca | 1140 |
| atggctctta atagagggaa gcgaaggagc gatccggagc aaacccccaaa aacagagtcc | 1200 |
| cagttcggat tgcaggctgc aacccgcctg catgaagcag gaatcgctag taatcgcagg | 1260 |
| tcagcatact gcggtgaata cgttcccggg ccttgtacac accgcccgtc acaccacgaa | 1320 |
| agtcattcac acccgaagcc ggtgaggtaa ccgtaaggag ccagccgtcg aaggtggggg | 1380 |
| cgatgattgg ggtgaagtcg taa | 1403 |

<210> SEQ ID NO 40
<211> LENGTH: 1369
<212> TYPE: DNA
<213> ORGANISM: Blautia luti

<400> SEQUENCE: 40

| | |
|---|---|
| ggtgagtaac gcgtgggtaa cctgccttat acaggggat aacagtcaga aatggctgct | 60 |
| aataccgcat aagcgcacag ggccgcatgg cccggtgtga aaaactgagg tggtataaga | 120 |
| tggacccgcg ttggattagc cagttggcag ggtaacggcc taccaaagcg acgatccata | 180 |
| gccggcctga gagggtgaac ggccacattg gactgagac acggcccaga ctcctacggg | 240 |
| aggcagcagt ggggaatatt gcacaatggg ggaaaccctg atgcagcgac gccgcgtgaa | 300 |
| ggaagaagta tctcggtatg taaacttcta tcagcaggga agaaaatgac ggtacctgac | 360 |
| taagaagccc cggctaacta cgtgccagca gccgcggtaa tacgtagggg gcaagcgtta | 420 |
| tccggattta ctgggtgtaa agggagcgta gacggcataa caagtctgat gtgaaaggct | 480 |
| ggggcttaac cccgggactg cattggaaac tgttaagctt gagtgccgga ggggtaagcg | 540 |
| gaattcctag tgtagcggtg aaatgcgtag atattaggag gaacaccagt ggcgaaggcg | 600 |
| gcttactgga cggtaactga cgttgaggct cgaaagcgtg gggagcaaac aggattagat | 660 |
| accctggtag tccacgccgt aaacgatgaa tactaggtgt cggggagcac agctcttcgg | 720 |
| tgccgccgca aacgcattaa gtattccacc tggggagtac gttcgcaaga atgaaactca | 780 |

-continued

```
aaggaattga cggggacccg cacaagcggt ggagcatgtg gtttaattcg aagcaacgcg      840 aagaaccta ccaagtcttg acatctgcct gaccggtgag taacgtcacc tttccttcgg       900
gacaggcaag acaggtggtg catggttgtc gtcagctcgt gtcgtgagat gttgggttaa      960
gtcccgcaac gagcgcaacc cctatcccca gtagccagca tgtaaaggtg ggcactctga     1020
ggagactgcc agggataacc tggaggaagg tggggatgac gtcaaatcat catgccccttt   1080 atgatttggg ctacacacgt gctacaatgg cgtaaacaga gggaagcgaa agggtgacct    1140
ggagcaaatc ccaaaaataa cgtcccagtt cggactgtag tctgcaaccc gactacacga    1200
agctggaatc gctagtaatc gcggatcaga atgccgcggt gaatacgttc ccgggtcttg    1260
tacacaccgc ccgtcacacc atgggagtca gtaacgcccg aagtcagtga cctaaccgaa    1320
agggaggagc tgccgaaggc gggacggatg actggggtga agtcgtaac               1369
```

<210> SEQ ID NO 41
<211> LENGTH: 1359
<212> TYPE: DNA
<213> ORGANISM: Bacteroides coprocola

<400> SEQUENCE: 41

```
gtatccaacc ttccgtttac tcagggatag cctttcgaaa gaaagattaa tacctgatag      60
tatggtaaga ttgcatgata ataccattaa agattcatcg gtaaacgatg gggatgcgtt     120
ccattaggta gtaggcgggg taacggccca cctagccgac gatggatagg ggttctgaga     180
ggaaggtccc ccacattgga actgagacac ggtccaaact cctacgggag gcagcagtga    240
ggaatattgg tcaatgggcg agagcctgaa ccagccaagt agcgtgaagg atgaaggttc    300
tatggattgt aaacttcttt tataagggaa taaagtgctt tacgtgtaga gttttgtatg    360
taccttatga ataagcatcg gctaactccg tgccagcagc cgcggtaata cggaggatgc    420
gagcgttatc cggatttatt gggtttaaag ggagcgtaga cgggatgtta agtcagctgt    480
gaaagtttgg ggctcaacct taaaattgca gttgaaactg gcgttcttga gtgcggtaga    540
ggcaggcgga attcgtggtg tagcggtgaa atgcttagat atcacgaaga accccgattg    600
cgaaggcagc ttgctggagc gtaactgacg ttgatgctcg aaagtgtggg tatcaaacag    660
gattagatac cctggtagtc cacacggtaa acgatggata ctcgctgttg gcgatatacg    720
gtcagcggcc aagcgaaagc attaagtatc ccacctgggg agtacgccgg caacggtgaa    780
actcaaagga attgacgggg gcccgcacaa gcggaggaac atgtggttta attcgatgat    840
acgcgaggaa ccttacccgg gcttaaatta tgcatgaatg atctggagac agatcagccg    900
caaggcatgt atgaaggtgc tgcatggttg tcgtcagctc gtgccgtgag gtgtcggctt    960
aagtgccata acgagcgcaa ccctttctgc cagttactaa caggcaatgc tgaggactct   1020
ggcggtactg ccatcgtaag atgtgaggaa ggtggggatg acgtcaaatc agcacggccc   1080
ttacgtccgg ggctacacac gtgttacaat gggggtaca gaaggcagct taccggcgac    1140
ggttggccaa tccctaaagc ccctctcagt tcggactgga gtctgcaacc cgactccacg    1200
aagctggatt cgctagtaat cgcgcatcag ccacggcgcg gtgaatacgt tcccgggcct   1260
tgtacacacc gcccgtcaag ccatgaaagc cgggagtacc tgaagtgcgt aaccgcgagg   1320
agcgccctag ggtaacactg gtaattgggg ctaagtcgt                          1359
```

<210> SEQ ID NO 42
<211> LENGTH: 1406
<212> TYPE: DNA

-continued

<213> ORGANISM: Bacteroides plebius

<400> SEQUENCE: 42

| | | | | | |
|---|---|---|---|---|---|
| ggggcagcat | gaacttagct | tgctaagttc | gatggcgacc | ggcgcaccgt | tgagtaacgc | 60 |
| gtatccaacc | ttccgtacac | tcaggaatag | cctttcgaaa | gaaagattaa | tacctgatgg | 120 |
| tatgatggga | ttgcatgaaa | tcatcattaa | agattcatcg | gtgtacgatg | gggatgcgtt | 180 |
| ccattagata | gtaggcgggg | taacggccca | cctagtcgac | gatggatagg | ggttctgaga | 240 |
| ggaaggtccc | ccacattgga | actgagacac | ggtccaaact | cctacgggag | gcagcagtga | 300 |
| ggaatattgg | tcaatgggcg | cgagcctgaa | ccagccaagt | agcgtgaagg | atgaaggtcc | 360 |
| tacggattgt | aaacttcttt | tataagggaa | taaagtcacc | cacgtgtggg | tgtttgtatg | 420 |
| taccttatga | ataagcatcg | gctaactccg | tgccagcagc | cgcggtaata | cggaggatgc | 480 |
| gagcgttatc | cggatttatt | gggtttaaag | ggagcgtaga | cgggtcgtta | agtcagctgt | 540 |
| gaaagttcgg | ggctcaacct | tgaaattgca | gttgatactg | gcgtccttga | gtacggttga | 600 |
| ggcaggcgga | attcgtggtg | tagcggtgaa | atgcttagat | atcacgaaga | accccgattg | 660 |
| cgaaggcagc | ctgctaaacc | gccactgacg | ttgaggctcg | aaagtgtggg | tatcaaacag | 720 |
| gattagatac | cctggtagtc | cacacggtaa | acgatggata | ctcgctgttg | gcgatagact | 780 |
| gtcagcggct | tagcgaaagc | gttaagtatc | ccacctgggg | agtacgccgg | caacggtgaa | 840 |
| actcaaagga | attgacgggg | gcccgcacaa | gcggaggaac | atgtggttta | attcgatgat | 900 |
| acgcgaggaa | ccttacccgg | gcttgaattg | cagacgaatt | gcttggaaac | aggcaagccg | 960 |
| caaggcgtct | gtgaaggtgc | tgcatggttg | tcgtcagctc | gtgccgtgag | gtgtcggctt | 1020 |
| aagtgccata | acgagcgcaa | ccctcgtgtc | cagttgctag | caggtagtgc | tgaggactct | 1080 |
| ggacagactg | ccatcgtaag | atgtgaggaa | ggtggggatg | acgtcaaatc | agcacggccc | 1140 |
| ttacgtccgg | ggctacacac | gtgttacaat | gggggtaca | gcaggcagct | accgggcgac | 1200 |
| cggatgccaa | tcccgaaagc | ctctctcagt | tcggactgga | gtctgcaacc | cgactccacg | 1260 |
| aagctggatt | cgctagtaat | cgcgcatcag | ccacggcgcg | gtgaatacgt | tcccgggcct | 1320 |
| tgtacacacc | gcccgtcaag | ccatgaaagc | cgggggtacc | tgaagtgcgt | aaccgcaagg | 1380 |
| agcgccctag | ggtaaaactg | gtaatt | | | | 1406 |

<210> SEQ ID NO 43
<211> LENGTH: 1420
<212> TYPE: DNA
<213> ORGANISM: Roseburia inulinivorans

<400> SEQUENCE: 43

| | | | | | |
|---|---|---|---|---|---|
| gcacttttgc | cgattttctt | cggaactgaa | gtaatagtga | ctgagtggcg | gacgggtgag | 60 |
| taacgcgtgg | ataacctgcc | tcacacaggg | ggataacagt | tagaaatgac | tgctaatacc | 120 |
| gcataagcgc | acagtaccgc | atggtacagt | gtgaaaaact | ccggtggtgt | gagatggatc | 180 |
| cgcgtctgat | tagccagttg | gcggggtaac | ggcccaccaa | agcgacgatc | agtagccggc | 240 |
| ctgagagggc | gaccggccac | attgggactg | agacacggcc | cagactccta | cgggaggcag | 300 |
| cagtggggaa | tattgcacaa | tgggggaaac | cctgatgcag | cgacgccgcg | tgagcgaaga | 360 |
| agtatttcgg | tatgtaaagc | tctatcagca | gggaagaaaa | tgacggtacc | tgactaagaa | 420 |
| gctccggcta | aatacgtgcc | agcagccgcg | gtaatacgta | tggagcaagc | gttatccgga | 480 |
| tttactgggt | gtaagggag | cgcaggcggt | atgacaagtc | tgatgtgaaa | ggctggggct | 540 |
| caaccccagg | actgcattgg | aaactgtcag | actagagtgt | cggagaggta | agtggaattc | 600 |

```
ctagtgtagc ggtgaaatgc gtagatatta ggaggaacac cagtggcgaa ggcggcttac      660
tggacgacaa ctgacgctga ggctcgaaag cgtggggagc aaacaggatt agataccctg      720
gtagtccacg ccgtaaacga tgaatactag gtgtcgggag gcagagcctt tcggtgccgc      780
agcaaacgca gtaagtattc cacctgggga gtacgttcgc aagaatgaaa ctcaaaggaa      840
ttgacgggga cccgcacaag cggtggagca tgtggtttaa ttcgaagcaa cgcgaagaac      900
cttaccaggc cttgacatcc ccctgacggg acagtaatgt gtccgttcct cgggacaga      960 ggagacaggt ggtgcatggt tgtcgtcagc tcgtgtcgtg agatgttggg ttaagtcccg     1020
caacgagcgc aacccttatc ctcagtagcc agcggataaa gccgggcact ctgtggagac     1080
tgccagggac aacctggagg aaggtgggga tgacgtcaaa tcatcatgcc ccttatggcc     1140
tgggctacac acgtgctaca atggcgtaaa caaagggaag cgaagctgtg aagtgaagca     1200
aatcccaaaa ataacgtctc agttcggatt gtagtctgca actcgactac atgaagctgg     1260
aatcgctagt aatcgcgaat cagaatgtcg cggtgaatac gttcccgggt cttgtacaca     1320
ccgcccgtca caccatggga gtcgggaatg cccgaagccg gtgacccaac cttaaggagg     1380
gagccgtcga aggcaggcct gataactggg gtgaagtcgt                            1420
```

<210> SEQ ID NO 44
<211> LENGTH: 1392
<212> TYPE: DNA
<213> ORGANISM: Ruminococcus albus

<400> SEQUENCE: 44

```
ctgatctagt ggcggacggg tgagtaacac gtgagcaatc tgcctttcag agggggatac       60
cgattggaaa cgatcgttaa taccgcataa cataattgaa ccgcatgatt tgattatcaa      120
agatttatcg ctgaaagatg agctcgcgtc tgattagcta gttggtaagg taacggctta      180
ccaaggcgac gatcagtagc cggactgaga ggttgatcgg ccacattggg actgagacac      240
ggcccagact cctacgggag gcagcagtgg ggaatattgc acaatggagg aaactctgat      300
gcagcgatgc cgcgtgaggg aagaaggttt taggattgta aacctctgtc ttcagggacg      360
aaaaaagacg gtacctgagg aggaagctcc ggctaactac gtgccagcag ccgcggtaat      420
acgtagggag cgagcgttgt ccggaattac tgggtgtaaa gggagcgtag gcgggatcgc      480
aagtcagatg tgaaaactat gggcttaacc cataaactgc atttgaaact gtggttcttg      540
agtgaagtag aggtaagcgg aattcctagt gtagcggtga aatgcgtaga tattaggagg      600
aacatcagtg gcgaaggcgg cttactgggc tttaactgac gctgaggctc gaaagcgtgg      660
ggagcaaaca ggattagata ccctggtagt ccacgccgta acgatgatt actaggtgtg      720 gggggactga ccccttccgt gccgcagcaa acgcaataag taatccacct ggggagtacg      780
accgcaaggt tgaaactcaa aggaattgac ggggcccgc acaagcagtg gagtatgtgg      840
attaattcga agcaacgcga agaaccttac caggtcttga catcgtatgc atagctcaga      900
gatgagtgaa atctcttcgg agacatatag acaggtggtg catggttgtc gtcagctcgt      960
gtcgtgagat gttgggttaa gtcccgcaac gagcgcaacc cttactgtta gttgctacgc     1020
aagagcactc tagcaggact gccgttgaca aaacggagga aggtggggat gacgtcaaat     1080
catcatgccc cttatgacct gggcctcaca cgtactacaa tggctgttaa cagagggatg     1140
caaagccgcg aggtagagcg aacccctaaa agcagtctta gttcggattg taggctgcaa     1200
cccgcctaca tgaagtcgga attgctagta atcgcagatc agcatgctgc ggtgaatacg     1260
```

```
ttcccgggcc ttgtacacac cgcccgtcac gccatgggag tcggtaacac ccgaagcctg    1320
tagtctaacc gcaaggagga cgcagtcgaa ggtgggattg atgactgggg tgaagtcgta    1380
acagggtaac cg                                                        1392
```

<210> SEQ ID NO 45
<211> LENGTH: 1414
<212> TYPE: DNA
<213> ORGANISM: Blautia producta

<400> SEQUENCE: 45

```
tggacagatt cttcggatga agtccttagt gactgagtgg cggacgggtg agtaacgcgt      60
gggtaacctg cctcatacag ggggataaca gttagaaatg gctgctaata ccgcataagc     120
gcacggtact gcatggtaca gtgtgaaaaa ctccggtggt atgagatgga cccgcgttgg     180
attagctagt tggcagggta acggcctacc aaggcgacga tccatagccg gcctgagagg     240
gtggacggcc acattgggac tgagacacgg cccagactcc tacgggaggc agcagtgggg     300
aatattgcac aatgggggaa accctgatgc agcgacgccg cgtgagcgaa gaagtatttc     360
ggtatgtaaa gctctatcag cagggaagaa aatgacggta cctgactaag aagccccggc     420
taactacgtg ccagcagccg cggtaatacg tagggggcaa gcgttatccg gatttactgg     480
gtgtaaaggg agcgtagacg gaatggcaag tctgatgtga aaggcggggg ctcaaccccg     540
ggactgcatt ggaaactgtc aatctagagt accgagggg taagtggaat tcctagtgta      600
gcggtgaaat gcgtagatat taggaggaac accagtggcg aaggcggctt actggacggt     660
aactgacgtt gaggctcgaa agcgtgggga gcaaacagga ttagataccc tggtagtcca     720
cgccgtaaac gatgaatact aggtgttggg gagcaaagct cttcggtgcc gcagcaaacg     780
caataagtat tccacctggg gagtacgttc gcaagaatga aactcaaagg aattgacggg     840
gacccgcaca agcggtggag catgtggttt aattcgaagc aacgcgaaga accttaccaa     900
atcttgacat cgatctgacc ggactgtaat gagtcctttc ccttcgggga cagagaagac     960
aggtggtgca tggttgtcgt cagctcgtgt cgtgagatgt tgggttaagt cccgcaacga    1020
gcgcaaccct tatcctcagt agccagcaag tgaagttggg cactctgtgg agactgccag    1080
ggataacctg gaggaaggtg gggatgacgt caaatcatca tgccccttat gatttgggct    1140
acacacgtgc tacaatggcg taaacaaagg gaagcgatca cgcgagtgtg agcaaatctc    1200
aaaaataacg tctcagttcg gattgtagtc tgcaactcga ctacatgaag ctggaatcgc    1260
tagtaatcgc aggtcagcat actgcggtga atacgttccc gggtcttgta cacaccgccc    1320
gtcacaccat gggagtcagt aacacccgaa gccggtgacc taaccgaaag gaaggagccg    1380
tcgaaggtgg gaccgataac tggggtgaag tcgt                                1414
```

<210> SEQ ID NO 46
<211> LENGTH: 1389
<212> TYPE: DNA
<213> ORGANISM: Clostridium nexile

<400> SEQUENCE: 46

```
gtttgtgact tagtggcgga cgggtgagta acgcgtgggt aacctgcctt atacaggggg      60
ataacagtta gaaatgactg ctaataccgc ataagcgcac agtctcgcat gggacagtgt     120
gaaaaactaa ggtggtataa gatggacccg cgtctgatta gctagttggt ggggtaaagg     180
cctaccaagg cgacgatcag tagccgacct gagagggtga tcggccacat tgggactgag     240
acacggccca aactcctacg ggaggcagca gtggggaata ttgcacaatg ggggaaaccc     300
```

```
tgatgcagca acgccgcgtg aaggaagaag tatctcggta tgtaaacttc tatcagcagg    360
gaagaaaatg acggtacctg actaagaagc tccggctaaa tacgtgccag cagccgcggt    420
aatacgtatg gagcaagcgt tatccggatt tactgggtgt aaagggagcg taggcggtta    480
tgcaagtcag atgtgaaagc ccggggctta accccgggac tgcatttgaa actgtgtaac    540
tagagtgtcg gagaggtaag tggaattcct agtgtagcgg tgaaatgcgt agatattagg    600
aggaacacca gtggcgaagg cggcttactg gacgataact gacgctgagg ctcgaaagcg    660
tggggagcaa acaggattag ataccctggt agtccacgcc gtaaacgatg aatactaggt    720
gttggggagc aaagctcttc ggtgccgcag caaacgcaat aagtattcca cctggggagt    780
acgttcgcaa gaatgaaact caaaggaatt gacggggacc cgcacaagcg gtggagcatg    840
tggtttaatt cgaagcaacg cgaagaacct taccaagtct tgacatctgg atgaccggac    900
cgtaatgggt cctttccttc gggacatcca agacaggtgg tgcatggttg tcgtcagctc    960
gtgtcgtgag atgttgggtt aagtcccgca acgagcgcaa cccttatcct tagtagccag   1020
cagtaagatg ggcactctag ggagactgcc ggagacaatc cggaggaagg tggggatgac   1080
gtcaaatcat catgcccctt atgacttggg ctacacacgt gctacaatgg cgtaaacaaa   1140
gggaagcgag accgcgaggt taagcaaatc tcaaaaataa cgtctcagtt cggattgtag   1200
tctgcaactc gactacatga agctggaatc gctagtaatc gcgaatcagc atgtcgcggt   1260
gaatacgttc ccgggtcttg tacacaccgc ccgtcacacc atgggagtcg ataacgcccg   1320
aagccggtga ctcaaccgaa aggagagagc cgtcgaaggc gggatggata actggggtga   1380
agtcgtaac                                                            1389
```

<210> SEQ ID NO 47
<211> LENGTH: 1404
<212> TYPE: DNA
<213> ORGANISM: Butyricicoccus pullicaecorum

<400> SEQUENCE: 47

```
atctcttcgg agatggaatt cttaacctag tggcggacgg gtgagtaacg cgtgagcaat     60
ctgcctttag gagggggata acagtcggaa acggctgcta ataccgcata atacgtttgg    120
gaggcatctc ttgaacgtca aagattttat cgcctttaga tgagctcgcg tctgattagc    180
tggttggcgg ggtaacggcc caccaaggcg acgatcagta gccggactga gaggttgaac    240
ggccacattg ggactgagac acggcccaga ctcctacggg aggcagcagt ggggaatatt    300
gcgcaatggg ggaaaccctg acgcagcaac gccgcgtgat tgaagaaggc cttcgggttg    360
taaagatctt taatcaggga cgaaaaatga cggtacctga gaataagct ccggctaact    420 acgtgccagc agccgcggta atacgtaggg agcaagcgtt atccggattt actgggtgta    480
aagggcgcgc aggcgggccg gcaagttggg agtgaaatcc cggggcttaa ccccggaact    540
gctttcaaaa ctgctggtct tgagtgatgg agaggcaggc ggaattccgt gtgtagcggt    600
gaaatgcgta gatatacgga ggaacaccag tggcgaaggc ggcctgctgg acattaactg    660
acgctgaggc gcgaaagcgt ggggagcaaa caggattaga taccctggta gtccacgccg    720
taaacgatgg atactaggtg tgggaggtat tgacccttc cgtgccgcag ttaacacaat    780
aagtatccca cctggggagt acggccgcaa ggttgaaact caaaggaatt gacggggcc    840 cgcacaagca gtggagtatg tggtttaatt cgaagcaacg cgaagaacct taccaggtct    900
tgacatcccg atgaccggcg tagagatacg ccctctcttc ggagcatcgg tgacaggtgg    960
```

```
tgcatggttg tcgtcagctc gtgtcgtgag atgttgggtt aagtcccgca acgagcgcaa   1020
cccttacggt tagttgatac gcaagatcac tctagccgga ctgccgttga caaaacggag   1080
gaaggtgggg acgacgtcaa atcatcatgc cccttatgac ctgggctaca cacgtactac   1140
aatggcagtc atacagaggg aagcaatacc gcgaggtgga gcaaatccct aaaagctgtc   1200
ccagttcaga ttgcaggctg caacccgcct gcatgaagtc ggaattgcta gtaatcgcgg   1260
atcagcatgc cgcggtgaat acgttcccgg gccttgtaca caccgcccgt cacaccatga   1320
gagccgtcaa tacccgaagt ccgtagccta accgcaaggg gggcgcggcc gaaggtaggg   1380
gtggtaatta gggtgaagtc gtac                                         1404

<210> SEQ ID NO 48
<211> LENGTH: 1407
<212> TYPE: DNA
<213> ORGANISM: Ruminococcus flavefaciens

<400> SEQUENCE: 48
agtcgacgga cgaggaggag cttgcttctc cgagttagtg gcggacgggt gagtaacacg     60
tgagcaacct acccttgaga gggggatagc ttctggaaac ggatggtaat accccataac    120
atatatttta ggcatctaag atatatcaaa gaaattcgct caaggatggg ctcgcgtctg    180
attagatagt tggtgaggta acggcccacc aagtcgacga tcagtagccg gactgagagg    240
ttgaacggcc acattgggac tgagacacgg cccagactcc tacggaggc agcagtgggg     300 aatattgcac aatgggggga accctgatgc agcgatgccg cgtggaggaa gaaggttttc    360
ggattgtaaa ctccttttaa cagggacgat aatgacggta cctgaagaaa agctccggc     420 taactacgtg ccagcagccg cggtaatacg tagggagcga cgttgtccg gaattactgg     480 gtgtaaaggg agcgtaggcg ggacggtaag tcaggtgtga atatacgtg ctcaacatgt     540 agactgcact tgaaactgct gttcttgagt gaagtagagg taagcggaat tcctagtgta    600
gcggtgaaat gcgtagatat taggaggaac atcggtggcg aaggcggctt actgggcttt    660
tactgacgct gaggctcgaa agcgtgggga gcaaacagga ttagataccc tggtagtcca    720
cgctgtaaac gatgattact aggtgtgggg ggactgaccc cttccgtgcc gcagttaaca    780
caataagtaa tccacctggg gagtacgacc gcaaggttga aactcaaagg aattgacggg    840
ggcccgcaca gcagtggag tatgtggttt aattcgaagc aacgcgaaga accttaccag    900
gtcttgacat cgtatgcata gtctagagat agatgaaatc ccttcgggga catatagaca    960
ggtggtgcat ggttgtcgtc agctcgtgtc gtgagatgtt gggttaagtc ccgcaacgag   1020 cgcaacccctt acctttagtt gctacgcaag agcactctag agggactgcc gttgacaaaa   1080
cggaggaagg tggggatgac gtcaaatcat catgcccctt atgacctggg ctacacacgt   1140
actacaatgg caattaacag agggaagcaa acagcgatg tggagcaaat cccgaaaaat   1200
tgtcccagtt cagattgcag gctgcaactc gcctgcatga agtcggaatt gctagtaatc   1260
gcagatcaga atgctgcggt gaatacgttc ccgggccttg tacaccgcc cgtcacacc    1320 atgggagtcg gtaacacccg aagcctgtag tctaacctta taggaggacg cagtcgaagg   1380
tgggattgat gactggggtg aagtcgt                                      1407

<210> SEQ ID NO 49
<211> LENGTH: 1349
<212> TYPE: DNA
<213> ORGANISM: Clostridium orbiscindens

<400> SEQUENCE: 49
```

```
aaagggaatg cttagtggcg gacgggtgag taacgcgtga gtaacctgcc ttggagtggg       60
gaataacagc cggaaacggc tgctaatacc gcatgatgta tctggatcgc atggttctgg     120
ataccaaaga tttatcgctc tgagatggac tcgcgtctga ttagctagtt ggtgaggtaa     180
cggctcacca aggcgacgat cagtagccgg actgagaggt tggccggcca cattgggact     240
gagacacggc ccagactcct acggaggca gcagtgggga atattgggca atgggcgaaa      300
gcctgaccca gcaacgccgc gtgaaggaag aaggccctcg ggttgtaaac ttcttttgtc     360
agggacgaag caagtgacgg tacctgacga ataagccacg gctaactacg tgccagcagc     420
cgcggtaata cgtaggtggc aagcgttatc cggatttact gggtgtaaag ggcgtgtagg     480
cgggagtgca agtcagatgt gaaaactatg ggctcaaccc atagcctgca tttgaaactg     540
tacttcttga gtgatggaga ggcaggcgga attccctgtg tagcggtgaa atgcgtagat     600
atagggagga acaccagtgg cgaaggcggc ctgctggaca ttaactgacg ctgaggcgcg     660
aaagcgtggg gagcaaacag gattagatac cctggtagtc cacgccgtaa acgatggata     720
ctaggtgtgg ggggtctgac cccctccgtg ccgcagttaa cacaataagt atcccacctg     780
gggagtacga tcgcaaggtt gaaactcaaa ggaattgacg ggcccccgca caagcggtgg     840
agtatgtggt ttaattcgaa gcaacgcgaa gaaccttacc aggacttgac atcctactaa     900
cgaagcagag atgcataagg tgcccttcgg ggaaagtaga gacaggtggt gcatggttgt     960
cgtcagctcg tgtcgtgaga tgttgggtta agtcccgcaa cgagcgcaac ccttattgtt    1020
agttgctacg caagagcact ctagcgagac tgccgttgac aaaacggagg aaggtgggga    1080
cgacgtcaaa tcatcatgcc ccttatgtcc tgggccacac acgtactaca atggcggtca    1140
acagagggaa gcaaagccgc gaggtggagc aaatccctaa aagccgtccc agttcggatt    1200
gcaggctgaa actcgcctgt atgaagtcgg aatcgctagt aatcgcggat cagcatgccg    1260
cggtgaatac gttcccgggc cttgtacaca ccgcccgtca caccatgaga gtcgggaaca    1320
cccgaagtcc gtagcctaac agcaatggg                                      1349

<210> SEQ ID NO 50
<211> LENGTH: 1420
<212> TYPE: DNA
<213> ORGANISM: Ruminococcus bromii

<400> SEQUENCE: 50
acgaagcttt gaggagcttg cttttttaagc ttagtggcgg acgggtgagt aacgcgtgag      60
caacctgcct ctcagagggg aataacgttt tgaaaagaac gctaataccg cataacatat     120
cggaaccgca tgattctgat atcaaggag caatccgctg agagatgggc tcgcgtccga      180
ttagttagtt ggtgaggtaa cggctcacca agactacgat cggtagccgg actgagaggt     240
tgatcggcca cattgggact gagacacggc ccagactcct acggaggca gcagtggggg      300 atattgcgca atgggggaaa ccctgacgca gcaacgccgc gtgaaggaag aaggtcttcg     360
gattgtaaac ttcttttgtc agggacgaag aaagtgacgg tacctgacga ataagctccg     420
gctaactacg tgccagcagc cgcggtaata cgtagggagc gagcgttgtc cggatttact     480
gggtgtaaag ggtgcgtagg cggccgagca agtcagttgt gaaaactatg gcttaaccc      540 ataacgtgca attgaaactg tccggcttga gtgaagtaga ggtagcggaa ttcccggtg      600 tagcggtgaa atgcgtagag atcgggagga acaccagtgg cgaaggcggc ctactgggct     660
ttaactgacg ctgaggcacg aaagcatggg tagcaaacag gattagatac cctggtagtc     720
```

| | |
|---|---|
| catgccgtaa acgatgatta ctaggtgtgg ggggactgac cccttccgtg ccgcagttaa | 780 |
| cacaataagt aatccacctg gggagtacgg ccgcaaggtt gaaactcaaa ggaattgacg | 840 |
| ggggcccgca caagcagtgg agtatgtggt ttaattcgaa gcaacgcgaa gaaccttacc | 900 |
| aggtcttgac atcctgagaa tccttaagag attagggagt gccttcggga actcagagac | 960 |
| aggtggtgca tggttgtcgt cagctcgtgt cgtgagatgt tgggttaagt cccgcaacga | 1020 |
| gcgcaaccct tgctattagt tgctacgcaa gagcactcta ataggactgc cgttgacaaa | 1080 |
| acggaggaag gtggggacga cgtcaaatca tcatgcccct tatgacctgg gctacacacg | 1140 |
| tactacaatg gccattaaca gagggaagca aaaccgcgag gcagagcaaa cccctaaaaa | 1200 |
| tggtcccagt tcggattgta ggctgcaacc cgcctacatg aagttggaat tgctagtaat | 1260 |
| cgcggatcag catgccgcgg tgaatacgtt cccgggcctt gtacacaccg cccgtcacac | 1320 |
| catgggagcc ggtaataccc gaagtcagta gtctaacagc aatgaggacg ctgccgaagg | 1380 |
| taggattggc gactggggtg aagtcgtaac aaggtaaccg | 1420 |

<210> SEQ ID NO 51
<211> LENGTH: 1490
<212> TYPE: DNA
<213> ORGANISM: Ruminococcus albus

<400> SEQUENCE: 51

| | |
|---|---|
| agagtttgat cctggctcag gacgaacgct ggcggcacgc ttaacacatg caagtcgaac | 60 |
| gagagaagag aagcttgctt ttctgatcta gtggcggacg ggtgagtaac acgtgagcaa | 120 |
| tctgcctttc agaggggggat accgattgga aacgatcgtt aataccgcat aacataattg | 180 |
| aaccgcatga tttgattatc aaagatttat cgctgaaaga tgagctcgcg tctgattagc | 240 |
| tagttggtaa ggtaacggct taccaaggcg acgatcagta gccggactga gaggttgatc | 300 |
| ggccacattg ggactgagac acggcccaga ctcctacggg aggcagcagt ggggaatatt | 360 |
| gcacaatgga ggaaactctg atgcagcgat gccgcgtgag ggaagaaggt tttaggattg | 420 |
| taaacctctg tcttcaggga cgaaaaaaaa gacggtacct gaggaggaag ctccggctaa | 480 |
| ctacgtgcca gcagccgcgg taatacgtag ggagcgagcg ttgtccggaa ttactgggtg | 540 |
| taaagggagc gtaggcggga tcgcaagtca gatgtgaaaa ctatgggctt aacccataaa | 600 |
| ctgcatttga aactgtggtt cttgagtgaa gtagaggtaa gcggaattcc tagtgtagcg | 660 |
| gtgaaatgcg tagatattag gaggaacatc agtggcgaag gcggcttact gggctttaac | 720 |
| tgacgctgag gctcgaaagc gtggggagca aacaggatta gataccctgg tagtccacgc | 780 |
| cgtaaacgat gattactagg tgtgggggga ctgacccctt ccgtgccgca gcaaacgcaa | 840 |
| taagtaatcc acctggggag tacgaccgca aggttgaaac tcaaaggaat tgacggggc | 900 |
| ccgcacaagc agtggagtat gtggattaat tcgaagcaac gcgaagaacc ttaccaggtc | 960 |
| ttgacatcgt atgcatagct cagagatgag tgaaatctct tcggagacat atagacaggt | 1020 |
| ggtgcatggt tgtcgtcagc tcgtgtcgtg agatgttggg ttaagtcccg caacgagcgc | 1080 |
| aacccttact gttagttgct acgcaagagc actctagcag gactgccgtt gacaaaacgg | 1140 |
| aggaaggtgg ggatgacgtc aaatcatcat gccccttatg acctgggcct cacacgtact | 1200 |
| acaatggctg tcaacagagg gatgcaaagc cgcgaggtgg agcgaacccc taaaagcagt | 1260 |
| cttagtcgg attgtaggct gcaacccgcc tacatgaagt cggaattgct agtaatcgca | 1320 |
| gatcagcatg ctgcggtgaa tacgttcccg ggccttgtac acaccgcccg tcacgccatg | 1380 |
| ggagtcggta acacccgaag cctgtagtct aaccgcaagg aggacgcagt cgaaggtggg | 1440 |

```
attgatgact ggggtgaagt cgtaacaagg tagccgtatc ggaaggtgcg          1490

<210> SEQ ID NO 52
<211> LENGTH: 20
<212> TYPE: DNA
<213> ORGANISM: Artificial Sequence
<220> FEATURE:
<223> OTHER INFORMATION: 16S rRNA forward primer

<400> SEQUENCE: 52
agagtttgat ymtggctcag                                          20

<210> SEQ ID NO 53
<211> LENGTH: 21
<212> TYPE: DNA
<213> ORGANISM: Artificial Sequence
<220> FEATURE:
<223> OTHER INFORMATION: 1510R reverse primer

<400> SEQUENCE: 53
acggytacct tgttacgact t                                        21

<210> SEQ ID NO 54
<211> LENGTH: 61
<212> TYPE: DNA
<213> ORGANISM: Artificial Sequence
<220> FEATURE:
<223> OTHER INFORMATION: 27F primer

<400> SEQUENCE: 54
aatgatacgg cgaccaccga gatctacact atggtaattc cagmgttyga tymtggctca    60
g                                                              61

<210> SEQ ID NO 55
<211> LENGTH: 66
<212> TYPE: DNA
<213> ORGANISM: Artificial Sequence
<220> FEATURE:
<223> OTHER INFORMATION: 338R primer

<400> SEQUENCE: 55
caagcagaag acggcatacg agatacgaga ctgattagtc agtcagaagc tgcctcccgt    60
aggagt                                                         66

<210> SEQ ID NO 56
<211> LENGTH: 20
<212> TYPE: DNA
<213> ORGANISM: Artificial Sequence
<220> FEATURE:
<223> OTHER INFORMATION: 338F primer

<400> SEQUENCE: 56
actcctacgg gaggcagcag                                          20

<210> SEQ ID NO 57
<211> LENGTH: 18
<212> TYPE: DNA
<213> ORGANISM: Artificial Sequence
<220> FEATURE:
<223> OTHER INFORMATION: 926R primer

<400> SEQUENCE: 57
ccgtcaattc mtttragt                                            18
```